US011331299B2

(12) United States Patent
Duke et al.

(10) Patent No.: US 11,331,299 B2
(45) Date of Patent: May 17, 2022

(54) MEDICINAL USE OF SERRULATANE DITERPENES

(71) Applicant: The University of Sydney, Sydney (AU)

(72) Inventors: Colin Charles Duke, Randwick (AU); Rujee Kyokajee Duke, Randwick (AU); Van Hoan Tran, Guilford (AU)

(73) Assignee: Kynan Duke IP, LLC, Greensboro, NC (US)

( * ) Notice: Subject to any disclaimer, the term of this patent is extended or adjusted under 35 U.S.C. 154(b) by 0 days.

(21) Appl. No.: 17/123,539

(22) Filed: Dec. 16, 2020

(65) Prior Publication Data
US 2021/0212982 A1   Jul. 15, 2021

Related U.S. Application Data

(63) Continuation-in-part of application No. 16/330,676, filed as application No. PCT/AU2017/050972 on Sep. 7, 2017, now Pat. No. 10,912,742.

(30) Foreign Application Priority Data

Sep. 7, 2016   (AU) .................................. 2016903585

(51) Int. Cl.
| *A61K 31/352* | (2006.01) |
| *A61K 31/05* | (2006.01) |
| *A61K 31/216* | (2006.01) |
| *A61K 36/80* | (2006.01) |
| *A61P 35/00* | (2006.01) |
| *A61K 31/085* | (2006.01) |
| *A61K 31/7068* | (2006.01) |

(52) U.S. Cl.
CPC ............ *A61K 31/352* (2013.01); *A61K 31/05* (2013.01); *A61K 31/085* (2013.01); *A61K 31/216* (2013.01); *A61K 36/80* (2013.01); *A61P 35/00* (2018.01); *A61K 31/7068* (2013.01)

(58) Field of Classification Search
CPC .................................................... A61K 31/352
USPC ....................................................... 549/388
See application file for complete search history.

(56) References Cited

U.S. PATENT DOCUMENTS 7,700,798 B1    4/2010  Davies et al.
2002/0091093 A1  7/2002  Jacobs et al.

FOREIGN PATENT DOCUMENTS

WO    WO 03065001 A2    8/2003
WO    WO 2012149608 A1  11/2012

OTHER PUBLICATIONS

Abell et al.; "Eremophilane and Serrulatane Terpenoids from Eremophila Rotundifolia;" Australian Journal of Chemistry; (1985); pp. 1263-1269; vol. 38, No. 8.

Abell et al.; "The Structure of a Stable Serrulatane Diterpenoid Acetal from Eremophila Rotundifolia;" Australian Journal of Chemistry; (1985); pp. 1837-1845; vol. 38, No. 12.

Adams-Cioaba et al.; "Crystal Structures of the Tudor Domains of Human PHF20 Reveal Novel Structural Variations on the Royal Family of Proteins;" FEBS Letters; (2012); pp. 859-865; vol. 586; <doi: 10.1016/j.febslet.2012.02.012 >.

Adcock et al.; "Abnormal Histone Acetylase and Deacetylase Expression and Function in Lung Inflammation;" Inflammation Research; (2006); pp. 311-313 21; vol. 5 5; <doi: 10.1007/00011-006-0081-1>.

Ahuja et al.; "The CXC Chemokines Growth-Regulated Oncogene (GRO) α GROβ, GROγ, Neutrophil-Activating Peptide-2, and Epithelial Cell-Derived Neutrophil-Activating Peptide-78 Are Potent Agonists for the Type B, but Not the Type A, Human Interleukin-8 Receptor;" The Journal of Biological Chemistry; (Aug. 23, 1996); pp. 20545-20550; vol. 271, No. 34.

Akdis et al.; "Interleukins (from IL-1 to IL-38), Interferons, Transforming Growth Factor β, and TNF-α: Receptors, Functions, and Roles in Diseases;" Journal of Allergy and Clinical Immunology; (Oct. 2016); pp. 984-1010; vol. 138, No. 4; <doi: 10.1016/j.jaci.2016.06.033 >.

Ali et al.; "Diverse Functions of PHD Fingers of the MLL/KMT2 Subfamily;" Biochim Biophys Acta; (Feb. 2014); pp. 366-371; vol. 1843, No. 2; <doi: 10.1016.j.bbamcr.2013.11.016 >.

Allali-Hassani et al.; "A Basic Post-SET Extension of NSDs is Essential for Nucleosome Binding in Vitro;" Journal of Biomolecular Screening; (2014); pp. 928-935; vol. 19, No. 6; <doi: 10.1177/1087057114525854 >.

Aminimoghadamfaroouj et al.; "Structure Elucidation and botanical Characterization of Diterpenes from a Specific Type of Bee Glue;" Molecules; (2017); pp. 10/13-11/13; vol. 22, No. 7; <doi: 10.3390/molecules22071185 >.

An et al.; "Crystal Structure of the Human Histone Methyltransferase ASH1L Catalytic Domain and Its Implications for the Regulatory Mechanism;" The Journal of Biological Chemistry; (Mar. 11, 2011); pp. 8369-8374; vol. 286, No. 10; <doi: 10.1074/jbcM110.203380 >.

Aoki et al.; "Enzymatic Properties of de novo-type Mouse DNA (Cytosine-5) Methyltransferases;" Nucleic Acids Research; (2001); pp. 3506-3512; vol. 20, No. 17.

Arrowsmith et al.; "Epigenetic Protein Families: A New Frontier for Drug Discovery;" Nature Reviews Drug Discovery; (Apr. 13, 2012); pp. 384-400; vol. 11; <doi: 10.1038/nrd3674 >.

Avvakumov et al.; "The MYST Family of Histone Acetyltransferases and their Intimate Links to Cancer;" Oncogene; (2007); pp. 5395-5407; vol. 26; <doi: 10.1038/sj.onc.1210608 >.

(Continued)

*Primary Examiner* — Taofiq A Solola
(74) *Attorney, Agent, or Firm* — Thorpe North & Western, LLP

(57) ABSTRACT

The present disclosure is drawn to methods of treating diseases or disorders, and uses of preparing medicaments. The methods of administering and/or preparation of medicaments can include the use of a compound of Formula (I) disclosed herein, or a geometric isomer, stereoisomer, and/or pharmaceutically acceptable salt or solvate thereof.

36 Claims, 21 Drawing Sheets

(56) References Cited

OTHER PUBLICATIONS

Baek; "When Signaling Kinases Meet Histones and Histone Modifiers in the Nucleus;" Molecular Cell; (2011); pp. 274-284; vol. 42, No. 3; <doi: 10.1016/j.molcel.2011.03.022 >.

Barnett et al.; "Identification and Characterization of Pleckstrin-Homology-Doman-Dependent and Isoenzyme-Specific Akt Inhibitors;" Biochem Journal; (2005); pp. 399-408; vol. 385.

Barretina et al.; "The Cancer Cell Line Encyclopedia Enables Predictive Modeling of Anticancer Drug Sensitivity;" Nature; (Sep. 29, 2012); pp. 603-607; vol. 483, No. 7391; <doi: 10.1038/nature11003 >.

Becker et al.; "Thioredoxin Reductase as a Pathophysiological Factor and Drug Target;" European Journal of Biochem; (2000); pp. 6118-6125; vol. 267.

Berry et al.; "KDM4/JMJD2 Histone Demethylases: Epigenetic Regulators in Cancer Cells;" Cancer Research; (May 15, 2013; pp. 2936-2942; vol. 73, No. 10; <doi: 10.1158/0008-5472.CAN-12-4300 >.

Biggar et al.; "Non-Histone Protein Methylation as a Regulator of Cellular Signalling and Function;" Nature Reviews Molecular Cell Biology; (Jan. 2015); pp. 1-17; vol. 16; <doi: 10.1038/nrm3915 >.

Blus et al.; "Epigenetic Virtues of Chromodomains;" Critical Reviews in Biochemistry and Molecular Biology; (Dec. 2011); pp. 507-526; vol. 46, No. 6; <doi: 10.3109/10409238.2011.619164 >.

Brigelius-Flohe et al.; "Basic Principles and Emerging Concepts in the Redox Control of Transcription Factors;" Antioxidants & Redox Signaling; (2011); pp. 2335-2381; vol. 15, No. 8; <doi: 10.1089/ars.2010.3534 >.

CAS Registry No. 1025822-75-6; STN Entry Date: Jun. 5, 2008; 1,2,4-NaphUiaienetrioi, 5-[(1S)-1,5-Dimethyl-4-Hexen-1-yl]-1,4,5,6,7,8-hexahydro-3,8-dimethyl- (5R,8S)-STN Entry.

CAS Registry No. 1026551-09-6; STN Entry Date: Jun. 8, 2008; 1,2-Napbthalenedione, 5-[(1S)-1,5-dimethyl-4-hexen-1-yl]-5,6,7,8-tetrahydroxy-3,8-dimethyl- (5R,8S)-STN Entry.

Bünning et al.; "Substrate Specificity and Kinetic Characteristics of Angiotensin Converting Enzyme;" Biochemistry; (1983); pp. 103-110; vol. 22, No. 1.

Casciello et al.; "Functional Role of G9a Histone Methyltransferase in Cancer;" Frontiers in Immunology; (Sep. 25, 2015); 12 pages; vol. 6, Article 487; <doi: 10.3389/fimmu.2015.00487 >.

Cheng et al.; "Small Molecule Regulators of Protein Arginine Methyltransferases;" The Journal of Biological Chemistry; (Jun. 4, 2004); pp. 23892-23899; vol. 279, No. 23; <doi: 10.1074/jbc.M401853200 >.

Chowdhury et al.; "The Oncometabolite 2-Hydroxyglutarate Inhibits Histone Lysine Demethylases;" European Molecular Biology Organization Reports; (2011); pp. 463-469; vol. 12, No. 5; <doi: 10.1038/embor.2011.43 >.

Ciceri et al.; "Dual Kinase-Bromodomain Inhibitors for Rationally Designed Polvpharmacologv;" Nature Chemical Biology, (Apr. 2014); pp. 305-312; vol. 10, No. 4; <doi: 10.10s8/nchembio.1471 >.

Ciró et al.; "ATAD2 Is a Novel Cofactor for MYC, Overexpressed and Amplified in Aggressive Tumors;" The Journal of Cancer Research; (Nov. 1, 2009); pp. 8491-8498; vol. 69, No. 21; <doi: 10.1158/0008-5472.CAN-09-2131 >.

Cobb et al.; "Functional Expression of Soluble ICAM-1 by Baculovirus-Infected Sf9 Cells;" Biochemical and Biophysical Research Communications; (Jun. 30, 1992); pp. 1022-1033; vol. 185, No. 3.

Combadiere et al.; "Identification of CX$^3$CR1: A Chemotactic Receptor for the Human CX$^3$C Chemokine Fractalkine and a Fusion Coreceptor for HIV-1;" The Journal of Biological Chemistry; (Sep. 11, 1998); pp. 23799-23804; vol. 273, No. 37.

Copeland et al.; "Protein Methyltransferases as a Target Class for Drug Discovery;" Nature Reviews—Drug Discovery; (Sep. 2009); pp. 724-732; vol. 8; <doi: 10.1038/nrd2974 >.

Couvelard et al.; "Overexpression of the Oxygen Sensors PHD-1, PHD-2, PHD-3, and FIH Is Associated with Tumor Aggressiveness in Pancreatic Endocrine Tumors;" Clinical Cancer Research; (Oct. 15, 2008); pp. 6634-6639; vol. 14, No. 20; <doi: 10.1158/1078-0432.CCR-07-5258 >.

Cowin et al.; "Selective Reduction of Sernulatenol as a Route to Seco-Pseudopterosin Analogues;" Journal of Natural Products; (1992); pp. 1790-1794; vol. 55, No. 12.

Croft et al.; "The Chemistry of Eremophilia spp. XVI. New Serrulatanes from *Eremophilia* spp.;" Australian Journal of Chemistry; (1981); pp. 1951-1957; vol. 34, No. 9.

Cyr et al.; "The Redox Basis of Epigenetic Modifications: From Mechanisms to Functional Consequences;" Antioxidants & Redox Signaling; (2011); pp. 551-589; vol. 15, No. 2; <doi: 10.1089/ars.2010.3492 >.

D'Lgnazio et al.; "NF-κB and HIF Crosstalk in Immune Responses;" Federation of European Biochemical Societies Journal; (2016); pp. 413-424; vol. 283; <doi: 10.1111/febs.13578 >.

Dai el al.; "Synthetic and Isolation Studies Related to Ilie Marine Natural Products (+)-Elisabethadione and (+)-Elisabethamine;" Journal of Organic Chemistry; (2007); pp. 1895-1900; vol. 72.

Davies et al.; "Application of the Combined C—H Activation/Cope Rearrangement as a Key step in the Total Syntheses of the Assigned Structure of (+)-Elisabethadione and a (+)-P-Benzoquinone Natural Product;" Tetrahedron; (2006): pp. 10477-10484; vol. 62, No. 45.

Davis et al.; "New Lamellarin Alkaloids from the Australian Ascidian, Didemnum Chartaceum;" Journal of Natural Products; (1999); pp. 419-424; vol. 62; <doi: 10.1021/np9803530 >.

De Backer et al.; "Genomic Cloning, Heterologous Expression and Pharmacological Characterization of a Human Histamine H1 Receptor;" Biochemical and Biophysical Research Communications; (Dec. 30, 1993); pp. 1601-1608; vol. 197, No. 3.

Dierks et al.; "A Method for the Simultaneous Evaluation of the Activities of Seven Major Human Drug-Metabolizing Cytochrome P450S using an in Vitro Cocktail of Probe Substrates and Fast Gradient Liquid Chromatography Tandem Mass Spectrometry;" Drug Metabolism and Disposition; (2001); pp. 23-29; vol. 29, No. 1.

Dittadi et al.; "Radioligand Binding Assay of Epidermal Growth Factor Receptor: Causes of Variability and Standardization of the Assay;" Clinical Chemistry; (1990); pp. 849-854; vol. 36, No. 6.

Du et al.; "Histone H3 K36 Methylation is Mediated by a Trans-Histone Methylation Pathway Involving an Interaction Between Set2 and Histone H4;" Genes & Development; (2008); pp. 2786-2798; vol. 22; <doi: 10.1101/gad.1700008 >.

Escarcena et al.; "Diterpenes Synthesized from the Natural Serrulatane Leubethanol and Their in Vitro Activities Against Mycobacterium tuberculosis;" Molecules; (2015); pp. 7245-7262; vol. 20, No. 4; < doi: 10.3390/molecules20047245 >.

Fallahi-Sichani et al.; "Metrics Other Than Potency Reveal Systematic Variation in Responses to Cancer Drugs;" Nature Chemical Biology; (Nov. 2013); pp. 708-714; vol. 9, No. 11; <doi: 10.1038/nchembio.1337 >.

Ferns, T., et al., "Oxidations of erogergiaene in pseudopterosin biosynthesis", Tetrahedron (2005), vol. 61(52), pp. 12358-12365.

Filippakopoulos et al.; "Histone Recognition and Large-Scale Structural Analysis of the Human Bromodomain Family;" Cell; (Mar. 30, 2012); pp. 214-231; vol. 149; <doi: 10.1016/j.cell.2012.02.013 >.

Filippakopoulos et al.; "The Bromodomain Interaction Module;" Federation of European Biochemical Societies Letters; (2012); pp. 2692-2704; vol. 586; <doi: 10.1016/j.febslet.2012.04.045 >.

Fu et al.; "Inhibition of BET Bromodomains as a Therapeutic Strategy for Cancer Drug Discovery;" Oncotarget; (Mar. 12, 2015); pp. 5501-5516; vol. 6, No. 8.

Fuhrmann et al.; "Chemical Biology of Protein Arginine Modifications in Epigenetic Regulation;" Chemical Reviews; (2015); pp. 5413-5461; vol. 115; <doi: 10.1021/acs.chemrev.5b00003 >.

Ghisalberti; "Review Article No. 87: The Phytochemistry of Myoporaceae;" Phytochemistry; (1994); pp. 7-33; vol. 35, No. 1.

Ghizzoni et al.; "Histone Acetyltransferases are Crucial Regulators in NF-κB Mediated Inflammation;" Drug Discovery Today; (Jun. 2011); pp. 504-511; vol. 16, Nos. 11/12; <doi: 10.1016/j.drudis.2011.03.009 >.

(56) References Cited

OTHER PUBLICATIONS

Ghosh et al.; "NF-κB Regulation: Lessons from Structures;" Immunological Reviews, Author Manuscript; (Mar. 2012); pp. 36-58; vol. 246, No. 1; <doi: 10.1111/j.1600-065X.2012.01097.x>.

Gong et al.; "Monocyte Chemotactic Protein-2 (MCP-2) Uses CCR1 and CCR2B as Its Functional Receptors;" The Journal of Biological Chemistry; (May 2, 1997); pp. n11682-n11685; vol. 272, No. 18; <doi: 10.1074/jbc.272.18.11682>.

Grabiec et al.; "Targeting Histone Deacetylase Activity in rheumatoid Arthritis and Asthma as Prototypes of Inflammatory Disease: Should We Keep Our HATs On?;" Arthritis Research & Therapy; (Oct. 17, 2008); 13 pages; vol. 10, No. 226; <doi: 10.1186/ar2489>.

Grob et al.; "Characterization of a Receptor for Human Monocyte-Derived Neutrophil Chemotactic Factor/Interleukin-8;" The Journal of Biological Chemistry'; (May 15, 1990); pp. 8311-8316; vol. 265, No. 14.

Han et al.; "Methylation-Mediated Control of Aurora Kinase B and Haspin with Epigenetically Modified Histone H3 N-Terminal Peptides;" Bioorganic & Medicinal Chemistry'; (2011); pp. 2373-23 77; vol. 19; <doi: 10.1016/j.bmc.2011.02.011>.

Hatano et al.; "Effects of Interaction of Tannins with Co-Existing Substances. VII. Inhibitory Effects of Tannins and Related Polyphenols on Xanthine Oxidase;" Chemical and Pharmaceutical Bulletin; (May 1990); pp. 1224-1229; vol. 3 8, No. 5.

Hayashi-Takanaka et al.; "Tracking Epigenetic Histone Modifications in Single Cells using Fab-Based Live Endogenous Modification Labeling;" Nucleic Acids Research; (2011); pp. 6475-6488; vol. 3 9, No. 15;<doi: 10.1093/nar/gkr343>.

He et al.; "KDM2b/JHDMIb, an H3K36me2-Specific Demethylase. is Required for Initiation and Maintenance of Acute Myeloid Leukemia;" Blood; (Apr. 7, 2011); pp. 3869-3880; vol. 117. No. 14; <doi: 10.1182/blood-2010-10-312736>.

Heightman; "Chemical Biology of Lysine Demethylases:" Current Chemical Genomics; (2011); pp. 62-71; vol. 5, (Suppl 1-M3).

Hesselgesser et al.; "Identification and Characterization of Small Molecule Functional Antagonists of the CCR1 Chemokine Receptor;" The Journal of Biological Chemistry; (Jun. 19, 1998); pp. 15687-15692; vol. 273, No. 25.

Hoerstermann et ah; "Synthesis of an Analog of the Cytotoxic Marine Diterpene Helioporin C Exploiting Arene-Cr(CO)3 Chemistry;" Tetrahedron; (1999); pp. 6905-6916; vol. 55, No. 22.

Hojfeldt et al.; "Histone Lysine Demethylases as Targets for Anticancer Therapy;" Nature Reviews; (Dec. 2013); pp. 917-930; vol. 12; <doi: 10.1038/nrd4154>.

Hong et al.; "Identification of JmjC Domain-Containing UTX and JMJD3 as Histone H3 Lysine 27 Demethylases;" Proceedings of the National Academy of Sciences of the United States of America; (Nov. 20, 2007); pp. 18439-18444; vol. 104, No. 47; <doi: 10.1073/pnas.0707292104>.

Horton et al.; "A Substrate for Deubiquitinating Enzymes Based on Time-Resolved Fluorescence Resonance Energy Transfer Between Terbium and Yellow Fluorescent Protein;" Analytical Biochemistry; (2007); pp. 138-143; vol. 360; <doi; 10.1016/j.ab.2006.06.031>.

Hu et al.; "Structure and Mechanisms of the Proteasome- Associated Deubiquitinating Enzyme USP14;" The European Molecular Biology Organization Journal; (2005); pp. 3747-3756; vol. 24, No. 21.

Iberg et al.; "Arginine Methylation of the Histone H3 Tail Impedes Effector Binding;" The Journal of Biological Chemistry; (Feb. 8, 2008); pp. 3006-3010; vol. 283, No. 6.

Iyer et al.; "Lysine Acetylation in Obesity, Diabetes and Metabolic Disease:" Immunology and Cell Biology; (2012); pp. 39-46; vol. 90; <doi 10.1038/icb.2011.99>.

Janssen-Heininger et al.; "Redox-Based Regulation of Signal Transduction: Principles, Pitfalls, and Promises;" Free Radical Biology and Medicine, Author Manuscript; (Jul. 1, 2008); pp. 1-17; vol. 45, No. 1.

Jiang et al.; "Regulation of Transcription by the MLL2 Complex and MLL Complex-Associated AKAP95;" Nature Structural & Molecular Biology, Author Manuscript; (Oct. 2013); pp. 1156-1163; vol. 20, No. 10; <doi: 10.1038/nsmb.2656>.

Kang et al.; "The Histone Methyltransferase, NSD2, Enhances Androgen Receptor-Mediated Transcription;" Federal of European Biochemical Societies Letters; (2009); pp. 1880-1886; vol. 583; <doi: 10.1016/j.febslet.2009.05.038>.

Kaustov et al.; "Recognition and Specificity Determinants of the Human Cbx Chromodomains;" Journal of Biological Chemistry; (Jan. 7, 2011); pp. 521-529; vol. 286, No. 1; <doi: 10.1074/jbc.M110.191411>.

Kim et al.; "SIRT7 an Emerging Sirtuin: Deciphering Newer Roles;" Journal of Physiology and Pharmacology; (2013); pp. 531-534; vol. 64, No. 5.

Kim et al.; "Tudor, MBT and Chromo Domains Gauge the Degree of Lysine Methylation;" European Molecular Biology Organization Reports; (2006); pp. 397-403; vol. 7, No. 4; <doi: 10.1038/sj.embor.7400625>.

King et al.; "Quantitative High-Throughput Screening Identifies 8-Hydroxyquinolines as Cell-Active Histone Demethylase Inhibitors;" PLos One; (Nov. 2010); 12 pages; vol. 5, Issue 11; e15535; <doi: 10.1371/journal.pone.001.5535>.

Kogure et al.; "Deregulation of the Histone Demethylase JMJD2A is Involved in Human Carcinogenesis Through Regulation of the G.sup.1/S Transition;" Cancer Letters; (2013); pp. 76-84; vol. 336; <doi: 10.1016/j.canlet.2013.04.009>.

Kohl et al.; "Pseudopterosin Biosynthesis-Pathway Elucidation, Enzymology, and a Proposed Production Method for Anti-Inflammatory Metabolites from Pseudopterogorgia Elisabethae;" Journal of Industrial Microbiology & Biotechnology; (2003): pp. 495-499: vol. 30, No. 8.

Krakstad et al.; ATAD2 Overexpression Links to Enrichment of B-MYB-Translational Signatures and Development of Aggressive Endometrial Carcinoma; Oncotarget; (Jul. 22, 2015); pp. 28440-28452; vol. 6, No. 29.

Kristensen et al.; "Studies of H3K4me3 Demethylation by KDM5B/Jarid1B/PLU1 Reveals Strong Substrate Recognition In Vitro and Identifies 2,4-Pyridine-Dicarboxylic Acid as an In Vitro and In Cell Inhibitor;" Federal of European Biochemical Societies Journal; (2012); pp. 1905-1914; vol. 279; <doi: 10.1111/j.1742-4658.2012.08567.x>.

Krueger et al.; "G Protein-Dependent Pharmacology of Histamine H.sup.3 Receptor Ligands: Evidence for Heterogeneous Active State Receptor Conformations;" The Journal of Pharmacology and Experimental Therapeutics; (2005); pp. 271-281; vol. 314, No. 1; <doi: 10.1124/jpet.104.078865>.

Kubicek et al.; "Reversal of H3K9me2 by a Small-Molecule Inhibitor for the G9a Histone Methyltransferase;" Molecular Cell; (Feb. 9, 2007); pp. 473-481; vol. 25; <doi: 10.1016/j.molcel.2007.01.017>.

Kubo et al.; "Differential Activity of 3-Hydroxy-3-Methylglutaryl Coenzyme A Reductase in Zones of the Adrenal Cortex;" Endocrinology; (1987); pp. 214-221; vol. 120, No. 1.

Lee et al.; "Combined Angiotensin Converting Enzyme Inhibition and Angiotensin AT[1] Receptor Blockade Up-Regulate4s Myocardial AT[2] Receptors in Remodeled Myocardium Post-Infarction;" Cardiovascular Research; (2001); pp. 131-139; vol. 51.

Lee et al.; "PRMT8, a New Membrane-Bound Tissue-Specific Member of the Protein Arginine Methyltransferase Family;" The Journal of Biological Chemistry; (Sep. 23, 2005); pp. 32890-32896; vol. 280, No. 38.

Lenardo et al.; "NF-κB: A Pleiotropic Mediator of Inducible and Tissue-Specific Gene Control;" Cell; (Jul. 28, 1989); pp. 227-229; vol. 58.

Li et al.; "Chemical and Biochemical Approaches in the Study of Histone Methylation and Demethylation;" Medicinal Research Reviews, Author Manuscript; (Jul. 2012); pp. 815-867; vol. 32, No. 4; <doi: 10.1002/mrr.20228>.

Liu et al.; "Comparison of Human, Mouse, Rat, and Guinea Pig Histamine H[4] Receptors Reveals Substantial Pharmacological Species Variation;" The Journal of Pharmacology and Experimental Therapeutics; (2001); pp. 121-130; vol. 299, No. 1.

(56) References Cited

OTHER PUBLICATIONS

Look et al.; "The Seco-Pseudopterosins, New Anti-Inflammatory Diterpene-Glycosides from a Caribbean Gorgonian Octocoral of the Genus Pseudopterogorgia;" Tetrahedron; (1987); pp. 3363-3370; vol. 43, No. 15.
Ludwig et al.; "Killing Two Cells with One Stone: Pharmacologic BCL-2 Family Targeting for Cancer Cell Death and Immune Modulation;" Frontiers in Pediatrics Review; (Dec. 2016); 13 pages; vol. 4, Article 135; <doi: 10.3389/fped.2016.00135 >.
Ma et al.; "The Challenge of Selecting Protein Kinase Assays for Lead Discovery Optimization;" Expert Opinion on Drug Discovery, Author Manuscript; (Jun. 2008); pp. 607-621; vol. 3, No. 6; <doi: 10.1517/17460441.3.6.607 >.
Mansuy et al.; "A New Potent Inhibitor of Lipid Peroxidation In Vitro and In Vivo, the Hepatoprotective Drug Anisyldithiolthione;" Biochemical and Biophysical Research Communications; (Mar. 28, 1986); pp. 1015-1021; vol. 135, No. 3.
Michan et al.; "Sirtuins in Mammals: Insights into their Biological Function;" Biochemical Journal, Author Manuscript; (May 15, 2007); pp. 1-13; vol. 404, No. 1; <doi: 10.1042/BJ20070140 >.
Michishita et al.; "SIRT6 is a Histone H3 Lysine 9 Deacetylase that Modulates Telomeric Chromatin;" Nature, Author Manuscript; (Mar. 27, 2008); pp. 492-496; vol. 452, No. 7186; <doi: 10.1038/nature06736 >.
Misaghi et al.; "Association of C-Terminal Ubiquitin Hydrolase BRCA1-Associated Protein 1 with Cell Cycle Regulator Host Cell Factor 1;" Molecular and Cellular Biology; (Apr. 2009); pp. 2181-2192; vol. 29, No. 8; <doi: 10.1128/MCB.01517-08 >.
Mohammad et al.; "Establishment of a Human Pancreatic Tumor Xenograft Model: Potential Application for Preclinical Evaluation of Novel Therapeutic Agents;" Pancreas; (1998); pp. 19-25; vol. 16, No. 1.
Montalibet et al.; "Protein Tyrosine Phosphatase: Enzymatic Assays;" Methods; (2005); pp. 2-8; vol. 35; <doi: 10.1016/j.ymeth.2004.07.002 >.
Müller-Enoch et al.; "6,7-Dihydroxycumarin (Aesculetin) als Substrat der Catechol-O-Methyltransferase;" Z. Naturforsch; (1976); pp. 280-284; vol. 31 c.
Munoz-Fuentes et al.; "Prdm9, a Major Determinant of Meiotic Recombination Hotspots, Is Not Functional in Dogs and Their Wild Relatives, Wolves and Coyotes;" PLoS One; (Nov. 2011); 7 pages; vol. 6, Issue 11, e25498; <doi: 10.1371/journal.pone.0025498 >.
Nayak et al.; "Composition, Recruitment and Regulation of PRC2 Complex;" Nucleus; (2011); pp. 277-282; vol. 23, No. 4; <doi: 10.4161/nucl.2.4.16266 >.
Noma et al.; "Histone H3 Lysine 4 Methylation is Mediated by Set1 and Promotes Maintenance of Active Chromatin States in Fission Yeast;" Proceedings of the National Academy of Sciences of the United States of America; (Dec. 10, 2002); pp. 16438-16445; vol. 99, Suppl. 4; <doi: 10.1073/pnas.182436399 >.
Nottke et al.; "Developmental Roles of the Histone Lysine Demethylases;" Development; (Mar. 15, 2009); pp. 879-889; vol. 136, No. 6; <doi: 10.1242/dev.020966 >.
O'Hora et al.; "Catalytic Asymmetric Crotvlation of Aldehydes: Application in Total Synthesis of (−)-Elisabethadione;" Chenustiy—A European Journal; (2015); pp. 4551-4555; vol. 21, No. 12.
Org et al.; "The Autoimmune Regulator PHD Finger Binds to Non-Methylated Histone H3K4 to Activate Gene Expression;" European Molecular Biology Organization Reports; (Feb. 2008); pp. 370-376; vol. 9, No. 4; <doi: 10.1038/embor.2008.11 >.
Parri et al.; "Redox Molecular Machines Involved in Tumor Progression;" Antioxidants & Redox Signaling; (2013); pp. 1828-1845; vol. 19, No. 15; 21 doi: 10.1089/ars.2012.5040 >.
Perkins; "The Diverse and Complex Roles of NF-.kappa.B Subunits in Cancer;" Nature Reviews; (Feb. 2012); pp. 121-132; vol. 12; <doi: 10.1038/nrc3204 >.
Philpott et al.; "Bromodomain-Peptide Displacement Assays for Interactome Mapping and Inhibitor Discovery;" Molecular BioSystems; (2011); pp. 2899-2908; vol. 7; <doi: 10.1039/c1mb05099k >.

Pirooznia et al.; "Targeting Specific HATs for Neurodegenerative Disease Treatment: Translating Basic Biology to Therapeutic Possibilities;" Frontiers in Cellular Neuroscience; (Mar. 28, 2013); 18 pages; vol. 7, Article 30; <doi: 10.3389/fncel.2013.00030 >.
Plass et al.; "Mutations in Regulators of the Epigenome and Their Connections to Global Chromatin Patterns in Cancer;" Nature Reviews: Genetics; (Nov. 2013); pp. 765-780; vol. 14; <doi: 10.1038/nrg3554 >.
Pradhan et al.; "Recombinant Human DNA (Cytosine-5) Methyltransferase: I. Expression, Purification, and Comparison of De Novo and Maintenance Methylation;" The Journal of Biological Chemistry; (Nov. 12, 1999); pp. 33002-33010; vol. 274, No. 46.
Preuss et al.; "Novel Mitosis-Specific Phosphorylation of Histone H3 at Thr11 Mediated by Dlk/ZIP Kinase;" Nucleic Acids Research; (2003); pp. 878-885; vol. 31, No. 3; <doi: 10.1093/nar/gkg176 >.
Prinjha et al.; "Place Your BETs: The Therapeutic Potential of Bromodomains;" Trends in Pharmacological Sciences; (Mar. 2012); pp. 146-153; vol. 33, No. 3; <doi: 10.1016/j.tips.2011.12.002 >.
Pufahl et al.; "Development of a Fluorescence-Based Enzyme Assay of Human 5-Lipoxygenase;" Analytical Biochemistry; (2007); pp. 204-212; vol. 364; <doi: 10.1016/j.ab.2007.02.009 >.
Rodriguez et al.; "New Pseudopterosin and Seco-Pseudopterosin Diterpene Glvcosides from Two Colombian Isolates of Pseudopterogorigia Elisabethae and their Diverse Biological Activities;" Journal of Natural Products: (2004); pp. 1672-1680; vol. 67. No. 10.
Roesch et al.; "A Temporarily Distinct Subpopulation of Slow-Cycling Melanoma Cells is Required for Continuous Tumor Growth;" Cell, Author Manuscript; (May 14, 2010); pp. 583-594; vol. 141, No. 4; <doi: 10.1016/j.cell.2010.04.020 >.
Romano et al.; "Lipoxin Synthase Activity of Human Platelet 12-Lipoxygenase;" Biochemical Journal; (1993); pp. 127-133; vol. 296.
Rotili et al.; "Targeting Histone Demethylases: A New Avenue for the Fight Against Cancer;" Genes & Cancer; (2011); pp. 663-679; vol. 2, No. 6; <doi: 10.1177/1947601911417976 >.
Ruat et al.; "Reversible and Irreversible Labeling and Autoradiographic Localization of the Cerebral Histamine $H^2$ Receptor using $[^{125}I]$iodinated Probes;" Proceedings of the National Academy of Sciences of the United States of American; (Mar. 1990); pp. 1658-1662; vol. 87, Neurobiology.
Rubin et al.; "SQ 14,225 (D-3-Mercapto-2-Methylpropanoyl-L-Proline), A Novel Orally Active Inhibitor of Angiotensin I-Converting Enzyme;" The Journal of Pharmacology and Experimental Therapeutics; (1978); pp. 271-280; vol. 204, No. 2.
Sabbattini et al.; "A Novel Role for the Aurora B Kinase in Epigenetic Marking of Silent Chromatin in Differentiated Postmitotic Cells;" The European Molecular Biology Organization Journal; (2007); pp. 4657-4669; vol. 26; <doi: 10.1038/sj.emboj.7601875 >.
Schultz et al. "SETDB1: A Novel KAP-1-Associated Histone H3, Lysine 9-Specific Methyltransferase that Contributes to HP1-Mediated Silencing of Euchromatic Genes by KRAB Zinc-Finger Proteins;" Genes & Development; (2002); pp. 919-932; vol. 16; <doi: 10.1101/gad.973302 >.
Selvi et al.; "Identification of a Novel Inhibitor of Coactivator-Associated Arginine Methyltransferase 1 (CARM1)-Mediated Methylation of Histone H3 Arg-17;" The Journal of Biological Chemistry; (Mar. 5, 2010); pp. 7143-7152; vol. 285, No. 10; <doi: 10.1074/jbc.M109.063933 >.
Selvi et al.; "Small Molecule Modulators of Histone Acetylation and Methylation: A Disease Perspective;" Biochimica et Biophysica Acta; (2010); pp. 810-828; vol. 1799; doi: 10.1016/j.bbagrm.2010.09.005 >.
Sen et al.; "Multiple Nuclear Factors Interact with the Immunoglobulin Enhancer Sequences;" Cell; (Aug. 29, 1986); pp. 706-716; vol. 46.
Sethi et al.; "Multifaceted Link Between Cancer and Inflammation;" Bioscience Reports; (2012);>.
Shankar et al.; "G9a, A Multipotent Regulator of Gene Expression;" Epigenetics; (2013); pp. 16-22; vol. 8, No. 1; <doi: 10.4161/epi.23331 >.
Shen et al.; "EZH1 Mediates Methylation on Histone H3 Lysine 27 and Complements EZH2 in Maintaining Stem Cell Identity and

(56) References Cited

OTHER PUBLICATIONS

Executing Pluripotency;" Molecular Cell, Author Manuscript; (Nov. 21, 2008); pp. 491-502; vol. 21, No. 4.
Stoltenborg et al.; "A Fluorescent Cellular Adhesion Assay using Insect Cell Produced Human VCAM1;" Journal of Immunological Methods; (1994); pp. 59-68; vol. 175.
Strahl et al.; "The Language of Covalent Histone Modifications;" Nature; (Jan. 6, 2000); pp. 41-45; vol. 403.
Suetake et al.; "DNMT3L Stimulates the DNA Methylation Activity of Dnmt3a and Dnmt3b through a Direct Interaction;" The Journal of Biological Chemistry; (Jun. 25, 2004); pp. 27816-27823; vol. 279, No. 26; <doi: 10.1074/jbc.M400181200 >.
Svensson et al.; "Peroxidase and Peroxidase-Oxidase Activities of Isolated Human Myeloperoxidases;" Biochemical Journal; (1987); pp. 673-680; vol. 242.
Taverna et al.; "How Chromatin-Binding Modules Interpret Histone Modifications: Lessons from Professional Pocket Pickers;" Nature Structural & Molecular Biology, Author Manuscript; (Nov. 2007); pp. 1025-1040; vol. 14, No. 11; <doi: 10.1038/nsmb1338 >.
The National Academies; Guide for the Care and Use of Laboratory Animals; (2011); 246 pages; Eighth Edition.
Tian et al.; "Characterization of Selective Ubiquitin and Ubiquitin-Like Protease Inhibitors using a Fluorescence-Based Multiplex Assay Format;" ASSAY and Drug Development Technologies; (Apr. 2011); pp. 165-173; vol. 9, No. 2; <doi: 10.1089/adt.2010.0317 >.
Tietge et al.; "Macrophage-Specific Expression of Group IIA sPLA$^2$ Results in Accelerated Atherogenesis by Increasing Oxidative Stress;" Journal of Lipid Research; (2005); pp. 1604-1614; vol. 46; <doi: 10.1194/jlr.M400469-JLR200 >.
Tippett et al.; "Serrulatane Diterpenes from Eremophila Duttonli:" Phytochemistry; (1993); pp. 417-421; vol. 33, No. 2.
Tough et al.; "International Union of Basic and Clinical Pharmacology Review: Epigenetic Pathway Targets for the Treatment of Disease: Accelerating Progress in the Development of Pharmacological Tools: IUPHAR Review 11;" British Journal of Pharmacology; (2014); pp. 4981-5010; vol. 171; <doi: 10.1111/bph.12848 >.
Tzatsos et al.; "KDM2B Promotes Pancreatic Cancer via Polycomb-Dependent and -Independent Transcriptional Programs;" The Journal of Clinical Investigation; (2013); pp. 727-739; vol. 123, No. 2; <doi: 10.1172/JCI64535 >.
Ullman et al.; "Luminescent Oxygen Channeling Immunoassay: Measurement of Particle Binding Kinetics by Chemiluminescence;" Proceedings of the National Academy of Sciences of the United States of America; (Jun. 1994); pp. 5426-5430; vol. 91, Biochemistry.
Urban et al.; "Comparative Membrane Locations and Activities of Human Monoamine Oxidases Expressed in Yeast;" Federation of European Biochemical Societies 09934; (Jul. 1991); pp. 142-146; vol. 286, No. 1, 2.
Valenzuela-Fernandez et al.; "Leukocyte Elastase Negatively Regulates Stromal Cell-Derived Factor-1 (SDF-1)/CXCR4 Binding and Functions by Amino-Terminal Processing of SDF-1 and CXCR4;" The Journal of Biological Chemistry; (May 3, 2002); pp. 15677-15689; vol. 277, No. 18; <doi: 10.1074/jbc.M111388200 >.
Venturini et al.; "TIF1γ, a Novel Member of the Transcriptional Intermediary Factor 1 Family;" Oncogene; (1999); pp. 1209-1217; vol. 18.
Weidner-Glunde et al.; "What do Viruses BET on?;" Frontiers in Bioscience; (Jan. 1, 2010); pp. 537-549; vol. 15.
Xia et al.; "Compound Cytotoxicity Profiling using Quantitative High-Throughput Screening;" Environmental Health Perspectives; (Mar. 2008); pp. 284-291; vol. 116, No. 3; <doi: 10.1289/ehp.10727 >.
Xiang et al.; "JARID1B is a Histone H3 Lysine 4 Demethylase Up-Regulated in Prostate Cancer;" Proceedings of the National Academy of Sciences of the United States of America; (Dec. 4, 2007); pp. 19226-19231; vol. 104, No. 49; <doi: 10.1073/pnas.0700735104 >.
Xie et al.; "UHRF1 Double Tudor Domain and the Adjacent PHD Finger Act Together to Recognize K9me3-Containing Histone H3 Tail;" Journal of Molecular Biology; (2012); pp. 318-328; vol. 415; <doi: 10.1016/j.jmb.2011.11.012 >.
Yamamoto et al.; "A Nonradioisotope, Enzymatic Assay for 2-Deoxyglucose Uptake in L6 Skeletal Muscle Cells Cultured in a 96-Well Microplate;" Analytical Biochemistry; (2006); pp. 139-145; vol. 351; <doi: 10.1016/j.ab.2005.12.011 >.
Ye et al.; "Polyubiquitin Binding and Cross-Reactivity in the USP Domain Deubiquitinase USP21;" European Molecular Biology Organization Reports; (2011); pp. 351-357; vol. 12, No. 4.
Yost et al.; "Targets in Epigenetics: Inhibiting the Methyl Writers of the Histone Code;" Current Chemical Genomics; (2011); pp. 72-84; vol. 5, (Suppl 1-M4).
Yu et al.; "Enantioselective Total Synetheses of Various Amphilectane and Serrulatane Diterpenoids via Cope Rearrangements;" Journal of the American Chemical Society: (2016); pp. 6261-6270; vol. 138.
Zhang et al.; "Human Histone Acetyltransferase 1 Protein Preferentially Acetylates H4 Histone Molecules in H3.1-H4 over H3.3-H4;" The Journal of Biological Chemistry; (Feb. 24, 2012); pp. 6573-6581; vol. 287, No. 9; <doi: 10.1074/jbc.M111.312637 >
Zurita-Lopez et al.; "Human Protein Arginine Methyltransferase 7 (PRMT7) is a Type III Enzyme Forming $N^G$-Monomethylated Arginine Residues;" Journal of Biological Chemistry; (Jan. 12, 2012); 24 pages; <doi: 10.1074/jbc.M111.336271 >.
Zu-Yue et al.; "A Novel in Vitro Model to Screen Steroid 5.alpha.-Reductase Inhibitors Against Benign Prostatic Hyperplasia;" Methods & Findings in Experimental & Clinical Pharmacology; (1998); pp. 283-287; vol. 20, No. 4.

MEDICINAL USE OF SERRULATANE DITERPENES

The present application is a Continuation in Part of U.S. application Ser. No. 16/330,676 filed on Mar. 5, 2019, which is a National Stage of International Application No. PCT/AU2017/050972 filed on Sep. 7, 2017, which claims priority to foreign application No. AU2016903585 filed on Sep. 7, 2016, each of which are incorporated herein by reference in its entirety.

TECHNICAL FIELD

This invention relates to terpenes and uses thereof. In particular, the invention relates to serrulatane diterpenes and to the use of such compounds in the treatment of diseases and disorders such as cancer.

Throughout this application, various publications are referred to by first author and year of publication. Full citations for these publications, in the order they appear in the application, are presented in a References section immediately before the claims.

BACKGROUND OF THE INVENTION

Plant secondary metabolites have been a major source of medicinal substances providing lead compounds for drug discovery and development.

Plants produce resins and exudates containing secondary metabolites to protect young flower and leaf buds against bacteria and fungi, and damage from sunlight. Accordingly, compounds from plant resins and exudates frequently possess antimicrobial and antioxidant/free radical scavenging activities. Worker honey bees (*Apis mellifera*) collect plant resins/exudates of young shoots and buds from certain trees and shrubs. The resulting mixture is called propolis, or so called bee glue. Propolis is a complex resinous substance and a rich source of bioactive substances. It is used by the bees to mix with wax to seal cracks and holes in their hives and as a disinfectant to protect against microbial infections. The medicinal properties of propolis have been exploited by man since Ancient civilizations.

Currently, propolis is extensively available as a natural health product, and is widely used in cosmetics. However, its modern use in medicine is limited, largely due to the wide variations in chemical compositions arising from honey bees collecting from different or a mixture of plant sources. The composition of propolis is dependent upon the surrounding flora to which the bees have access, and as such, differences in flora may result in differences in propolis compositions. For example, it is known that flavonoids are the major pharmacologically active compounds in European propolis, polyprenylated benzophenones are the main substances in Cuban and Venuzuelan propolis, and prenylated cinnamic acid derivatives are predominant in Brazilian propolis.

Recognition of the botanical origin of the propolis produced by honey bees enables beehives to be placed in favourable locations such that propolis from a single botanical source may be produced to enable manufacture of medicines of high quality and efficacy.

The medicinal uniqueness of propolis is determined by the selective collecting ability of honey bees, as they can recognise natural materials that are relatively non-polar and have antibiotic properties. As reported, the common source of propolis is leaf and flower bud exudates, which are of high antibiotic character in order to protect the delicate growing of plant tissue from attack by microorganisms. It has also been reported that honey bees collect exudates from wounded or diseased plant tissues. Such sources are potentially rich in antibiotic substances produced by plants in response to wounding or attack from insects, microorganisms and viruses.

Medicinal properties of a propolis are associated with the biological activities of the individual plant resins/exudates. It is not clear from previous studies whether the bees simply collect a plant material that is known as propolis, or if there is metabolic modification or addition from the bees. However, there does not appear to be evidence of significant amounts of material added from honey bees, or strong evidence for metabolic transformation. Thus, a better understanding is required regarding the composition of propolis in specific geographical locations to be able to utilize it to its full benefit in the development of new agents in the treatment of diseases and disorders such as cancer.

SUMMARY OF THE INVENTION

In work leading up to the present invention a survey of propolis samples isolated from Kangaroo Island (South Australia) was conducted. Surprisingly, the Inventors found that unlike other propolis which commonly contains flavonoids as active constituents, Kangaroo Island propolis from the *Myoporum* genus of plants, in particular *Myoporum insulare*, contains serrulatane diterpenes. Thus, the present invention relates to compounds isolated from the resins/exudates of leaves and leaf buds of *Myoporum insulare*, propolis sourced from the same plant and uses thereof.

*Myoporum insulare* species is a shrub occurring on ridges and coastal cliffs in Australia. Common names include boobialla, native juniper and, in Western Australia, blueberry tree. *Myoporum* is a genus of approximately 30 species, of which sixteen are found in Australia. *Myoporum insulare* species has a variable growth habitat and may be a dense or an open shrub or a small tree up to 6 metres. The leaves are lance-shaped to elliptical, 30-100 mm long by 10-20 mm wide with glossy green colour. The flowers occur in groups of up to 8 in the leaf axils in late spring and summer and are usually white or occasionally pale pink.

The Inventors have isolated five major compounds, namely compounds 1 to 5, from propolis obtained from *Myoporum insulare*. Compounds 1 to 5 are shown in Table 1. The conventional numbering for serrulatane compounds is shown with respect to Compound 1. In general, serrulatane diterpenes have the (1R,4S)-configuration (Ghisalberti, 1994).

Compound 1 gives a derivative, Compound 6, on oxidation. Further in regard to derivatization, the compounds can also be acylated, alkylated, alkenylated or benzoylated through the free hydroxyl groups. For example, compounds 1 and 2 can be acetylated to give derivatives 7 and 8 while benzoylation can give derivatives 9 and 10.

TABLE 1
Representative serrulatane diterpenoid compounds.
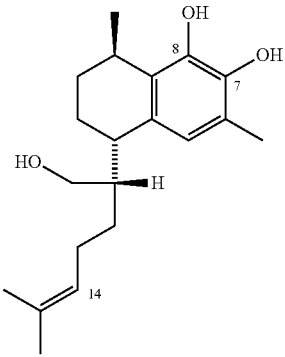 [SMILES: CC(C)=CCC[C@H](CO)[C@@H]1CC[C@@H](C)c2c1cc(C)c(O)c2O]
1
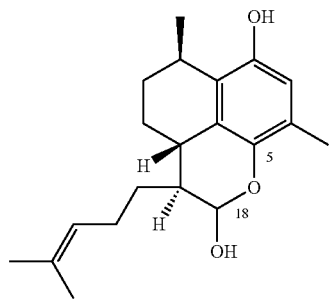 [SMILES: CC(C)=CCC[C@@H]1C(O)Oc2c(C)cc(O)c3c2[C@H]1CC[C@H]3C]
2
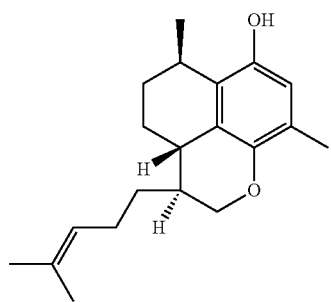 [SMILES: CC(C)=CCC[C@@H]1COc2c(C)cc(O)c3c2[C@H]1CC[C@H]3C]
3
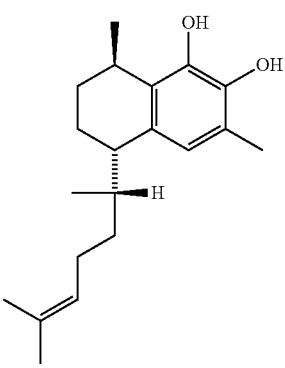 [SMILES: CC(C)=CCC[C@H](C)[C@@H]1CC[C@@H](C)c2c1cc(C)c(O)c2O]
4
TABLE 1-continued
Representative serrulatane diterpenoid compounds.
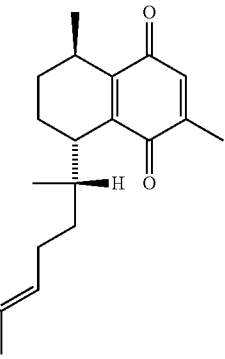
5
TABLE 2
Serrulatane diterpenoid derivatives.
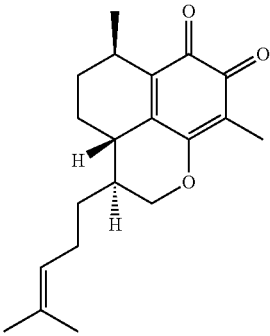 [SMILES: CC(C)=CCC[C@@H]1COC2=C(C)C(=O)C(=O)C3=C2[C@H]1CC[C@H]3C]
6
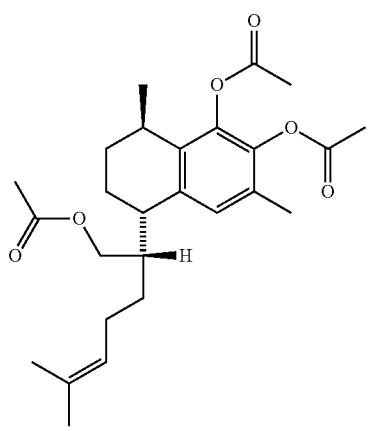
7

TABLE 2-continued

Serrulatane diterpenoid derivatives.

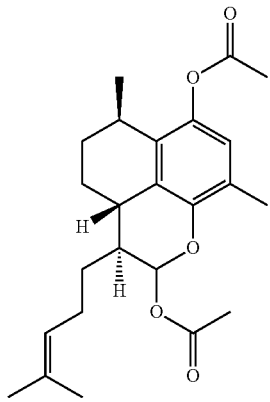 [SMILES: CC(=O)Oc1cc(C)c2c3c1[C@H](C)CC[C@H]3[C@H](CCC=C(C)C)C(OC(C)=O)O2]

8

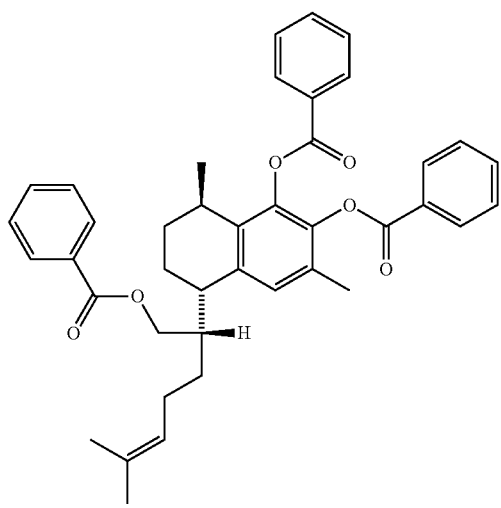 [SMILES: CC(C)=CCC[C@H](COC(=O)c1ccccc1)[C@@H]1CC[C@@H](C)c2c1cc(C)c(OC(=O)c1ccccc1)c2OC(=O)c1ccccc1]

9

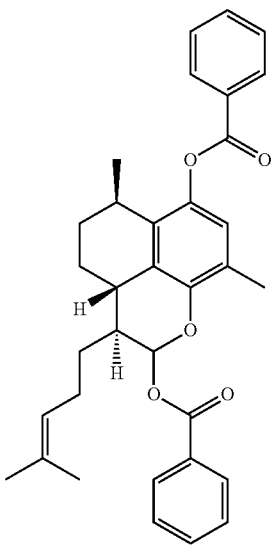 [SMILES: CC(C)=CCC[C@@H]1C(OC(=O)c2ccccc2)Oc2c(C)cc(OC(=O)c3ccccc3)c3c2[C@H]1CC[C@H]3C]

10

TABLE 2-continued

Serrulatane diterpenoid derivatives.

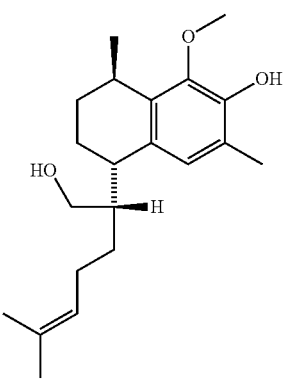 [SMILES: COc1c(O)c(C)cc2c1[C@H](C)CC[C@H]2[C@@H](CO)CCC=C(C)C]

11

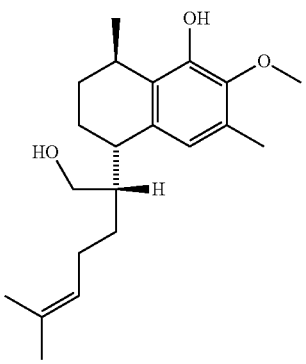 [SMILES: COc1c(C)cc2c(c1O)[C@H](C)CC[C@H]2[C@@H](CO)CCC=C(C)C]

12

Representative compounds were evaluated for pharmacological activity and were found to be useful in modulating a number of diseases or disorders. For example, the compounds were found to inhibit cancer cell proliferation and showed moderate to strong inhibition of various targets associated with cancer pathology. This indicates that the serrulatane diterpene compounds of the present disclosure may be useful as therapeutic agents e.g. for the treatment of cancer. The compounds were also found to effectively inhibit inflammatory activity and modulate immune response, showing moderate to strong inhibition of COX1 and COX2, the release of proinflammatory cytokines, lipoxygenase and the nuclear transcription factor NF-κB. Therefore, the serrulatane diterpenes described herein provide a potentially attractive lead for pharmaceutical research and development and as biological tools for further understanding the pathophysiology of diseases and disorders such as cancer, and diseases and disorders associated with inflammation, such as skin inflammatory conditions.

Accordingly, in a first aspect, there is provided a method of treating a cancer, the method comprising administering a therapeutically effective amount of a compound of Formula (I),

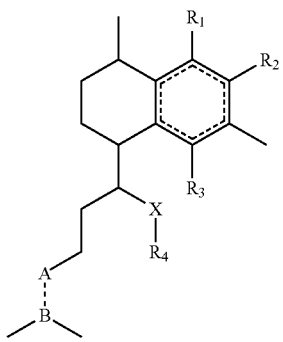

a geometric isomer, stereoisomer, pharmaceutically acceptable salt or solvate thereof, or pharmaceutical composition including said compounds, to a subject in need thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and A-B is CH=C or $CH_2$—CH.

According to a second aspect, there is provided use of a compound of Formula (I),

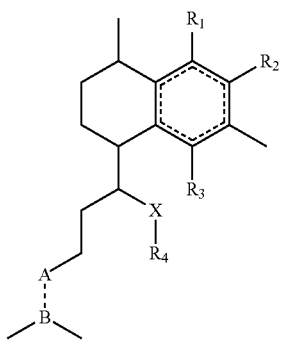

a geometric isomer, stereoisomer, pharmaceutically acceptable salt or solvate thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC_{4-5}$alkadienyl, $OC(O)C_{1-5}$ alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and A-B is CH=C or $CH_2$—CH, in the preparation of a medicament for treating a cancer.

According to a third aspect, there is provided use of a compound of Formula (I),

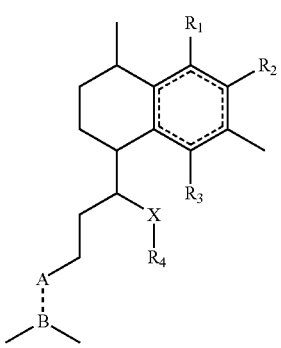

a geometric isomer, stereoisomer, pharmaceutically acceptable salt or solvate thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and A-B is CH=C or $CH_2$—CH, in treating a cancer.

According to a fourth aspect, there is provided a compound of Formula (I),

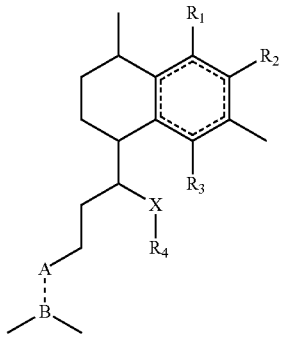

a geometric isomer, stereoisomer, pharmaceutically acceptable salt or solvate thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC_{4-5}$alkadienyl, $OC(O)C_{1-5}$ alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and A-B is CH=C or $CH_2$—CH, for use in treating a cancer.

According to a fifth aspect, there is provided a compound of Formula (I),

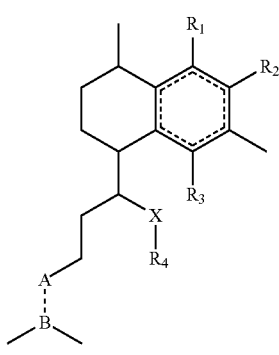

a geometric isomer, stereoisomer, pharmaceutically acceptable salt or solvate thereof, wherein:

X is $CH_2$, CHOH or C(O);

$R_1$ is independently H, OH, $OC_{1-5}$alkyl, $OCH_2Ph$, $OC_{2-5}$ alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$ alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC_{4-5}$alkadienyl, $OC(O)C_{1-5}$ alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and A-B is CH=C or $CH_2$—CH.

According to a sixth aspect, there is provided a pharmaceutical composition comprising a compound, geometric isomer, stereoisomer, pharmaceutically acceptable salt or solvate thereof, according to the fifth aspect and a pharmaceutically acceptable excipient.

According to a seventh aspect, there is provided a pharmaceutical composition comprising a compound, geometric isomer, stereoisomer, pharmaceutically acceptable salt or solvate thereof, according to the fifth aspect, or a mixture thereof, and a pharmaceutically acceptable excipient.

According to an eighth aspect, there is provided a compound as defined in the fifth aspect isolated from propolis, wherein the propolis originates from plants of the *Myoporum* genus.

According to a ninth aspect, there is provided a compound as defined in the fifth aspect isolated from the resin, gum or exudate of *Myoporum* genus.

According to a tenth aspect, there is provided a method of treating a disease or disorder, the method comprising administering a therapeutically effective amount of a compound according to the fifth aspect or a composition according to the sixth or seventh aspect.

According to an eleventh aspect, there is provided use of a compound according to the fifth aspect in the preparation of a medicament for treating a disease or disorder.

According to a twelfth aspect, there is provided use of a compound according to the fifth aspect or a composition according to the sixth aspect or seventh aspect in treating a disease or disorder.

According to a thirteenth aspect of the present invention, there is provided a compound according to the fifth aspect or a composition according to the sixth aspect or seventh aspect for use in treating a disease or disorder.

BRIEF DESCRIPTION OF DRAWINGS

FIG. 3 shows ASH1L (h) bromodomain binding curve.

FIG. 4 shows CECR2(h) bromodomain binding curve.

FIG. 5 shows SP140 (h) bromodomain binding curve.

FIG. 6 shows UHRF1(108-286) (h) binding curve.

Figure 1:
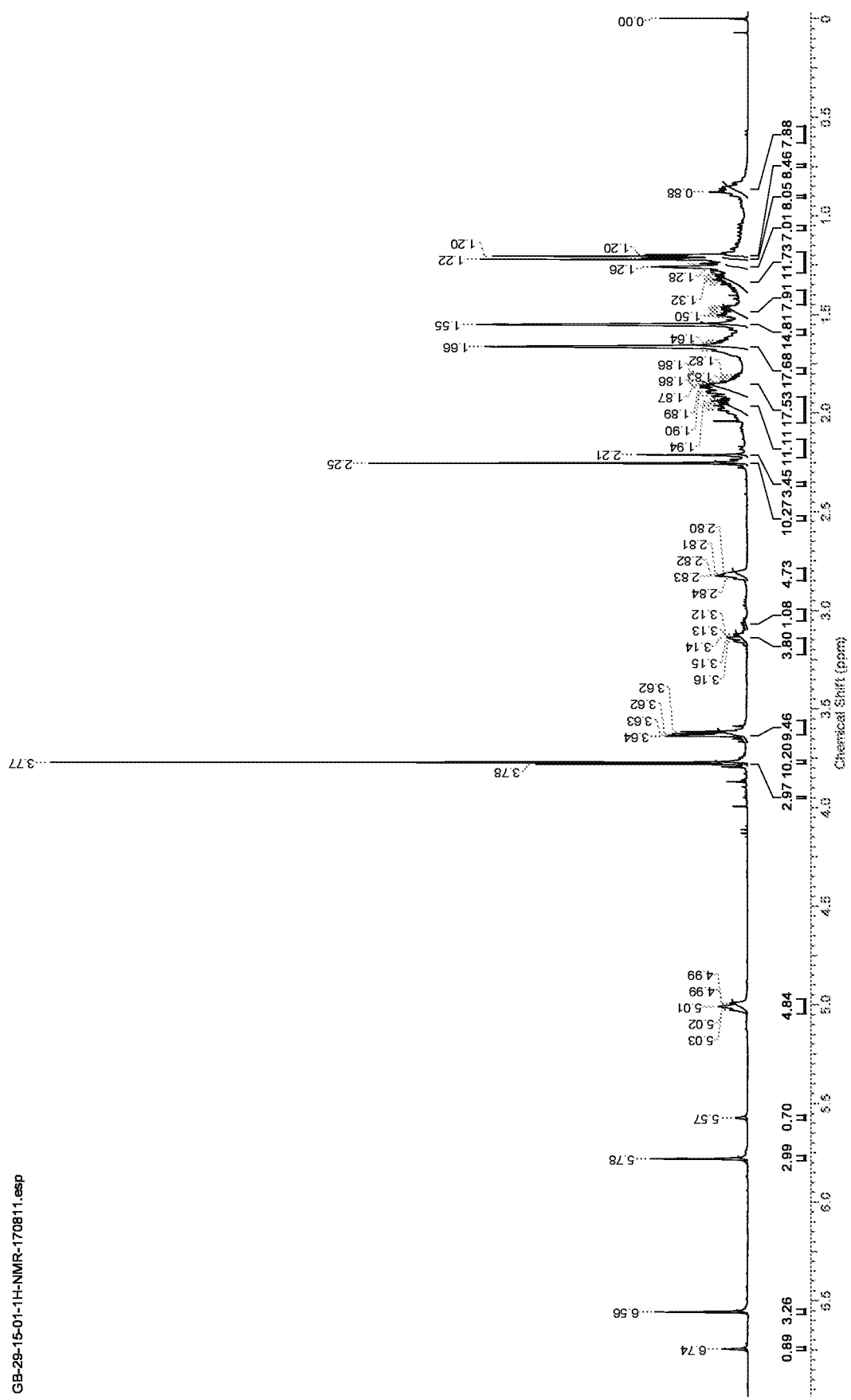
FIG. 1 shows representative $^1$H NMR (400 MHz, $CDCl_3$) spectrum of the 4:1 mixture of mono-methylated products (compounds 11 and 12).

Specific embodiments of the disclosure are described below. It will be appreciated that these embodiments are illustrative and not restrictive.

DETAILED DESCRIPTION OF THE INVENTION

Disclosed herein is a method of treating a cancer, the method comprising administering a therapeutically effective amount of a compound of Formula (I),

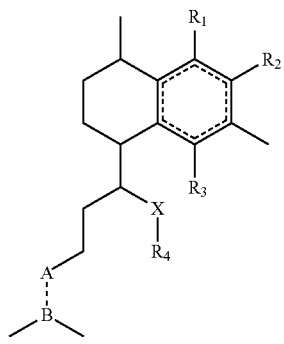

a geometric isomer, stereoisomer, pharmaceutically acceptable salt or solvate thereof, or pharmaceutical composition including said compounds, to a subject in need thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl. $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC_{4-5}$alkadienyl, $OC(O)C_{1-5}$ alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or OC(O)$C_{4-5}$ alkadienyl; and A-B is CH=C or $CH_2$—CH.

Preferably:

X is $CH_2$, CHOH or C(O);

$R_1$ is independently H, OH, $OC_{1-5}$alkyl, $OCH_2Ph$, $OC_{2-5}$alkenyl, $OC(O)C_{1-5}$alkyl, OC(O)Ph, $OC(O)C_{2-5}$alkenyl or =O;

$R_2$ is independently H, OH, $OC_{1-5}$alkyl, $OCH_2Ph$, $OC_{2-5}$alkenyl, $OC(O)C_{1-5}$alkyl, OC(O)Ph, $OC(O)C_{2-5}$alkenyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC(O)C_{1-5}$alkyl, OC(O)Ph or $OC(O)C_{2-5}$alkenyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC(O)C_{1-5}$alkyl, OC(O)Ph or $OC(O)C_{2-5}$alkenyl; and A-B is CH=C or $CH_2$—CH.

Preferably:

X is $CH_2$, CHOH or C(O);

$R_1$ is independently H, OH, $OC_{1-5}$alkyl, $OCH_2Ph$, OC(O)$C_{1-5}$alkyl, OC(O)Ph or =O;

$R_2$ is independently H, OH, $OC_{1-5}$alkyl, $OCH_2Ph$, OC(O)$C_{1-5}$alkyl, OC(O)Ph or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC(O)C_{1-5}$alkyl or OC(O)Ph; and A-B is CH=C or $CH_2$—CH.

Preferably:

X is $CH_2$, CHOH or C(O);

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is $CH_2$;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is CHOH;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is C(O);

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably, the compound is a compound of Formula (Ia):

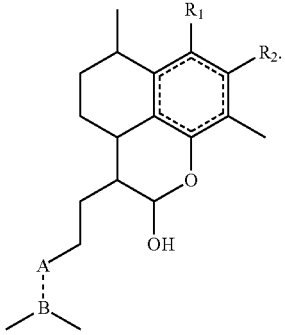

(Ia)

Preferably, the compound is a compound of Formula (Ib):

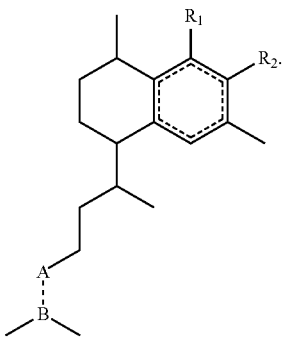

(Ib)

Preferably, the compound is a compound of Formula (Ic):

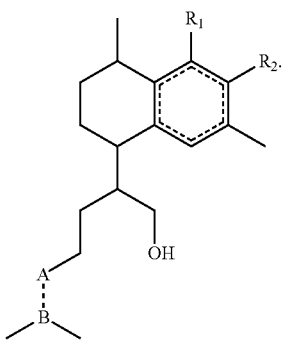

(Ic)

Preferably, the compound is a compound of Formula (Id):

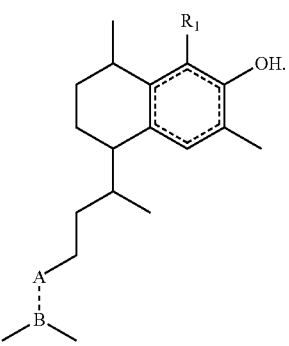

(Id)

Preferably, the compound is a compound of Formula (Ie):
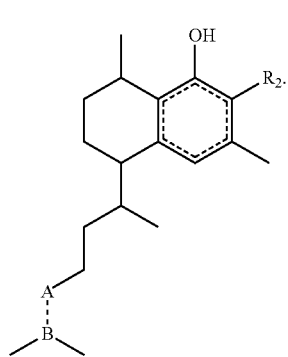
(Ie)
Preferably, the compound is a compound of Formula (If):
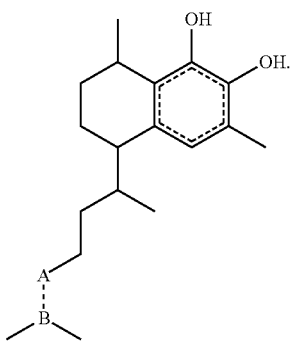
(If)
Preferably, the compound is a compound of Formula (Ig):
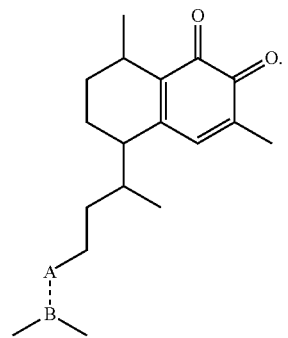
(Ig)
Preferably, the compound is a compound of Formula (Ih):
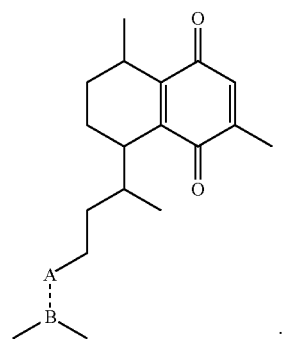
(Ih)
Preferably, the compound is a compound of Formula (Ii):
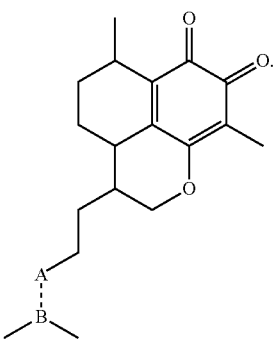
(Ii)
Preferably, A-B is CH=C.
The compound is preferably selected from the group consisting of:
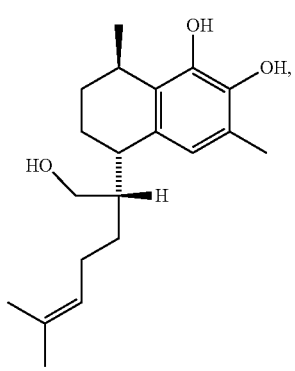 [SMILES: CC(C)=CCC[C@H](CO)[C@@H]1CC[C@@H](C)c2c1cc(C)c(O)c2O]
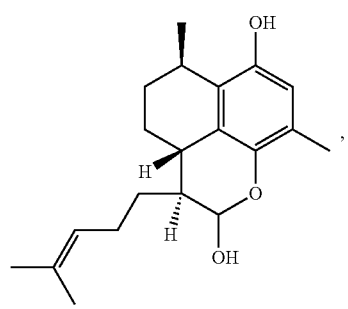
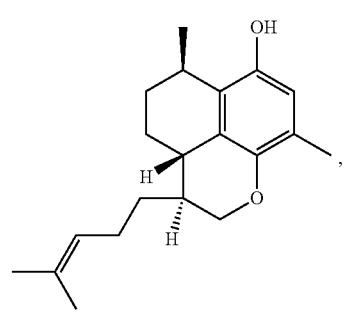

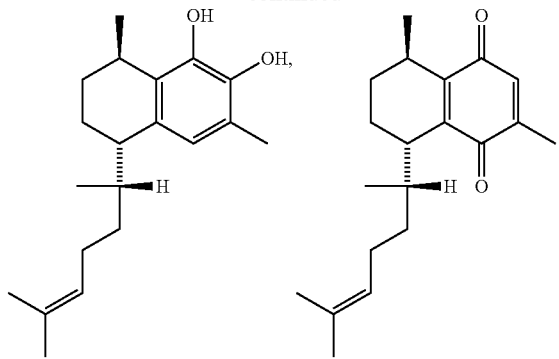
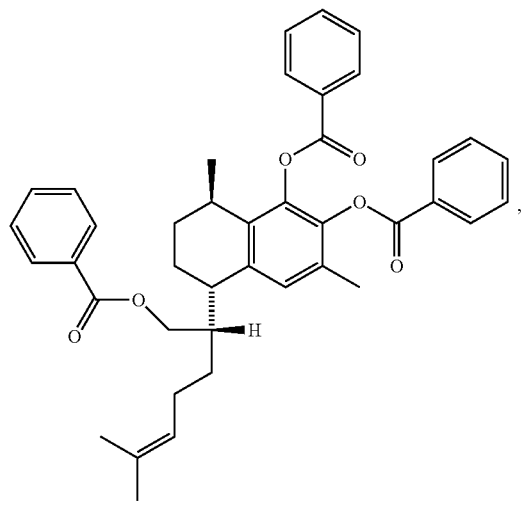
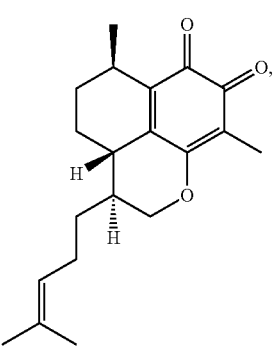
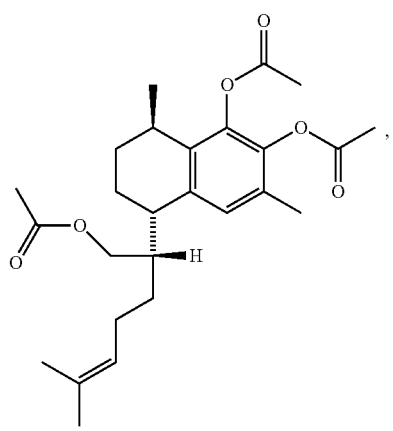
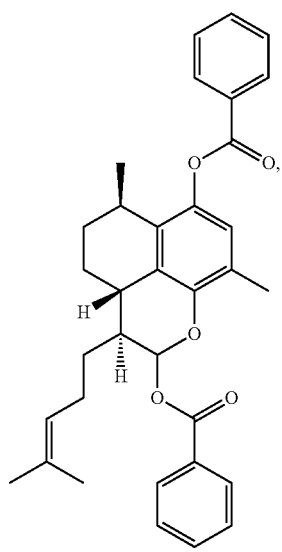
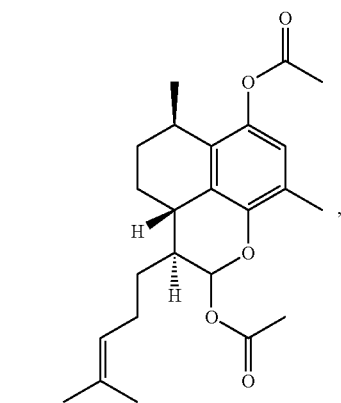
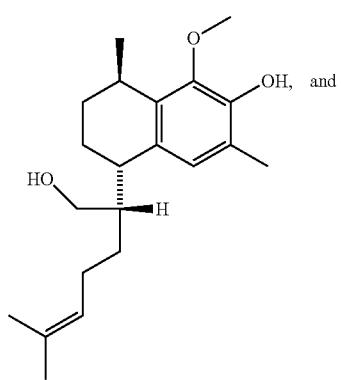

-continued
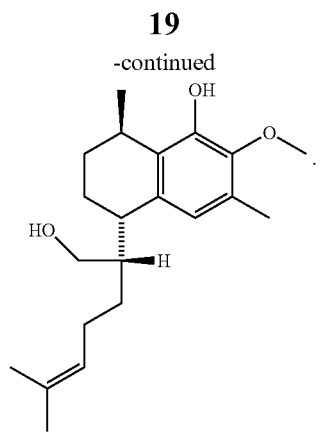
-continued
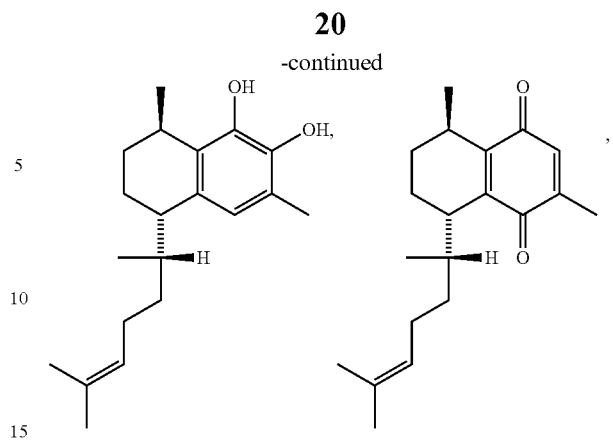
Preferably, the compound is selected from the group consisting of:
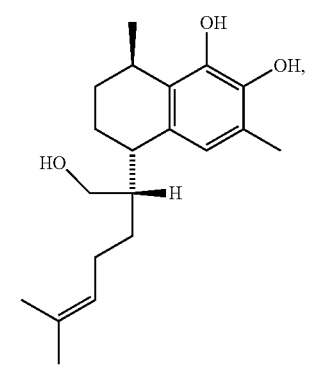
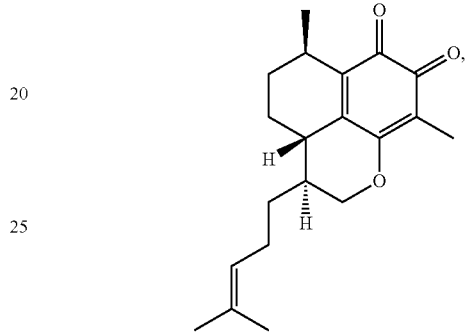
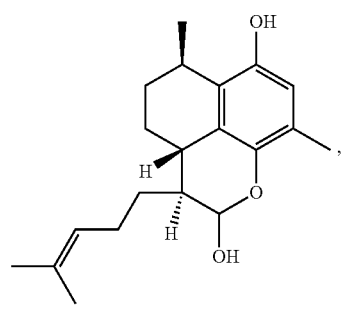
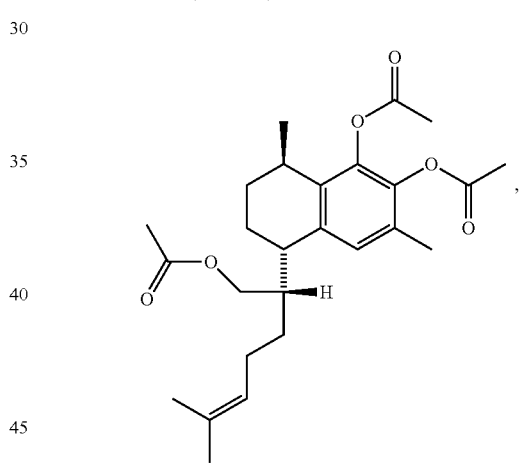
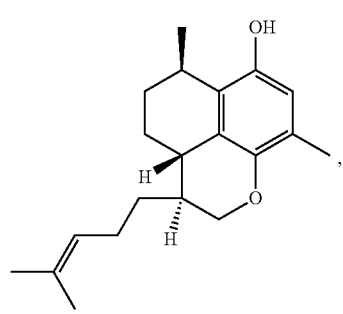
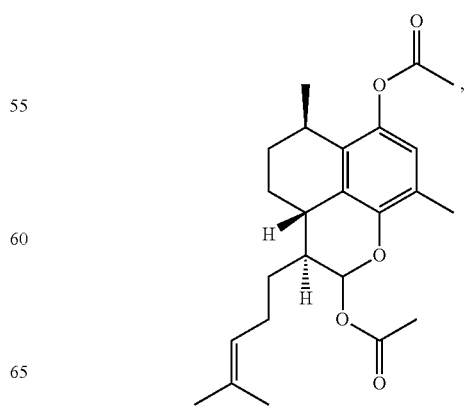

The compound is preferably selected from the group consisting of:

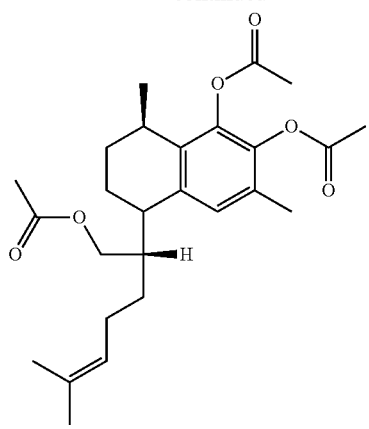
, and
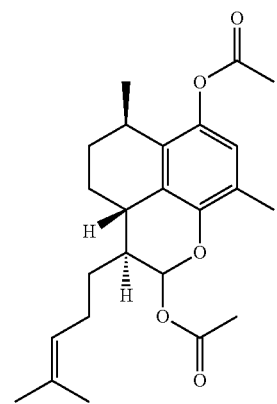
Preferably, the compound is selected from the group consisting of:
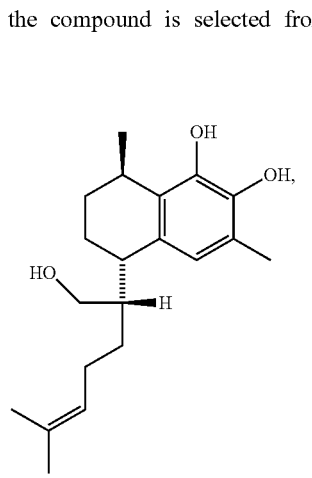
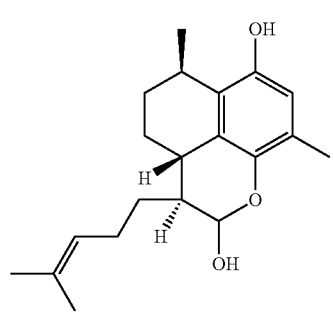
,
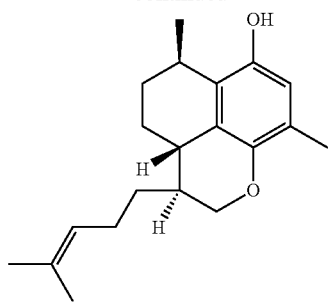
,
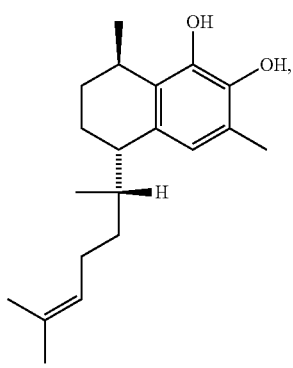
,
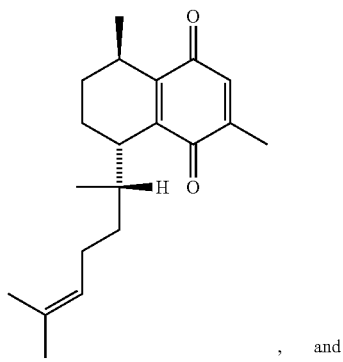
, and
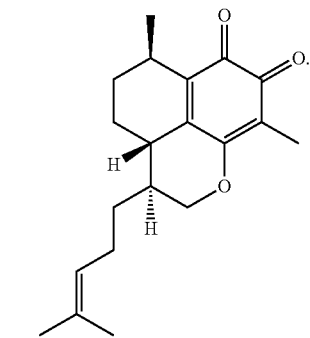
.

The compound is preferably:

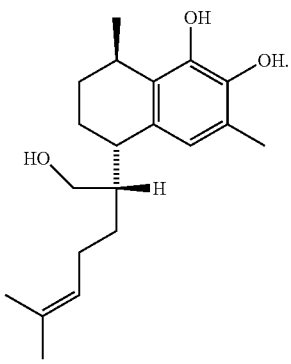

Preferably, the compound is:

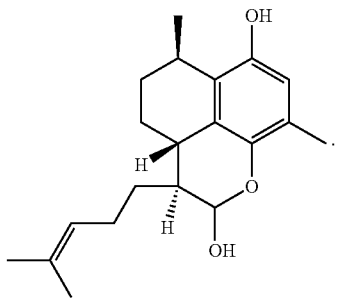 [SMILES: CC(C)=CCC[C@@H]1C(O)Oc2c(C)cc(O)c3c2[C@H]1CC[C@H]3C]

The compound is preferably:

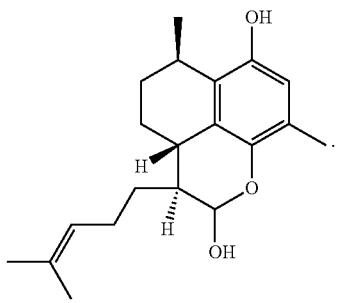 [SMILES: CC(C)=CCC[C@@H]1C(O)Oc2c(C)cc(O)c3c2[C@H]1CC[C@H]3C]

Preferably, the compound is:

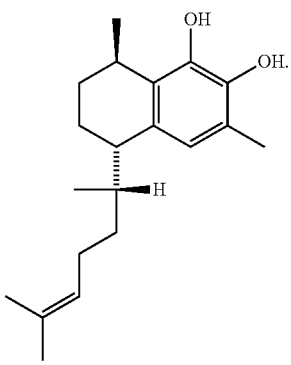 [SMILES: CC(C)=CCC[C@H](C)[C@@H]1CC[C@@H](C)c2c1cc(C)c(O)c2O]

The compound is preferably:

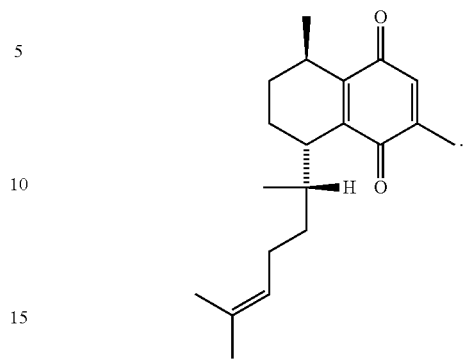

Preferably, the compound is:

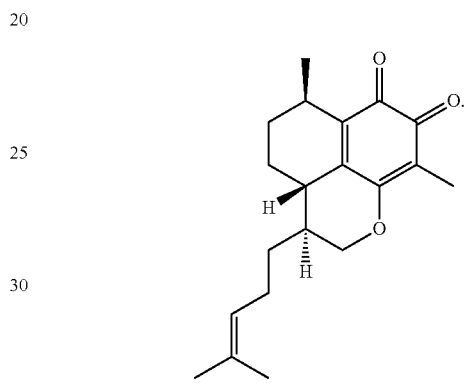

Preferably, the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

The cancer of the central nervous system is preferably a glioma. Preferably, the cancer of the central nervous system is a medulloblastoma. The cancer of the central nervous system is preferably a neuroblastoma.

Preferably, the lung cancer is a non-small cell lung cancer. The lung cancer is preferably a small cell lung cancer.

Preferably, the carcinoma is adenosquamous cell carcinoma or squamous cell carcinoma.

The sarcoma is preferably a liposarcoma, rhabdomyosarcoma, or fibrosarcoma. Preferably, the sarcoma is a soft tissue sarcoma. The soft tissue sarcoma is preferably a soft tissue osteosarcoma.

Preferably, the lymphoma is Burkitt's lymphoma, Hodgkin's lymphoma, or non-Hodgkin's lymphoma.

While it is possible that, for use in therapy a therapeutically effective amount of the compounds as defined herein, or a pharmaceutically acceptable salt or solvate thereof, may be administered as the raw chemical; in the first aspect of the present invention the active ingredient is administered as a pharmaceutical composition. Thus, the present invention also contemplates a pharmaceutical composition comprising a compound of formula (I) to (Ii), or a pharmaceutically acceptable salt or a solvate thereof, and a pharmaceutically acceptable excipient. The excipient must be acceptable in the sense of being compatible with the other ingredients of the formulation and not deleterious to the recipient thereof.

When applicable, the compounds of the present invention, including the compounds of formula (I) to (Ii) may be in the form of and/or may be administered as a pharmaceutically acceptable salt.

As used herein the term "pharmaceutically acceptable salt" refers to salts which are toxicologically safe for systemic administration. The pharmaceutically acceptable salts may be selected from alkali or alkaline earth metal salts, including, sodium, lithium, potassium, calcium, magnesium and the like, as well as non-toxic ammonium, quaternary ammonium, and amine cations, including, but not limited to ammonium, tetramethylammonium, tetraethyl ammonium, methylamine, dimethylamine, trimethylamine, tri ethyl amine, ethylamine, triethanolamine and the like.

As used herein the term "pharmaceutically acceptable excipient" refers to a solid or liquid filler, carrier, diluent or encapsulating substance that may be safely used in administration. Depending upon the particular route of administration, a variety of carriers, well known in the art may be used. These carriers or excipients may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water.

As used herein, the term "solvate" refers to a complex of variable stoichiometry formed by a solute (in this disclosure, a compound of formula (I) to (Ii) or a salt or physiologically functional derivative thereof) and a solvent. Such solvents for the purpose of the disclosure may not interfere with the biological activity of the solute. Examples of suitable solvents include, but are not limited to, water, methanol, ethanol and acetic acid. In particular the solvent used is a pharmaceutically acceptable solvent. Examples of suitable pharmaceutically acceptable solvents include, without limitation, water, ethanol, acetic acid, glycerol, liquid polyethylene glycols and mixtures thereof. A particular solvent is water.

Administration of compounds of the formula (I) to (Ii) may be in the form of a "prodrug". A prodrug is an inactive form of a compound which is transformed in vivo to the active form. Suitable prodrugs include esters, phosphonate esters etc, of the active form of the compound.

It should be understood that in addition to the ingredients particularly mentioned above, the formulations may include other agents conventional in the art having regard to the type of formulation in question.

The compounds of the present disclosure may be suitable for the treatment of diseases in a human or animal subject. In one example, the subject is a mammal including a human, horse, dog, cat, sheep, cow, or primate. In another example, the subject is a human. In a further example, the subject is not a human. The terms "subject" and "patient" are used interchangeably herein.

As used herein, the term "effective amount" means that amount of a drug or pharmaceutical agent that will elicit the biological or medical response of a tissue, system, animal or human that is being sought, for instance, by a researcher or clinician.

Furthermore, the term "therapeutically effective amount" means any amount which, as compared to a corresponding subject who has not received such amount, results in improved treatment, healing or amelioration of a disease, disorder, or side effect, or a decrease in the rate of advancement of a disease or disorder. The term also includes within its scope amounts effective to enhance normal physiological function. The term also includes within its scope amounts effective to prevent a disease, disorder, or side effect.

As used herein the term "treatment" refers to defending against or inhibiting a symptom, treating a symptom, delaying the appearance of a symptom, reducing the severity of the development of a symptom, and/or reducing the number or type of symptoms suffered by an individual, as compared to not administering a pharmaceutical composition comprising a compound of the invention. The term also includes within its scope prevention of a disease, disorder, or side effect. The term "treatment" encompasses use in a palliative setting The antitumor effect of the compounds of the present disclosure may be applied as a sole therapy or as a combination therapy i.e. where two or more serrulatane diterpenoids may be administered in combination. Therapy may also involve administration of a mixture of two or more serrulatane diterpenoids. Therapy may involve, in addition, administration of one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer such as a combination of surgery, radiotherapy and/or chemotherapy. In particular, it is known that irradiation or treatment with antiangiogenic and/or vascular permeability reducing agents can enhance the amount of hypoxic tissue within a tumour. Therefore the effectiveness of the compounds of the present invention may be improved by conjoint treatment with radiotherapy and/or with an antiangiogenic agent.

The individual components of such combinations can be administered separately at different times during the course of therapy or concurrently in divided or single combination forms. The present disclosure is therefore to be understood as embracing all such regimes of simultaneous or alternating treatment and the term "administering" is to be interpreted accordingly. It will be understood that the scope of combinations of the compounds of this invention with other anti-neoplastic agents includes in principle any combination with any pharmaceutical composition useful for treating cancer.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

Pharmaceutical compositions of the present disclosure may be formulated for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Therefore, the pharmaceutical compositions of the invention may be formulated, for example, as tablets, capsules, powders, granules, lozenges, creams or liquid preparations, such as oral or sterile parenteral solutions or suspensions. Such pharmaceutical formulations may be prepared by any method known in the art of pharmacy, for example by bringing into association the active ingredient with the carrier(s) or excipient(s). Such pharmaceutical formulations may be prepared as enterically coated granules, tablets or capsules suitable for oral administration and delayed release formulations.

When a compound is used in combination with a second therapeutic agent active against the same disease, the dose of each compound may differ from that when the compound is used alone. Appropriate doses will be readily appreciated by those skilled in the art.

Also disclosed herein is use of a compound of Formula (I),

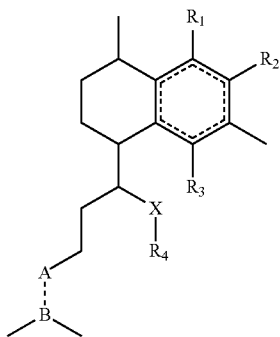

wherein:
X is CH$_2$, CHOH or C(O);
R$_1$ is independently H, OH, OC$_{1-5}$alkyl, OCH$_2$Ph, OC$_{2-5}$alkenyl, OC$_{4-5}$alkadienyl. OC(O)C$_{1-5}$alkyl, OC(O)Ph, OC(O)C$_{2-5}$alkenyl, OC(O)C$_{4-5}$alkadienyl or =O;
R$_2$ is independently H, OH, OC$_{1-5}$alkyl, OCH$_2$Ph, OC$_{2-5}$alkenyl, OC$_{4-5}$alkadienyl, OC(O)C$_{1-5}$alkyl, OC(O)Ph, OC(O)C$_{2-5}$alkenyl, OC(O)C$_{4-5}$alkadienyl or =O;
R$_3$ is independently H, OH, OC$_{1-5}$alkyl, OC(O)C$_{1-5}$alkyl or =O;
and no more than one of R$_1$, R$_2$ and R$_3$ can be H;
where X is CH$_2$, CHOH or C(O), R$_4$ is H, OH, OC$_{1-5}$alkyl, OCH$_2$Ph, OC$_{2-5}$alkenyl, OC$_{4-5}$alkadienyl, OC(O)C$_{1-5}$alkyl, OC(O)Ph, OC(O)C$_{2-5}$alkenyl or OC(O)C$_{4-5}$alkadienyl;
or X and R$_3$ form a six-membered ether ring or lactone ring, or a six membered ring containing a hemiacetal carbon atom or an acetal carbon atom wherein R$_4$ is respectively OH or OC$_{1-5}$alkyl, OCH$_2$Ph, OC$_{2-5}$alkenyl, OC$_{4-5}$alkadienyl, OC(O)C$_{1-5}$alkyl, OC(O)Ph, OC(O)C$_{2-5}$alkenyl or OC(O)C$_{4-5}$ alkadienyl; and
A-B is CH=C or CH$_2$—CH,
in the preparation of a medicament for treating a cancer.
Preferably:
X is CH$_2$, CHOH or C(O);
R$_1$ is independently H, OH, OC$_{1-5}$alkyl, OCH$_2$Ph, OC$_{2-5}$alkenyl, OC(O)C$_{1-5}$alkyl, OC(O)Ph, OC(O)C$_{2-5}$alkenyl or =O;
R$_2$ is independently H, OH, OC$_{1-5}$alkyl, OCH$_2$Ph, OC$_{2-5}$alkenyl, OC(O)C$_{1-5}$alkyl, OC(O)Ph, OC(O)C$_{2-5}$alkenyl or =O;
R$_3$ is independently H, OH, OC$_{1-5}$alkyl, OC(O)C$_{1-5}$alkyl or =O;
and no more than one of R$_1$, R$_2$ and R$_3$ can be H;
where X is CH$_2$, CHOH or C(O), R$_4$ is H, OH, OC$_{1-5}$alkyl, OCH$_2$Ph, OC$_{2-5}$alkenyl, OC(O)C$_{1-5}$alkyl, OC(O)Ph or OC(O)C$_{2-5}$alkenyl;
or X and R$_3$ form a six-membered ether ring or lactone ring, or a six membered ring containing a hemiacetal carbon atom or an acetal carbon atom wherein R$_4$ is respectively OH or OC$_{1-5}$alkyl, OCH$_2$Ph, OC$_{2-5}$alkenyl, OC(O)C$_{1-5}$alkyl, OC(O)Ph or OC(O)C$_{2-5}$alkenyl; and
A-B is CH=C or CH$_2$—CH.
Preferably:
X is CH$_2$, CHOH or C(O);
R$_1$ is independently H, OH, OC$_{1-5}$alkyl, OCH$_2$Ph, OC(O)C$_{1-5}$alkyl, OC(O)Ph or =O;
R$_2$ is independently H, OH, OC$_{1-5}$alkyl, OCH$_2$Ph, OC(O)C$_{1-5}$alkyl, OC(O)Ph or =O;
R$_3$ is independently H, OH, OC$_{1-5}$alkyl, OC(O)C$_{1-5}$alkyl or =O;
and no more than one of R$_1$, R$_2$ and R$_3$ can be H;
where X is CH$_2$, CHOH or C(O), R$_4$ is H, OH, OC$_{1-5}$alkyl, OCH$_2$Ph, OC(O)C$_{1-5}$alkyl or OC(O)Ph;
or X and R$_3$ form a six-membered ether ring or lactone ring, or a six membered ring containing a hemiacetal carbon atom or an acetal carbon atom wherein R$_4$ is respectively OH or OC$_{1-5}$alkyl, OCH$_2$Ph, OC(O)C$_{1-5}$alkyl or OC(O)Ph; and
A-B is CH=C or CH$_2$—CH.
Preferably:
X is CH$_2$, CHOH or C(O);
R$_1$ is independently H, OH, OC$_{1-5}$alkyl, OC(O)C$_{1-5}$alkyl or =O;
R$_2$ is independently H, OH, OC$_{1-5}$alkyl, OC(O)C$_{1-5}$alkyl or =O;
R$_3$ is independently H, OH, OC$_{1-5}$alkyl, OC(O)C$_{1-5}$alkyl or =O;
and no more than one of R$_1$, R$_2$ and R$_3$ can be H;
where X is CH$_2$, CHOH or C(O), R$_4$ is H, OH, OC$_{1-5}$alkyl, OCH$_2$Ph, OC(O)C$_{1-5}$alkyl or OC(O)Ph;
or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and
A-B is CH=C or CH$_2$—CH.
Preferably:
X is CH$_2$;
R$_1$ is independently H, OH, OC$_{1-5}$alkyl, OC(O)C$_{1-5}$alkyl or =O;
R$_2$ is independently H, OH, OC$_{1-5}$alkyl, OC(O)C$_{1-5}$alkyl or =O;
R$_3$ is independently H, OH, OC$_{1-5}$alkyl, OC(O)C$_{1-5}$alkyl or =O;
and no more than one of R$_1$, R$_2$ and R$_3$ can be H;
R$_4$ is H, OH, OC$_{1-5}$alkyl, OCH$_2$Ph, OC(O)C$_{1-5}$alkyl or OC(O)Ph;
or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and
A-B is CH=C or CH$_2$—CH.
Preferably:
X is CHOH;
R$_1$ is independently H, OH, OC$_{1-5}$alkyl, OC(O)C$_{1-5}$alkyl or =O;
R$_2$ is independently H, OH, OC$_{1-5}$alkyl, OC(O)C$_{1-5}$alkyl or =O;
R$_3$ is independently H, OH, OC$_{1-5}$alkyl, OC(O)C$_{1-5}$alkyl or =O;
and no more than one of R$_1$, R$_2$ and R$_3$ can be H;
R$_4$ is H, OH, OC$_{1-5}$alkyl, OCH$_2$Ph, OC(O)C$_{1-5}$alkyl or OC(O)Ph;
or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and
A-B is CH=C or CH$_2$—CH.
Preferably:
X is C(O);
R$_1$ is independently H, OH, OC$_{1-5}$alkyl, OC(O)C$_{1-5}$alkyl or =O;
R$_2$ is independently H, OH, OC$_{1-5}$alkyl, OC(O)C$_{1-5}$alkyl or =O;
R$_3$ is independently H, OH, OC$_{1-5}$alkyl, OC(O)C$_{1-5}$alkyl or =O;
and no more than one of R$_1$, R$_2$ and R$_3$ can be H;
R$_4$ is H, OH, OC$_{1-5}$alkyl, OCH$_2$Ph, OC(O)C$_{1-5}$alkyl or OC(O)Ph;
or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and
A-B is CH=C or CH$_2$—CH.

Preferably, the compound is a compound of Formula (Ia):

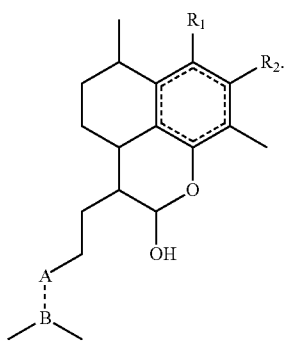

(Ia)

Preferably, the compound is a compound of Formula (Ib):

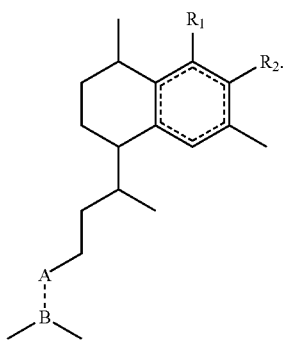

(Ib)

Preferably, the compound is a compound of Formula (Ic):

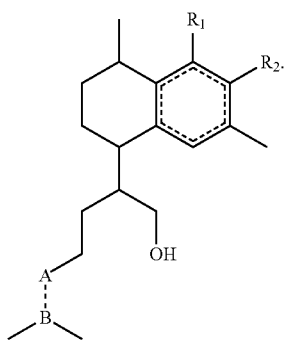

(Ic)

Preferably, the compound is a compound of Formula (Id):

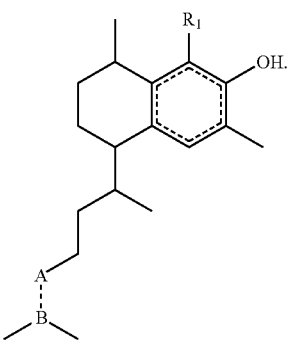

(Id)

Preferably, the compound is a compound of Formula (Ie):

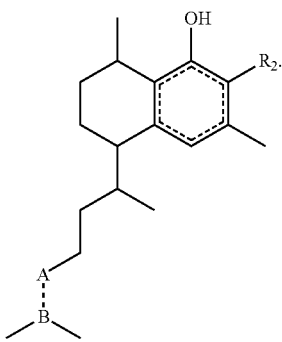

(Ie)

Preferably, the compound is a compound of Formula (If):

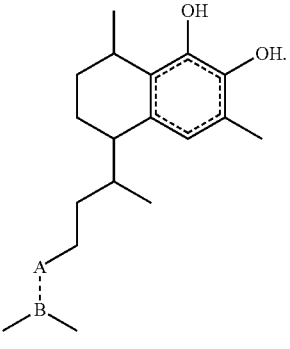

(If)

Preferably, the compound is a compound of Formula (Ig):

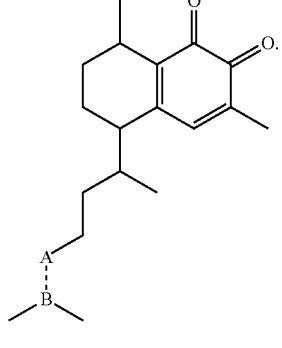

(Ig)

Preferably, the compound is a compound of Formula (Ih):

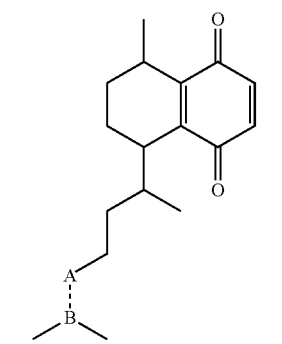

(Ih)

Preferably, the compound is a compound of Formula (Ii):
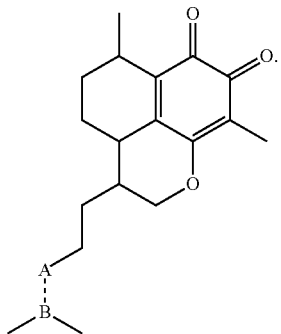
(Ii)
Preferably, A-B is CH=C.
The compound is preferably selected from the group consisting of:
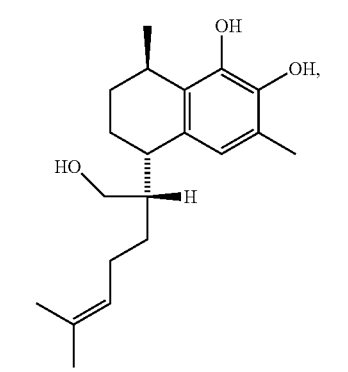
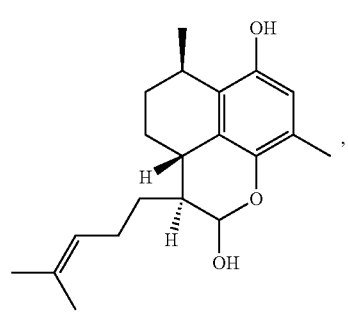
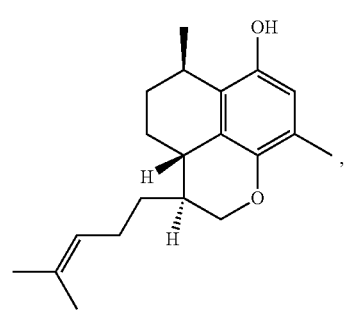
-continued
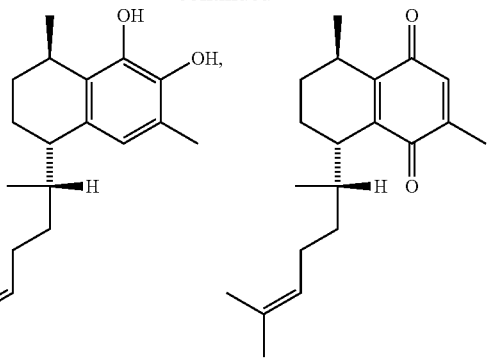
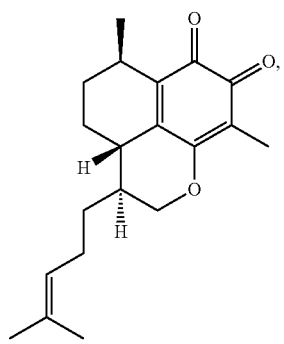 [SMILES: CC(C)=CCC[C@@H]1COC2=C(C)C(=O)C(=O)C3=C2[C@H]1CC[C@H]3C]
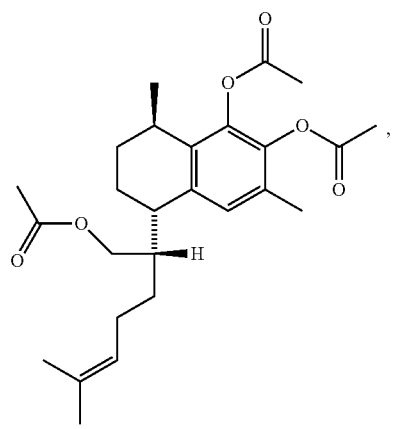
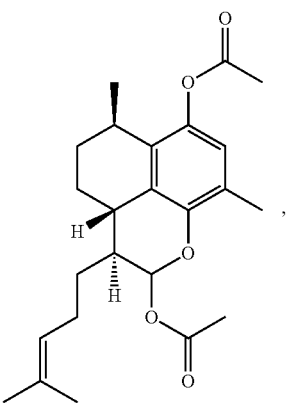

35
-continued
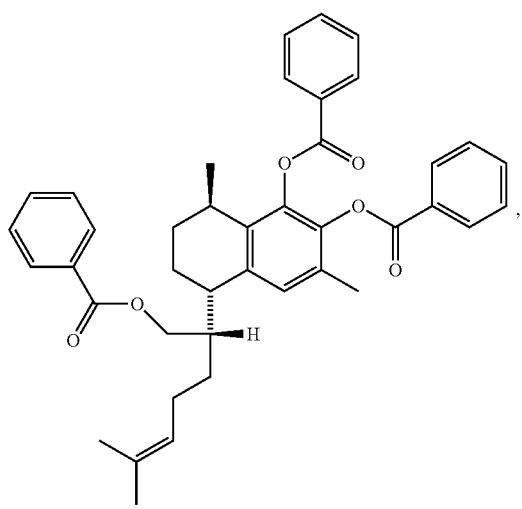
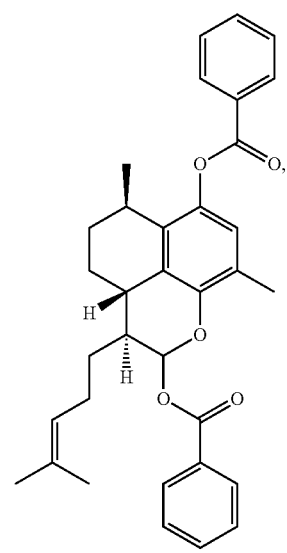
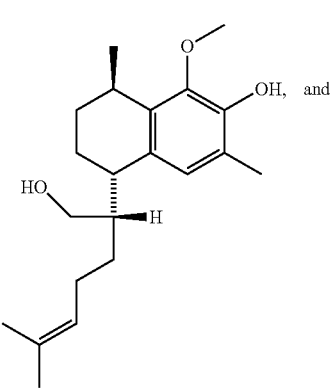
36
-continued
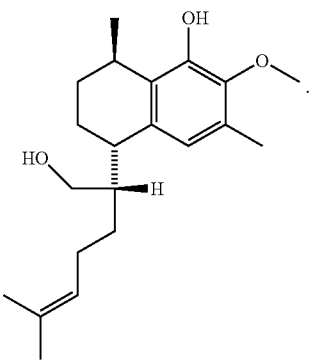
Preferably, the compound is selected from the group consisting of:
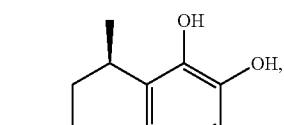
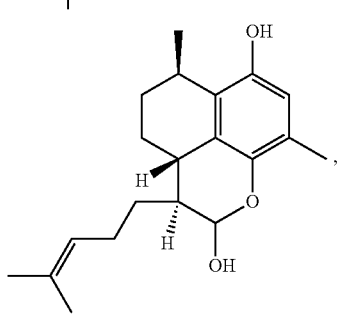
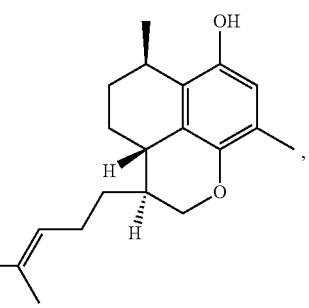

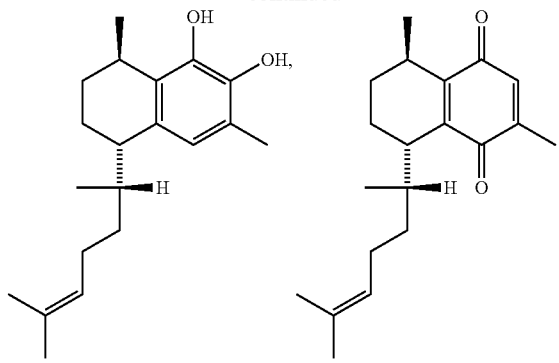
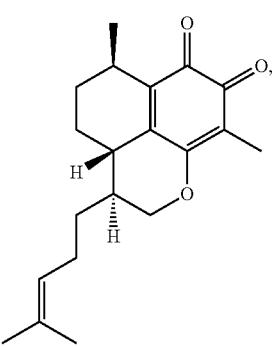 [SMILES: CC(C)=CCC[C@@H]1COC2=C(C)C(=O)C(=O)C3=C2[C@H]1CC[C@H]3C]
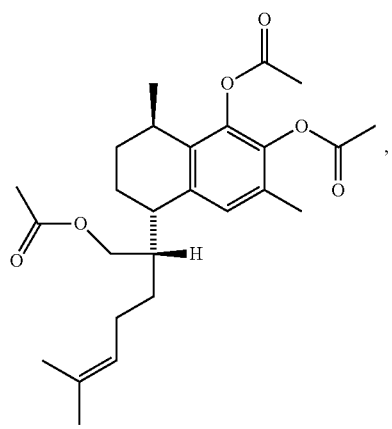
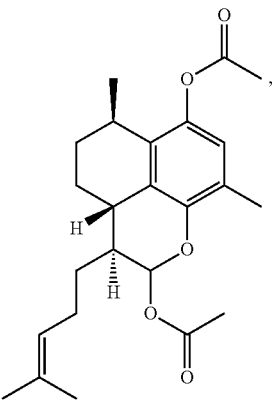
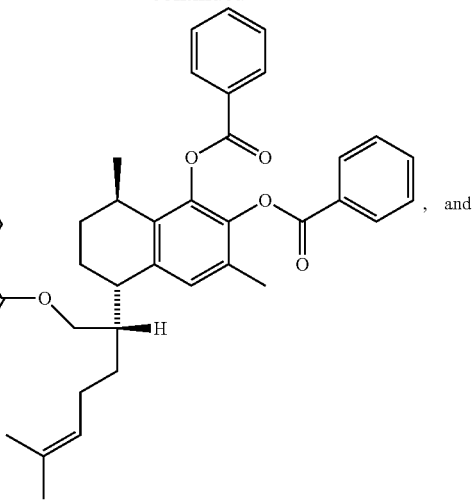
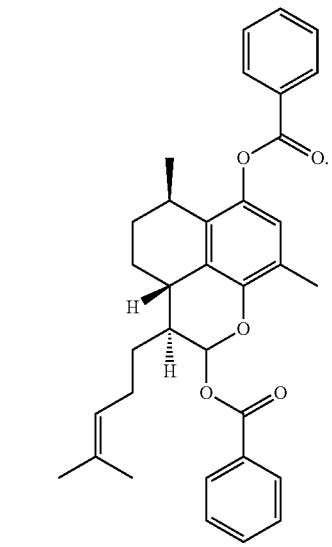
The compound is preferably selected from the group consisting of:
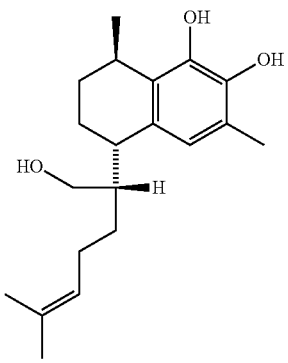

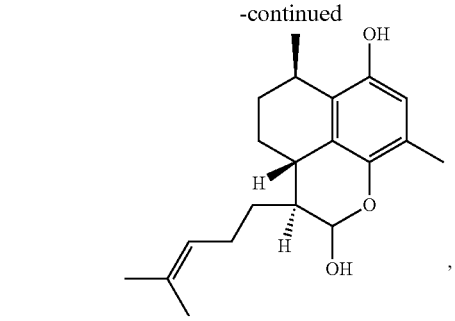
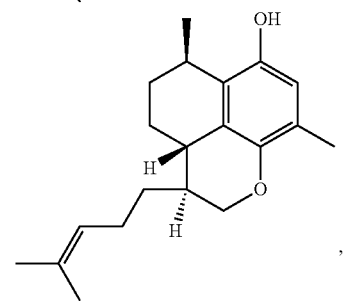
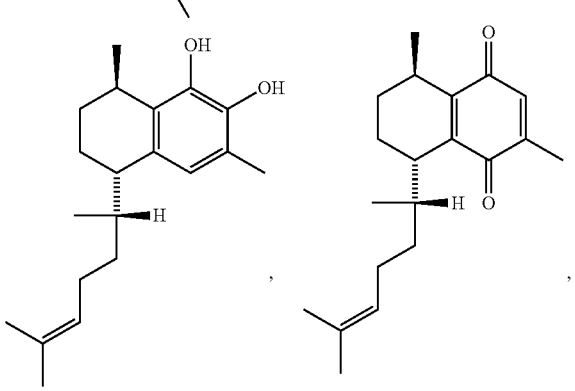
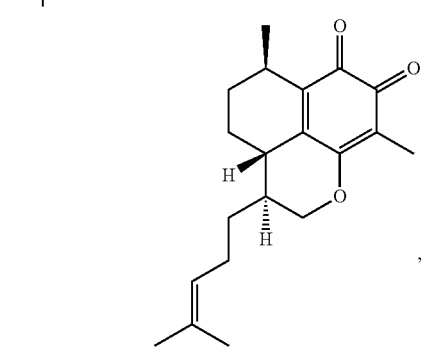
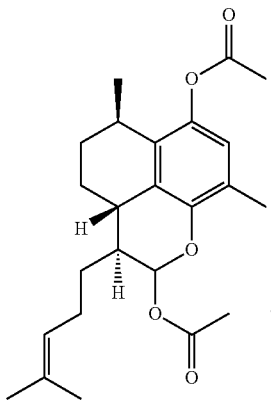
Preferably, the compound is selected from the group consisting of:
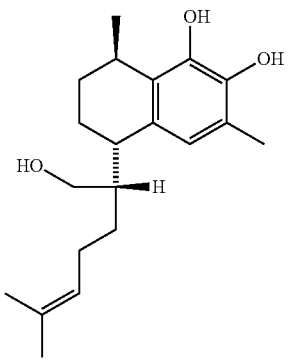
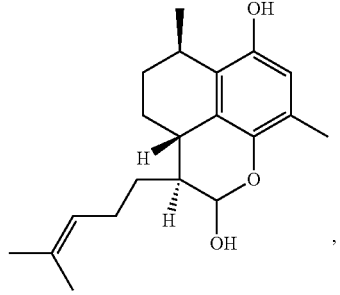
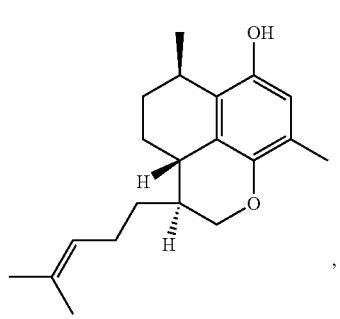

-continued
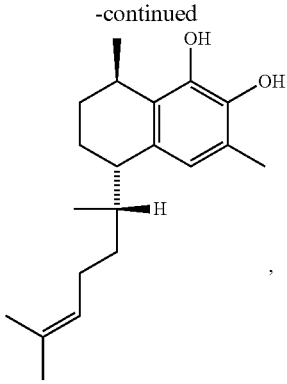
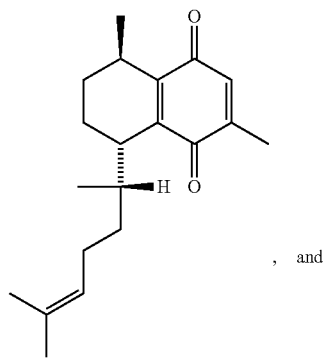
, and
The compound is preferably:
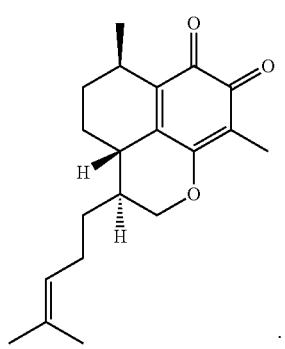 [SMILES: CC(C)=CCC[C@@H]1COC2=C(C)C(=O)C(=O)C3=C2[C@H]1CC[C@H]3C]
Preferably, the compound is:
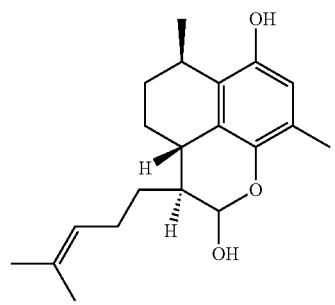
The compound is preferably:
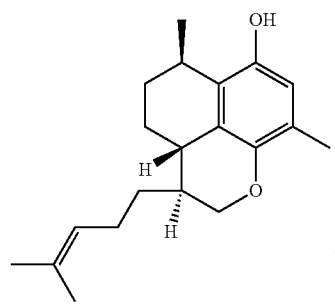
Preferably, the compound is:
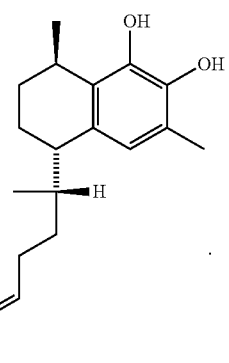
The compound is preferably:
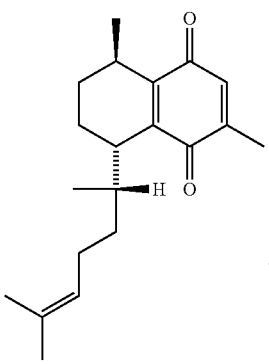
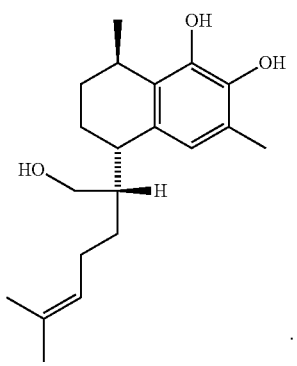

Preferably, the compound is:

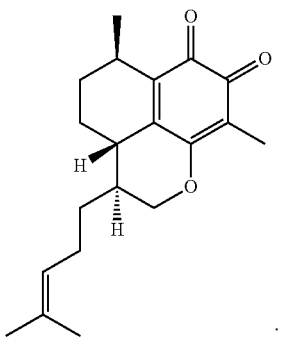

Preferably, the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

The cancer of the central nervous system is preferably a glioma. Preferably, the cancer of the central nervous system is a medulloblastoma. The cancer of the central nervous system is preferably a neuroblastoma.

Preferably, the lung cancer is a non-small cell lung cancer. The lung cancer is preferably a small cell lung cancer.

Preferably, the carcinoma is adenosquamous cell carcinoma or squamous cell carcinoma.

The sarcoma is preferably a liposarcoma, rhabdomyosarcoma, or fibrosarcoma. Preferably, the sarcoma is a soft tissue sarcoma. The soft tissue sarcoma is preferably a soft tissue osteosarcoma.

Preferably, the lymphoma is Burkitt's lymphoma, Hodgkin's lymphoma, or non-Hodgkin's lymphoma.

Also disclosed herein is use of a compound of Formula (I),

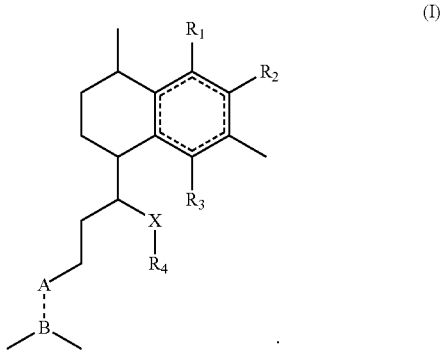

a geometric isomer, stereoisomer, pharmaceutically acceptable salt, or solvate thereof,
wherein:
X is $CH_2$, CHOH or C(O);
$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$alkadienyl;
or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and
A-B is CH=C or $CH_2$—CH,
in treating a cancer.
Preferably:
X is $CH_2$, CHOH or C(O);
$R_1$ is independently H, OH, $OC_{1-5}$alkyl, $OCH_2Ph$, $OC_{2-5}$alkenyl, $OC(O)C_{1-5}$alkyl, OC(O)Ph, $OC(O)C_{2-5}$alkenyl or =O;
$R_2$ is independently H, OH, $OC_{1-5}$alkyl, $OCH_2Ph$, $OC_{2-5}$alkenyl, $OC(O)C_{1-5}$alkyl, OC(O)Ph, $OC(O)C_{2-5}$alkenyl or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC_{2-5}$alkenyl, $OC(O)C_{1-5}$alkyl, OC(O)Ph or $OC(O)C_{2-5}$alkenyl;
or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC(O)C_{1-5}$alkyl, OC(O)Ph or $OC(O)C_{2-5}$alkenyl; and
A-B is CH=C or $CH_2$—CH.
Preferably:
X is $CH_2$, CHOH or C(O);
$R_1$ is independently H, OH, $OC_{1-5}$alkyl, $OCH_2Ph$, $OC(O)C_{1-5}$alkyl, OC(O)Ph or =O;
$R_2$ is independently H, OH, $OC_{1-5}$alkyl, $OCH_2Ph$, $OC(O)C_{1-5}$alkyl, OC(O)Ph or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC(O)C_{1-5}$alkyl or OC(O)Ph;
or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC(O)C_{1-5}$alkyl or OC(O)Ph; and
A-B is CH=C or $CH_2$—CH.
Preferably:
X is $CH_2$, CHOH or C(O);
$R_1$ is independently H, OH, $OC_{1-5}$alkyl, $OC(O)C_{1-5}$alkyl or =O;
$R_2$ is independently H, OH, $OC_{1-5}$alkyl, $OC(O)C_{1-5}$alkyl or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC(O)C_{1-5}$alkyl or OC(O)Ph;
or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is $CH_2$;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or $OC(O)Ph$;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is CHOH;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or $OC(O)Ph$;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is C(O);

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or $OC(O)Ph$;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably, the compound is a compound of Formula (Ia):

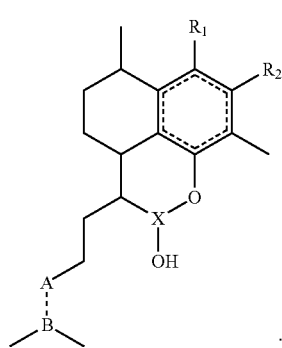

(Ia)

Preferably, the compound is a compound of Formula (Ib):

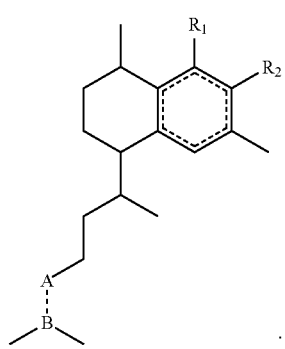

(Ib)

Preferably, the compound is a compound of Formula (Ic):

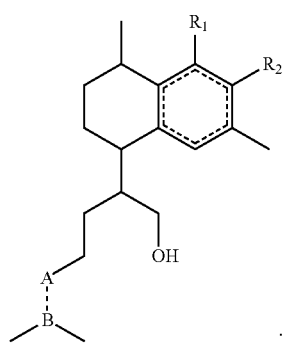

(Ic)

Preferably, the compound is a compound of Formula (Id):

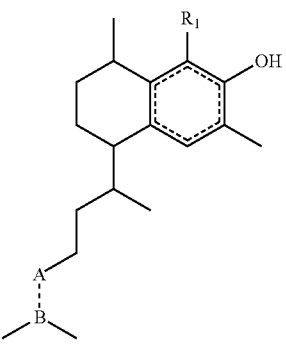

(Id)

Preferably, the compound is a compound of Formula (Ie):

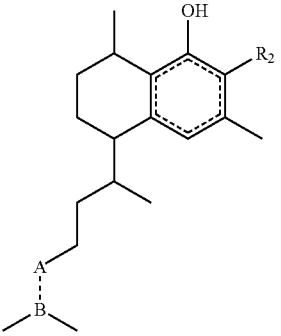

(Ie)

Preferably, the compound is a compound of Formula (If):
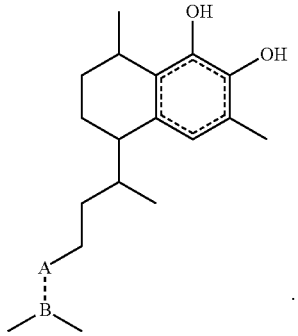
(If)
Preferably, the compound is a compound of Formula (Ig):
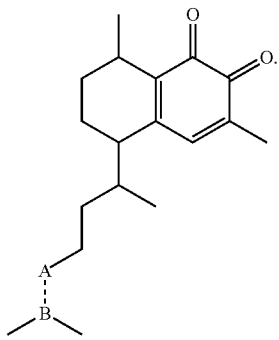
(Ig)
Preferably, the compound is a compound of Formula (Ih):
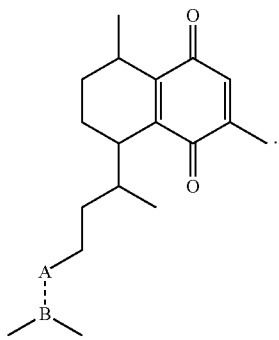
(Ih)
Preferably, the compound is a compound of Formula (Ii):
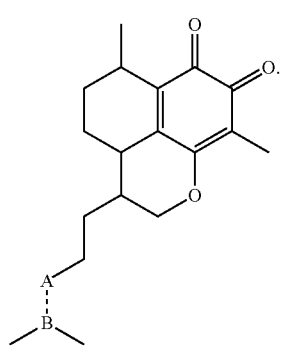
(Ii)
Preferably, A-B is CH=C.
The compound is preferably selected from the group consisting of:
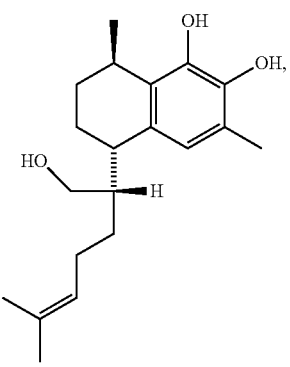
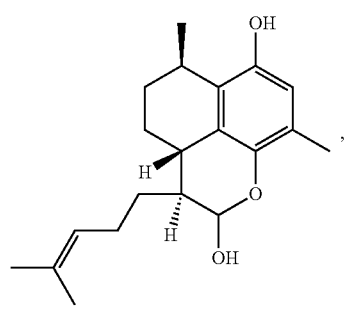
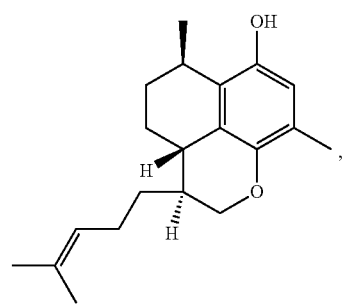
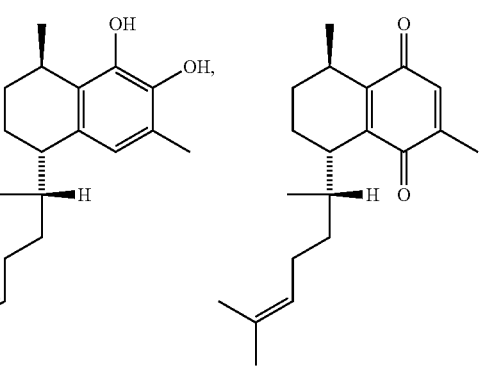

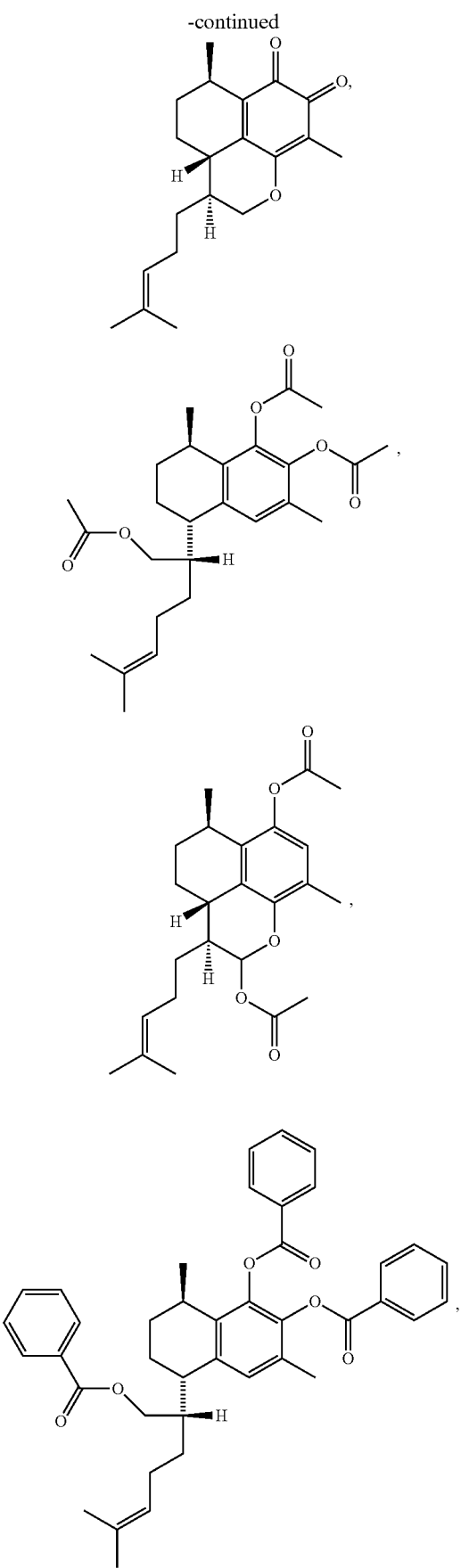
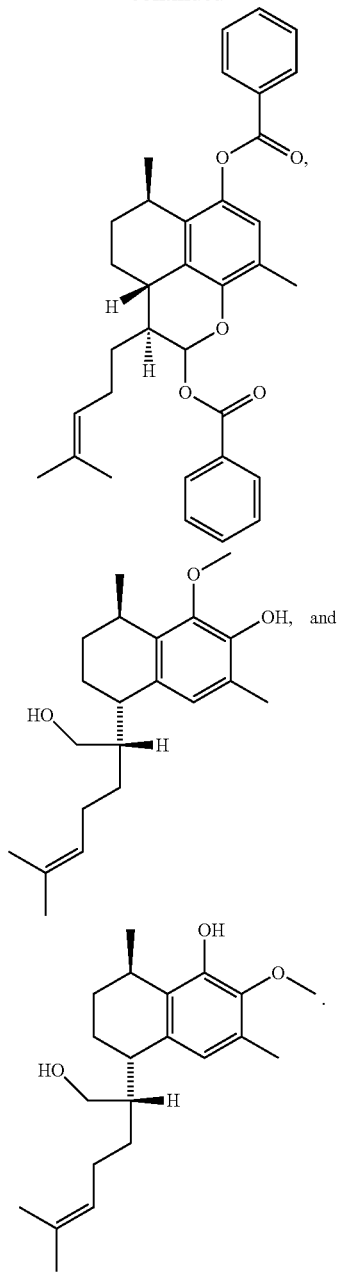
Preferably, the compound is selected from the group consisting of:
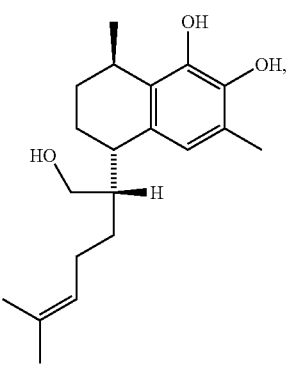

-continued
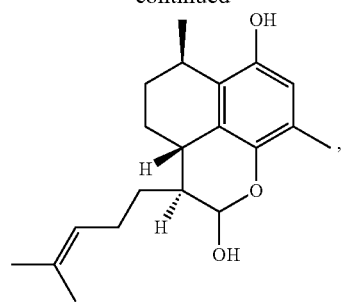
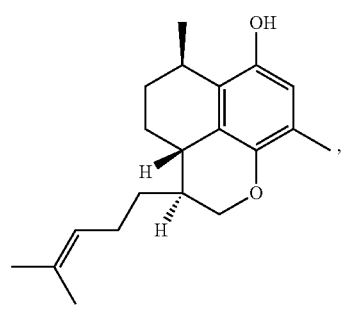
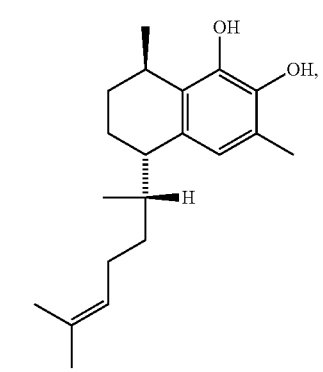
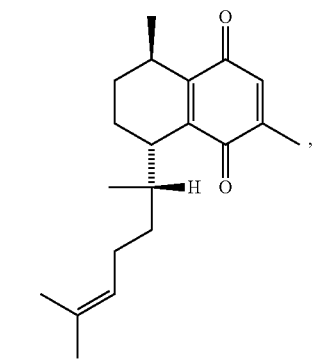
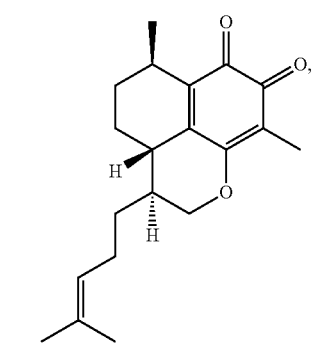
-continued
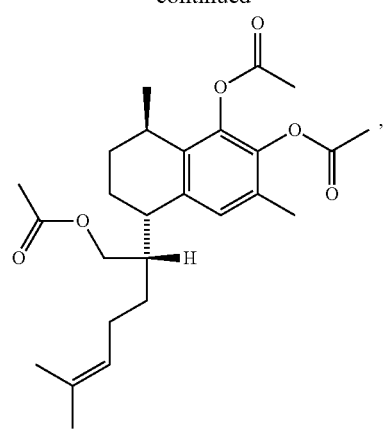
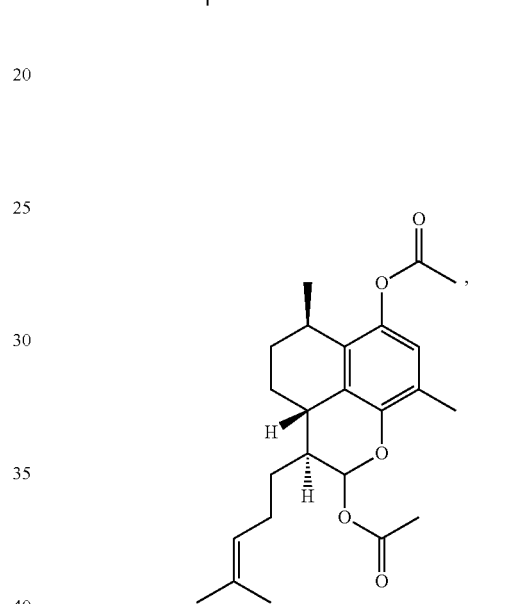
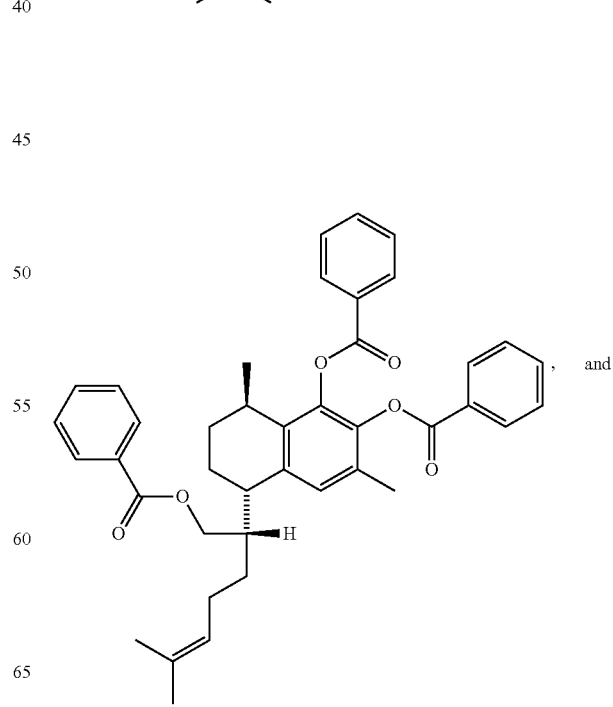
, and

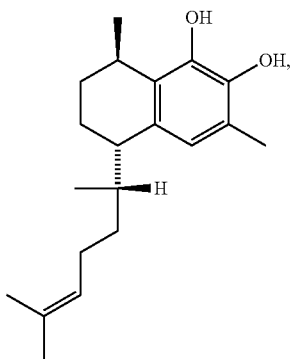
The compound is preferably selected from the group consisting of:
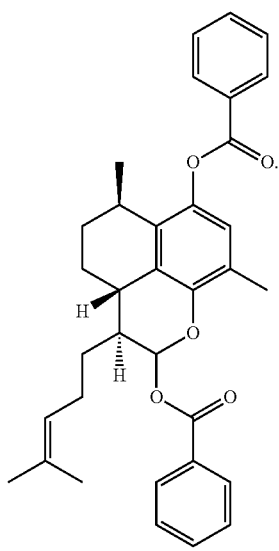
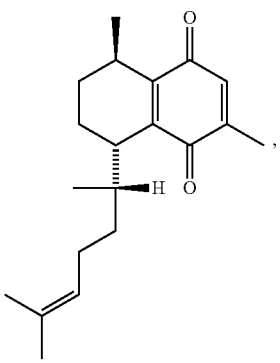
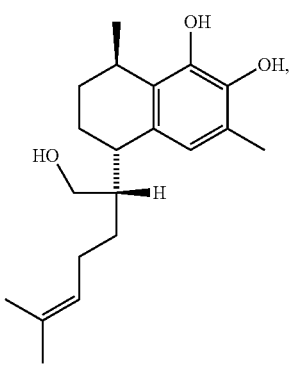
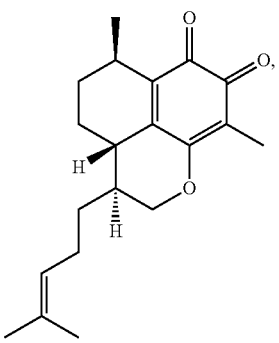
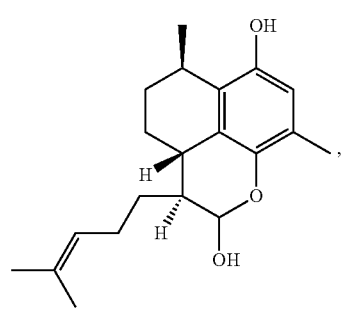
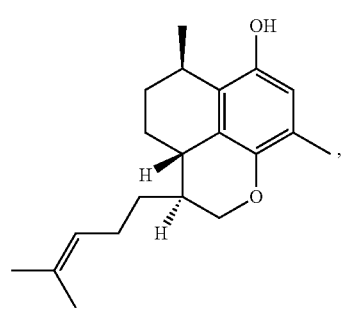, and

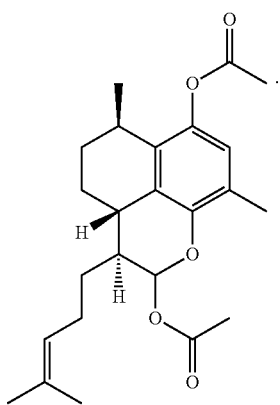
Preferably, the compound is selected from the group consisting of:
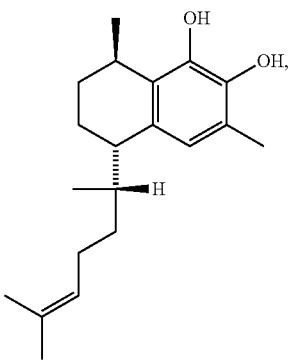
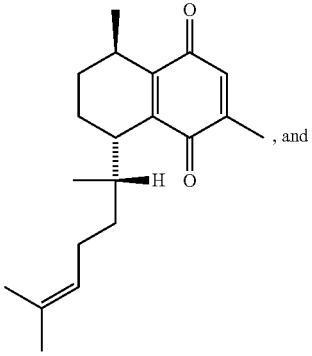
The compound is preferably:
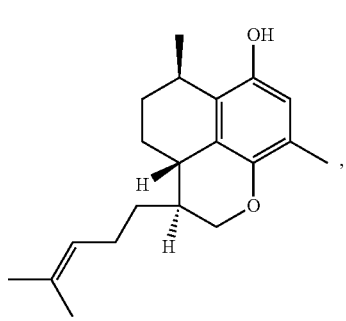

Preferably, the compound is:

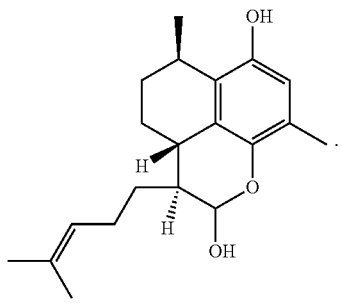 [SMILES: CC(C)=CCC[C@@H]1C(O)Oc2c(C)cc(O)c3c2[C@H]1CC[C@H]3C]

The compound is preferably:

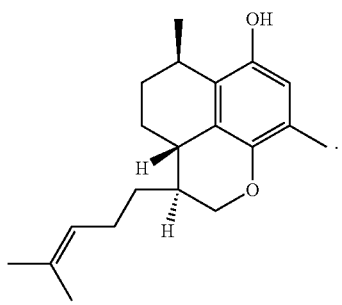 [SMILES: CC(C)=CCC[C@@H]1COc2c(C)cc(O)c3c2[C@H]1CC[C@H]3C]

Preferably, the compound is:

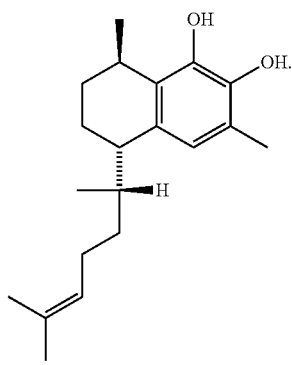 [SMILES: CC(C)=CCC[C@H](C)[C@@H]1CC[C@@H](C)c2c1cc(C)c(O)c2O]

The compound is preferably:

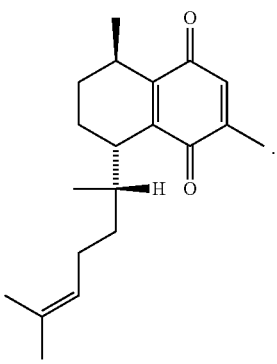 [SMILES: CC(C)=CCC[C@H](C)[C@@H]1CC[C@@H](C)C2=C1C(=O)C(C)=CC2=O]

Preferably, the compound is:

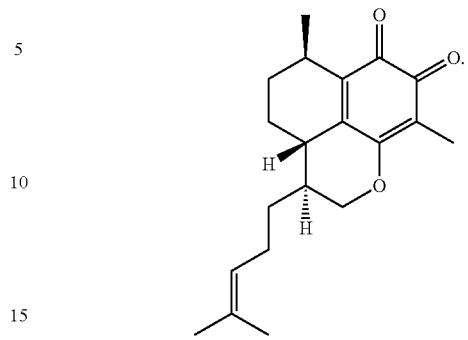

Preferably, the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

The cancer of the central nervous system is preferably a glioma. Preferably, the cancer of the central nervous system is a medulloblastoma. The cancer of the central nervous system is preferably a neuroblastoma.

Preferably, the lung cancer is a non-small cell lung cancer. The lung cancer is preferably a small cell lung cancer.

Preferably, the carcinoma is adenosquamous cell carcinoma or squamous cell carcinoma.

The sarcoma is preferably a liposarcoma, rhabdomyosarcoma, or fibrosarcoma. Preferably, the sarcoma is a soft tissue sarcoma. The soft tissue sarcoma is preferably a soft tissue osteosarcoma.

Preferably, the lymphoma is Burkitt's lymphoma, Hodgkin's lymphoma, or non-Hodgkin's lymphoma.

Also disclosed herein is a compound of Formula (I),

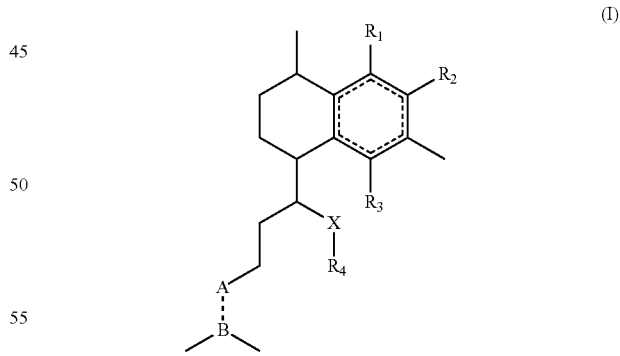

(I)

a geometric isomer, stereoisomer, pharmaceutically acceptable salt or solvate thereof,
wherein:
X is $CH_2$, CHOH or C(O);
$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;
$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC_{4-5}$alkadienyl, $OC(O)C_{1-5}$ alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or OC(O) $C_{4-5}$ alkadienyl; and A-B is CH=C or $CH_2$—CH, for use in treating a cancer.

Preferably:

X is $CH_2$, CHOH or C(O);

$R_1$ is independently H, OH, $OC_{1-5}$alkyl, $OCH_2Ph$, $OC_{2-5}$ alkenyl, $OC(O)C_{1-5}$alkyl, OC(O)Ph, $OC(O)C_{2-5}$alkenyl or =O;

$R_2$ is independently H, OH, $OC_{1-5}$alkyl, $OCH_2Ph$, $OC_{2-5}$ alkenyl, $OC(O)C_{1-5}$alkyl, OC(O)Ph, $OC(O)C_{2-5}$alkenyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC_{2-5}$alkenyl, $OC(O)C_{1-5}$alkyl, OC(O)Ph or $OC(O)C_{2-5}$alkenyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC(O)C_{1-5}$alkyl, OC(O)Ph or $OC(O)C_{2-5}$alkenyl; and A-B is CH=C or $CH_2$—CH.

Preferably:

X is $CH_2$, CHOH or C(O);

$R_1$ is independently H, OH, $OC_{1-5}$alkyl, $OCH_2Ph$, OC(O) $C_{1-5}$alkyl, OC(O)Ph or =O;

$R_2$ is independently H, OH, $OC_{1-5}$alkyl, $OCH_2Ph$, OC(O) $C_{1-5}$alkyl, OC(O)Ph or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC(O)C_{1-5}$alkyl or OC(O)Ph; and A-B is CH=C or $CH_2$—CH.

Preferably:

X is $CH_2$, CHOH or C(O);

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$ alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is $CH_2$;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is CHOH;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably:

X is C(O);

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

Preferably, the compound is a compound of Formula (Ia):

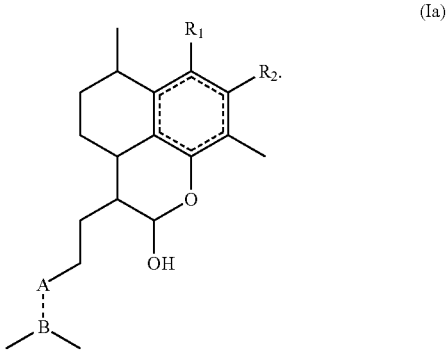

Preferably, the compound is a compound of Formula (Ib):

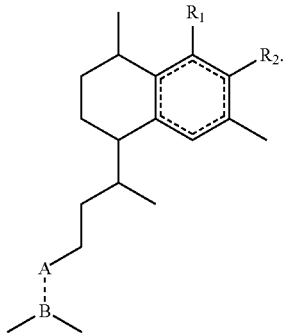

(Ib)

Preferably, the compound is a compound of Formula (Ic):

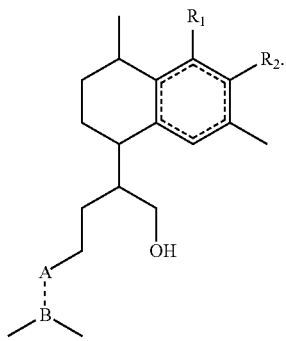

(Ic)

Preferably, the compound is a compound of Formula (Id):

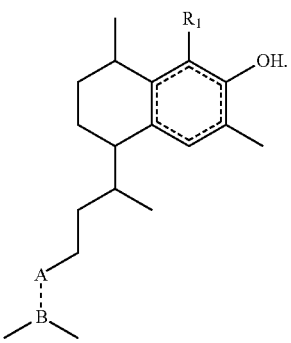

(Id)

Preferably, the compound is a compound of Formula (Ie):

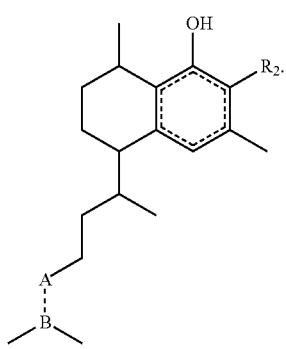

(Ie)

Preferably, the compound is a compound of Formula (If):

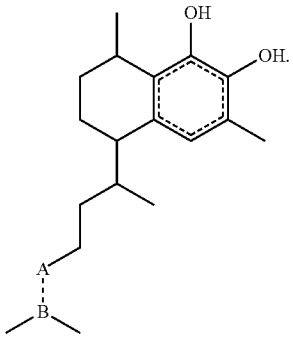

(If)

Preferably, the compound is a compound of Formula (Ig):

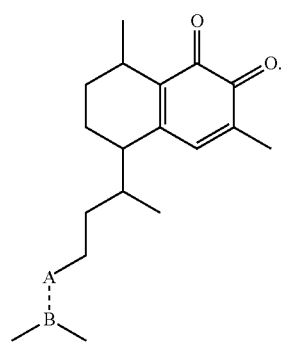

(Ig)

Preferably, the compound is a compound of Formula (Ih):

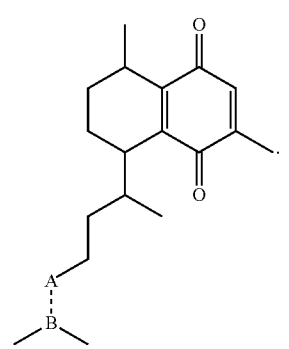

(Ih)

Preferably, the compound is a compound of Formula (Ii):

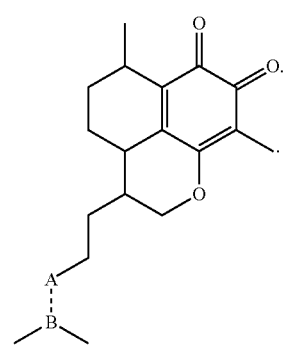

(Ii)

Preferably, A-B is CH=C.
The compound is preferably selected from the group consisting of:
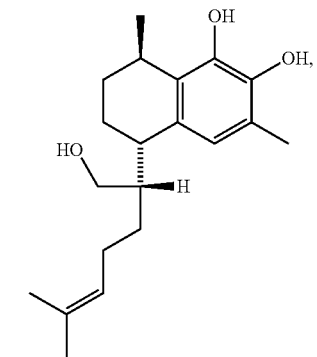
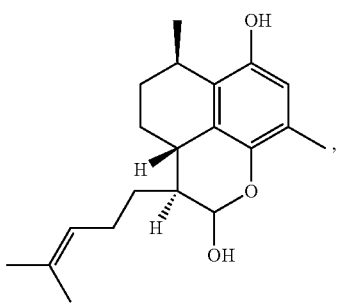
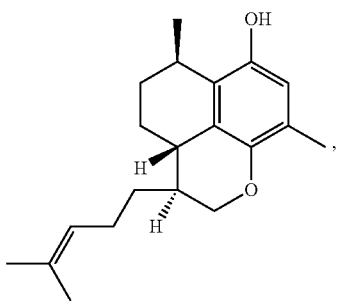
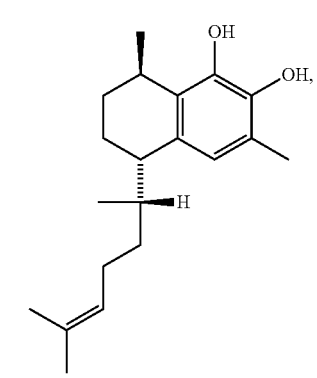
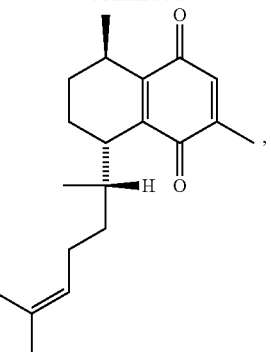
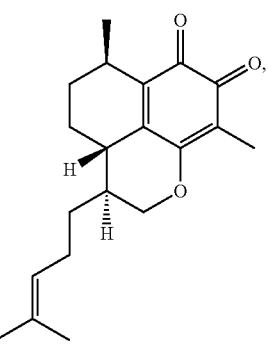
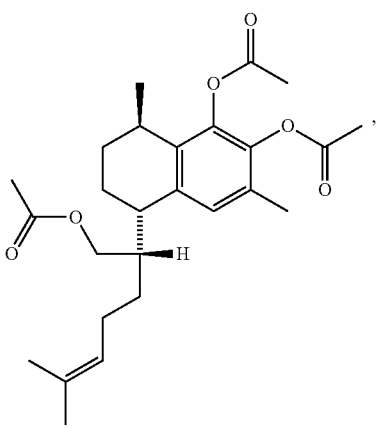
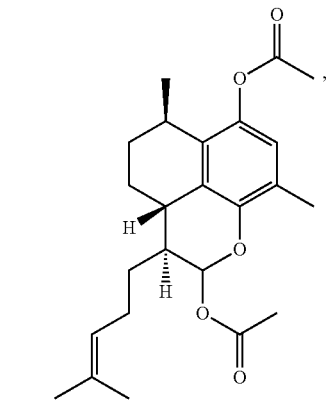

65
-continued
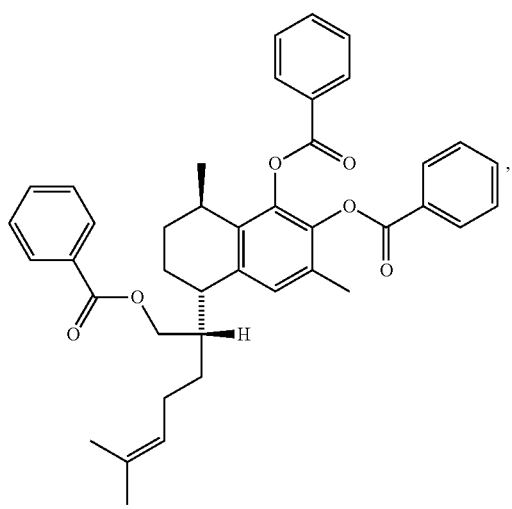
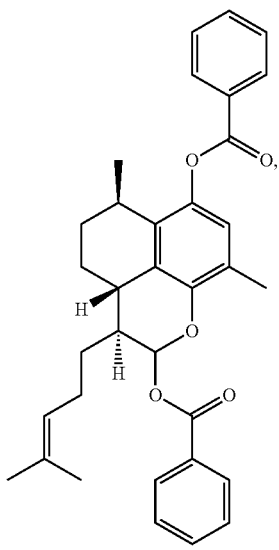
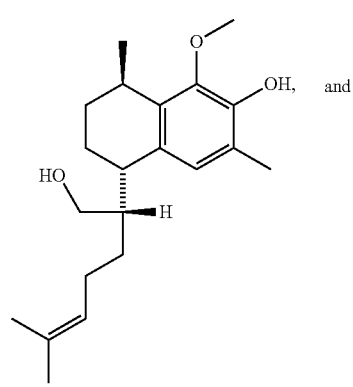
66
-continued
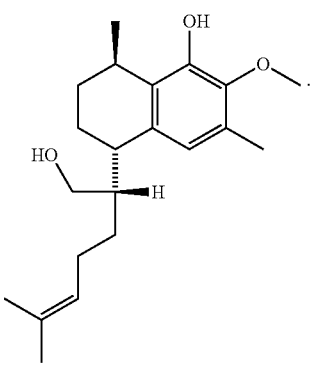
Preferably, the compound is selected from the group consisting of:
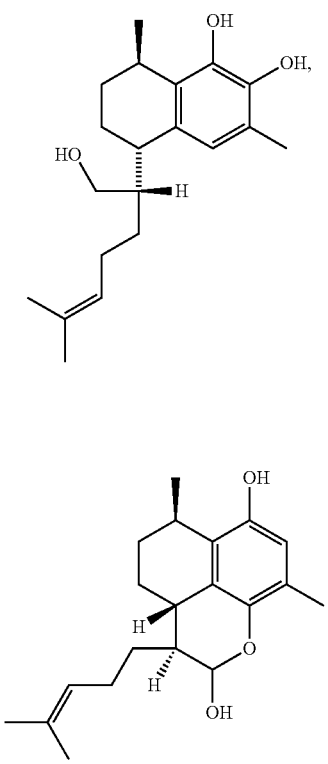
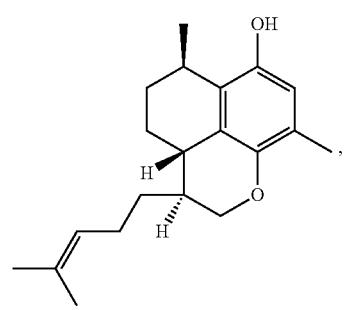

67
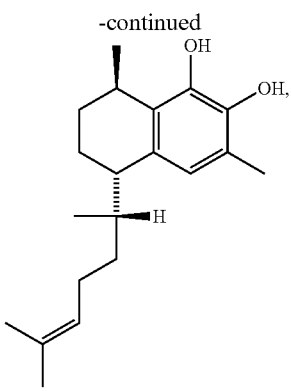
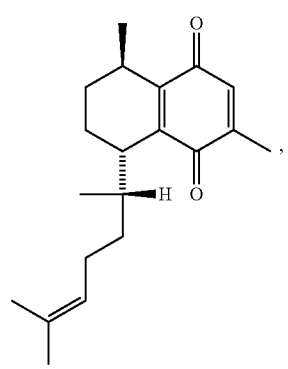
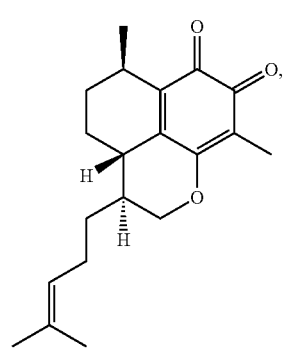
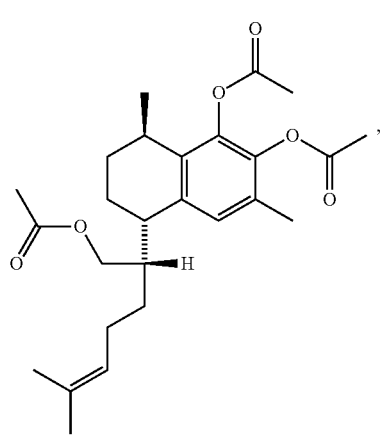
68
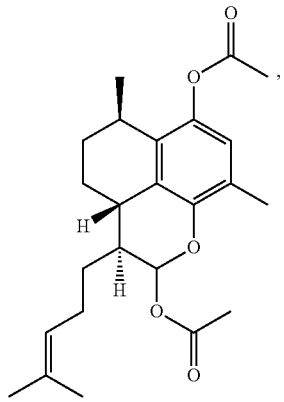
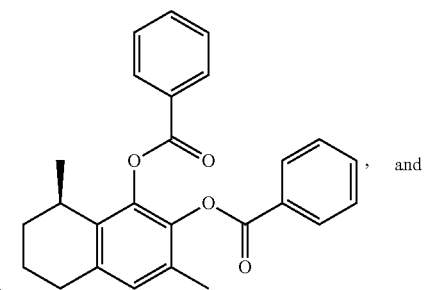, and
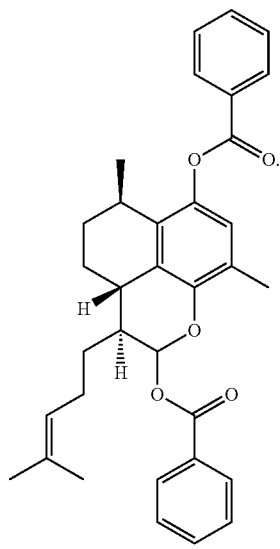

The compound is preferably selected from the group consisting of:
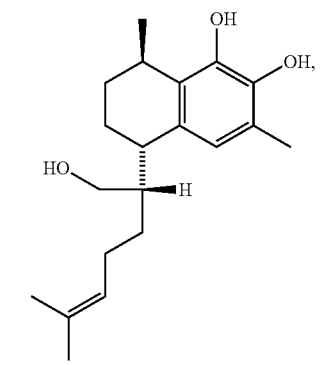
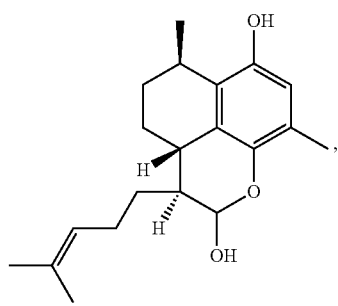
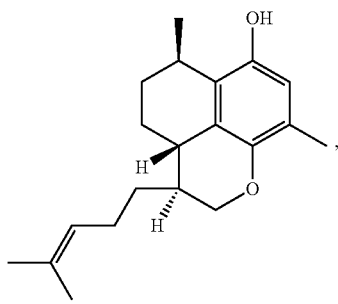
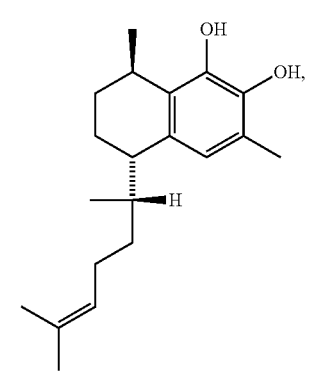
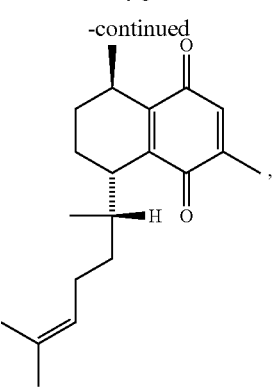
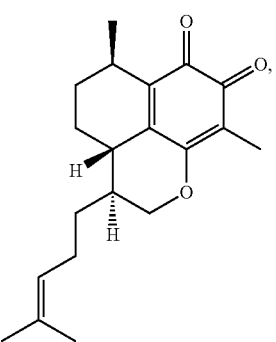 [SMILES: CC(C)=CCC[C@@H]1COC2=C(C)C(=O)C(=O)C3=C2[C@H]1CC[C@H]3C]
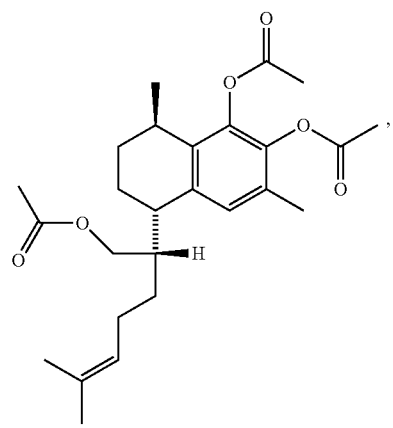, and
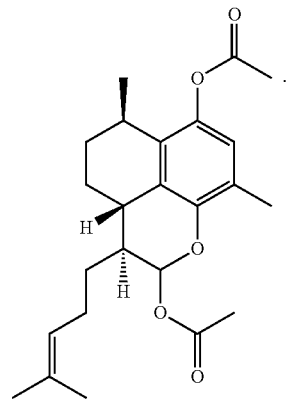.

Preferably, the compound is selected from the group consisting of:
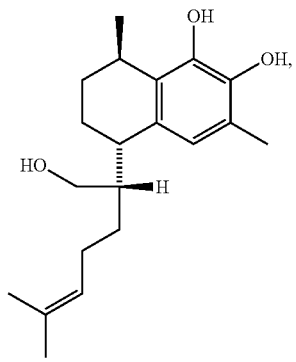
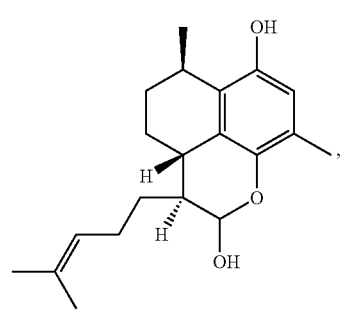
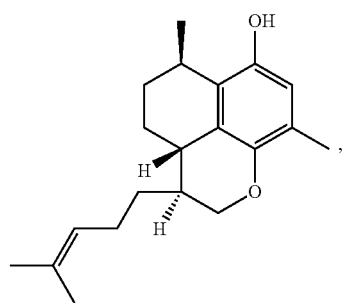
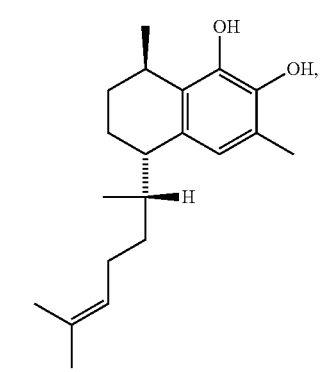
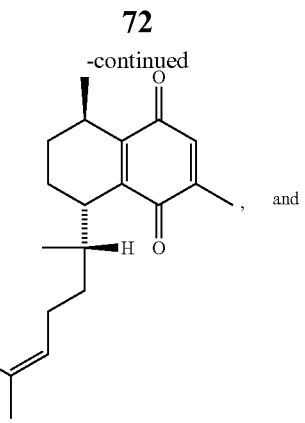, and
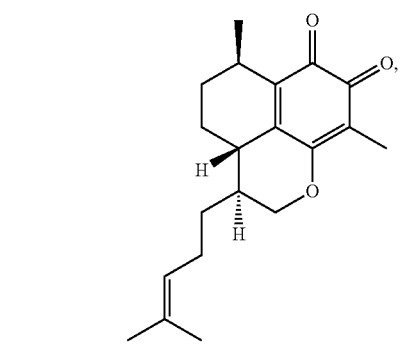
The compound is preferably:
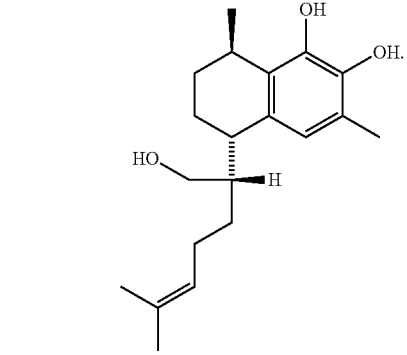 [SMILES: CC(C)=CCC[C@H](CO)[C@@H]1CC[C@@H](C)c2c1cc(C)c(O)c2O]
Preferably, the compound is:
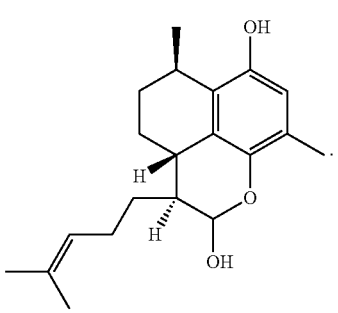

The compound is preferably:

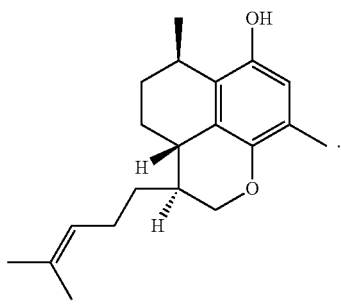 [SMILES: CC(C)=CCC[C@@H]1COc2c(C)cc(O)c3c2[C@H]1CC[C@H]3C]

Preferably, the compound is:

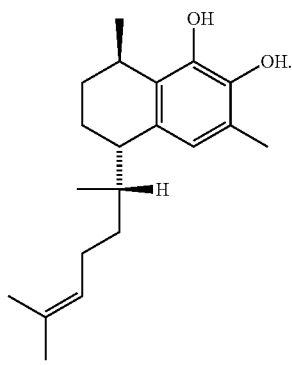 [SMILES: CC(C)=CCC[C@H](C)[C@@H]1CC[C@@H](C)c2c1cc(C)c(O)c2O]

The compound is preferably:

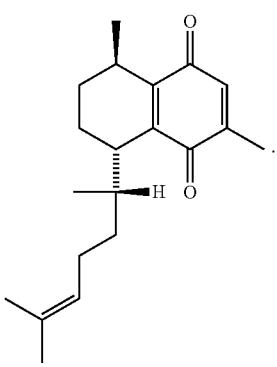 [SMILES: CC(C)=CCC[C@H](C)[C@@H]1CC[C@@H](C)C2=C1C(=O)C(C)=CC2=O]

Preferably, the compound is:

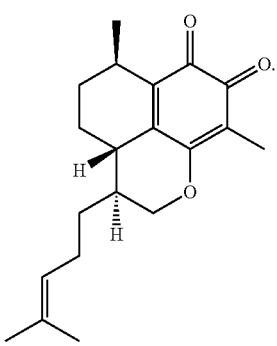 [SMILES: CC(C)=CCC[C@@H]1COC2=C(C)C(=O)C(=O)C3=C2[C@H]1CC[C@H]3C]

Preferably, the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

The cancer of the central nervous system is preferably a glioma. Preferably, the cancer of the central nervous system is a medulloblastoma. The cancer of the central nervous system is preferably a neuroblastoma.

Preferably, the lung cancer is a non-small cell lung cancer. The lung cancer is preferably a small cell lung cancer.

Preferably, the carcinoma is adenosquamous cell carcinoma or squamous cell carcinoma.

The sarcoma is preferably a liposarcoma, rhabdomyosarcoma, or fibrosarcoma. Preferably, the sarcoma is a soft tissue sarcoma. The soft tissue sarcoma is preferably a soft tissue osteosarcoma.

Preferably, the lymphoma is Burkitt's lymphoma, Hodgkin's lymphoma, or non-Hodgkin's lymphoma.

Also disclosed herein is a compound of Formula (I),

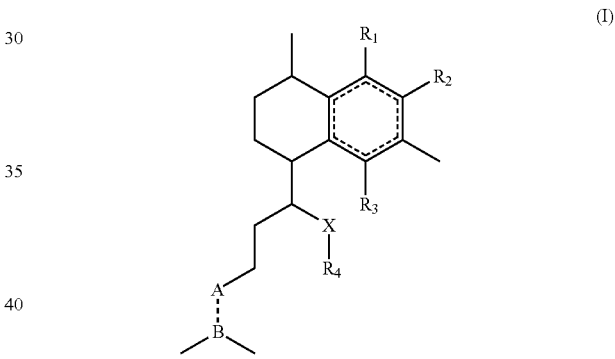

a geometric isomer, stereoisomer, pharmaceutically acceptable salt or solvate thereof,
wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl. $OC(O)C_{1-5}$alkyl, OC(O)Ph, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$alkadienyl; and A-B is CH=C or $CH_2$—CH.

Preferably:

X is CH$_2$, CHOH or C(O);

R$_1$ is independently H, OH, OC$_{1-5}$alkyl, OCH$_2$Ph, OC$_{2-5}$alkenyl, OC(O)C$_{1-5}$alkyl, OC(O)Ph, OC(O)C$_{2-5}$alkenyl or =O;

R$_2$ is independently H, OH, OC$_{1-5}$alkyl, OCH$_2$Ph, OC$_{2-5}$alkenyl, OC(O)C$_{1-5}$alkyl, OC(O)Ph, OC(O)C$_{2-5}$alkenyl or =O;

R$_3$ is independently H, OH, OC$_{1-5}$alkyl, OC(O)C$_{1-5}$alkyl or =O;

and no more than one of R$_1$, R$_2$ and R$_3$ can be H;

where X is CH$_2$, CHOH or C(O), R$_4$ is H, OH, OC$_{1-5}$alkyl, OCH$_2$Ph, OC$_{2-5}$alkenyl, OC(O)C$_{1-5}$alkyl, OC(O)Ph or OC(O)C$_{2-5}$alkenyl;

or X and R$_3$ form a six-membered ether ring or lactone ring, or a six membered ring containing a hemiacetal carbon atom or an acetal carbon atom wherein R$_4$ is respectively OH or OC$_{1-5}$alkyl, OCH$_2$Ph, OC$_{2-5}$alkenyl, OC(O)C$_{1-5}$alkyl, OC(O)Ph or OC(O)C$_{2-5}$alkenyl; and A-B is CH=C or CH$_2$—CH.

Preferably:

X is CH$_2$, CHOH or C(O);

R$_1$ is independently H, OH, OC$_{1-5}$alkyl, OCH$_2$Ph, OC(O)C$_{1-5}$alkyl, OC(O)Ph or =O;

R$_2$ is independently H, OH, OC$_{1-5}$alkyl, OCH$_2$Ph, OC(O)C$_{1-5}$alkyl, OC(O)Ph or =O;

R$_3$ is independently H, OH, OC$_{1-5}$alkyl, OC(O)C$_{1-5}$alkyl or =O;

and no more than one of R$_1$, R$_2$ and R$_3$ can be H;

where X is CH$_2$, CHOH or C(O), R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl, OCH$_2$Ph, OC(O)C$_{1-5}$alkyl or OC(O)Ph; and A-B is CH=C or CH$_2$—CH.

Preferably:

X is CH$_2$, CHOH or C(O);

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

where X is CH$_2$, CHOH or C(O), R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

Preferably:

X is CH$_2$;

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

Preferably:

X is CHOH;

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

Preferably:

X is C(O);

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

Preferably, the compound is a compound of Formula (Ia):

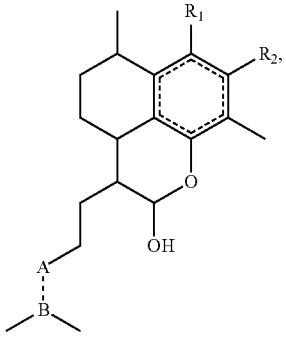

(Ia)

Preferably, the compound is a compound of Formula (Ib):

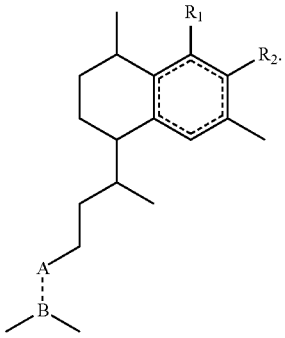

(Ib)

Preferably, the compound is a compound of Formula (Ic):

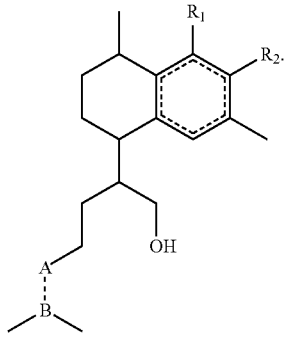
(Ic)

Preferably, the compound is a compound of Formula (Id):

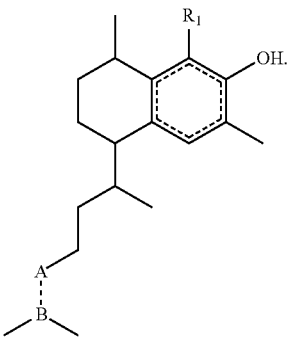
(Id)

Preferably, the compound is a compound of Formula (Ie):

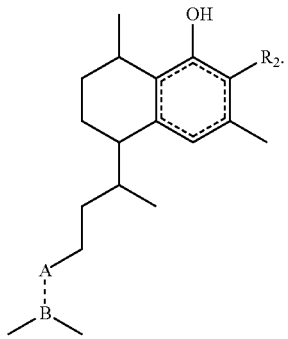
(Ie)

Preferably, the compound is a compound of Formula (If):

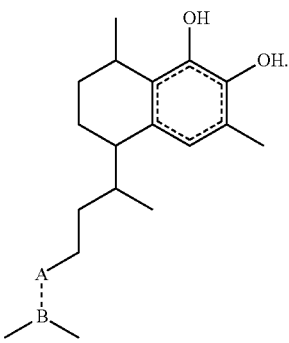
(If)

Preferably, the compound is a compound of Formula (Ig):

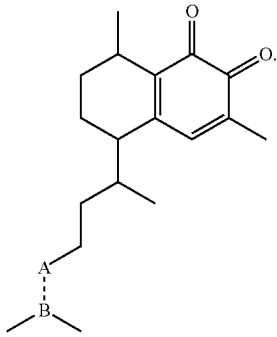
(Ig)

Preferably, the compound is a compound of Formula (Ih):

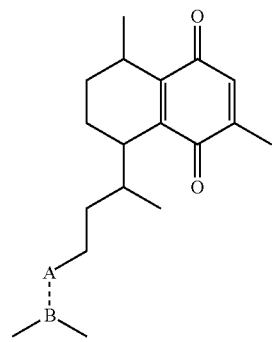
(Ih)

Preferably, the compound is a compound of Formula (Ii):

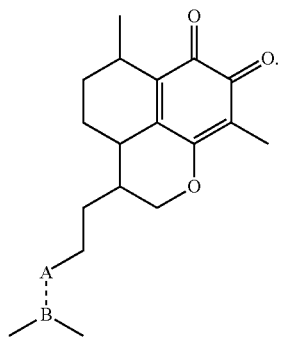
(Ii)

Preferably, A-B is CH=CH.

The compound is preferably selected from the group consisting of:

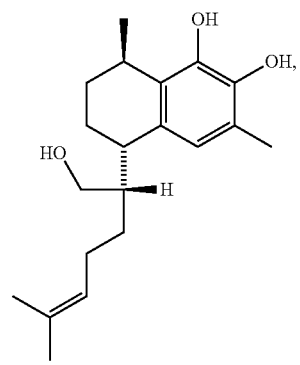

79
-continued
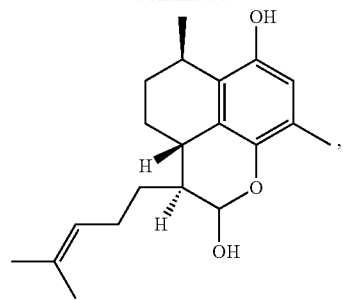
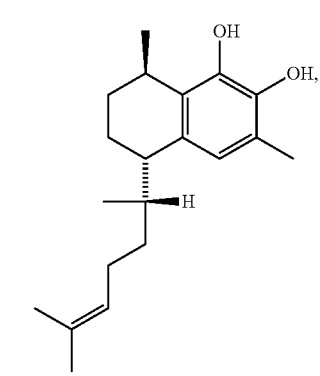
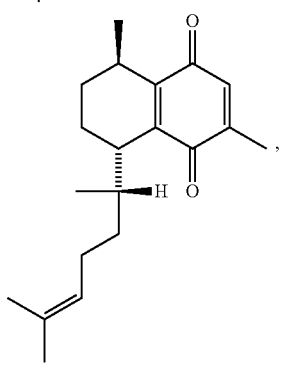
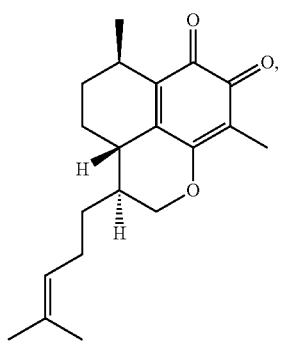
80
-continued
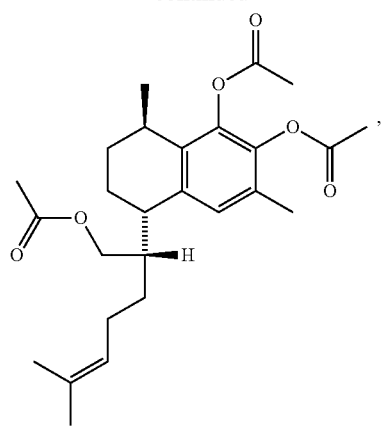
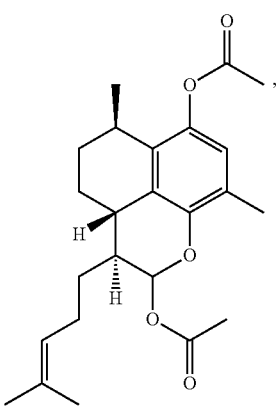
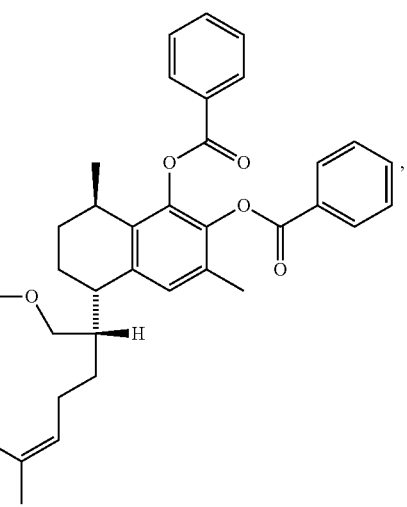

-continued
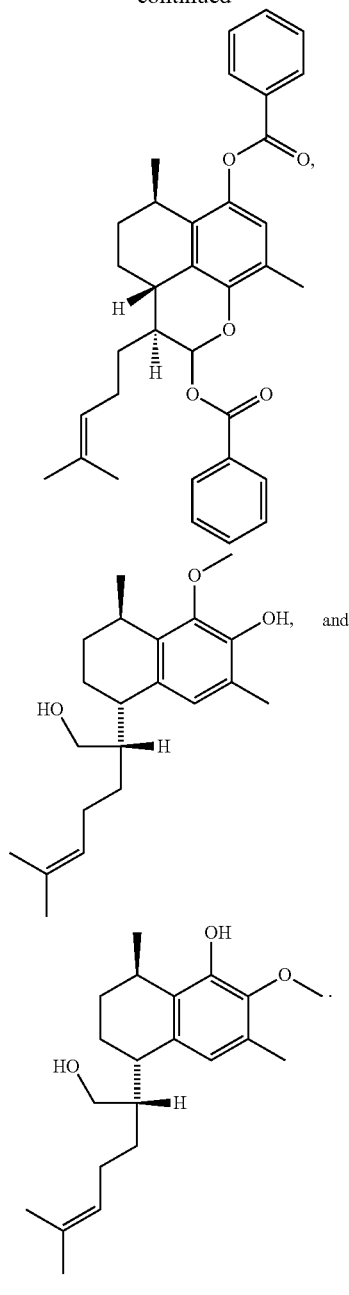
Preferably, the compound is selected from the group consisting of:
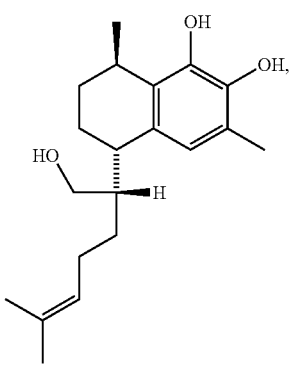
-continued
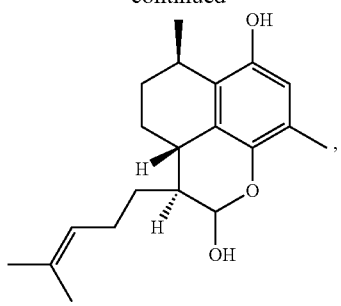
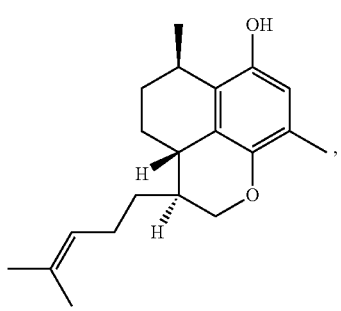
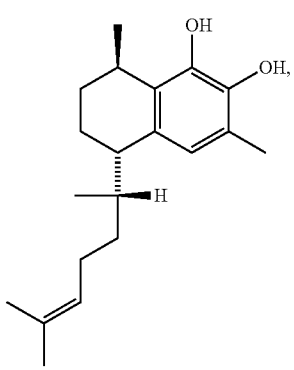
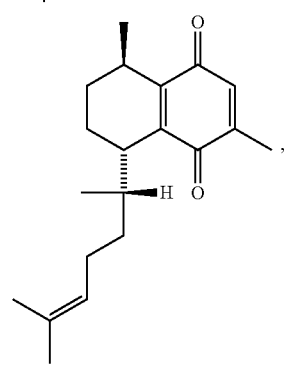
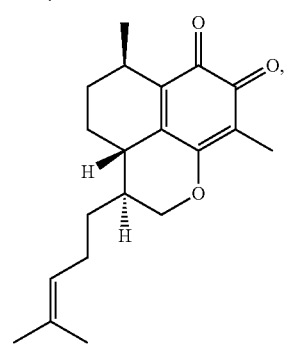

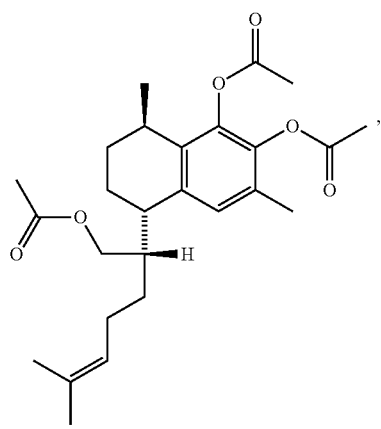
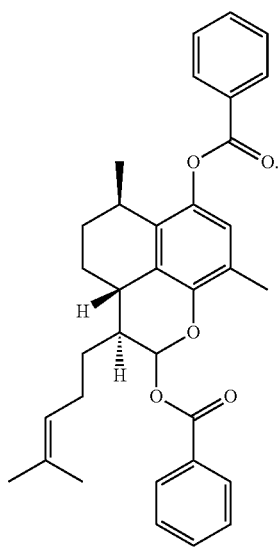
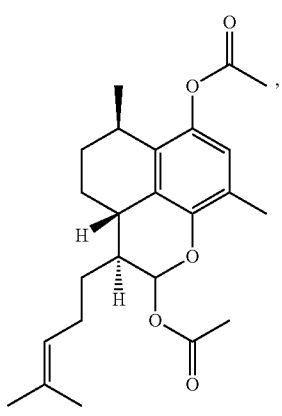
The compound is preferably selected from the group consisting of:
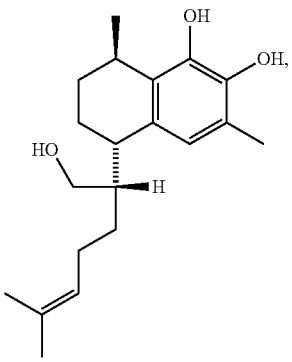
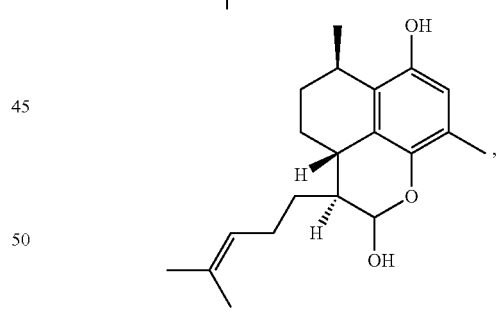
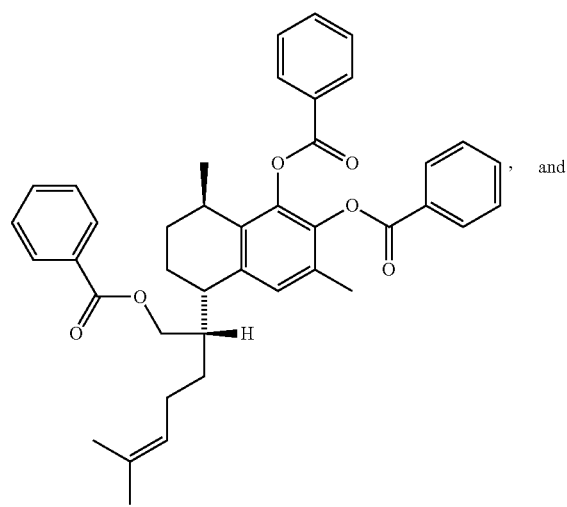
, and
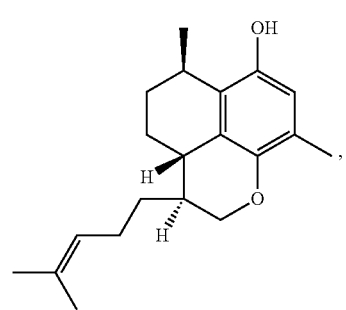

85
-continued
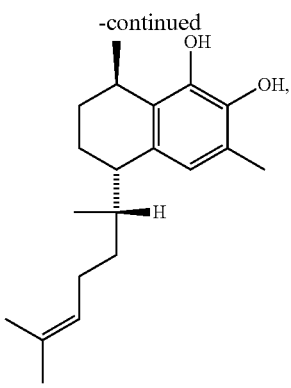
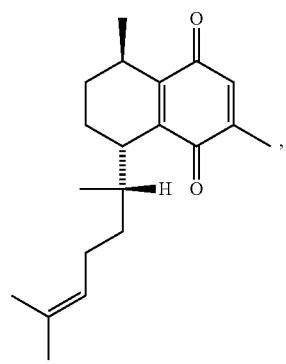
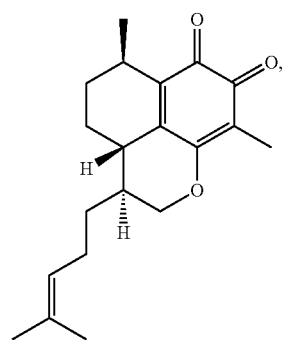 [SMILES: CC(C)=CCC[C@@H]1COC2=C(C)C(=O)C(=O)C3=C2[C@H]1CC[C@H]3C]
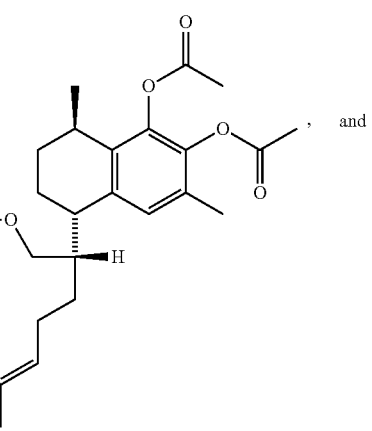, and
86
-continued
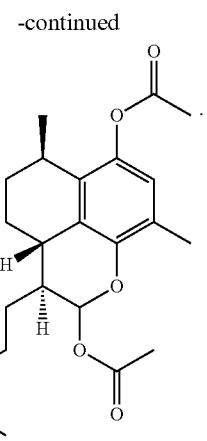
Preferably, the compound is selected from the group consisting of:
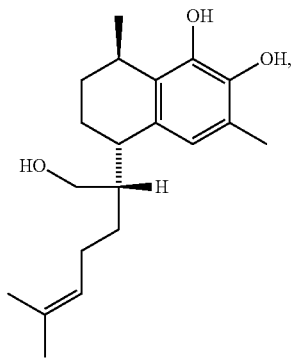 [SMILES: CC(C)=CCC[C@H](CO)[C@@H]1CC[C@@H](C)c2c1cc(C)c(O)c2O]
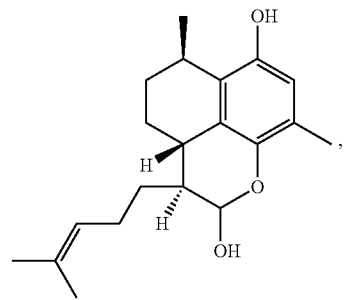,
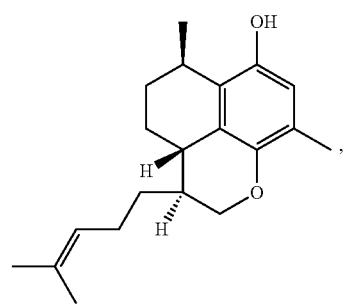,

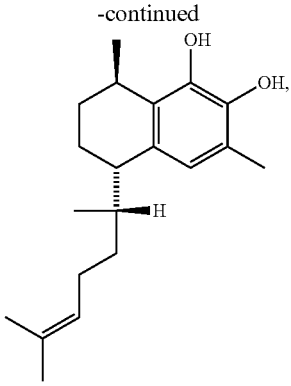
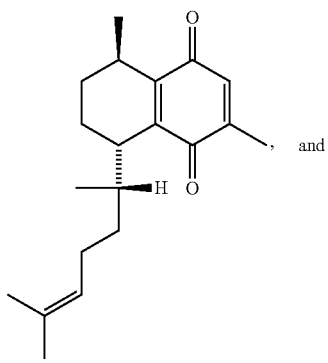, and
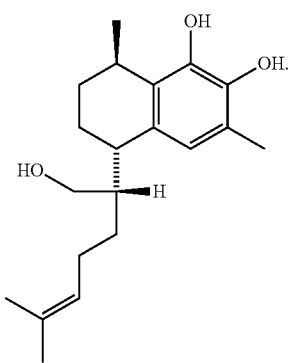
The compound is preferably:
Preferably, the compound is:
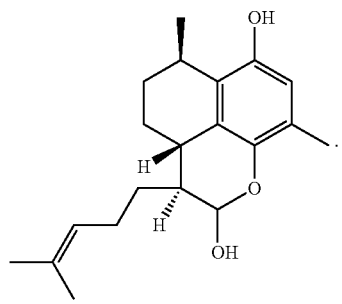 [SMILES: CC(C)=CCC[C@@H]1C(O)Oc2c(C)cc(O)c3c2[C@H]1CC[C@H]3C]
The compound is preferably:
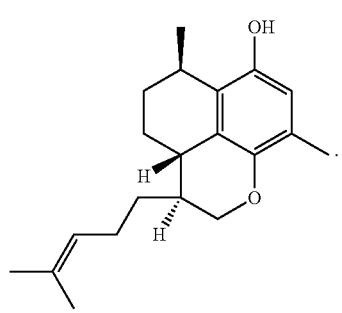 [SMILES: CC(C)=CCC[C@@H]1COc2c(C)cc(O)c3c2[C@H]1CC[C@H]3C]
Preferably, the compound is:
The compound is preferably:
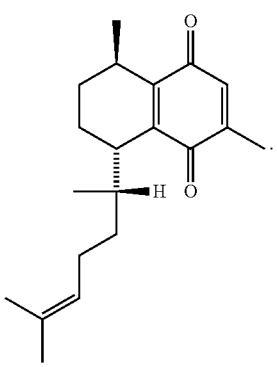 [SMILES: CC(C)=CCC[C@H](C)[C@@H]1CC[C@@H](C)C2=C1C(=O)C(C)=CC2=O]

Preferably, the compound is:

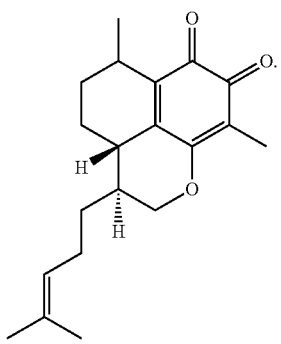 [SMILES: CC(C)=CCC[C@@H]1COC2=C(C)C(=O)C(=O)C3=C2[C@H]1CCC3C]

Also disclosed herein is a pharmaceutical composition comprising a compound, geometric isomer, stereoisomer, pharmaceutically acceptable salt or solvate thereof, as described herein, and a pharmaceutically acceptable excipient.

Also disclosed herein is a pharmaceutical composition comprising a compound, geometric isomer, stereoisomer, pharmaceutically acceptable salt or solvate thereof, as described herein, or a mixture thereof, and a pharmaceutically acceptable excipient.

The compounds or pharmaceutical compositions disclosed above are preferably for use as a medicament.

The compounds or pharmaceutical compositions disclosed above are preferably for use in therapy.

Also disclosed is a compound described above isolated from propolis, wherein the propolis originates from plants of the *Myoporum* genus. Preferably, the propolis originates from *Myoporum insulare*.

Also disclosed is a compound described above isolated from the resin, gum or exudate of *Myoporum* genus. Preferably, the compound is isolated from the resin, gum or exudate of *Myoporum insulare*.

Also disclosed is a method of treating a disease or disorder, the method comprising administering a therapeutically effective amount of a compound or a composition described herein.

Also disclosed is use of a compound described herein in the preparation of a medicament for treating a disease or disorder.

Also disclosed herein is use of a compound or a composition described herein in treating a disease or disorder.

Also disclosed herein is a compound or a composition described herein for use in treating a disease or disorder.

Preferably, the disease or disorder is selected from the group consisting of: acute coronary syndrome, an aging-related disease or disorder; an allergic disease or a related condition; Alzheimer's disease, atherosclerosis, an autoimmune disease; a bacterial infection, cancer; dementia, depression or a related condition; diabetes; dyslipidemia, hyperlipidemia, hypertension, itchytosis, an immune disease; a metabolic disease or disorder; a neurological disease or disorder; obesity; Parkinson's disease; pain; rheumatoid arthritis, a disease or disorder associated with inflammation, such as skin inflammatory conditions, and a skin disease or disorder.

The disease or disorder is preferably cancer.

Preferably, the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

The cancer of the central nervous system is preferably a glioma. Preferably, the cancer of the central nervous system is a medulloblastoma. The cancer of the central nervous system is preferably a neuroblastoma.

Preferably, the lung cancer is a non-small cell lung cancer. The lung cancer is preferably a small cell lung cancer.

Preferably, the carcinoma is adenosquamous cell carcinoma or squamous cell carcinoma.

The sarcoma is preferably a liposarcoma, rhabdomyosarcoma, or fibrosarcoma.

Preferably, the sarcoma is a soft tissue sarcoma. The soft tissue sarcoma is preferably a soft tissue osteosarcoma.

Preferably, the lymphoma is Burkitt's lymphoma, Hodgkin's lymphoma, or non-Hodgkin's lymphoma.

The skin disease or disorder is preferably selected from the group consisting of: eczema, psoriasis, acne, a wound, a scar, inflammation including psoriasis and atopic dermatitis, a burn, sunburn, skin damage and skin irritation.

Representative compounds were evaluated for pharmacological activity and were found to be useful in modulating a number of diseases or disorders. For example, the compounds were found to inhibit cancer cell proliferation and showed moderate to strong inhibition of various targets associated with cancer pathology. The compounds were also found to effectively inhibit inflammatory activity and modulate immune response, showing moderate to strong inhibition of COX1 and COX2, the release of proinflammatory cytokines, lipoxygenase and the nuclear transcription factor NF-κB. Further discussion of compound activity is presented below in the Examples.

Example Embodiments

1. A method of treating a cancer, the method comprising administering a therapeutically effective amount of a compound of Formula (I),

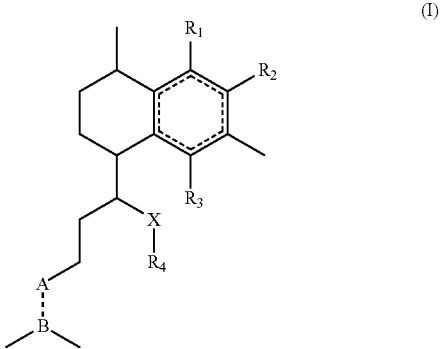

a geometric isomer, stereoisomer, pharmaceutically acceptable salt or solvate thereof, or pharmaceutical composition including said compounds, to a subject in need thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl. $OC(O)C_{1-5}$alkyl, $OC(O)Ph$, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$ alkadienyl; and A-B is CH=C or $CH_2$—CH.

2. Use of a compound of Formula (I), a geometric isomer, stereoisomer, pharmaceutically acceptable salt or solvate thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl. $OC(O)C_{1-5}$alkyl, $OC(O)Ph$, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$ alkadienyl; and A-B is CH=C or $CH_2$—CH, in the preparation of a medicament for treating a cancer.

3. Use of a compound of Formula (I), a geometric isomer, stereoisomer, pharmaceutically acceptable salt or solvate thereof, wherein:

X is $CH_2$, CHOH or C(O);

$R_1$ is independently H, OH, $OC_{1-5}$alkyl, $OCH_2Ph$, $OC_{2-5}$alkenyl, $OC_{4-5}$alkadienyl. $OC(O)C_{1-5}$alkyl, $OC(O)Ph$, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl, $OC(O)C_{4-5}$alkadienyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$alkadienyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$ alkadienyl; and A-B is CH=C or $CH_2$—CH, in treating a cancer.

4. The method according to example embodiment 1 or the use according to example embodiment 2 or example embodiment 3, wherein:

X is $CH_2$, CHOH or C(O);

$R_1$ is independently H, OH, $OC_{1-5}$alkyl, $OCH_2Ph$, $OC_{2-5}$alkenyl, $OC(O)C_{1-5}$alkyl, $OC(O)Ph$, $OC(O)C_{2-5}$alkenyl or =O;

$R_2$ is independently H, OH, $OC_{1-5}$alkyl, $OCH_2Ph$, $OC_{2-5}$alkenyl, $OC(O)C_{1-5}$alkyl, $OC(O)Ph$, $OC(O)C_{2-5}$alkenyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC_{2-5}$alkenyl, $OC(O)C_{1-5}$alkyl, $OC(O)Ph$ or $OC(O)C_{2-5}$alkenyl;

or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC(O)C_{1-5}$alkyl, $OC(O)Ph$ or $OC(O)C_{2-5}$alkenyl; and A-B is CH=C or $CH_2$—CH.

5. The method according to example embodiment 1 or the use according to example embodiment 2 or example embodiment 3, wherein:

X is CH$_2$, CHOH or C(O);

R$_1$ is independently H, OH, OC$_{1-5}$alkyl, OCH$_2$Ph, OC(O)C$_{1-5}$alkyl, OC(O)Ph or =O;

R$_2$ is independently H, OH, OC$_{1-5}$alkyl, OCH$_2$Ph, OC(O)C$_{1-5}$alkyl, OC(O)Ph or =O;

R$_3$ is independently H, OH, OC$_{1-5}$alkyl, OC(O)C$_{1-5}$alkyl or =O;

and no more than one of R$_1$, R$_2$ and R$_3$ can be H;

where X is CH$_2$, CHOH or C(O), R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl, OCH$_2$Ph, OC(O)C$_{1-5}$alkyl or OC(O)Ph; and A-B is CH=C or CH$_2$—CH.

6. The method according to example embodiment 1 or the use according to example embodiment 2 or example embodiment 3, wherein:

X is CH$_2$, CHOH or C(O);

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

where X is CH$_2$, CHOH or C(O), R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

7. The method according to example embodiment 1 or the use according to example embodiment 2 or example embodiment 3, wherein:

X is CH$_2$;

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

8. The method according to example embodiment 1 or the use according to example embodiment 2 or example embodiment 3, wherein:

X is CHOH;

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

9. The method according to example embodiment 1 or the use according to example embodiment 2 or example embodiment 3, wherein:

X is C(O);

R$_1$ is independently H, OH, OC$_{1-5}$alkyl, OC(O)C$_{1-5}$alkyl or =O;

R$_2$ is independently H, OH, OC$_{1-5}$alkyl, OC(O)C$_{1-5}$alkyl or =O;

R$_3$ is independently H, OH, OC$_{1-5}$alkyl, OC(O)C$_{1-5}$alkyl or =O;

and no more than one of R$_1$, R$_2$ and R$_3$ can be H;

R$_4$ is H, OH, OC$_{1-5}$alkyl, OCH$_2$Ph, OC(O)C$_{1-5}$alkyl or OC(O)Ph;

or X and R$_3$ form a six-membered ether ring or lactone ring, or a six membered ring containing a hemiacetal carbon atom or an acetal carbon atom wherein R$_4$ is respectively OH or OC$_{1-5}$alkyl or OC(O)C$_{1-5}$alkyl; and A-B is CH=C or CH$_2$—CH.

10. The method according to example embodiment 1 or the use according to example embodiment 2 or example embodiment 3, wherein the compound is a compound of Formula (Ia):

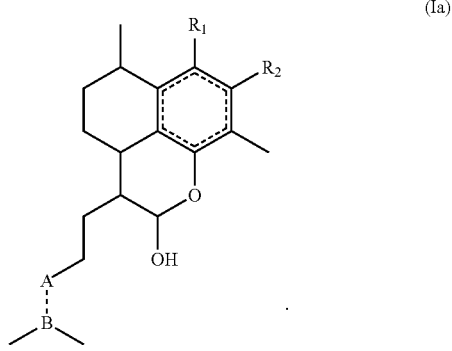

(Ia)

11. The method according to example embodiment 1 or the use according to example embodiment 2 or example embodiment 3, wherein the compound is a compound of Formula (Ib):

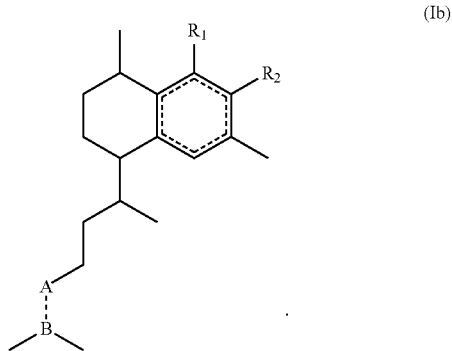

(Ib)

12. The method according to example embodiment 1 or the use according to example embodiment 2 or example embodiment 3, wherein the compound is a compound of Formula (Ic):

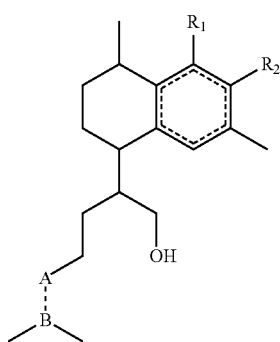

(Ic)

13. The method according to example embodiment 1 or the use according to example embodiment 2 or example embodiment 3, wherein the compound is a compound of Formula (Id):

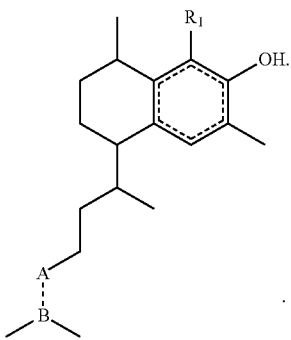

(Id)

14. The method according to example embodiment 1 or the use according to example embodiment 2 or example embodiment 3, wherein the compound is a compound of Formula (Ie):

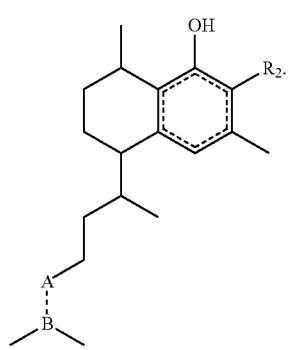

(Ie)

15. The method according to example embodiment 1 or the use according to example embodiment 2 or example embodiment 3, wherein the compound is a compound of Formula (If):

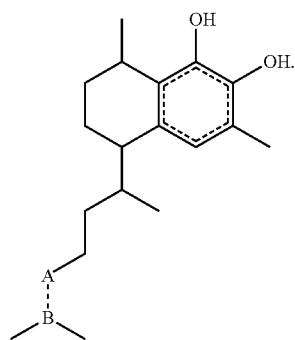

(If)

16. The method according to example embodiment 1 or the use according to example embodiment 2 or example embodiment 3, wherein the compound is a compound of Formula (Ig):

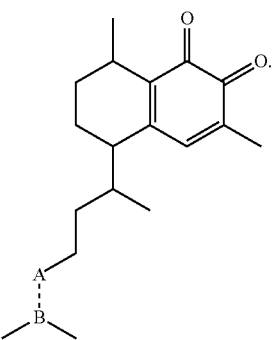

(Ig)

17. The method according to example embodiment 1 or the use according to example embodiment 2 or example embodiment 3, wherein the compound is a compound of Formula (Ih):

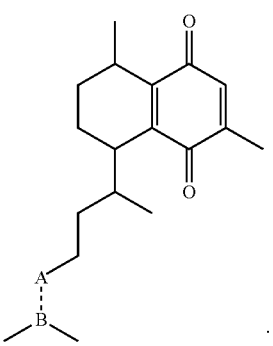

(Ih)

18. The method according to example embodiment 1 or the use according to example embodiment 2 or example embodiment 3, wherein the compound is a compound of Formula (Ii):

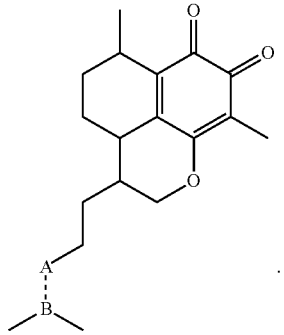

19. The method or use according to any one of example embodiments 1 to 16, wherein A-B is CH═C.

20. The method according to any one of example embodiments 1 to 19 or the use according to any one of example embodiments 2 to 19, wherein the compound is selected from the group consisting of:

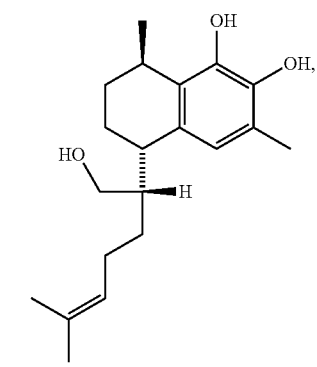

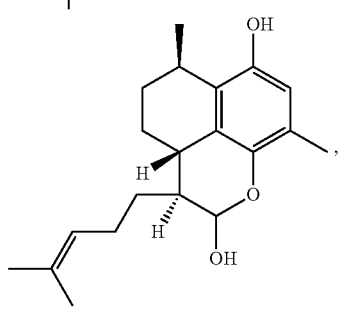

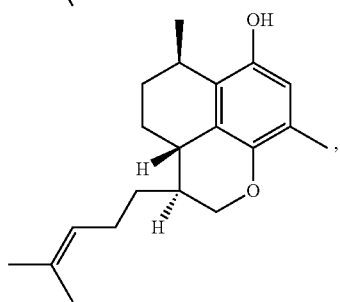

-continued

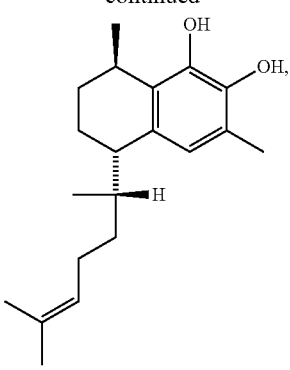

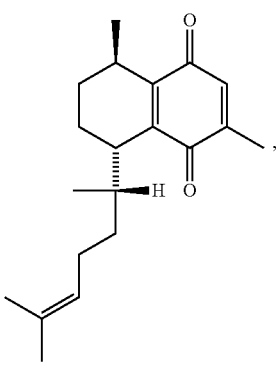

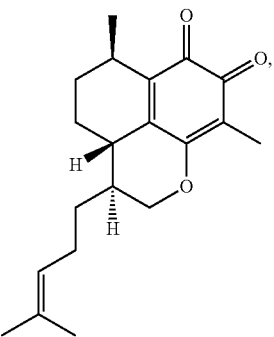

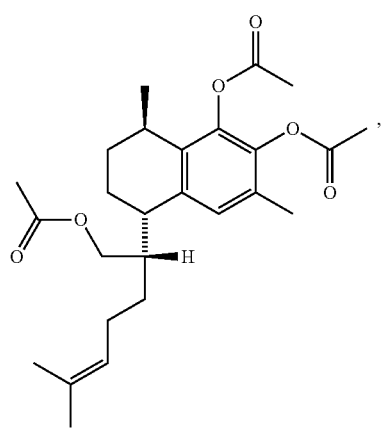

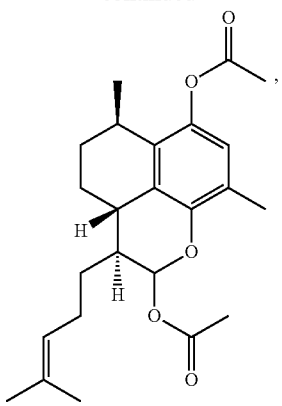
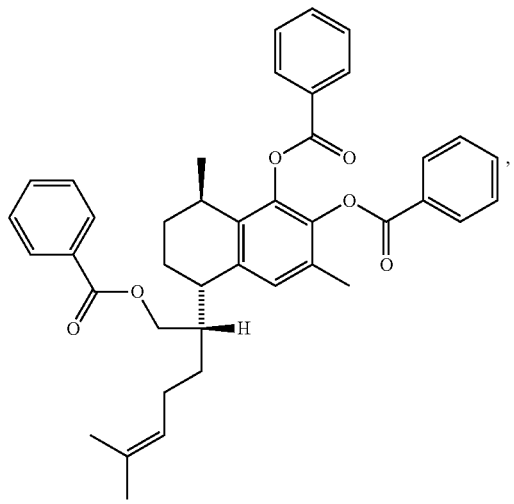
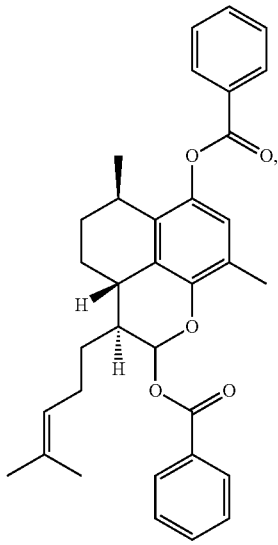
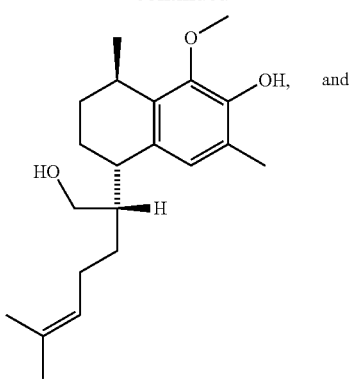
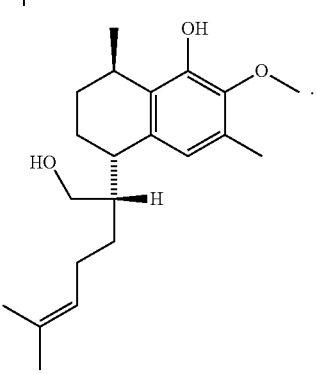
21. The method or use according to example embodiment 20, wherein the compound is selected from the group consisting of:
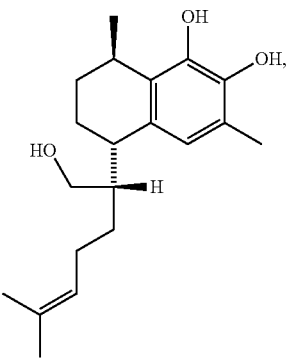
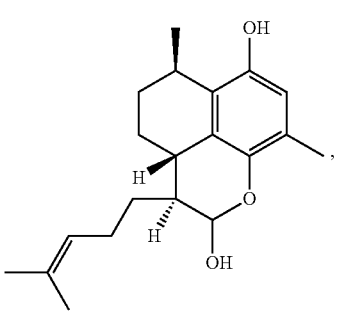

| 101 | 102 |
|---|---|
| -continued | -continued |
| 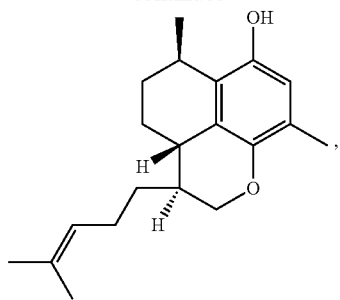 | 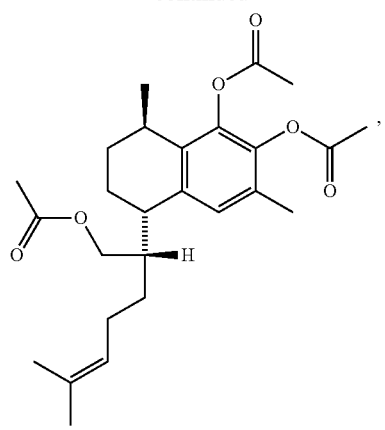 |
| 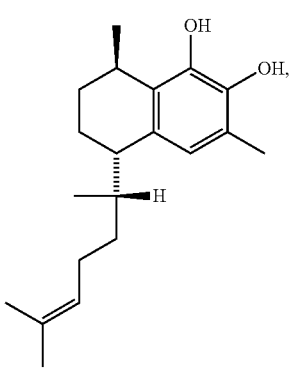 | |
| 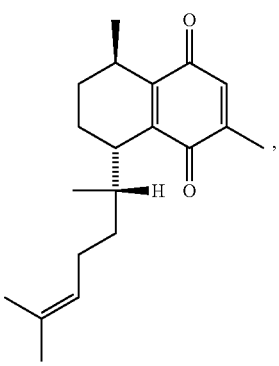 | 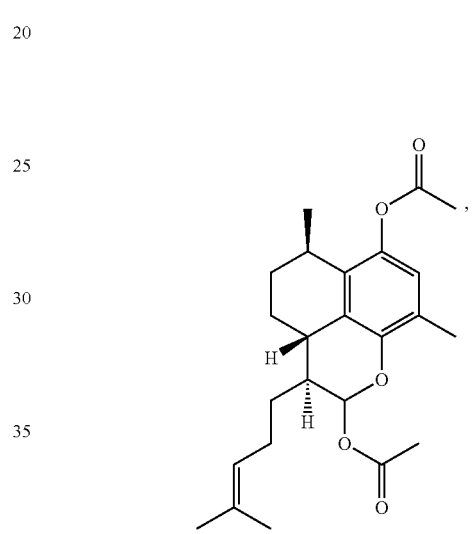 |
| 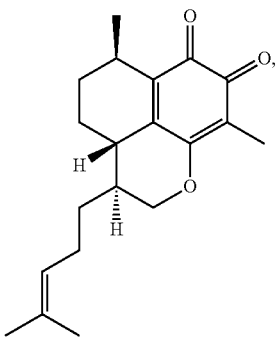 | 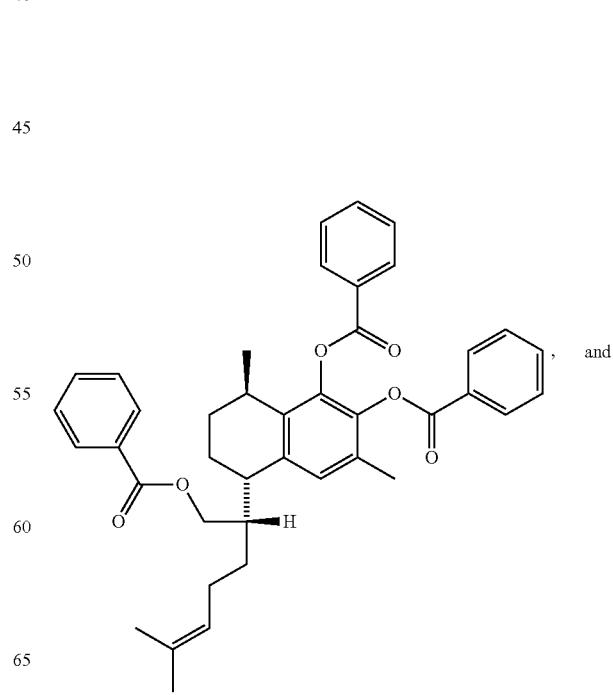, and |

103
-continued
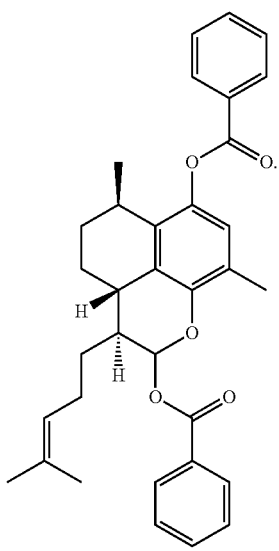
22. The method or use according to example embodiment 21, wherein the compound is selected from the group consisting of:
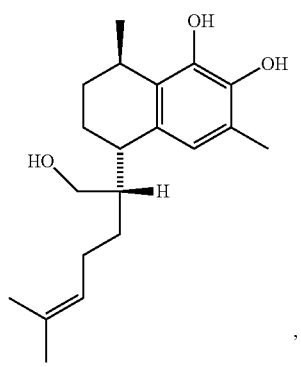
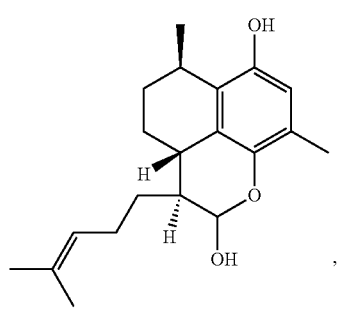
104
-continued
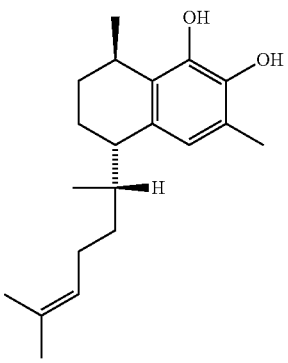
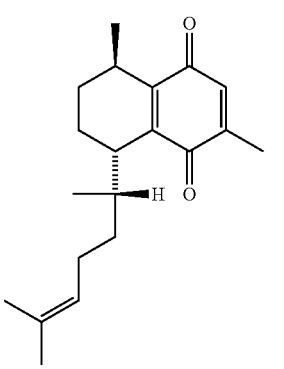
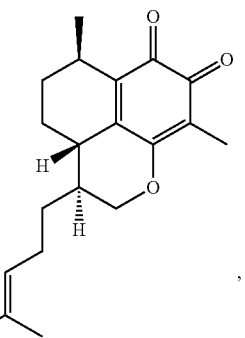
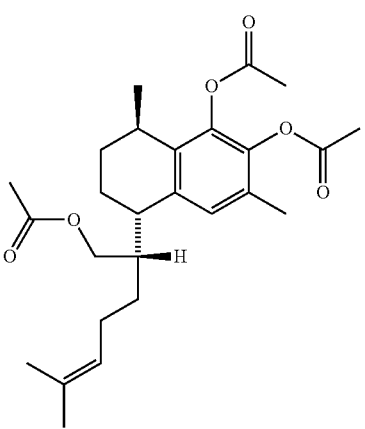
, and 105
-continued
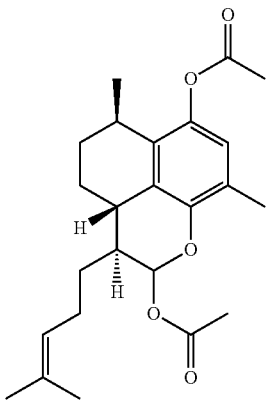
23. The method or use according to example embodiment 22, wherein the compound is selected from the group consisting of:
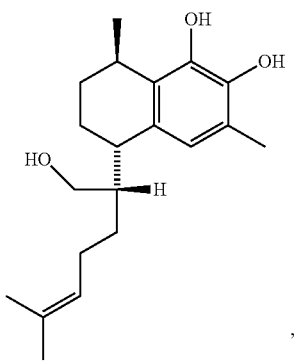
,
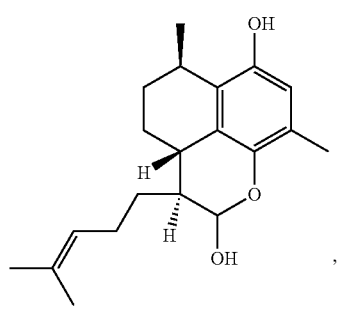
,
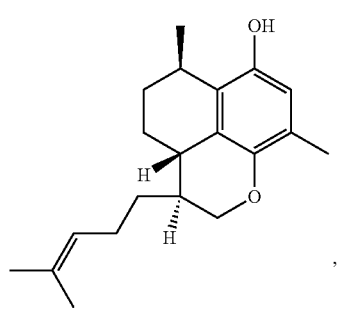
,
106
-continued
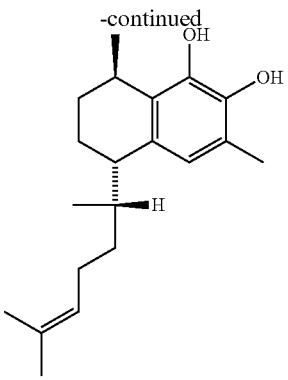
,
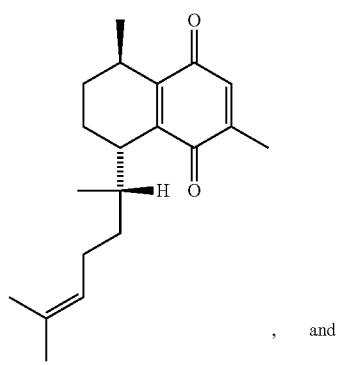
, and
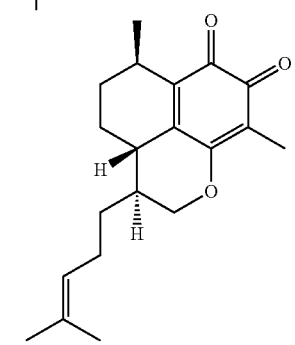
24. The method or use according to example embodiment 23, wherein the compound is:
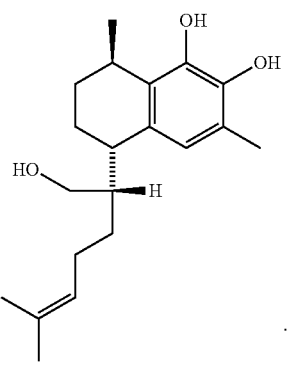 [SMILES: CC(C)=CCC[C@H](CO)[C@@H]1CC[C@@H](C)c2c1cc(C)c(O)c2O]

25. The method or use according to example embodiment 23, wherein the compound is:

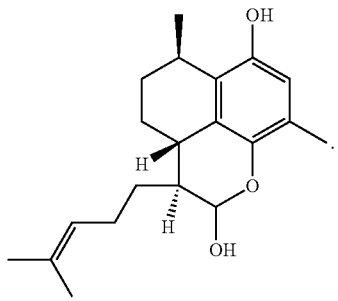 [SMILES: CC(C)=CCC[C@@H]1C(O)Oc2c(C)cc(O)c3c2[C@H]1CC[C@H]3C]

26. The method or use according to example embodiment 23, wherein the compound is:

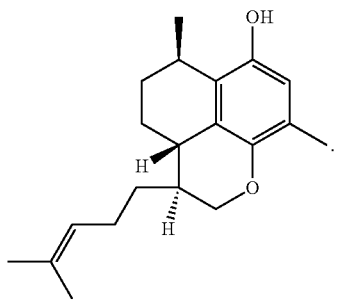 [SMILES: CC(C)=CCC[C@@H]1COc2c(C)cc(O)c3c2[C@H]1CC[C@H]3C]

27. The method or use according to example embodiment 23, wherein the compound is:

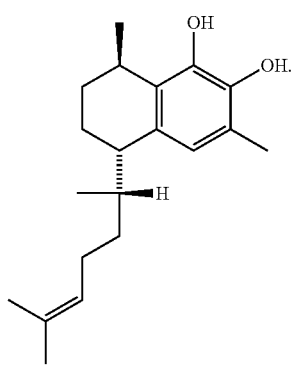 [SMILES: CC(C)=CCC[C@H](C)[C@@H]1CC[C@@H](C)c2c1cc(C)c(O)c2O]

28. The method or use according to example embodiment 23, wherein the compound is:

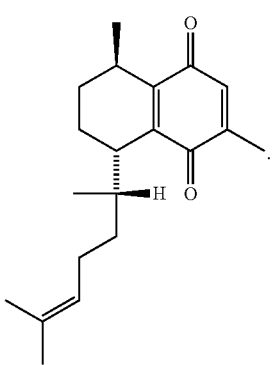 [SMILES: CC(C)=CCC[C@H](C)[C@@H]1CC[C@@H](C)C2=C1C(=O)C(C)=CC2=O]

29. The method or use according to example embodiment 23, wherein the compound is:

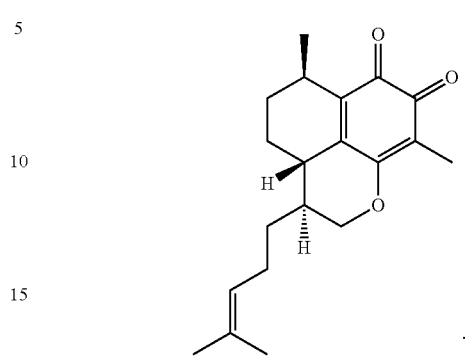

30. The method according to any one of example embodiments 1 to 29 or the use according to any one of example embodiments 2 to 29, wherein the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

31. The method or use according to example embodiment 30, wherein the cancer of the central nervous system is a glioma.

32. The method or use according to example embodiment 30, wherein the cancer of the central nervous system is a medulloblastoma.

33. The method or use according to example embodiment 30, wherein the cancer of the central nervous system is a neuroblastoma.

34. The method or use according to example embodiment 30, wherein the lung cancer is a non-small cell lung cancer.

35. The method or use according to example embodiment 30, wherein the lung cancer is a small cell lung cancer.

36. The method or use according to example embodiment 30, wherein the carcinoma is adenosquamous cell carcinoma or squamous cell carcinoma.

37. The method or use according to example embodiment 30, wherein the sarcoma is a liposarcoma, rhabdomyosarcoma, or fibrosarcoma.

38. The method or use according to example embodiment 30, wherein the sarcoma is a soft tissue sarcoma.

39. The method or use according to example embodiment 38, wherein the soft tissue sarcoma is a soft tissue osteosarcoma.

40. The method according to example embodiment 30, wherein the lymphoma is Burkitt's lymphoma, Hodgkin's lymphoma, or non-Hodgkin's lymphoma.

41. A compound of Formula (I), (I)

a geometric isomer, stereoisomer, pharmaceutically acceptable salt or solvate thereof,
wherein:
X is $CH_2$, CHOH or C(O);
$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;
$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$alkadienyl;
or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and
A-B is CH=C or $CH_2$—CH.

42. A compound of Formula (I), (I)

a geometric isomer, stereoisomer, pharmaceutically acceptable salt or solvate thereof,
wherein:
X is $CH_2$, CHOH or C(O);
$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;
$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl, $OC(O)C_{4-5}$alkadienyl or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$alkadienyl;
or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC_{4-5}$alkadienyl, $OC(O)C_{1-5}$alkyl, OC(O)Ph, $OC(O)C_{2-5}$alkenyl or $OC(O)C_{4-5}$ alkadienyl; and
A-B is CH=C or $CH_2$—CH,
for use in treating a cancer.

43. The compound according to example embodiment 41 or example embodiment 42,
wherein:
X is $CH_2$, CHOH or C(O);
$R_1$ is independently H, OH, $OC_{1-5}$alkyl, $OCH_2Ph$, $OC_{2-5}$alkenyl, $OC(O)C_{1-5}$alkyl, OC(O)Ph, $OC(O)C_{2-5}$alkenyl or =O;
$R_2$ is independently H, OH, $OC_{1-5}$alkyl, $OCH_2Ph$, $OC_{2-5}$alkenyl, $OC(O)C_{1-5}$alkyl, OC(O)Ph, $OC(O)C_{2-5}$alkenyl or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC_{2-5}$alkenyl, $OC(O)C_{1-5}$alkyl, OC(O)Ph or $OC(O)C_{2-5}$alkenyl;
or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC_{2-5}$alkenyl, $OC(O)C_{1-5}$alkyl, OC(O)Ph or $OC(O)C_{2-5}$alkenyl; and
A-B is CH=C or $CH_2$—CH.

44. The compound according to example embodiment 41 or example embodiment 42,
wherein:
X is $CH_2$, CHOH or C(O);
$R_1$ is independently H, OH, $OC_{1-5}$alkyl, $OCH_2Ph$, $OC(O)C_{1-5}$alkyl, OC(O)Ph or =O;
$R_2$ is independently H, OH, $OC_{1-5}$alkyl, $OCH_2Ph$, $OC(O)C_{1-5}$alkyl, OC(O)Ph or =O;
$R_3$ is independently H, OH, $OC_{1-5}$alkyl, $OC(O)C_{1-5}$alkyl or =O;
and no more than one of $R_1$, $R_2$ and $R_3$ can be H;
where X is $CH_2$, CHOH or C(O), $R_4$ is H, OH, $OC_{1-5}$alkyl, $OCH_2Ph$, $OC(O)C_{1-5}$alkyl or OC(O)Ph;
or X and $R_3$ form a six-membered ether ring or lactone ring, or a six membered ring containing a hemiacetal carbon atom or an acetal carbon atom wherein $R_4$ is respectively OH or $OC_{1-5}$alkyl, $OCH_2Ph$, $OC(O)C_{1-5}$alkyl or OC(O)Ph; and
A-B is CH=C or $CH_2$—CH.

45. The compound according to example embodiment 41 or example embodiment 42,
wherein:
X is $CH_2$, CHOH or C(O);
$R_1$ is independently H, OH, $OC_{1-5}$alkyl, $OC(O)C_{1-5}$alkyl or =O;
$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

where X is $CH_2$, CHOH or C(O), $R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

46. The compound according to example embodiment 41 or example embodiment 42, wherein:

X is $CH_2$;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

47. The compound according to example embodiment 41 or example embodiment 42, wherein:

X is CHOH;

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

48. The compound according to example embodiment 41 or example embodiment 42, wherein:

X is C(O);

$R_1$ is independently H, OH, $OC_{1-5}$alkyl, $OC(O)C_{1-5}$alkyl or =O;

$R_2$ is independently H, OH, $OC_{1-5}$alkyl, $OC(O)C_{1-5}$alkyl or =O;

$R_3$ is independently H, OH, $OC_{1-5}$alkyl, $OC(O)C_{1-5}$alkyl or =O;

and no more than one of $R_1$, $R_2$ and $R_3$ can be H;

$R_4$ is H, OH, $OC_{1-5}$alkyl, $OCH_2Ph$, $OC(O)C_{1-5}$alkyl or OC(O)Ph;

or X and $R_3$ form a six-membered ether ring or lactone ring, or a six membered ring containing a hemiacetal carbon atom or an acetal carbon atom wherein $R_4$ is respectively OH or $OC_{1-5}$alkyl or $OC(O)C_{1-5}$alkyl; and A-B is CH=C or $CH_2$—CH.

49. The compound according to example embodiment 41 or example embodiment 42, wherein the compound is a compound of Formula (Ia):

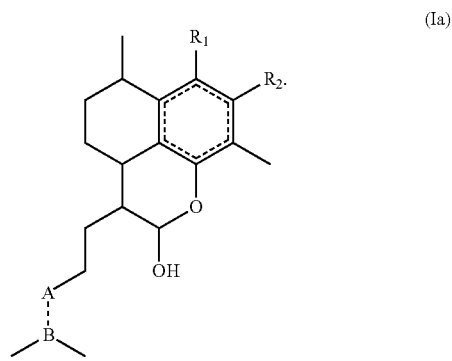

50. The compound according to example embodiment 41 or example embodiment 42, wherein the compound is a compound of Formula (Ib):

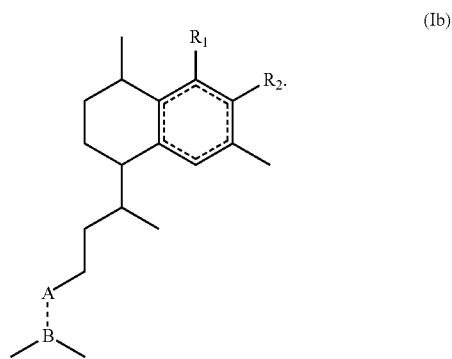

51. The compound according to example embodiment 41 or example embodiment 42, wherein the compound is a compound of Formula (Ic):

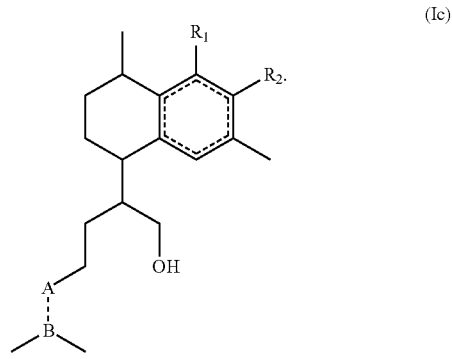

52. The compound according to example embodiment 41 or example embodiment 42, wherein the compound is a compound of Formula (Id):

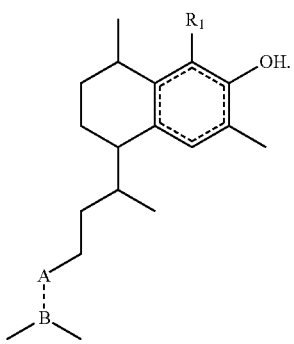

(Id)

53. The compound according to example embodiment 41 or example embodiment 42, wherein the compound is a compound of Formula (Ie):

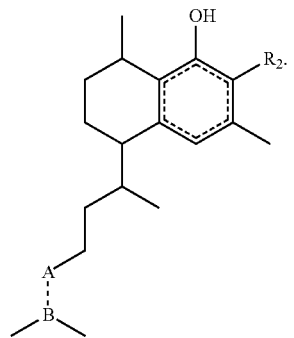

(Ie)

54. The compound according to example embodiment 41 or example embodiment 42, wherein the compound is a compound of Formula (If):

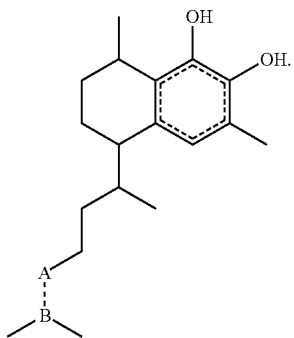

(If)

55. The compound according to example embodiment 41 or example embodiment 42, wherein the compound is a compound of Formula (Ig):

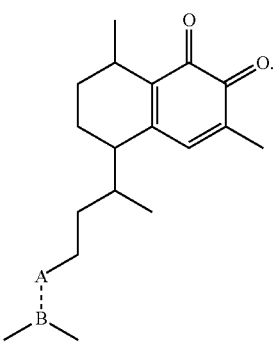

(Ig)

56. The compound according to example embodiment 41 or example embodiment 42, wherein the compound is a compound of Formula (Ih):

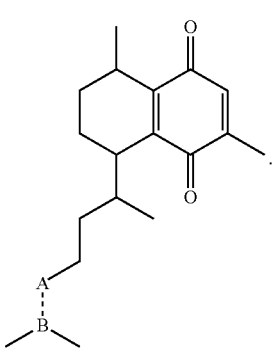

(Ih)

57. The compound according to example embodiment 41 or example embodiment 42, wherein the compound is a compound of Formula (Ii):

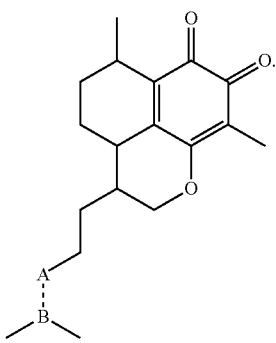

(Ii)

58. The compound according to any one of example embodiments 41 to 57, wherein A-B is CH=C.

59. The compound according to any one of example embodiments 41 to 58, wherein the compound is selected from the group consisting of:
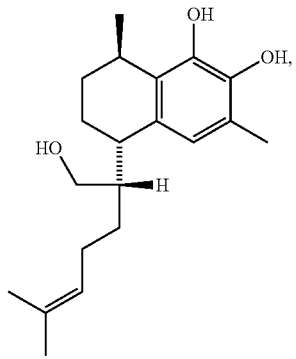
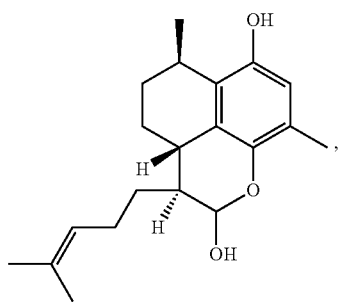
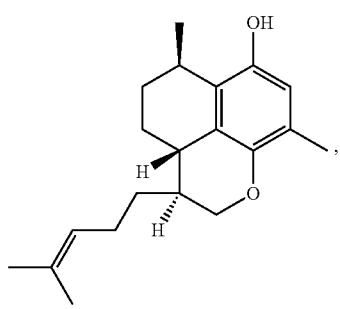
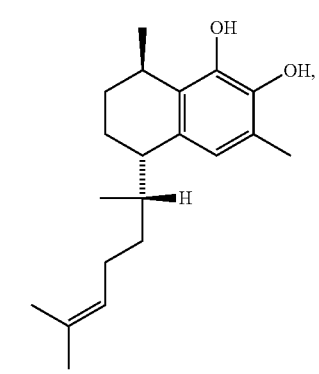
-continued
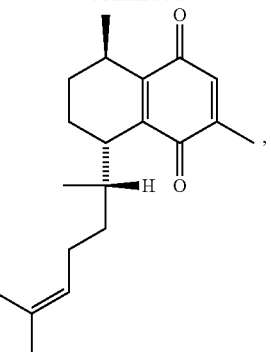
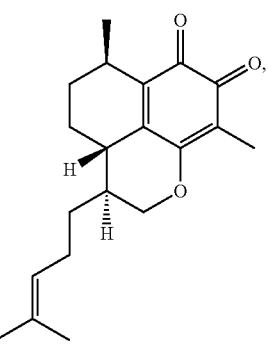
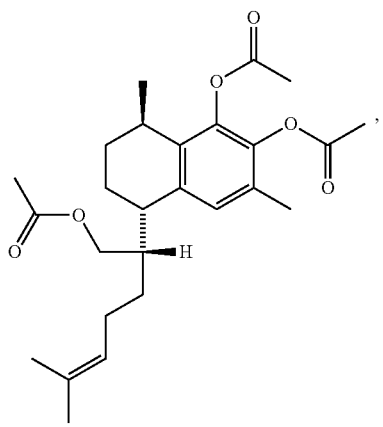
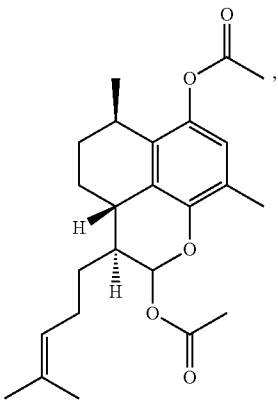

117
-continued
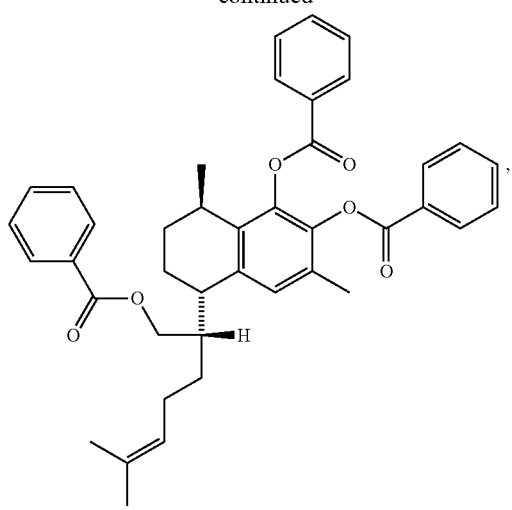
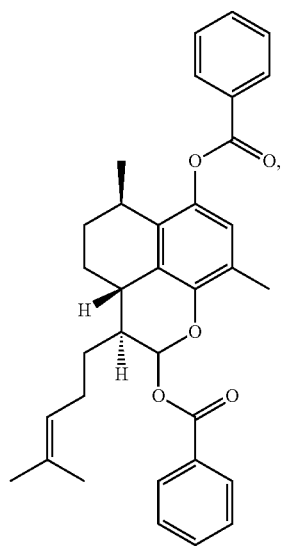
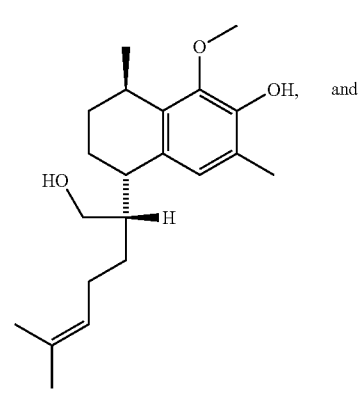
and
118
-continued
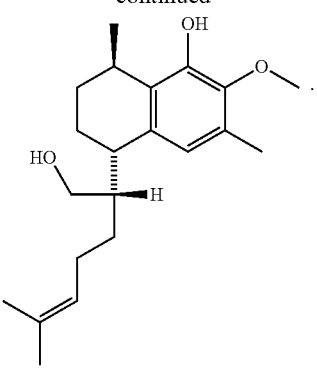
60. The compound according to example embodiment 59, wherein the compound is selected from the group consisting of:
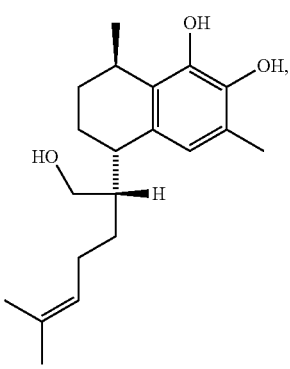
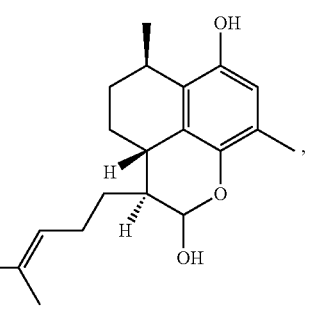
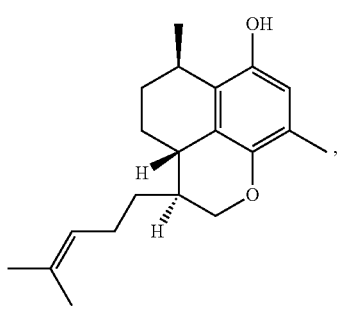

119
-continued
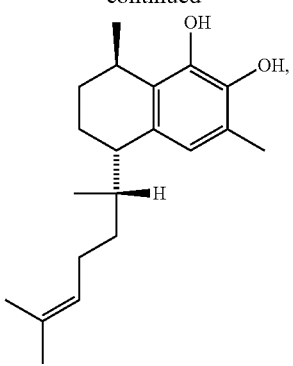
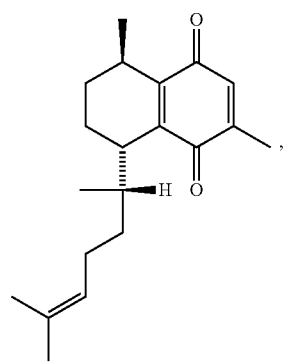
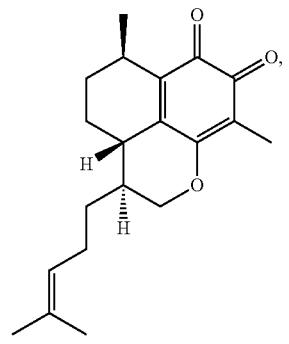 [SMILES: CC(C)=CCC[C@@H]1COC2=C(C)C(=O)C(=O)C3=C2[C@H]1CC[C@H]3C]
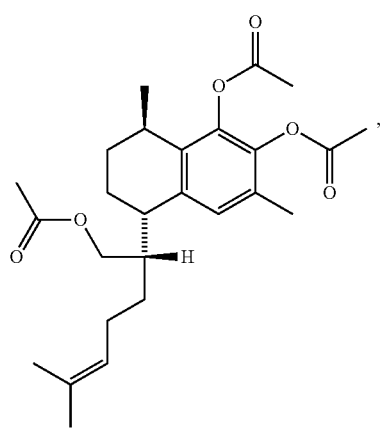
120
-continued
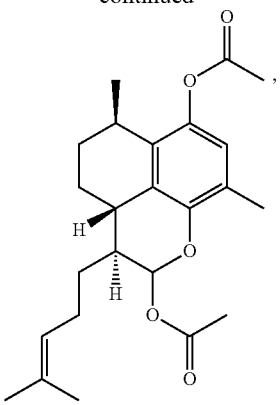
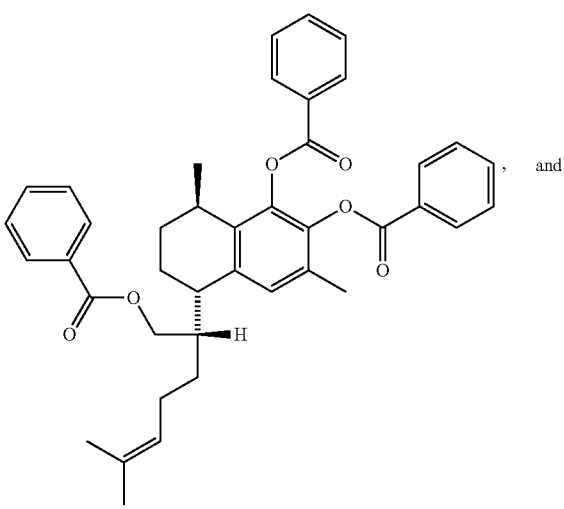
, and
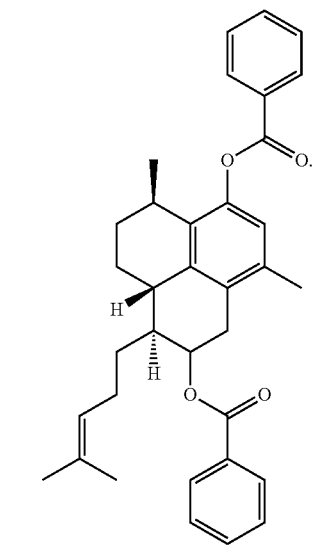

61. The compound according to example embodiment 60, wherein the compound is selected from the group consisting of:
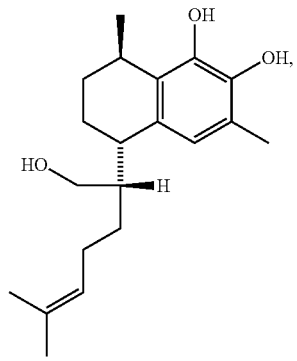
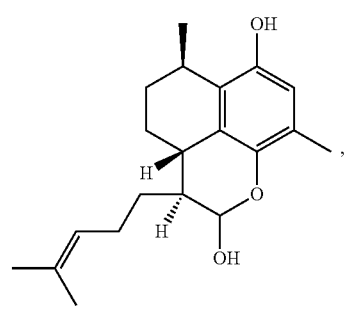
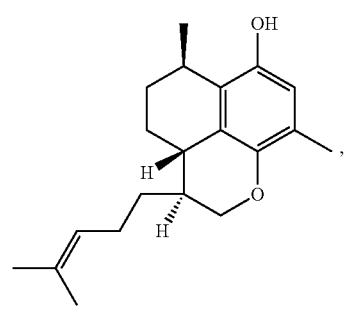
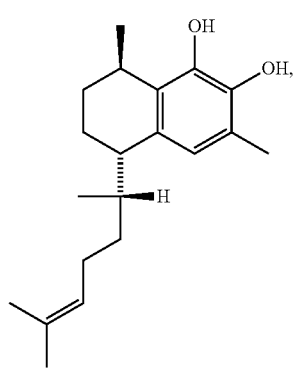
-continued
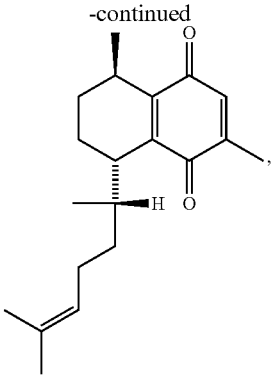
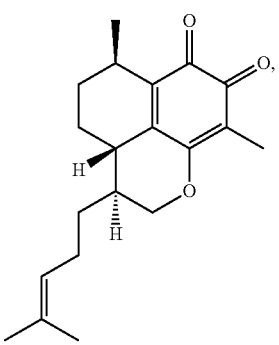 [SMILES: CC(C)=CCC[C@@H]1COC2=C(C)C(=O)C(=O)C3=C2[C@H]1CC[C@H]3C]
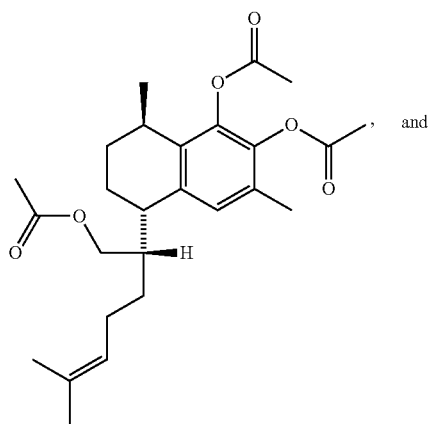, and
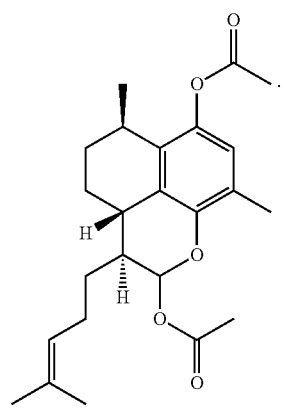.

62. The compound according to example embodiment 61, wherein the compound is selected from the group consisting of:
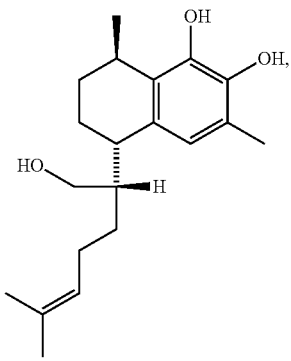
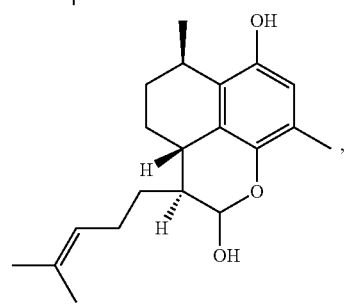
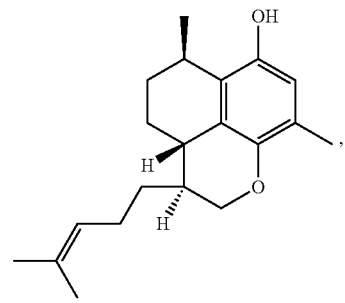
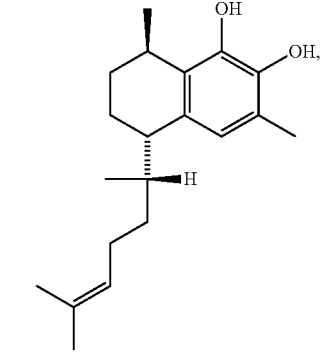
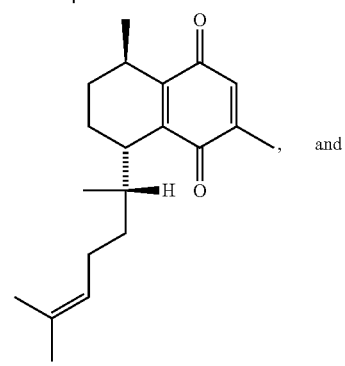
and
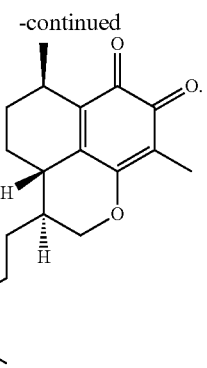
63. The compound according to example embodiment 62, wherein the compound is:
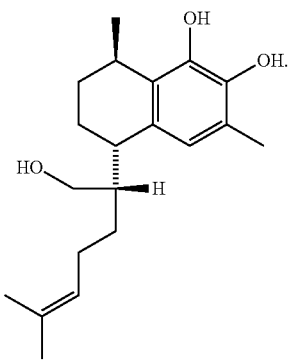 [SMILES: CC(C)=CCC[C@H](CO)[C@@H]1CC[C@@H](C)c2c1cc(C)c(O)c2O]
64. The compound according to example embodiment 62, wherein the compound is:
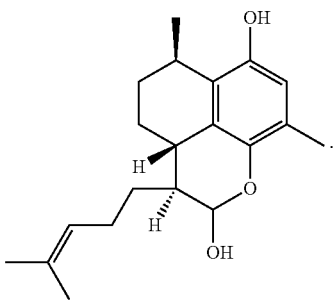 [SMILES: CC(C)=CCC[C@@H]1C(O)Oc2c(C)cc(O)c3c2[C@H]1CC[C@H]3C]
65. The compound according to example embodiment 62, wherein the compound is:
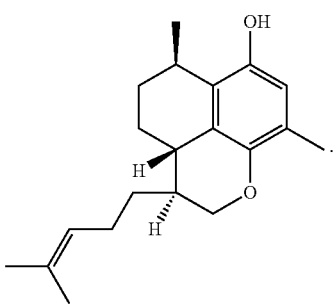 [SMILES: CC(C)=CCC[C@@H]1COc2c(C)cc(O)c3c2[C@H]1CC[C@H]3C]

66. The compound according to example embodiment 62, wherein the compound is:

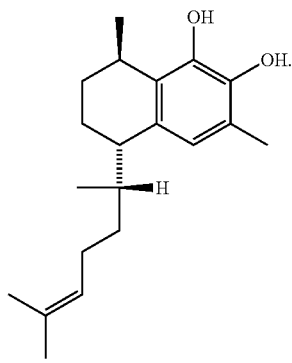 [SMILES: CC(C)=CCC[C@H](C)[C@@H]1CC[C@@H](C)c2c1cc(C)c(O)c2O]

67. The compound according to example embodiment 62, wherein the compound is:

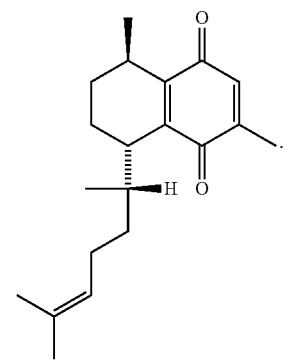 [SMILES: CC(C)=CCC[C@H](C)[C@@H]1CC[C@@H](C)C2=C1C(=O)C(C)=CC2=O]

68. The compound according to example embodiment 62, wherein the compound is:

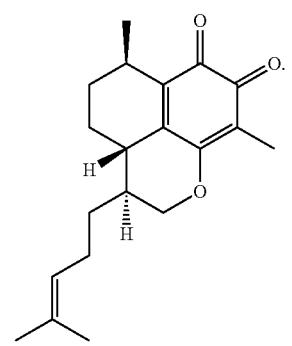 [SMILES: CC(C)=CCC[C@@H]1COC2=C(C)C(=O)C(=O)C3=C2[C@H]1CC[C@H]3C]

69. The compound according to any one of example embodiments 42 to 68, wherein the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

70. The compound according to example embodiment 69, wherein the cancer of the central nervous system is a glioma.

71. The compound according to example embodiment 69, wherein the cancer of the central nervous system is a medulloblastoma.

72. The compound or use according to example embodiment 69, wherein the cancer of the central nervous system is a neuroblastoma.

73. The compound according to example embodiment 69, wherein the lung cancer is a non-small cell lung cancer.

74. The compound according to example embodiment 69, wherein the lung cancer is a small cell lung cancer.

75. The compound according to example embodiment 69, wherein the carcinoma is adenosquamous cell carcinoma or squamous cell carcinoma.

76. The compound according to example embodiment 69, wherein the sarcoma is a liposarcoma, rhabdomyosarcoma, or fibrosarcoma.

77. The compound according to example embodiment 69, wherein the sarcoma is a soft tissue sarcoma.

78. The compound according to example embodiment 77, wherein the soft tissue sarcoma is a soft tissue osteosarcoma.

79. The compound according to example embodiment 69, wherein the lymphoma is Burkitt's lymphoma, Hodgkin's lymphoma, or non-Hodgkin's lymphoma.

80. A pharmaceutical composition comprising a compound, geometric isomer, stereoisomer, pharmaceutically acceptable salt or solvate thereof, according to example embodiment 41 or any one of example embodiments 43 to 68, and a pharmaceutically acceptable excipient.

81. A pharmaceutical composition comprising a compound, geometric isomer, stereoisomer, pharmaceutically acceptable salt or solvate thereof, according to example embodiment 41 or any one of example embodiments 43 to 68, or a mixture thereof, and a pharmaceutically acceptable excipient.

82. The compound according to example embodiment 41 or any one of example embodiments 43 to 68, or the pharmaceutical composition according to example embodiment 80 or example embodiment 81, for use as a medicament.

83. The compound according to example embodiment 41 or any one of example embodiments 43 to 68, or the pharmaceutical composition according to example embodiment 80 or example embodiment 81, for use in therapy.

84. A compound as defined in any one of example embodiments 42 to 68 isolated from propolis, wherein the propolis originates from plants of the *Myoporum* genus.

85. The compound according to example embodiment 84, wherein the propolis originates from *Myoporum insulare*.

86. A compound as defined in example embodiment 41 or any one of example embodiments 43 to 68 isolated from the resin, gum or exudate of *Myoporum* genus.

87. The compound according to example embodiment 86 isolated from the resin, gum or exudate of *Myoporum insulare*.

88. A method of treating a disease or disorder, the method comprising administering a therapeutically effective amount of a compound example embodiment 41 or any one of example embodiments 43 to 68 or a composition according to example embodiment 80 or example embodiment 81.

89. Use of a compound according to example embodiment 41 or any one of example embodiments 43 to 68 in the preparation of a medicament for treating a disease or disorder.

90. Use of a compound according to example embodiment 41 or any one of example embodiments 43 to 68 or a composition according to example embodiment 80 or example embodiment 81 in treating a disease or disorder.

91. A compound according to example embodiment 41 or any one of example embodiments 43 to 68 or a composition according to example embodiment 80 or example embodiment 81 for use in treating a disease or disorder.

92. The method according to example embodiment 88 or use according to example embodiment 89 or example embodiment 90 or compound according to example embodiment 91, wherein the disease or disorder is selected from the group consisting of: acute coronary syndrome, an aging-related disease or disorder; an allergic disease or a related condition; Alzheimer's disease, atherosclerosis, an autoimmune disease; a bacterial infection, cancer; dementia, depression or a related condition; diabetes; dyslipidemia, hyperlipidemia, hypertension, itchyosis, an immune disease; a metabolic disease or disorder; a neurological disease or disorder; obesity; Parkinson's disease; pain; rheumatoid arthritis, a disease or disorder associated with inflammation, such as skin inflammatory conditions, and a skin disease or disorder.

93. The method or use or compound according to example embodiment 92, wherein the disease or disorder is cancer.

94. The method or use or compound according to example embodiment 93, wherein the cancer is bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, sarcoma, eye cancer, esophageal cancer, bile duct cancer or vulva cancer.

95. The method or use or compound according to example embodiment 94, wherein the cancer of the central nervous system is a glioma.

96. The method or use or compound according to example embodiment 94, wherein the cancer of the central nervous system is a medulloblastoma.

97. The method or use or compound according to example embodiment 94, wherein the cancer of the central nervous system is a neuroblastoma.

98. The method or use or compound according to example embodiment 94, wherein the lung cancer is a non-small cell lung cancer.

99. The method or use or compound according to example embodiment 94, wherein the lung cancer is a small cell lung cancer.

100. The method or use or compound according to example embodiment 94, wherein the carcinoma is adenosquamous cell carcinoma or squamous cell carcinoma.

101. The method or use or compound according to example embodiment 94, wherein the sarcoma is a liposarcoma, rhabdomyosarcoma, or fibrosarcoma.

102. The method or use or compound according to example embodiment 94, wherein the sarcoma is a soft tissue sarcoma.

103. The method or use or compound according to example embodiment 102, wherein the soft tissue sarcoma is a soft tissue osteosarcoma.

104. The method or use or compound according to example embodiment 94, wherein the lymphoma is Burkitt's lymphoma, Hodgkin's lymphoma, or non-Hodgkin's lymphoma.

105. The method or use or compound according to example embodiment 92, wherein the skin disease or disorder is selected from the group consisting of: eczema, psoriasis, acne, a wound, a scar, inflammation including psoriasis and atopic dermatitis, a burn, sunburn, skin damage and skin irritation.

EXAMPLES

In order to better understand the nature of the invention a number of examples will now be described as follows:
Experimental
Materials Honey bees observed collecting from the boobialla trees and shrubs (*Myoporum insulare*) were captured in plastic tubes, capped and frozen. Sections of the bee hind legs holding propolis were cut and pooled. Plant samples were obtained and dried at 40° C. in a ventilated oven (Thermoline, NSW Australia) a few days to provide voucher specimens for identification by botanist, A/Prof Murray Henwood, John Ray Herbarium, University of Sydney, Sydney, Australia, and registered as *Myoporum insulare* voucher number Duke-131202-01. Resin extracted from plant samples was stored at −20° C. until analysis or further processing.

Propolis was obtained from apiary sites with from 1 to 10 colonies of European honey bee (*Apis mellifera ligustica*) in standard 10-frame box hives, each fixed with a propolis mat under the hive cover lid. The propolis samples were collected and provided by a few beekeepers in eight apiary sites located in different parts of Kangaroo Island, South Australia. These sites were located in the vicinity of Hanson Bay, Vivonne Bay, Flour Cask Bay, Island Beach, Kingscote, Brownlow, Rainy Creek and Eleanor River. These locations are known to be a habitat for the plant *Myoporum insulare* on Kangaroo Island. This provided 23 propolis samples which, based on TLC analysis and $^1$H NMR techniques, were estimated to be at least 90% sourced from *M. insulare*. The samples were stored at −20° C. until further analysis and processing.

Thin layer chromatography sheets precoated with silica gel 60 $F_{254}$ and silica gel 60H for normal-phase short-column vacuum chromatography (NPSCVC) were purchased from Merck. TLC plates were visualized with a UVGL-58 mineral-light lamp, Multiband UV-2544/366.

All the chemicals used in the isolation and synthesis, including deuterated NMR solvents such as d-chloroform, $d_4$-methanol and $d_6$-dimethyl sulfoxide were purchased from Novachem Pty Ltd (Collingwood, Vic, Australia). Solvents including hexane, dichloromethane, ethyl acetate, isopropanol, ethanol, methanol, and acetic acid were of analytical grade and purchased from Chem Supply, Gillman, SA, Australia.
General Methods Rotavapor model R-114 rotary evaporator with a water bath temperature ranging between 40-60° C. was used to evaporate the solvent fraction. Vacuum pump V-700 or Vacuubrand MD 4C NT diaphragm pump (Vacuubrand GMBH, Wertheim, Germany) with vacuum controller V-800 or V-850 is used. Final drying is carried out by a Napco 5831 vacuum oven (NAPCO, Salt Lake City, USA) using a DirectTorr vacuum pump (Sargent-Welch, Buffalo, USA).

Isocratic analytical HPLC was performed on a Shimadzu UFLC, LC-20AD pump, SIL-20A HT autosampler, with a Hewlett-Packard Column, NUCLEOSIL 100 $C_{18}$, 5 µm, 4 mm×125 mm, injection volume 20 µl, eluted at 1 ml/min and detected at 230 nm with a UV-Vis detector (Shimadzu SPD-20A). The column was eluted with methanol-water-acetic acid (65:34.8:0.2).

Gradient analytical HPLC was performed on a Shimadzu Nexera X2 LC-30AD system, SIL-30 autosampler, with a Hewlett-Packard Column, NUCLEOSIL 100 $C_{18}$, 5 μm, 4 mm×125 mm, injection volume 10 μl, eluted at 1 ml/min and detected at 320 nm with a SPD-M30A UV-Vis diode array detector. The column was eluted with a gradient system made up of methanol (phase A), and methanol:water:acetic acid (40:59.8:0.2) (phase B). A solvent gradient was applied as follows: 0-2 min: 32-50% A, 2-9 min: 50-90% A, 9-12 min: 90-100% A, 12-14 min, 100% A, and finally 14-15 min: 100-32% A, maintained over 5 min.

$^1$H and $^{13}$C Nuclear magnetic resonance (NMR) analyses were carried out on Varian 400 MHz System with a SMS autosampler (Palo Alto, Calif., USA). Chemical shifts (5) of peaks in NMR spectra are reported in parts per million (ppm) and are referenced to tetramethylsilane ($Si(CH_3)_4$, TMS). $^1$H NMR data is reported as chemical shift (5), relative integral, multiplicity (abbreviations: s=singlet, d=doublet, I=triplet, id=triplet of doublets, q=quartet, dd=doublet of doublets, ddd=doublet of doublet of doublets, bs=broad singlet, hi=broad triplet), coupling constant (Jin Hz) and assignment. $^{13}$C NMR data is reported as chemical shift (5) and assignment.

For low resolution ESI-MS, the samples were analyzed by Finnigan Polaris Ion Trap MS/MS system (Finnigan Corporation, San Jose, USA) using an Xcalibur 1.2 data system, in Electrospray Ionization (ESI) negative and positive modes using infusion technique.

High resolution ESI-MS were measured on a Bruker Daltonics Apex Ultra Fourier Transform Ion Cyclotron Resonance 7 Tesla Mass Spectrometer, mass spectrometry unit, School of Chemistry, The University of Sydney.

Determination of the $^1$H-NMR Chemical Profiles of the Plant and Propolis Specimens Young leaf shoots (25 g), bee hind leg (0.01 g) and beehive propolis (1.0 g) were extracted with dichloromethane at room temperature for 15 min. The extracts were filtered, dried under reduced pressure and analyzed by $^1$H-NMR and HPLC. Samples were found to contain serrulatane diterpenes. Propolis and plant samples were subsequently selected for isolation of the components.

Preparation of Myoporum insulare Resin Extract

Fresh young leaves and young shoot tips were harvested from several Myoporum insulare trees. The leaves were stored in plastic bags on ice until processing within 5 days. To extract the external resin/exudate the leaves and shoot tips (4 Kg) were mixed with dichloromethane (4 litres) and after 1 hour standing the dichloromethane extract was filtered and the dichloromethane was removed from the filtrate by evaporation under reduced pressure using a rotary evaporator to give a brown partially solid dried resin (12.5 g, yield 0.31%).

Isolation and Identification of Serrulatane Diterpenes from Myoporum insulare Propolis from Kangaroo Island.

General Method

Propolis (100 g) was extracted with dichloromethane at room temperature with stirring for 1 hr. The extract was subjected to purification using normal-phase short column vacuum chromatography (NPSCVC). A step-wise gradient of mobile phase (2×100 mL) consisting of dichloromethane (DCM) and ethyl acetate (EtOAc) at 0, 1, 2, 4, 8, 10, 15, 20, 50 and 100% was employed to elute the components which were analysed by TLC and NMR. Further purification of the compounds, if required, was subsequently carried out on the same NPSCVC with different mobile phases consisting of either hexane and EtOAc or hexane and isopropanol. Structures and identity of these purified compounds were characterized by $^1$H- and $^{13}$C-NMR and mass spectrometry including high resolution mass spectrometry. Detailed structural analyses of the isolated compound were also carried out when needed by 2D-NMR using Gradient Heteronuclear Multiple Bond Coherence (GHMBC). The major serrulatane diterpenoid was determined to be 7,8,18-trihydroxyserrulat-14-ene (1).

Isolated Serrulatane Diterpenes from the Plant, Myoporum insulare.

7,8,18-trihydroxyserrulat-14-ene (1)

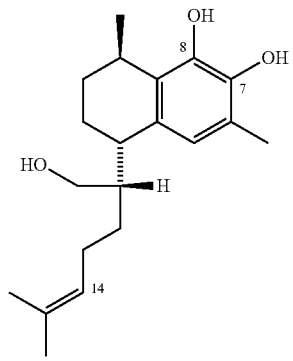 [SMILES: CC(C)=CCC[C@H](CO)[C@@H]1CC[C@@H](C)c2c1cc(C)c(O)c2O]

Yellowish liquid, yield 50 mg, $[\alpha]_D^{20}$ −27.3° (C=1.0, $CHCl_3$). UV ($CH_3OH$) $\lambda_{max}$ nm (log ε) 279 (3.37) and 320 (2.49). IR (v): 3381, 2924, 2864, 1625, 1581, 1448 $cm^{-1}$. HRESIMS: 341.2089 m/z $[M+Na]^+$ (calcd 341.2087) $C_{20}H_{30}O_3$. $^1$H NMR (400 MHz, $CDCl_3$) δ: 6.56, (1H, 5, H-5), 5.04 (1H, bt, J=7.0 Hz, H-14), 3.63 (2H, d, J=6.2 Hz, H-18), 3.07 (1H, pentet of d, J=6.8, 1.6 Hz, H-1), δ 2.76 (1H, td, J=5.6, 2.6 Hz, H-4), 2.20 (3H, 5, H-19), 1.99 (1H, m, H-13A), 1.90 (1H, m, H-13B), 1.90 (1H, m, H-3A), 1.86 (1H, m, H-2A), 1.83 (1H, m, H-11), 1.68 (3H, 5, H-16), 1.66 (1H, m, H-2B), 1.58 (3H, 5, H-17), 1.51 (1H, m, H-3B), 1.25 (1H, m, H-12A), 1.36 (2H, m, H-12B), 1.21 (3H, d, J=7.0 Hz, H-20). $^{13}$C NMR (100 MHz, $CDCl_3$) δ: 15.54 (C-19), 17.68 (C-17), 20.51 (C-2), 21.11 (C-20), 25.70 (C-16), 26.16 (C-13), 26.47 (C-3), 26.98 (C-1), 29.85 (C-12), 37.91 (C-4), 45.45 (C-11), 64.38 (C-18), 121.31 (C-6), 122.00 (C-5), 124.43 (C-14), 127.18 (C-9), 130.70 (C-10), 131.75 (C-15), 139.74 (C-7), 141.61 (C-8).

5,18-epoxyserrulat-14-en-8,18-diol (2)

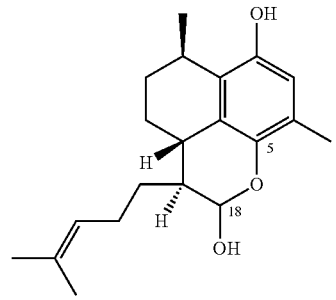 [SMILES: CC(C)=CCC[C@@H]1C(O)Oc2c(C)cc(O)c3c2[C@H]1CC[C@H]3C]

Red liquid, yield 84 mg, $[\alpha]_D^{20}$ −21.5° (C=1.0, $CHCl_3$). UV ($CH_3OH$) $\lambda_{max}$ nm (log ε) 293 (3.36) and 334 (2.91). IR (v): 3327, 2970, 2926, 2860, 1647, 1558, 1448, 1043 $cm^{-1}$.

HRESIMS: 315.1970 m/z [M–H]⁻ (calcd 315.1966). C₂₀H₂₈O₃. ¹H NMR (400 MHz, CDCl₃) δ 6.48 (1H, 5, H-7), 5.59 (1H, bs, H-18), 5.14 (1H, bt, J=7.0 Hz, H-14), 3.11 (1H, sextet, J=7.6, H-1), 2.54 (1H, td, J=11.4, 3.6 Hz, H-4), 2.25 (1H, m, H-2A), 2.20 (1H, m, H-13A), 2.13 (3H, 5, H-19), 2.09 (1H, m, H-13B), 2.08 (1H, m, H-3A), 1.69 (1H, m, H-12A), 1.70 (3H, 5, H-16), 1.63 (3H, s, H-17), 1.52 (1H, m, H-11), 1.41 (1H, m, H-2B), 1.28 (3H, d, J=6.9 Hz, H-20), 1.27 (1H, m, H-12B), 1.05 (1H, m, H-3B). ¹³C NMR (100 MHz, CDCl₃) δ 15.88 (C-19), 17.75 (C-17), 22.89 (C-20), 25.36 (C-13), 25.70 (C-16), 26.62 (C-3), 27.79 (C-1), 28.90 (C-12), 31.75 (C-2), 31.99 (C-4), 40.48 (C-11), 91.88 (C-18), 115.94 (C-7), 122.94 (C-6), 124.09 (C-14), 124.29 (C-10), 125.21 (C-9), 131.99 (C-15), 141.71 (C-5), 146.85 (C-8).

5,18-epoxy-8-hydroxyserrulat-14-ene (3)

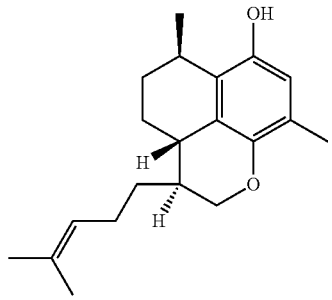 [SMILES: CC(C)=CCC[C@@H]1COc2c(C)cc(O)c3c2[C@H]1CC[C@H]3C]

Shiny yellow liquid, yield 87 mg, [α]$_D^{20}$ –8.9° (C=1.0, CHCl₃). UV (CH₃OH) λ$_{max}$ nm (log ε) 296 (3.55) and 334 (2.66). IR (v): 3502, 2922, 2856, 1622, 1597, 1421, 1230 cm⁻¹. HRESIMS: 301.21635 m/z [M+H]⁺ (calcd 301.21621) C₂₀H₂₈O₂. ¹H NMR (400 MHz, CDCl₃) δ: 6.46 (1H, 5, H-7), 5.13 (1H, bt, J=6.9 Hz, H-14), 4.35 (1H, dd, J=10.5, 3.7 Hz, H-18A), 3.70 (1H, t, J=10.8 Hz, H-18B), 3.13 (1H, sextet, J=7.4 Hz, H-1), 2.31 (1H, m, H-4), 2.24 (1H, m, H-2A), 2.16 (1H, m, H-13A), 2.15 (1H, m, H-3A), 2.12 (3H, s, H-19), 2.02 (1H, m, H-13B), 1.74 (1H, m, H-12A), 1.70 (3H, 5, H-16), 1.63 (3H, 5, H-17), 1.55, (1H, m, H-11), 1.40 (1H, m, H-2B), 1.28 (3H, d, J=7.0 Hz, H-20), 1.18 (1H, m, H-12B), 1.06 (1H, td J=12.2, 4.4 Hz, H-3B). ¹³C NMR (100 MHz, CDCl₃) δ: 15.82 (C-19), 17.73 (C-17), 23.12 (C-20), 25.44 (C-13), 25.70 (C-16), 26.97 (C-3), 27.61 (C-1), 29.97 (C-12), 31.47 (C-2), 37.17 (C-11), 39.00 (C-4), 69.52 (C-18), 115.79 (C-7), 122.64 (C-6), 124.12 (C-14), 124.26 (C-9), 125.70 (C-10), 131.99 (C-15), 145.27 (C-5), 146.16 (C-8).

7,8-dihydroxyserrulat-14-ene (4)

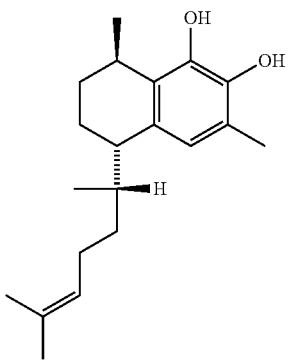 [SMILES: CC(C)=CCC[C@H](C)[C@@H]1CC[C@@H](C)c2c1cc(C)c(O)c2O]

Yellowish liquid, yield 56 mg, [α]$_D^{20}$ –21.1° (C=1.0, CHCl₃). UV (CH₃OH) λ$_{max}$ nm (log ε) 278 (3.36) and 329 (2.95). IR (v): 3396, 2954, 2924, 2868, 1635, 1577, 1456 cm⁻¹. HRESIMS: 325.21413 m/z [M+Na]⁺ (calcd 325.21380) C₂₀H₃₀O₂. ¹H NMR (400 MHz, CDCl₃) δ 6.53 (1H, 5, H-5), 5.00 (1H, bt, J=7.0 Hz, H-14), 3.06 (1H, pentet of d, J=6.7, 2.8 Hz, H-1), 2.53 (1H, td, J=5.5, 3.4 Hz, H-4), 2.22 (3H, 5, H-19), 2.00 (1H, m, H-13A), 1.95 (1H, m, H-2A), 1.84 (1H, m, H-11), 1.82 (1H, m, H-3A), 1.80 (1H, m, H-13B), 1.70 (1H, m, H-3B), 1.67 (3H, 5, H-16), 1.59 (3H, 5, H-17), 1.48 (1H, m, H-2B), 1.29 (1H, m, H-12A), 1.12 (3H, d, J=6.8 Hz, H-20), 1.05 (1H, m, H-12B), 0.95 (3H, d, J=6.8, H-18). ¹³C NMR (100 MHz, CDCl₃) δ: 15.53 (C-19), 17.62 (C-17), 18.66 (C-18), 19.63 (C-3), 21.10 (C-20), 25.71 (C-16), 26.25 (C-13), 27.1 (C-1), 27.43 (C-2), 33.35 (C-12), δ 37.8 (C-11), δ 41.88 (C-4), δ 120.50 (C-6), δ 122.46 (C-5), δ 124.96 (C-14), δ 127.09 (C-9), δ 131.10 (C-15), δ 131.90 (C-10), δ 139.19 (C-7), δ 140.93 (C-8).

Serrulat-14-en-5,8-dione (5)

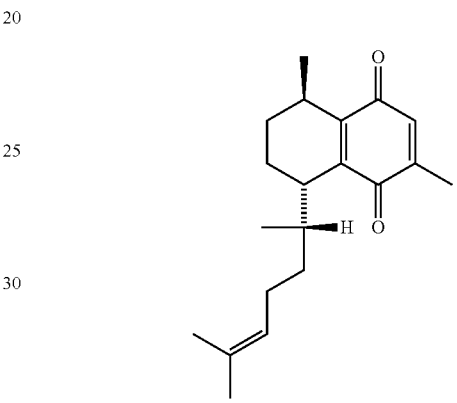

Light orange liquid, yield 30 mg. ¹H NMR (400 MHz, CDCl₃) δ 6.68 (1H, 5, H-5), 5.02 (1H, bt, J=7.1 Hz, H-14), 2.85 (1H, m, H-1), 2.20 (1H, m, H-4), 2.12 (1H, m, H-3A), 2.03 (1H, m, H-13A), 1.95 (3H, 5, H-19), 1.88 (1H, m, H-11), 1.85 (1H, m, H-13B), 1.69 (1H, m, H-2A), 1.67 (3H, 5, H-16), 1.58 (3H, 5, H-17), 1.34 (1H, m, H-2B), 1.30 (1H, m, H-12A), 1.20 (1H, m, H-3B), 1.12 (1H, m, H-12B), 1.07 (6H, d, J=6.9 Hz, H-18 and H-20). ¹³C NMR (100 MHz, CDCl₃) δ 15.21 (C-19), 17.69 (C-17), 18.67 (C-20), 18.75 (C-18), 20.55 (C-3), 25.71 (C-16), 26.10 (C-13), 26.56 (C-1), 26.59 (C-2), 33.41 (C-12), 34.9 (C-11), 43.83 (C-4), 124.13 (C-14), 132.00 (C-15), 135.36 (C-6), 140.04 (C-7), 140.70 (C-9), 150.13 (C-10), 179.85 (C-5), 181.55 (C-8).

5,18-epoxyserrulat-14-en-7,8-dione (6)

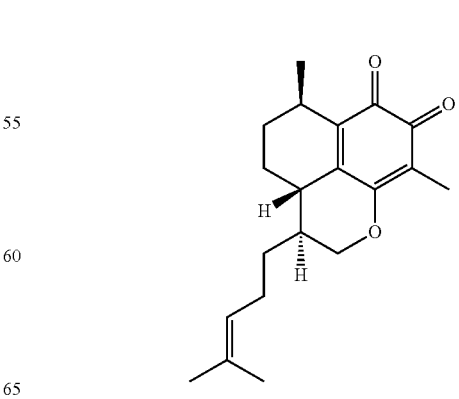

Purple liquid, yield 50 mg, HRESIMS: 315.19573 m/z [M+H]+(calcd 315.19547) C₂₀H₂₆O₃. ¹H NMR (400 MHz, CDCl$_3$) δ 5.07 (1H, bt, J=6.8 Hz, H-14), 4.49 (1H, dd, J=11.0, 3.8 Hz, H-18A), 3.86 (1H, t, J=11.1 Hz, H-18B), 2.82 (1H, m, H-1), 2.14 (1H, m, H-4), 2.15 (1H, m, H-2A), 2.13 (1H, m, H-3A), 2.09 (1H, m, H-13A), 1.97 (1H, m, H-13B), 1.81 (3H, 5, H-19), 1.76 (1H, m, H-12A), 1.74 (1H, m, H-11), 1.71 (3H, 5, H-16), 1.63 (3H, 5, H-17), 1.23 (1H, m, H-2B), 1.19 (1H, m, H-12B), 1.13 (3H, d, H-20) 1.11 (1H, m, H-3B). $^{13}$C NMR (100 MHz, CDCl$_3$) δ 7.57 (C-19), 17.78 (C-17), 21.67 (C-20), 24.66 (C-13), 25.32 (C-3), 25.71 (C-16), 28.74 (C-1), 29.15 (C-12), 30.77 (C-2), 37.07 (C-11), 40.09 (C-4), 71.85 (C-18), 114.44 (C-6), 123.06 (C-14), 132.87 (C-15), 139.43 (C-9), 149.67 (C-10), 162.76 (C-5), 179.38 (C-7), 181.91 (C-8).

Compound 6 was observed to be formed from oxidation of Compound 1.

Acetylation of Serrulatane Diterpenes 7,8,18-triacetyloxyserrulat-14-ene (7)

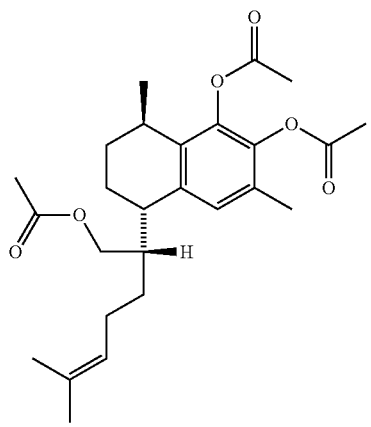 [SMILES: CC(=O)OC[C@@H](CCC=C(C)C)C1CC[C@@H](C)c2c1cc(C)c(OC(C)=O)c2OC(C)=O]

The serrulatane (1) (400 mg) was dissolved in acetic anhydride (1 mL) and in dry pyridine (1 mL) and stirred at room temperature overnight (Davis et al., 1999). The reaction mixture was quenched with distilled water (30 mL), and was extracted with dichloromethane (3×40 mL). The dichloromethane solution was extracted with aqueous 0.1 M hydrochloric acid (30 mL) to remove the residual trace of pyridine. The dichloromethane solutions were dried with Na$_2$SO$_4$, filtered and concentrated on a rotary evaporator to give a yellow oily residue. Finally, using normal-phase short-column vacuum chromatography (NPSCVC) with dichloromethane and ethyl acetate (100:0 to 90:10, v/v) the compound (7) (434 mg, 77%) was purified and isolated as a pale yellow oil, yield 27 mg. HRESIMS: 467.2404 m/z [M+Na]$^+$ (calcd 467.2206). C$_{26}$H$_{36}$O$_6$. $^1$H NMR (400 MHz, CDCl$_3$) δ 6.92 (1H, 5, H-5), 4.97 (1H, bt, J=7.1 Hz, H-14), 4.11 (2H, d, J=6.3 Hz, H-18), 2.92 (1H, m, H-1), 2.88 (1H, m, H-4), 2.31 (3H, 5, H-26), 2.29 (3H, s, H-24), 2.14 (3H, 5, H-19), 2.12 (1H, m, H-11), 2.06 (3H, 5, H-22), 1.99 (1H, m, H-13A), 1.87 (1H, m, H-13B), 1.87 (1H, m, H-3A), 1.87 (1H, m, H-2A), 1.68 (1H, m, H-3B), 1.66 (3H, 5, H-16), 1.54 (3H, 5, H-17), 1.50 (1H, m, H-2B), 1.33 (1H, m, H-12A), 1.23 (1H, m, H-12B), 1.15 (3H, d, J=7.0 Hz, H-20). $^{13}$C NMR (100 MHz, CDCl$_3$) δ 16.08 (C-19), 17.60 (C-17), 19.16 (C-3), 20.36 (C-24), 20.51 (C-26), 20.97 (C-22), 21.45 (C-20), 25.68 (C-16), 26.11 (C-13), 26.96 (C-2), 27.58 (C-1), 28.32 (C-12), 36.92 (C-4), 41.92 (C-11), 65.88 (C-18), 123.94 (C-14), 128.09 (C-5), 128.31 (C-6), 132.04 (C-15), 139.26 (C-7), 140.56 (C-8), 134.06 (C-9), 137.11 (C-10), 168.1 (C-23), 168.34 (C-25), 171.18 (C-21).

5,18-epoxyserrulat-14-ene-8,18-diacetate (8)

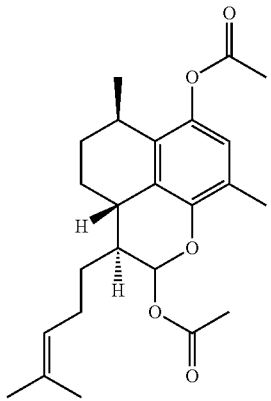 [SMILES: CC(=O)Oc1cc(C)c2c3c1[C@H](C)CC[C@H]3[C@H](CCC=C(C)C)C(OC(C)=O)O2]

To acetylate compound (2), 80 mg of serrulatane (2) was dissolved in acetic anhydride (1 mL) and in dry pyridine (1 mL) and stirred at room temperature overnight, and with the same workup procedure and using short-column vacuum chromatography with hexane and ethyl acetate (100:0 to 80:20, v/v) the compound (8) (57.8 mg, 58%) was purified and isolated. Red coloured liquid, yield 18 mg, HRESIMS: m/z 423.2143 [M+Na]$^+$ calcd 423.2142. C$_{24}$H$_{32}$O$_5$. $^1$H NMR (400 MHz, CDCl$_3$) δ: 6.69 (1H, 5, H-7), 6.53 (1H, d, J=1.7 Hz, H-18), 5.08 (1H, bt, J=6.5 Hz, H-14), 2.96 (1H, sextet, J=7.4 Hz, H-1), 2.54 (1H, td, J=11.6, 3.8 Hz, H-4), 2.3 (3H, 5, H-24), 2.19 (1H, m, H-13A), 2.19 (1H, m, H-2A), 2.14 (3H, 5, H-19), 2.12 (1H, m, H-3A), 2.09 (3H, 5, H-22), 2.02, (1H, m, H-13B), 1.70 (1H, m, H-12A), 1.69 (3H, 5, H-16), 1.62 (3H, 5, H-17), 1.65 (1H, m, H-11), 1.42 (1H, m, H-2B), 1.30 (1H, m, H-12B), 1.23 (3H, d, J=6.8 Hz, H-12), 1.10 (1H, m, H-3B). $^{13}$C NMR (100 MHz, CDCl$_3$) δ: 15.88 (C-19), 17.68 (C-17), 21.09 (C-22), 21.23 (C-24), 22.78 (C-20), 25.15 (C-13), 25.70 (C-16), 26.22 (C-3), 28.26 (C-1), 28.29 (C-12), 31.41 (C-2), 32.3 (C-4), 38.93 (C-11), 90.18 (C-18), 41.92 (C-11), 122.53 (C-7), 123.48 (C-14), 123.77 (C-10), 123.96 (C-6), 130.9 (C-9), 132.57 (C-15), 142.44 (C-8), 145.63 (C-5), 170.05 (C-23), 170.19 (C-21).

Methylation of Serrulatane Diterpenes 8-methoxy-7,18-dihydroxyserrulat-14-ene (11) and 7-methoxy-8,18-dihydroxyserrulat-14-ene (12)

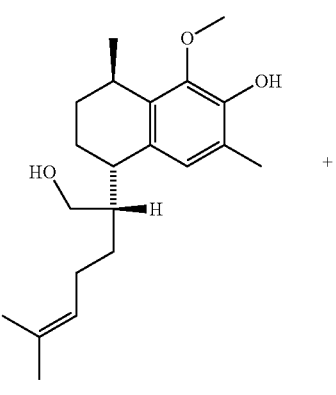

11

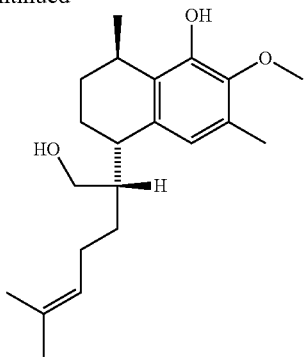

12

Compound 1 (140 mg) was treated with diazomethane (excess equiv) in diethyl ether at 0° C. to room temperature overnight to give an undetermined 4 to 1 ($^1$H-NMR) mixture of mono-methylated products 11 and 12 (35 mg, 88% purity by HPLC).

Compounds 11 and 12

Yellow oil Mass Spectrum (positive mode) m/z=333.2 (12%, (M+H)$^+$), 315.2 (100%, (M+H—H$_2$O)$^+$), 205.2 (18%, (M+H—C$_8$H$_{16}$O)$^+$). HPLC analysis: Wavelength, 210 nm, bandwidth 4; Column, SorbTech C18AQ, 2.1×50 mm, 3 µm; Retention time 7.474 min; Mobile phase acetonitrile/formic acid/water; Gradient method, 5-95% CAN+0.1% Formic acid in Water+0.1% Formic acid in 14 min, hold at 95% CAN+Formic acid for 4 min. U$_{Vmax}$, 275 nm and 210 nm, shoulder at 225 nm. $^1$H-NMR analysis indicated a 4:1 undetermined mixture of 11 and 12 (interchangeable major and minor isomers). $^1$H NMR (400 MHz, CDCl$_3$) δ: 6.74 (1H, 5, H-5)[minor], 6.56, (1H, 5, H-5)[major], 5.78 (1H, OH)[major], 5.57 (1H, OH)[minor], 5.01 (1H, bt, J=6.3 Hz, H-14), 3.78 (3H, 5, CH$_3$O)[minor], 3.77 (3H, 5, CH$_3$O)[major], 3.63 (2H, m, H-18), 3.14 (1H, m, H-1)[major], 3.07 (1H, m, H-1)[minor], δ 2.81 (1H, m, H-4), 2.25 (3H, 5, H-19)[major], 2.21 (3H, 5, H-19)[minor], 2.0-1.8 (5H, m, H-13, H-3A, H-2A, H-11), 1.7-1.6 (1H, m, H-2B), 1.66 (3H, bs, H-16), 1.55 (3H, bs, H-17), 1.52-1.46 (1H, m, H-3B), 1.35-1.23 (2H, m, H-12), 1.21 (3H, d, J=6.8 Hz, H-20) [major] 1.20 (3H, d, J=6.8 Hz, H-20)[minor], $^{13}$C NMR (100 MHz, CDCl$_3$) δ: 15.50 (C-19)[minor], 15.77 (C-19)[major], 17.62 (C-17), 20.22 (C-2)[major], 20.44 (C-2)[minor], 21.08 (C-20)[major], 22.22 (C-20)[minor], 25.66 (C-16), 26.27 (C-13), 26.81 (C-3), 27.14 (C-1)[major], 27.87 (C-1)[minor], 29.14 (C-12)[minor], 29.26 (C-12)[major], 37.53 (C-4) [minor], 37.55 (C-4)[major], 45.43 (C-11)[minor], 45.53 (C-11)[major], 60.64 (OCH$_3$)[major], 60.89 (OCH$_3$)[minor], 64.17 (C-18)[major], 64.30 (C-18)[minor], 121.89 (C-5), 124.55 (C-14), 126.39, 126.70, 127.69, 130.42, 131.63, 131.66, 133.17, 135.11, 143.15, 144.85, 145.26, 146.27.

Figure 2:
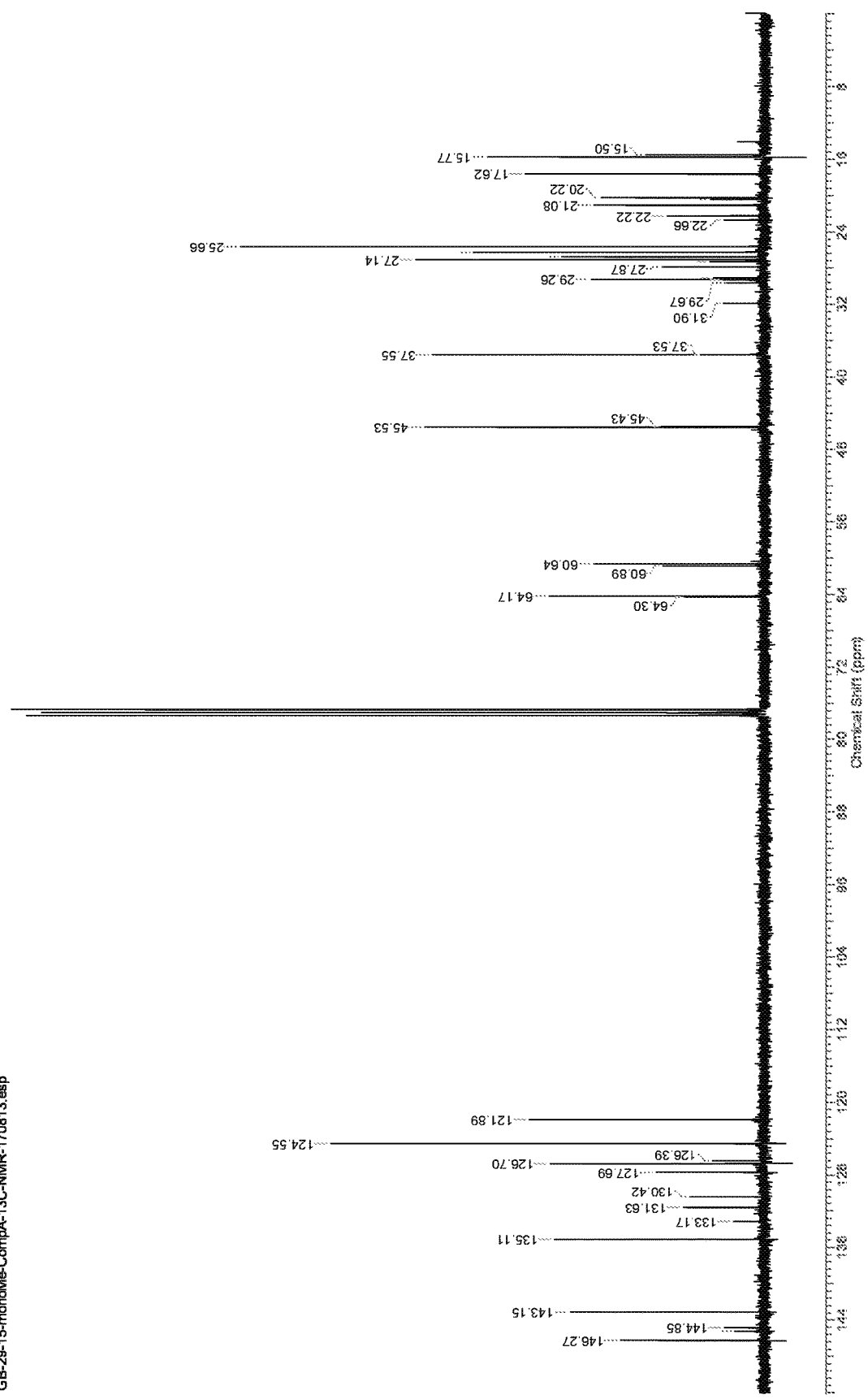
FIG. 2 shows representative $^{13}$C NMR (100 MHz, $CDCl_3$) spectrum of the 4:1 mixture of mono-methylated products (compounds 11 and 12).
Figure 3:
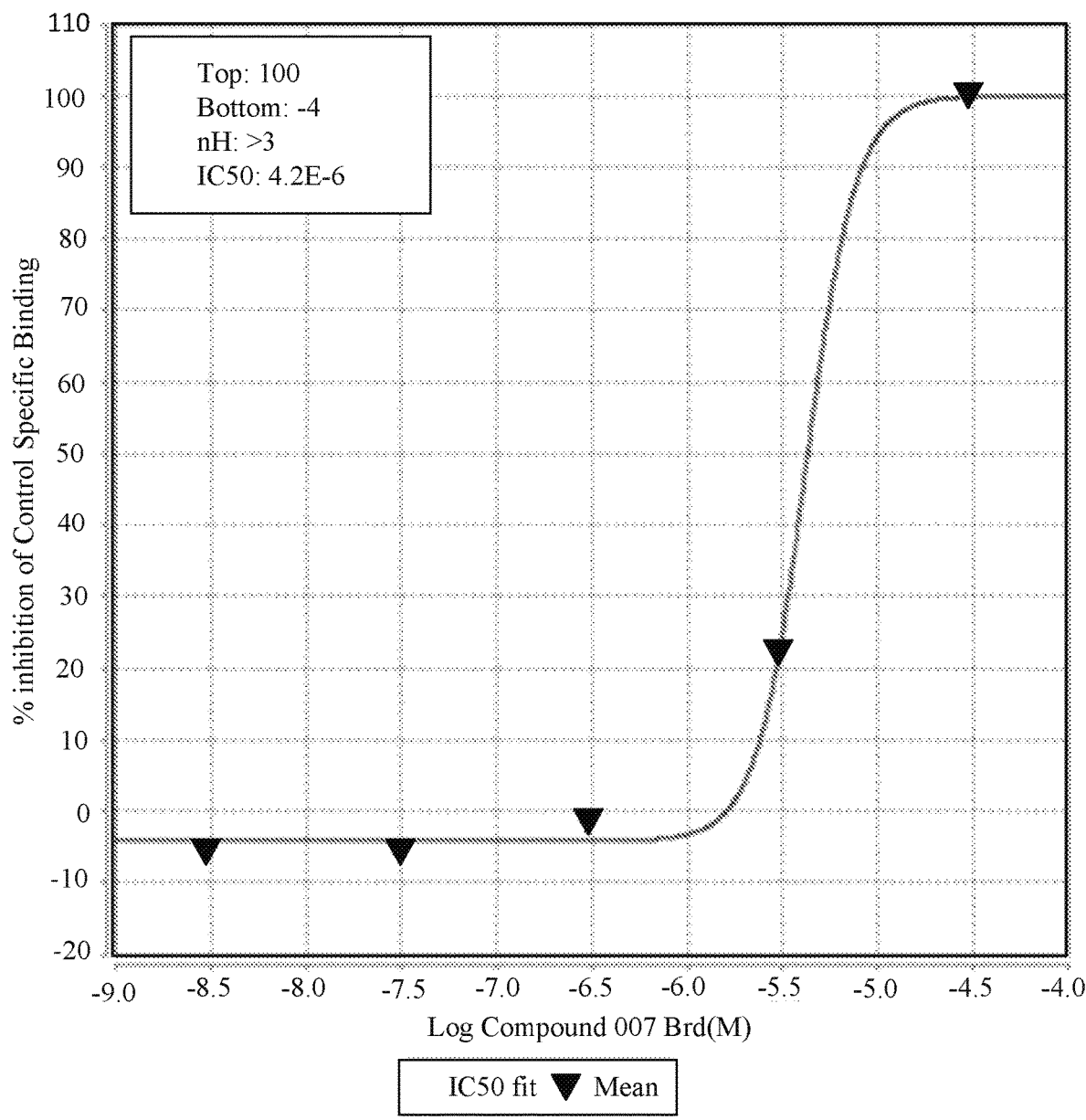
FIG. 3 to FIG. 6 show example binding curves for Compound 1 against epigenetic targets.
Figure 4:
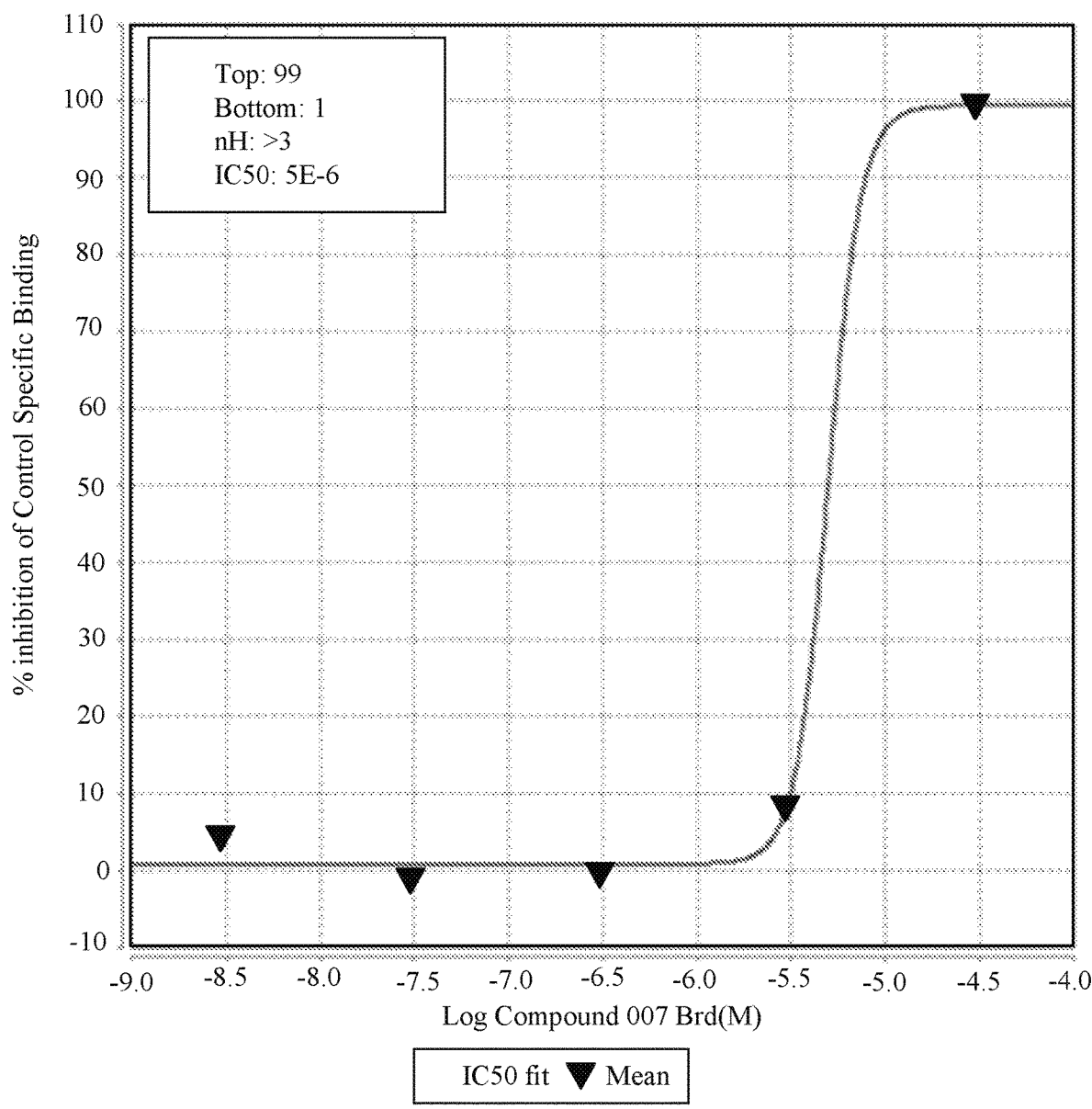
Figure 5:
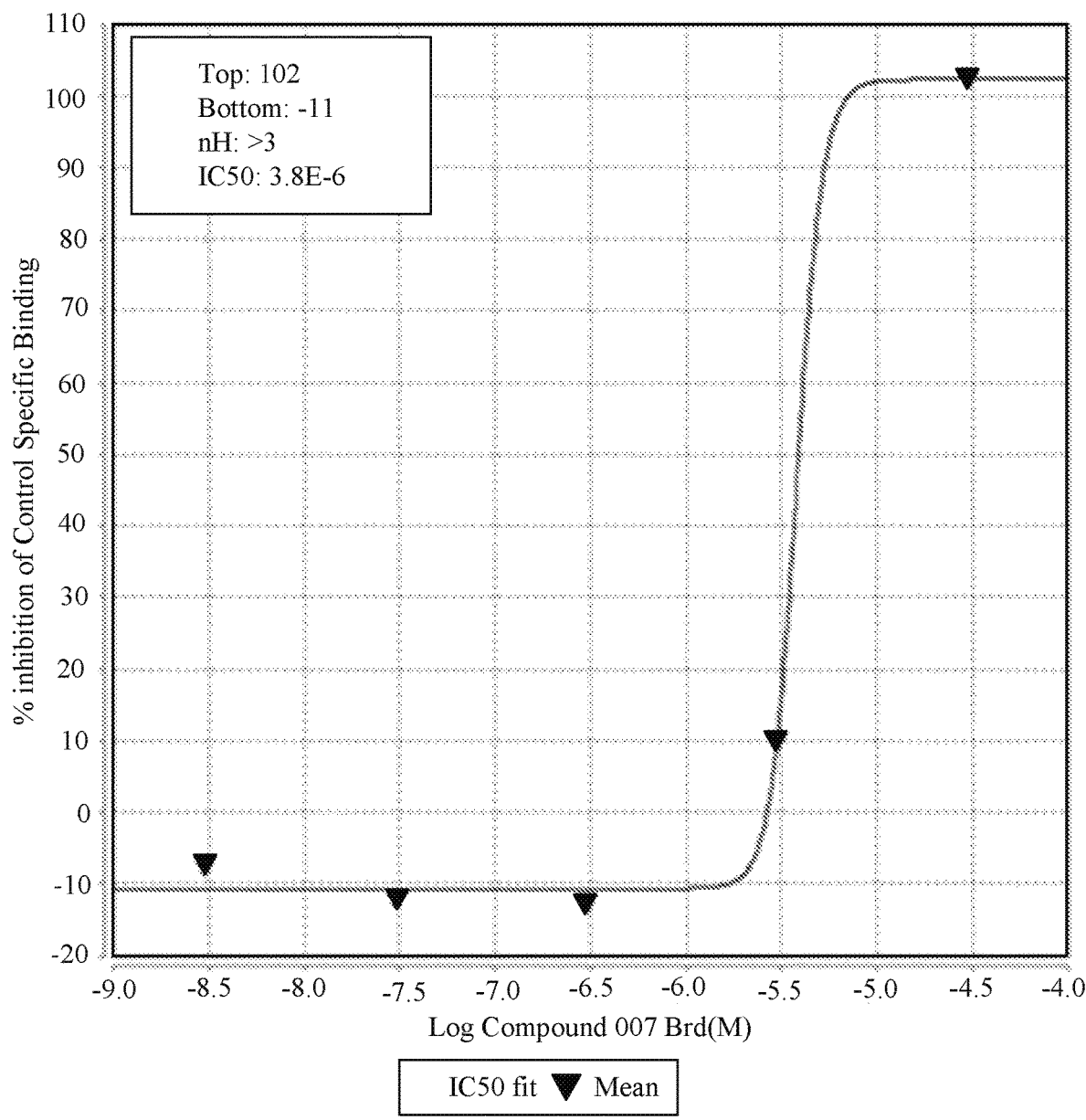
Figure 6:
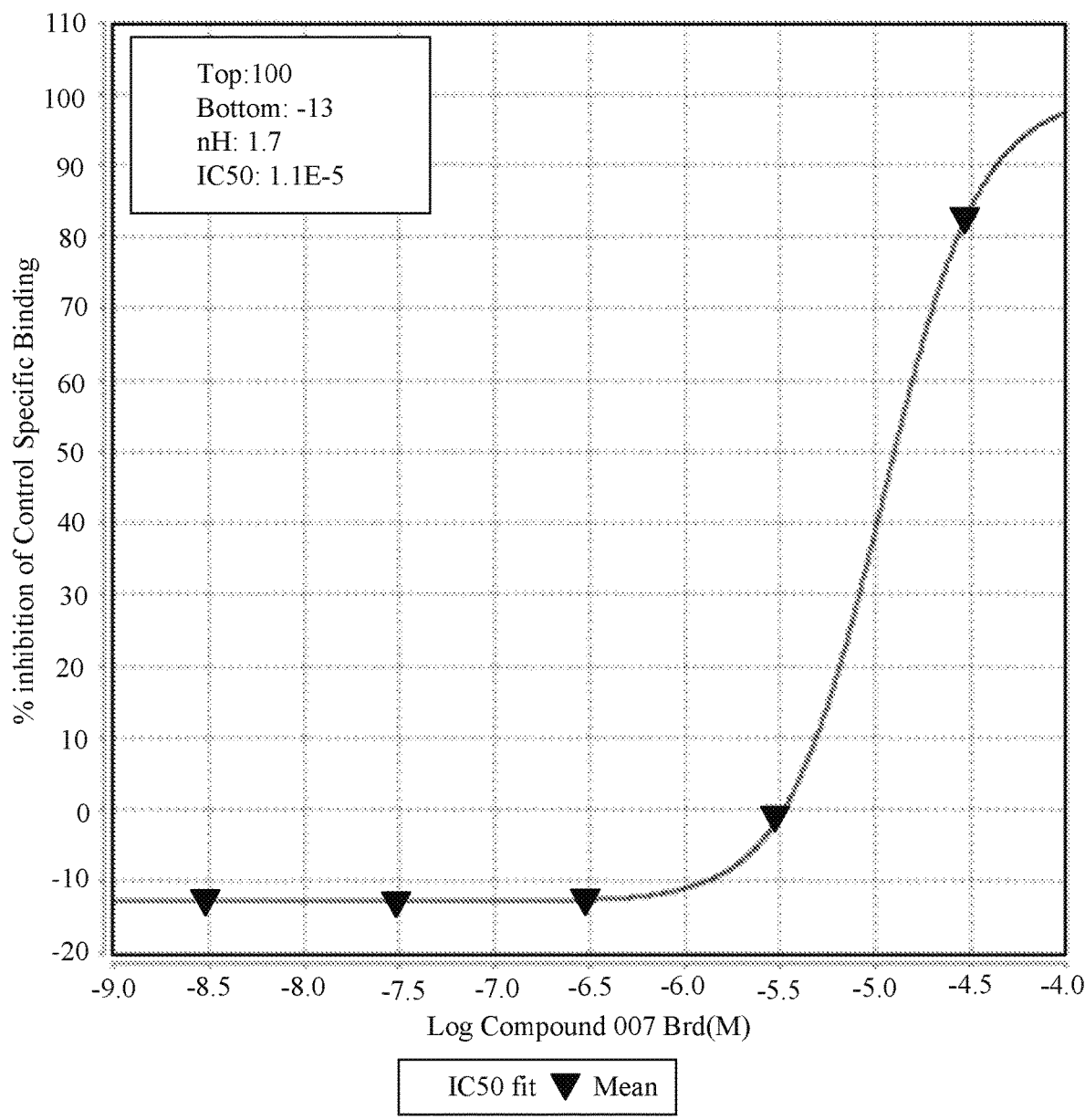

FIG. 1 and FIG. 2 show the $^1$H NMR (400 MHz, CDCl$_3$) and the $^{13}$C NMR (100 MHz, CDCl$_3$) spectra of the 4:1 mixture of compounds 11 and 12.

Biological Evaluation of Serrulatane Terpene Compounds

The serrulatane diterpenes 1 to 3 were evaluated for in vitro biological activities using assays for epigenetics (Tables 3 to 12). Table 3 shows the experimental conditions used in epigenetic binding assays. Table 4 shows the results of inhibition of compounds 1 to 3 on binding of epigenetic interacting protein modules. Tables 5 to 8 show representative inhibition data for Compound 1 on binding example epigenetic targets (Table 5: ASH1L (h) bromodomain; Table 6: CECR2(h) bromodomain; Table 7: SP140 (h) bromodomain; Table 8: UHRF1(108-286) (h)). Corresponding binding curves for the data displayed in Tables 5 to 8 are shown in FIGS. 3 to 6. Table 9 shows IC$_{50}$ values from inhibition/ concentration-response curves of compounds 1 and 2 for binding of epigenetic interacting protein modules against reference compounds.

Table 10 shows the inhibition of compounds 1 to 3 at 10 µM on activity of epigenetic enzymes against references.

Table 11 shows IC$_{50}$ values from inhibition/concentration-response curves of compounds 1, 2 and 4 for inhibition of epigenetic enzymes against reference compounds. Table 12 shows the pharmacological activity of compounds 1 to 3. Diterpenes 1 to 3 were also evaluated for in vitro pharmacological activity (Tables 13 to 16). Table 13 shows pharmacology assay methods. Table 14 shows pharmacological activity of compounds 1 to 3 at 10 µM. Table 15 shows activity of Compound 1 against 5-lipoxygenase, lipid peroxidase and monoamine oxidase (MAO-A) IC$_{50}$ (µM) and reference compounds. Table 16 shows the effect of compounds 1 to 4 at 10 µM on 2-deoxy-D-glucose uptake into muscle cells.

Table 17 shows dose response and IC$_{50}$ values for the pharmacological activity of representative serrulatane diterpenes.

Diterpenes 1 to 4 and *Myoporum insulare* resin were evaluated in a cell viability assay (Table 18)

Diterpenes 1, 2, 4 and *Myoporum insulare* resin were assayed for cell cancer cell proliferation in an OncoPanel assay (Table 19 to 29). Table 21 shows Oncopanel cell proliferation results for Compounds 11 and 12.

Epigenetic Assays

Epigenetic binding assays were carried out by Eurofins CEREP (France). The conditions used in the assays including: enzymes, source of enzymes, substrate, substrate concentration, ligand, ligand concentration, tracer, incubation, detection method, and reference compound and concentration are detailed in Table 3. Appropriate literature references are also provided. The AlphaScreen detection method refers to an Amplified Luminescent Proximity Homogeneous Assay used to study biomolecular interactions (see Ullman el al. 1994). LANCE and LanthaScreen assays are based on the principle of time-resolved fluorescence energy transfer (TR-FRET) and are described, for example, in Ma et al. 2008.

The IC$_{50}$ values (concentration causing a half-maximal inhibition of control specific activity) were determined by non-linear regression analysis of the inhibition/concentration-response curves generated with mean replicate values using Hill equation curve fitting. Inhibition/concentration-response curve concentrations were 30, 3, 0.3, 0.03 and 0.003 µM.

TABLE 3

| Assay | Main Feature | |
|---|---|---|
| Epigenetic binding assay details | | |
| Bromodomain | | |
| ATAD2B bromodomain [Filippakopoulos et al. 2012] | Source | human recombinant (*E. coli*) |
| | Ligand | biotin-H4 tetra acetyl Lys 5/8/12/16 |
| | Ligand concentration | 75 nM |
| | Incubation | 30 min/RT |
| | Detection method | AlphaScreen |
| | Reference: | Ischemin sodium salt (IC50: 76.6 μM) |
| ASH1L bromodomain [Filippakopoulos et al. 2012] | Source | human recombinant (*E. coli*) |
| | Ligand | biotin-H4 di acetyl Lys 5/8 |
| | Ligand concentration | 75 nM |
| | Incubation | 30 min/RT |
| | Detection method | AlphaScreen |
| | Reference: | JQ-1 (IC50: 13.8 μM) |
| BAZ2A bromodomain [Filippakopoulos and Knapp 2012] | Source | human recombinant (*E. coli*) |
| | Ligand | biotin-H4 tetra acetyl Lys 5/8/12/16 |
| | Ligand concentration | 25 nM |
| | Incubation | 30 min/RT |
| | Detection method | AlphaScreen |
| | Reference: | G5K2801 (IC50: 1.8 μM) |
| BRPF1-1 bromodomain [Filippakopoulos et al. 2012] | Source | human recombinant (*E. coli*) |
| | Ligand | biotin-H4 tetra acetyl Lys 5/8/12/16 |
| | Ligand concentration | 10 nM |
| | Incubation | 30 min/RT |
| | Detection method | AlphaScreen |
| | Reference: | Bromosporine (IC50: 0.026 μM) |
| CECR2 bromodomain [Filippakopoulos et al. 2012] | Source | human recombinant (*E. coli*) |
| | Ligand | biotin-H4 tetra acetyl Lys 5/8/12/16 |
| | Ligand concentration | 10 nM |
| | Incubation | 30 min/RT |
| | Detection method | AlphaScreen |
| | Reference: | Bromosporine (IC50: 0.062 μM) |
| EP300 bromodomain [Filippakopoulos and Knapp 2012] | Source | human recombinant (*E. coli*) |
| | Ligand | biotin-H3 acetyl Lys56 |
| | Ligand concentration | 25 nM |
| | Incubation | 30 min/RT |
| | Detection method | AlphaScreen |
| | Reference: | SGC-CBP30 (IC50: 0.050 μM) |
| KAT2A (GCN5L2) bromodomain [Filippakopoulos et al. 2012] | Source | human recombinant (*E. coli*) |
| | Ligand | biotin-H4 tetra acetyl Lys 5/8/12/16 |
| | Ligand concentration | 30 nM |
| | Incubation | 15 min/RT |
| | Detection method | AlphaScreen |
| | Reference: | JQ-1 (IC50: 45 μM) |
| PCAF bromodomain [Filippakopoulos and Knapp 2012] | Source | human recombinant (*E. coli*) |
| | Ligand | biotin-H4 tetra acetyl Lys 5/8/12/16 |
| | Ligand concentration | 100 nM |
| | Incubation | 30 min/RT |
| | Detection method | AlphaScreen |
| | Reference: | JQ-1 (IC50: 12 μM) |
| PB1(2) bromodomain [Filippakopoulos et al. 2012] | Source | human recombinant (*E. coli*) |
| | Ligand | biotin-H3 acetyl Lys 14 |
| | Ligand concentration | 60 nM |
| | Incubation | 15 min/RT |
| | Detection method | AlphaScreen |
| | Reference: | PFI-3 (IC50: 68 μM) |
| PB1(3) bromodomain [Filippakopoulos et al. 2012] | Source | human recombinant (*E. coli*) |
| | Ligand | biotin-H3 acetyl Lys14 |
| | Ligand concentration | 50 nM |
| | Incubation | 30 min/RT |
| | Detection method | AlphaScreen |
| | Reference: | JQ-1 (IC50: 47 μM) |
| PB1(4) bromodomain [Filippakopoulos et al. 2012] | Source | human recombinant (*E. coli*) |
| | Ligand | biotin-H3 acetyl Lys14 |
| | Ligand concentration | 50 nM |
| | Incubation | 30 min/RT |
| | Detection method | AlphaScreen |
| | Reference: | Ischemin sodium salt (IC50: 6.8 μM) |

TABLE 3-continued

Epigenetic binding assay details

| Assay | Main Feature | |
|---|---|---|
| PHIP(2) bromodomain [Filippakopoulos et al. 2012] | Source | human recombinant (*E. coli*) |
| | Ligand | biotin-H4 diacetyl Lys5/8 |
| | Ligand concentration | 100 nM |
| | Incubation | 30 min/RT |
| | Detection method | AlphaScreen |
| | Reference: | SGC-CBP30 (IC50: 0.130 μM) |
| SP140 bromodomain [Filippakopoulos et al. 2012] | Source | human recombinant (*E. coli*) |
| | Ligand | biotin-H3 acetyl Lys 9 |
| | Ligand concentration | 50 nM |
| | Incubation | 30 min/RT |
| | Detection method | AlphaScreen |
| | Reference: | Ischemin (IC50: 86 μM) |
| SMARCA2 bromodomain [Filippakopoulos et al. 2012] | Source | human recombinant (*E. coli*) |
| | Ligand | Biotin H3 mono acetyl Lys 14 |
| | Ligand concentration | 5 nM |
| | Incubation | 30 min/RT |
| | Detection method | AlphaScreen |
| | Reference: | PFI-3 (IC50: 0.47 μM) |
| TAF1(1) bromodomain [Filippakopoulos and Knapp 2012] | Source | human recombinant (*E. coli*) |
| | Ligand | biotin-H4 tetra acetyl Lys 5/8/12/16 |
| | Ligand concentration | 100 nM |
| | Incubation | 30 min/RT |
| | Detection method | AlphaScreen |
| | Reference: | G5K2801 (IC50: 4.4 μM) |
| SMARCA4 bromodomain [Filippakopoulos et al. 2012] | Source | human recombinant (*E. coli*) |
| | Ligand | Biotin-H3 mono acetyl Lys14 |
| | Ligand concentration | 15 nM |
| | Incubation | 30 min/RT |
| | Detection method | AlphaScreen |
| | Reference: | PFI-3 (IC50: 3 μM) |
| TAF1(2) bromodomain [Filippakopoulos and Knapp 2012] | Source | human recombinant (*E. coli*) |
| | Ligand | biotin-H4 tetra acetyl Lys 5/8/12/16 |
| | Ligand concentration | 100 nM |
| | Incubation | 30 min/RT |
| | Detection method | AlphaScreen |
| | Reference: | G5K2801 (IC50: 10 μM) |
| BAZ2B bromodomain [Philpott et al. 2011] | Source | human recombinant (*E. coli*) |
| | Ligand | biotin-H3 acetyl Lys14 |
| | Ligand concentration | 25 nM |
| | Incubation | 30 min/RT |
| | Detection method | AlphaScreen |
| | Reference: | G5K2801 (IC50: 1.8 μM) |
| ATAD2A bromodomain [Filippakopoulos and Knapp 2012] | Source | human recombinant (*E. coli*) |
| | Ligand | biotin-H4 tetra acetyl Lys 5/8/12/16 |
| | Ligand concentration | 100 nM |
| | Incubation | 30 min/RT |
| | Detection method | AlphaScreen |
| | Reference: | JQ-1 (IC50: 70 μM) |
| BRD2(1) bromodomain [Philpott et al. 2011] | Source | human recombinant (*E. coli*) |
| | Ligand | biotin-H4 tetra acetyl Lys 5/8/12/16 |
| | Ligand concentration | 50 nM |
| | Incubation | 30 min/RT |
| | Detection method | AlphaScreen |
| | Reference: | JQ-11 (IC50: 0.510 μM) |
| BRD2(2) bromodomain [Filippakopoulos and Knapp 2012] | Source | human recombinant (*E. coli*) |
| | Ligand | biotin-H4 tetra acetyl Lys 5/8/12/16 |
| | Ligand concentration | 50 nM |
| | Incubation | 30 min/RT |
| | Detection method | AlphaScreen |
| | Reference: | JQ-1 (IC50: 0.017 μM) |
| BRD3(1) bromodomain [Filippakopoulos and Knapp 2012] | Source | human recombinant (*E. coli*) |
| | Ligand | biotin-H4 tetra acetyl Lys 5/8/12/16 |
| | Ligand concentration | 25 nM |
| | Incubation | 30 min/RT |
| | Detection method | AlphaScreen |
| | Reference: | JQ-1 (IC50: 0.040 μM) |
| BRD3(2) bromodomain [Filippakopoulos and Knapp 2012] | Source | human recombinant (*E. coli*) |
| | Ligand | biotin-H4 di acetyl Lys 5/8 |
| | Ligand concentration | 100 nM |
| | Incubation | 30 min/RT |
| | Detection method | AlphaScreen |
| | Reference: | PFI-1 (IC50: 0.79 μM) |

TABLE 3-continued

Epigenetic binding assay details

| Assay | | Main Feature |
|---|---|---|
| BRD4(1) bromodomain [Philpott et al. 2011] | Source | human recombinant (*E. coli*) |
| | Ligand | biotin-H4 tetra acetyl Lys 5/8/12/16 |
| | Ligand concentration | 50 nM |
| | Incubation | 30 min/RT |
| | Detection method | AlphaScreen |
| | Reference: | JQ-1 (IC50: 0.018 µM) |
| BRD4(2) bromodomain [Filippakopoulos and Knapp 2012] | Source | human recombinant (*E. coli*) |
| | Ligand | biotin-H4 tetra acetyl Lys 5/8/12/16 |
| | Ligand concentration | 50 nM |
| | Incubation | 30 min/RT |
| | Detection method | AlphaScreen |
| | Reference: | PFI-1 (IC50: 1.3 µM) |
| BRDT(1) bromodomain [Filippakopoulos and Knapp 2012] | Source | human recombinant (*E. coli*) |
| | Ligand | biotin-H4 tetra acetyl Lys 5/8/12/16 |
| | Ligand concentration | 25 nM |
| | Incubation | 30 min/RT |
| | Detection method | AlphaScreen |
| | Reference: | JQ-1 (IC50: 0.110 µM) |
| CREBBP bromodomain [Philpott et al. 2011] | Source | human recombinant (*E. coli*) |
| | Ligand | biotin-H3 acetyl Lys56 |
| | Ligand concentration | 50 nM |
| | Incubation | 30 min/RT |
| | Detection method | AlphaScreen |
| | Reference: | SGC-CBP30 (IC50: 0.120 µM) |
| FALZ bromodomain [Philpott et al. 2011] | Source | human recombinant (*E. coli*) |
| | Ligand | biotin-H4 tetra acetyl Lys 5/8/12/16 |
| | Ligand concentration | 50 nM |
| | Incubation | 30 min/RT |
| | Detection method | AlphaScreen |
| | Reference: | I-CBP112 (IC50: 24.5 µM) |
| Chromodomain | | |
| CBX1 [Kaustov et al. 2011] | Source | human recombinant (*E. coli*) |
| | Ligand | biotin-H3 trimethylated Lys9 |
| | Ligand concentration | 5 nM |
| | Incubation | 30 min/RT |
| | Detection method | AlphaScreen |
| | Reference: | NA |
| CBX2 [Kaustov et al. 2011] | Source | human recombinant (*E. coli*) |
| | Ligand | biotin-H3 trimethylated Lys27 |
| | Ligand concentration | 20 nM |
| | Incubation | 30 min/RT |
| | Detection method | AlphaScreen |
| | Reference: | NA |
| CBX4 [Kaustov et al. 2011] | Source | human recombinant (*E. coli*) |
| | Ligand | biotin-H3 trimethylated Lys27 |
| | Ligand concentration | 8 nM |
| | Incubation | 30 min/RT |
| | Detection method | AlphaScreen |
| | Reference: | NA |
| CBX6 [Kaustov et al. 2011] | Source | human recombinant (*E. coli*) |
| | Ligand | biotin-H3 trimethylated Lys27 |
| | Ligand concentration | 5 nM |
| | Incubation | 30 min/RT |
| | Detection method | AlphaScreen |
| | Reference: | NA |
| CBX5 [Kaustov et al. 2011] | Source | human recombinant (*E. coli*) |
| | Ligand | biotin-H3 trimethylated Lys9 |
| | Ligand concentration | 6 nM |
| | Incubation | 15 min/RT |
| | Detection method | AlphaScreen |
| | Reference: | NA |
| CBX7 [Kaustov et al. 2011] | Source | human recombinant (*E. coli*) |
| | Ligand | biotin-H3 trimethylated Lys27 |
| | Ligand concentration | 10 nM |
| | Incubation | 30 min/RT |
| | Detection method | AlphaScreen |
| | Reference: | NA |
| CBX8 [Kaustov et al. 2011] | Source | human recombinant (*E. coli*) |
| | Ligand | biotin-H3 trimethylated Lys27 |
| | Ligand concentration | 55 nM |
| | Incubation | 30 min/RT |
| | Detection method | AlphaScreen |
| | Reference: | NA |

TABLE 3-continued

Epigenetic binding assay details

| Assay | | Main Feature |
|---|---|---|
| MBT domain | | |
| L3MBTL1 [Kim et al. 2006] | Source | human recombinant (*E. coli*) |
| | Ligand | biotin- H3 methylated Lys4 |
| | Ligand concentration | 50 nM |
| | Incubation | 15 min/RT |
| | Detection method | AlphaScreen |
| | Reference: | NA |
| L3MBTL3 [Kim et al. 2006] | Source | human recombinant (*E. coli*) |
| | Ligand | biotin-H4 dimethylated lysine 20 |
| | Ligand concentration | 60 nM |
| | Incubation | 15 min/RT |
| | Detection method | AlphaScreen |
| | Reference: | NA |
| PHD Domain | | |
| SP140 [Org et al. 2008] | Source | human recombinant (*E. coli*) |
| | Ligand | Biotin H3K4me |
| | Ligand concentration | 15 nM |
| | Incubation | 30 min/RT |
| | Detection method | AlphaScreen |
| | Reference: | NA |
| TRIM 33 [Venturini et al. 1999] | Source | human recombinant (*E. coli*) |
| | Ligand | biotin-H3 trimethylated Lys9 |
| | Ligand concentration | 8 nM |
| | Incubation | 30 min/RT |
| | Detection method | AlphaScreen |
| | Reference: | NA |
| UHRF1(108-286) [Xie et al. 2012] | Source | human recombinant (*E. coli*) |
| | Ligand | biotin-H3 trimethylated Lys9 |
| | Ligand concentration | 15 nM |
| | Incubation | 15 min/RT |
| | Detection method | AlphaScreen |
| | Reference: | NA |
| PHF20(1) [Adams-Cioba et al. 2012] | Source | human recombinant (*E. coli*) |
| | Ligand | biotin-H4 dimethylated Lys20 |
| | Ligand concentration | 100 nM |
| | Incubation | 30 min/RT |
| | Detection method | AlphaScreen |
| | Reference: | NA |
| Cell-based detection methyl modifications | | |
| H3K27 ac [Hayashi-Takanaka et al. 2011] | Source | HeLa Cells |
| | Incubation | 24 h/37° C. |
| | Detection method | AlphaScreen |
| | Reference: | NA |
| H3K27 me2-1 [Kubicek, S. et al. 2007] | Source | MCF7 cells |
| | Incubation | 24 h/37° C. |
| | Detection method | AlphaScreen |
| | Reference: | NA |
| H3K27 me3 [Kubicek, S. et al. 2007] | Source | SU-DHL-6 cells |
| | Incubation | 24 h/37° C. |
| | Detection method | AlphaScreen |
| | Reference: | NA |
| H3K36 me2 [Kubicek, S. et al. 2007] | Source | HeLa cells |
| | Incubation | 24 h/37° C. |
| | Detection method | AlphaScreen |
| | Reference: | NA |
| H3K4 me2 [Ken-ichi Noma and Grewal 2002] | Source | HeLa cells |
| | Incubation | 24 h/37° C. |
| | Detection method | AlphaScreen |
| | Reference: | NA |
| H3K79 me2 [Kubicek, S. et al. 2007] | Source | MCF7 cells |
| | Incubation | 24 h/37° C. |
| | Detection method | AlphaScreen |
| | Reference: | NA |
| H3K9 ac [Hayashi-Takanaka et al. 2011] | Source | HeLa cells |
| | Incubation | 24 h/37° C. |
| | Detection method | AlphaScreen |
| | Reference: | NA |
| H3K9 me2 [Kubicek, S. et al. 2007] | Source | HeLa cells |
| | Incubation | 24 h/37° C. |
| | Detection method | AlphaScreen |
| | Reference: | NA |

TABLE 3-continued

Epigenetic binding assay details

| Assay | | Main Feature |
|---|---|---|
| Demethylases (KDMs) | | |
| FBXL10 (h) [Rotili and Mai 2011] | Source | human recombinant (Sf9 cells) |
| | Substrate | biotin-H3K36me2 (24 nM) |
| | Incubation | 10 min/RT |
| | Detection method | LANCE |
| | Reference: | 2,4 PDCA (IC50: 0.61 μM) |
| FBXL11 (h) [Chowdhury 2011] | Source | human recombinant (E. coli) |
| | Ligand | biotin- H3K36me2 |
| | Ligand concentration | 50 nM |
| | Incubation | 10 min/RT |
| | Detection method | LANCE |
| | Reference: | 2,4 PDCA (IC50: 1.5 μM) |
| JARID1A (h) [Nottke et al. 2009] | Source | human recombinant (Sf9 cells) |
| | Ligand | biotin-H3K4me3 |
| | Ligand concentration | 100 nM |
| | Incubation | 10 min/RT |
| | Detection method | LANCE |
| | Reference: | 2,4 PDCA (IC50: 0.18 μM) |
| JARID1B (h) [Kristensen 2012] | Source | human recombinant (Sf9 cells) |
| | Ligand | biotin-H3K4me3 |
| | Ligand concentration | 60 nM |
| | Incubation | 30 min/RT |
| | Detection method | LANCE |
| | Reference: | 2,4 PDCA (IC50: 0.15 μM) |
| JARID1C (h) [Nottke et al. 2009] | Source | human recombinant (Sf9 cells) |
| | Substrate | biotin-H3K4me3 |
| | Substrate concentration | 15 nM |
| | Incubation | 30 min/RT |
| | Detection method | LANCE |
| | Reference: | 2,4 PDCA (IC50: 0.23 μM) |
| JMJD1A (h) [Heightman 2011] | Source | human recombinant (E. coli) |
| | Substrate | biotin-H3K4me1 |
| | Substrate concentration | 25 nM |
| | Incubation | 10 min/RT |
| | Detection method | LANCE |
| | Reference: | 2,4 PDCA (IC50: 0.76 μM) |
| JMJD2A (h) [King et al. 2010] | Source | human recombinant (E. coli) |
| | Ligand | biotin-H3K9me3 |
| | Ligand concentration | 100 nM |
| | Incubation | 10 min/RT |
| | Detection method | LANCE |
| | Reference: | 2,4 PDCA (IC50: 0.083 μM) |
| JMJD2B (h) [King et al. 2010] | Source | human recombinant (E. coli) |
| | Ligand | biotin-H3K9me3 |
| | Ligand concentration | 100 nM |
| | Incubation | 10 min/RT |
| | Detection method | LANCE |
| | Reference: | 2,4 PDCA (IC50: 0.14 μM) |
| JMJD2C (h) [King et al. 2010] | Source | human recombinant (E. coli) |
| | Ligand | biotin-H3K9me3 |
| | Ligand concentration | 100 nM |
| | Incubation | 10 min/RT |
| | Detection method | LANCE |
| | Reference: | 2,4 PDCA (IC50: 0.091 μM) |
| JMJD2D (h) [Hong et al. 2007] | Source | human recombinant (Sf9 cells) |
| | Ligand | biotin-H3K27me3 |
| | Ligand concentration | 50 nM |
| | Incubation | 10 min/RT |
| | Detection method | LANCE |
| | Reference: | 2,4 PDCA (IC50: 0.091 μM) |
| JMJD2E (h) [Hong et al. 2007] | Source | human recombinant (Sf9 cells) |
| | Ligand | biotin-H3K27me3 |
| | Ligand concentration | 50 nM |
| | Incubation | 10 min/RT |
| | Detection method | LANCE |
| | Reference: | 2,4 PDCA (IC50: 0.061 μM) |
| JMJD3 (h) [Hong et al. 2007] | Source | human recombinant (Sf9 cells) |
| | Ligand | biotin-H3K27me3 |
| | Ligand concentration | 50 nM |
| | Incubation | 10 min/RT |
| | Detection method | LANCE 1198 |
| | Reference: | 2,4 PDCA (IC50: 52 μM) |

TABLE 3-continued

Epigenetic binding assay details

| Assay | | Main Feature |
|---|---|---|
| LSD1 (h) [Hong et al. 2007] | Source | human recombinant (Sf9 cells) |
| | Ligand | biotin-H3K27me3 |
| | Ligand concentration | 50 nM |
| | Incubation | 10 min/RT |
| | Detection method | LANCE |
| | Reference: | Tranylcypromine (IC50: 22 µM) |
| PHF8(h) [Hong et al. 2007] | Source | human recombinant (Sf9 cells) |
| | Ligand | biotin-H3K27me3 |
| | Ligand concentration | 50 nM |
| | Incubation | 10 min/RT |
| | Detection method | LANCE 1198 |
| | Reference: | Daminozide (IC50: 0.28 µM) |
| UTX (h) [Hong et al. 2007] | Source | human recombinant (Sf9 cells) |
| | Ligand | biotin-H3K27me3 |
| | Ligand concentration | 50 nM |
| | Incubation | 10 min/RT |
| | Detection method | LANCE |
| | Reference: | IOX1 (0.15 µM) |
| DNA methyltransferases (DNMTs) | | |
| DNMT1 (h) [Pradhan et al. 1999] | Source | human recombinant (*E. coli*) |
| | Substrate | Poly (dI-dC)-Poly(dIdC) [6 mU/mL] |
| | Tracer | [3H] SAM (50 nM) |
| | Incubation | 30 min/37° C. |
| | Detection method | Scintillation counting |
| | Reference: | SAH (IC50: 0.23 µM) |
| DNMT3b [Hong et al. 2007] | Source | human recombinant (Sf9 cells) |
| | Ligand | biotin- H3K27me3 |
| | Ligand concentration | 50 nM |
| | Incubation | 10 min/RT |
| | Detection method | LANCE |
| | Reference: | SAH (IC50: 0.094 µM) |
| DNMT3B/DNMT3L (h) [Suetake et al. 2004] | Source | human recombinant (Sf9 cells) |
| | Substrate | Poly (dI-dC)-Poly(dIdC) [0.15 mU/mL] |
| | Tracer | [3H] SAM (200 nM) |
| | Incubation | 20 min/37° C. |
| | Detection method | Scintillation counting |
| | Reference: | SAH (IC50: 0.045 µM) |
| hDNMT3a [Aoki et al. 2001] | Source | human recombinant (Sf9 cells) |
| | Substrate | Poly (dI-dC)-Poly(dIdC) |
| | Tracer | [3H] SAM (200 nM) |
| | Incubation | 20 min/37° C. |
| | Detection method | Scintillation counting |
| | Reference: | SAH (IC50: 0.052 µM) |
| Histone acetyl-transferases (HATs) | | |
| CREBBP(h) [Hong et al. 2007] | Source | human recombinant (*E. coli*) |
| | Ligand | biotin-H3K27me3 |
| | Ligand concentration | 50 nM |
| | Incubation | 10 min/RT |
| | Detection method | LANCE |
| | Reference: | Garcinol (IC50: 1.5 µM) |
| GCN5L2(h) [Hong et al. 2007] | Source | human recombinant (Sf9 cells) |
| | Ligand | biotin-H3K27me3 |
| | Ligand concentration | 50 nM |
| | Incubation | 10 min/RT |
| | Detection method | LANCE |
| | Reference: | Anacardic acid (IC50: 4.7 µM) |
| HAT1(h) [Zhang et al. 2012] | Source | human recombinant (*E. coli*) |
| | Ligand | biotin-H3K27me3 |
| | Ligand concentration | 50 nM |
| | Incubation | 10 min/RT |
| | Detection method | Scintillation counting |
| | Reference: | Garcinol (IC50: 1.5 µM) |
| MYST3(h) [Zhang et al. 2012] | Source | human recombinant (*E. coli*) |
| | Ligand | biotin-H3K27me3 |
| | Ligand concentration | 50 nM |
| | Incubation | 10 min/RT |
| | Detection method | Scintillation counting |
| | Reference: | Garcinol (IC50: 1.8 µM) |

TABLE 3-continued

Epigenetic binding assay details

| Assay | | Main Feature |
|---|---|---|
| MYST4 (h) [Zhang et al. 2012] | Source | human recombinant (*E. coli*) |
| | Ligand | biotin-H3K27me3 |
| | Ligand concentration | 50 nM |
| | Incubation | 10 min/RT |
| | Detection method | Scintillation counting 1293 |
| | Reference: | Curcumin (IC50: 11 μM) |
| pCAF(h) [Zhang et al. 2012] | Source | human recombinant (*E. coli*) |
| | Ligand | biotin-H3K27me3 |
| | Ligand concentration | 50 nM |
| | Incubation | 10 min/RT |
| | Detection method | Scintillation counting 1293 |
| | Reference: | Garcinol (IC50: 2.9 μM) |
| TIP60 (h) [Zhang et al. 2012] | Source | human recombinant (Sf 21 cells) |
| | Ligand | biotin-H3K27me3 |
| | Ligand concentration | 50 nM |
| | Incubation | 10 min/RT |
| | Detection method | Scintillation counting 1293 |
| | Reference: | Garcinol (IC50: 1.5 μM) |
| Histone deacetylase (HDACs) [Strahl and Allis 2000] | | |
| HDAC1 (h) | Source | human recombinant |
| | Substrate | fluorogenic HDAC substrate |
| | Substrate concentration | 20 μM |
| | Incubation | 10 min/RT |
| | Detection method | fluoro-lysine fluorimetry |
| | Reference: | trichostatin A (IC50: 0.0052 μM) |
| HDAC2 (h) | Source | human recombinant fluorogenic HDAC substrate |
| | Ligand | NA |
| | Substrate concentration | 20 μM |
| | Incubation | 15 min/RT |
| | Detection method | fluoro-lysine fluorimetry 896 |
| | Reference: | trichostatin A (IC50: 0.024 μM) |
| HDAC3 (h) | Source | human recombinant |
| | Substrate | fluorogenic HDAC substrate |
| | Substrate concentration | 50 μM |
| | Incubation | 10 min/RT |
| | Detection method | fluoro-lysine fluorimetry |
| | Reference: | trichostatin A (IC50: 0.0068 μM) |
| HDAC4 (h) | Source | human recombinant |
| | Substrate | fluorogenic HDAC substrate |
| | Substrate concentration | 20 μM |
| | Incubation | 30 min/RT |
| | Detection method | fluoro-lysine fluorimetry |
| | Reference: | trichostatin A (IC50: 4.0 μM) |
| HDAC5 (h) | Source | human recombinant |
| | Ligand | fluorogenic HDAC substrate |
| | Substrate concentration | 20 μM |
| | Incubation | 30 min/RT |
| | Detection method | fluoro-lysine fluorimetry |
| | Reference: | trichostatin A (IC50: 1.0 μM) |
| HDAC6 (h) | Source | human recombinant |
| | Substrate | fluorogenic HDAC substrate |
| | Substrate concentration | 25 μM |
| | Incubation | 30 min/RT |
| | Detection method | fluoro-lysine fluorimetry |
| | Reference: | trichostatin A (IC50: 0.0074 μM) |
| HDAC7 (h) | Source | human recombinant |
| | Substrate | fluorogenic HDAC substrate class 2a |
| | Substrate concentration | 50 μM |
| | Incubation | 45 min/RT |
| | Detection method | fluoro-lysine fluorimetry |
| | Reference: | trichostatin A (IC50: 1.8 μM) |
| HDAC8 (h) | Source | human recombinant |
| | Substrate | fluorogenic HDAC substrate class 2a |
| | Substrate concentration | 50 μM |
| | Incubation | 45 min/RT |
| | Detection method | fluoro-lysine fluorimetry 896 |
| | Reference: | trichostatin A (IC50: 0.41 μM) |
| HDAC9 (h) | Source | human recombinant |
| | Substrate | fluorogenic HDAC substrate class 2a |
| | Substrate concentration | 50 μM |
| | Incubation | 30 min/RT |
| | Detection method | fluoro-lysine fluorimetry 896 |
| | Reference: | trichostatin A (IC50: 9.1 μM) |

TABLE 3-continued

Epigenetic binding assay details

| Assay | | Main Feature |
|---|---|---|
| HDAC10 (h) | Source | human recombinant |
| | Substrate | fluorogenic HDAC substrate class 2a |
| | Substrate concentration | 50 µM |
| | Incubation | 45 min/RT |
| | Detection method | fluoro-lysine fluorimetry 896 |
| | Reference: | trichostatin A (IC50: 0.009 µM) |
| HDAC11 (h) | Source | human recombinant (*E. coli*) |
| | Substrate | fluorogenic HDAC substrate class 2a |
| | Substrate concentration | 50 µM |
| | Incubation | 30 min/37° C. |
| | Detection method | fluoro-lysine fluorimetry 896 |
| | Reference: | Scriptaid (IC50: 8.9 µM) |
| Sirtuins | | |
| sirtuin 1 (h) (inhibitor effect) | Source | human recombinant (*E. coli*) |
| [Strahl and Allis 2000] | Substrate | fluorogenic HDAC substrate class 2a |
| | Substrate concentration | 50 µM |
| | Incubation | 30 min/37° C. |
| | Detection method | fluoro-lysine fluorimetry |
| | Reference: | Suramin (IC50: 7.9 µM) |
| sirtuin 2 (h) (inhibitor effect) | Source | human recombinant (*E. coli*) |
| [Michan and Sinclair 2007] | Substrate | fluoro-lysine sirtuin 2 deacetylase substrate |
| | Substrate concentration | 150 µM |
| | Incubation | 60 min/RT |
| | Detection method | fluoro-lysine fluorimetry |
| | Reference: | Suramin (IC50: 21 µM) |
| sirtuin 3 (h) (inhibitor effect) | Source | human recombinant (*E. coli*) |
| [Strahl and Allis 2000] | Substrate | fluorogenic HDAC substrate class 2a |
| | Substrate concentration | 50 µM |
| | Incubation | 30 min/37° C. |
| | Detection method | fluoro-lysine fluorimetry |
| | Reference: | Niacinamide (IC50: 21 µM) |
| Sirtuin 6 (h) | Source | human recombinant (*E. coli*) |
| [Michishita et al. | Substrate | Fluorogenic HDAC |
| 2008] | Substrate concentration | 50 µM |
| | Incubation | 180 min/RT |
| | Detection method | fluoro-lysine fluorimetry |
| | Reference | EX-527 (IC50: 550 µM) |
| Sirtuin 7 (h) [Kim and Kim | Source | human recombinant (Sf9 cells) |
| 2013] | Substrate | fluorogenic HDAC |
| | Substrate concentration | 25 µM |
| | Incubation | 60 min/37° C. |
| | Detection method | fluoro-lysine fluorimetry |
| | Reference: | JFD00244 (IC50: 1300 µM) |
| Methyltransferases (MTs) | | |
| ASH1L [An et al. 2011] | Source | human recombinant (*E. coli*) |
| | Substrate | polynucleosome (1.5 µg/mL) |
| | Tracer | [3H] SAM (150 nM) |
| | Incubation | 15 min/RT |
| | Detection method | Scintillation counting |
| | Reference: | SAH (IC50: 9.1 µM) |
| DOT1L (h) [An et al. 2011] | Source | human recombinant (*E. coli*) |
| | Substrate | polynucleosome (2.5 µg/mL) |
| | Tracer | [3H] SAM (150 nM) |
| | Incubation | 15 min/RT |
| | Detection method | Scintillation counting |
| | Reference: | SAH (IC50: 0.14 µM) |
| EHMT1 (h) [Yost et al. 2011] | Source | human recombinant (*E. coli*) |
| | Substrate (concentration) | histone H3 full length (10 nM) |
| | Co-substrate (concentration) | [3H] SAM (25 nM) |
| | Incubation | 120 min/RT |
| | Detection method | Scintillation counting |
| | Reference: | SAH (IC50: 0.18 µM) |
| EZH1/EED/SUZ12 (h) [Shen | Source | human recombinant |
| et al. 2008] | Substrate (concentration) | histone H3 full length (70 nM) |
| | Co-substrate (concentration) | [3H] SAM (120 nM) |
| | Incubation | 90 min/RT |
| | Detection method | Scintillation counting |
| | Reference: | SAH (IC50: 8.4 µM) |
| EZH2/EED/SUZ12 (h) | Source | human recombinant (Sf9 cells) |
| (PRC2 complex) [Philpott et | Substrate (concentration) | histone H3 full length (50 nM) |
| al. 2011] | Co-substrate (concentration) | [3H] SAM (35 nM) |
| | Incubation | 120 min/RT |
| | Detection method | Scintillation counting |
| | Reference: | [3H] (IC50: 22 µM) |

TABLE 3-continued

Epigenetic binding assay details

| Assay | | Main Feature |
|---|---|---|
| G9a (h) [Yost et al. 2011] | Source | human recombinant (*E. coli*) |
| | Substrate | histone H3 full length (5 nM) |
| | Co-substrate | [3H] SAM (25 nM) |
| | Incubation | 120 min/RT |
| | Detection method | Scintillation counting |
| | Reference: | SAH (2.1 μM) |
| hSMYD2 [An et al. 2011] | Source | human recombinant (Sf9 cells) |
| | Substrate | histone H4 full length (25 nM) |
| | Co-substrate | [3H] SAM 150 nM |
| | Incubation | 10 min/RT |
| | Detection method | Scintillation counting |
| | Reference: | SAH (0.16 μM) |
| MLL complex (h) [Jiang et al. 2013] | Source | human recombinant (*E. coli*) |
| | Substrate | Histone H3 full length (35 nM) |
| | Tracer | [3H] SAM (200 nM) |
| | Incubation | 30 min/RT |
| | Detection method | Scintillation counting |
| | Reference: | [3H] (0.97 μM) |
| MLL2(h) complex [Jiang et al. 2013] | Source | human recombinant (*E. coli*) |
| | Substrate | Histone H3 full length (35 nM) |
| | Tracer | [3H] SAM (200 nM) |
| | Incubation | 30 min/RT |
| | Detection method | Scintillation counting |
| | Reference: | SAH (0.97 μM) |
| MLL3(h) complex [Ali et al. 2014] | Source | human recombinant (*E. coli*) |
| | Substrate | Core histone (20 nM) |
| | Tracer | [3H] SAM (200 nM) |
| | Incubation | 20 min/RT |
| | Detection method | Scintillation counting |
| | Reference: | SAH (0.97 μM) |
| MLL4(h) complex [Ali et al. 2014] | Source | human recombinant (*E. coli*) |
| | Substrate | Core histone (30 nM) |
| | Tracer | [3H] SAM (200 nM) |
| | Incubation | 10 min/RT |
| | Detection method | Scintillation counting |
| | Reference: | SAH (0.97 μM) |
| NSD1 (h) [Allali-Hassani et al. 2014] | Source | human recombinant (*E. coli*) |
| | Substrate | Histone H3 full length (35 nM) |
| | Tracer | [3H] SAM (200 nM) |
| | Incubation | 30 min/RT |
| | Detection method | Scintillation counting |
| | Reference: | SAH (0.97 μM) |
| NSD3/WHSC1L1 (h) [Selvi et al. 2010] | Source | human recombinant (*E. coli*) |
| | Substrate | Histone H3 full length (35 nM) |
| | Tracer | [3H] SAM (200 nM) |
| | Incubation | 30 min/RT |
| | Detection method | Scintillation counting |
| | Reference: | [3H] (0.97 μM) |
| PRDM9 (h) [Munoz-Fuentes et al. 2011] | Source | human recombinant (*E. coli*) |
| | Substrate | Histone H3 full length (250 nM) |
| | Co-Substrate | [3H] SAM (60 nM) |
| | Incubation | 30 min/RT |
| | Detection method | Scintillation counting |
| | Reference: | SAH (370 μM) |
| PRMT1 (h) [Cheng et al. 2004] | Source | human recombinant (*E. coli*) |
| | Substrate | histone H4 full length (25 nM) |
| | Co-substrate | [3H] SAM (60 nM) |
| | Incubation | 90 min/RT |
| | Detection method | Scintillation counting |
| | Reference: | SAH (0.094 μM) |
| PRMT3 (h) [Li et al. 2012] | Source | human recombinant (*E. coli*) |
| | Substrate | histone H4 full length (25 nM) |
| | Co-substrate | [3H] SAM (60 nM) |
| | Incubation | 90 min/RT |
| | Detection method | Scintillation counting |
| | Reference: | SAH (0.86 μM) |
| PRMT4 (h) [Selvi et al. 2010] | Source | human recombinant (Sf9 cells) |
| | Substrate | histone H4 full length (25 nM) |
| | Co-substrate | [3H] SAM (60 nM) |
| | Incubation | 120 min/RT |
| | Detection method | Scintillation counting |
| | Reference: | SAH (0.094 μM) |

TABLE 3-continued

Epigenetic binding assay details

| Assay | | Main Feature |
|---|---|---|
| PRMT5 complex (h) [Yost et al. 2011] | Source | human recombinant (Sf9 cells) |
| | Substrate | histone H4 full length (250 nM) |
| | Co-substrate | [3H] SAM (600 nM) |
| | Incubation | 120 min/RT |
| | Detection method | Scintillation counting |
| | Reference: | SAH (0.65 µM) |
| PRMT6 (h) [Iberg et al. 2007] | Source | human recombinant (Sf9 cells) |
| | Substrate | histone H4 full length (250 nM) |
| | Co-substrate | [3H] SAM (600 nM) |
| | Incubation | 120 min/RT |
| | Detection method | Scintillation counting |
| | Reference: | SAH (0.65 µM) |
| PRMT7 (h)[Zurita-Lopez et al. 2012] | Source | human recombinant (Sf9 cells) |
| | Substrate | histone H2B (21-41) biotin labeled (4 nM) |
| | Co-substrate | [3H] SAM (250 nM) |
| | Incubation | 90 min/RT |
| | Detection method | Scintillation counting |
| | Reference: | SAH (0.65 µM) |
| PRMT8 (h) [Lee et al. 2005] | Source | human recombinant (Sf9 cells) |
| | Substrate | histone H4 full length (250 nM) |
| | Co-substrate | [3H] SAM (600 nM) |
| | Incubation | 120 min/RT |
| | Detection method | Scintillation counting |
| | Reference: | SAH (0.65 µM) |
| SETD2(h) [Du et al. 2008] | Source | human recombinant (*E. coli*) |
| | Substrate | Nucleosome (0.5 µg/mL) |
| | Co-substrate | [3H] SAM (250 nM) |
| | Incubation | 10 min/RT |
| | Detection method | Scintillation counting |
| | Reference: | SAH (1.2 µM) |
| SETD7 (h) [Li et al. 2012] | Source | human recombinant (*E. coli*) |
| | Substrate | histone H3 full length (120 nM) |
| | Co-substrate | [3H] SAM (850 nM) |
| | Incubation | 30 min/RT |
| | Detection method | Scintillation counting |
| | Reference: | SAH (24 µM) |
| SETD8 (h) [Yost et al. 2011] | Source | human recombinant (*E. coli*) |
| | Substrate | histone H3 full length (120 nM) |
| | Co-substrate | [3H] SAM (850 nM) |
| | Incubation | 30 min/RT |
| | Detection method | Scintillation counting |
| | Reference: | SAH (24 µM) |
| SETDB1 (h) [Schultz et al. 2002] | Source | human recombinant (Sf9 cells) |
| | Substrate | histone H3 full length (15 nM) |
| | Co-substrate | [3H] SAM (25 nM) |
| | Incubation | 120 min/RT |
| | Detection method | Scintillation counting |
| | Reference: | SAH (1.8 µM) |
| SUV39H2 (h) [Yost et al. 2011] | Source | human recombinant (Sf9 cells) |
| | Substrate | histone H3 full length (500 nM) |
| | Co-substrate | [3H] SAM (350 nM) |
| | Incubation | 120 min/RT |
| | Detection method | Scintillation counting |
| | Reference: | SAH (24 µM) |
| SUV4-20H2 (h) [Li et al. 2012] | Source | human recombinant (*E. coli*) |
| | Substrate | Nucleosome (1.5 µg/ml) |
| | Co-substrate | [3H] SAM (75 nM) |
| | Incubation | 15 min/RT |
| | Detection method | Scintillation counting |
| | Reference: | SAH (24 µM) |
| WHSC1(h) (NSD2(h)) [Kang et al. 2009] | Source | huma recombinant (*E. coli*) |
| | Substrate | Core Histone (1500 nM) |
| | Tracer | [3H] SAM (250 nM) |
| | Incubation | 15 min/RT |
| | Detection method | Scintillation counting |
| | Reference: | Chaetocin (IC50: 0.48 µM) |
| Kinases | | |
| Aurora B (h) (substrate histone H3 full length) [Sabbattini et al. 2007] | Source | Baculovirus |
| | Substrate | Histone H3 full length (150 nM) |
| | Tracer | [33P] ATP |
| | Incubation | 10 min/RT |
| | Detection method | Scintillation counting |
| | Reference: | Staurosporine (0.038 µM) |

TABLE 3-continued

Epigenetic binding assay details

| Assay | | Main Feature |
|---|---|---|
| DAPK3/ZIP (substrate histone H3 full length) [Preuss et al. 2003] | Source | Baculovirus |
| | Substrate | Histone H3 full length(50 nM) |
| | Tracer | [33P] ATP |
| | Incubation | 10 min/RT |
| | Detection method | Scintillation counting |
| | Reference: | Staurosporine (IC50: 0.0073 µM) |
| Haspin (h) (substrate histone H3 full length) [Han et al. 2011] | Source | human recombinant (*E. coli*) |
| | Substrate | baculovirus Histone H3 full length (250 nM) |
| | Tracer | [33P] ATP |
| | Incubation | 10 min/RT |
| | Detection method | Scintillation counting |
| | Reference: | Staurosporine (IC50: 0.0073 µM) |
| IKK alpha(h) (substrate histone H3 full length) [Baek 2011] | Source | human recombinant (Sf21 cells) |
| | Substrate | Histone H3 full length (50 nM) |
| | Tracer | [33P] ATP |
| | Incubation | 10 min/RT |
| | Detection method | Scintillation counting |
| | Reference: | Staurosporine (IC50: 0.03 µM) |
| MSK1(h)(substrate histone H3 full length) [Baek 2011] | Source | human recombinant insect cells |
| | Substrate | Histone H3 full length (100 nM) |
| | Tracer | [33P] ATP |
| | Incubation | 10 min/RT |
| | Detection method | Scintillation counting |
| | Reference: | Staurosporine (IC50: 0.015 µM) |
| MSK2(h) (substrate histone H3 full length) [Baek 2011] | Source | human recombinant (insect cells) |
| | Substrate | Histone H3 full length (20 nM) |
| | Tracer | [33P] ATP |
| | Incubation | 10 min/RT |
| | Detection method | Scintillation counting |
| | Reference: | Staurosporine (IC50: 0.0058 µM) |
| PIM1(h) (histone H3 full length substrate) [Baek 2011] | Source | human recombinant (Sf21 cells) |
| | Substrate | Histone H3 full length (50 nM) |
| | Tracer | [33P] ATP |
| | Incubation | 10 min/RT |
| | Detection method | Scintillation counting |
| | Reference: | Staurosporine (IC50: 0.03 µM) |
| PKBalpha/AKT1(h) (substrate histone H3 full length) [Barnett et al. 2005] | Source | human recombinant (Sf21 cells) |
| | Substrate | Histone H3 full length (50 nM) |
| | Tracer | [33P] ATP |
| | Incubation | 10 min/RT |
| | Detection method | Scintillation counting |
| | Reference: | Staurosporine (IC50: 0.03 µM) |
| PKBbeta/AKT2(h) (substrate histone H3 full length) [Barnett et al. 2005] | Source | human recombinant (baculovirus) |
| | Substrate | Histone H3 full length (100 nM) |
| | Tracer | [33P] ATP |
| | Incubation | 10 min/RT |
| | Detection method | Scintillation counting |
| | Reference: | Staurosporine (IC50: 0.03 µM) |
| PKBganuna/AKT3(h) (substrate histone H3 full length) [Baek 2011] | Source | human recombinant (baculovirus) |
| | Substrate | Histone H3 full length (150 nM) |
| | Tracer | [33P] ATP |
| | Incubation | 10 min/RT |
| | Detection method | Scintillation counting |
| | Reference: | Staurosporine (IC50: 0.03 µM) |
| Rsk2(h) (substrate histone H3 full length) [Baek 2011] | Source | human recombinant (baculovirus) |
| | Substrate | Histone H3 full length (250 nM) |
| | Tracer | [33P] ATP |
| | Incubation | 10 min/RT |
| | Detection method | Scintillation counting |
| | Reference: | Staurosporine (IC50: 0.007 µM) |
| Small molecule methyltransferases | | |
| Catechol O-methyltransferase (h) | Source | human recombinant (*E. coli*) |
| | Substrate | Pyrocatechol (250 nM) |
| | Tracer | SAM (10 µM) |
| | Incubation | 15 min/37° C. |
| | Detection method | MS |
| | Reference: | SAH-d4 (IC50: 14 µM) |
| Glycine N-methyltransferase (h) | Source | human recombinant (*E. coli*) |
| | Substrate | Glycine (100 µM) |
| | Tracer | SAM (20 µM) |
| | Incubation | 30 min/22° C. |
| | Detection method | MS |
| | Reference: | SAH-d4 (IC50: 17 µM) |

TABLE 3-continued

Epigenetic binding assay details

| Assay | | Main Feature |
|---|---|---|
| Guanidinoacetate N-methyltransferase (h) | Source | human recombinant (*E. coli*) |
| | Substrate | Guanidineacetic acid (4 µM) |
| | Tracer | SAM (7 µM) |
| | Incubation | 30 min/22° C. |
| | Detection method | MS |
| | Reference: | SAH-d4 (IC50: 2.3 µM) |
| Histamine N-methyltransferase (h) | Source | human recombinant (*E. coli*) |
| | Substrate | Histamine (4 µM) |
| | Tracer | SAM (4 µM) |
| | Incubation | 30 min/22° C. |
| | Detection method | MS |
| | Reference: | SAH-d4 (IC50: 13 µM) |
| Nicotinamide N-methyltransferase (h) | Source | human recombinant (*E. coli*) |
| | Substrate | Nicotinamide (8 µM) |
| | Tracer | SAM (6 µM) |
| | Incubation | 15 min/22° C. |
| | Detection method | MS |
| | Reference: | SAH-d4 (IC50: 13 µM) |
| Phenylethanolamine N-methyltransferase (h) | Source | human recombinant (*E. coli*) |
| | Substrate | DL-Normetanephrine SAM (35 µM) |
| | Tracer | SAM (6 µM) |
| | Incubation | 45 min/22° C. |
| | Detection method | MS |
| | Reference: | SAH-d4 (IC50: 13 µM) |
| Thiopurine S-methyltransferase (h) | Source | human recombinant (*E. coli*) |
| | Substrate | 6-mercaptopurine (1.5 µM) |
| | Tracer | SAM (1.5 µM) |
| | Incubation | 30 min/22° C. |
| | Detection method | MS |
| | Reference: | SAH-d4 (IC50: 2.3 µM) |
| Ubiquitin modifying enzymes | | |
| BAP1 (h) [Misaghi et al. 2009] | Source | human recombinant (*E. coli*) |
| | Substrate | LanthaScreen DUB substrate |
| | Substrate concentration | 20 nM |
| | Incubation | 180 min/RT |
| | Detection method | LanthaScreen |
| | Reference: | Ubiquitin aldehyde (IC50: 0.23 µM) |
| USP 10 (h) [Horton et al. 2007] | Source | human recombinant (Sf9 cells) |
| | Substrate | LanthaScreen DUB substrate |
| | Substrate concentration | 10 nM |
| | Incubation | 60 min/22° C. |
| | Detection method | LanthaScreen |
| | Reference: | Ubiquitin aldehyde (IC50: 0.23 µM) |
| USP 14 (h) [Hu et al. 2005] | Source | human recombinant (Sf9 cells) |
| | Substrate | LanthaScreen DUB substrate |
| | Substrate concentration | 10 nM |
| | Incubation | 240 min/RT |
| | Detection method | LanthaScreen |
| | Reference: | Ubiquitin Aldehyde (0.004 µM) |
| USP 16 (h) [Horton et al. 2007] | Source | Human recombinant HEK 293 cells |
| | Substrate | LanthaScreen DUB substrate |
| | Substrate concentration | 20 nM |
| | Incubation | 180 min/22° C. |
| | Detection method | LanthaScreen |
| | Reference: | Iodoacetamide (3.5 µM) |
| USP 21(h) [Ye et al. 2011] | Source | human recombinant (*E. coli*) |
| | Substrate | LanthaScreen DUB substrate |
| | Substrate concentration | 10 nM |
| | Incubation | 15 min/RT |
| | Detection method | LanthaScreen |
| | Reference: | Ubiquitin aldehyde (IC50: 0.17 µM) |
| USP 7 (h) [Tian et al. 2011] | Source | human recombinant (Sf21 cells) |
| | Substrate | LanthaScreen DUB substrate |
| | Substrate concentration | 10 nM |
| | Incubation | 60 min/RT |
| | Detection method | LanthaScreen |
| | Reference: | Ubiquitin Aldehyde (0.11 µM) |

Results for the binding assays are shown below in Table 4.

Representative inhibition data for Compound 1 on binding example epigenetic targets is shown in Tables 5 to 8.

TABLE 4

Inhibition of Compounds 1 to 3 at 10 µM on binding of epigenetic interacting protein modules against reference compounds.

| Binding Assay | % Inhibition[A] Comp 1 | Comp 2 | Comp 3 | Reference Compound | IC$_{50}$ µM |
|---|---|---|---|---|---|
| Bromodomain | | | | | |
| ATAD2B (h) | 52 | 25 | 28 | Ischemin sodium salt | 76.6 |
| ASH1L (h) | 95 | 59 | 42 | JQ-1 | 13.8 |
| BAZ2A (h) | 56 | 17 | 16 | GSK2801 | 1.8 |
| BRPF1-1 (h) | −25 | −25 | −4 | Bromosporine | 0.026 |
| CECR2 (h) | 100 | 25 | 15 | Bromosporine | 0.062 |
| EP300 (h) | 89 | 37 | 40 | SGC-CBP30 | 0.050 |
| KAT2A (GCN5L2) (h) | 76 | 19 | 18 | JQ-1 | 45 |
| PCAF (h) | 37 | 16 | 3 | JQ-1 | 12 |
| PB1(2) (h) | 31 | 22 | 13 | PFI-3 | 68 |
| PB1(3) (h) | 38 | 13 | 6 | JQ-1 | 47 |
| PB1(4) (h) | 41 | −3 | 16 | Ischemin sodium salt | 6.8 |
| PHIP(2) (h) | 61 | 30 | 23 | SGC-CBP30 | 0.130 |
| SP140 (h) | 84 | 43 | 1 | Ischemin | 86 |
| SMARCA2 (h) | 83 | 21 | 18 | PFI-3 | 0.47 |
| TAF1(1) (h) | 48 | 17 | 17 | GSK2801 | 4.4 |
| SMARCA4 (h) | 53 | 16 | 13 | PFI-3 | 3 |
| TAF1(2)(h) | 62 | 28 | 22 | GSK2801 | 10 |
| BAZ2B (h) | 58 | 23 | 21 | GSK2801 | 1.8 |
| ATAD2A (h) | 100 | 16 | 9 | JQ-1 | 70 |
| BRD2(1) (h) | 60 | 89 | 19 | JQ-1 | 0.510 |
| BRD2(2) (h) | 58 | 22 | 18 | JQ-1 | 0.017 |
| BRD3(1) (h) | 47 | 17 | 13 | JQ-1 | 0.040 |
| BRD3(2) (h) | 35 | 25 | 1 | PFI-1 | 0.79 |
| BRD4(1) (h) | 49 | 11 | 8 | JQ-1 | 0.018 |
| BRD4(2) (h) | 76 | 16 | 13 | PFI-1 | 1.3 |
| BRDT(1) (h) | 43 | 23 | 29 | JQ-1 | 0.110 |
| CREBBP (h) | 65 | 21 | 17 | SGC-CBP30 | 0.120 |
| FALZ (h) | 42 | 18 | 5 | I-CBP112 | 24.5 |
| Chromodomain | | | | | |
| CBX1 (h) | 15 | 0 | −1 | NA | |
| CBX2 (h) | 17 | 6 | 3 | NA | |
| CBX4 (h) | 25 | 29 | 40 | NA | |
| CBX6 (h) | −1 | 27 | 58 | NA | |
| CBX5 (h) | 25 | 24 | 25 | NA | |
| CBX7 (h) | 25 | 33 | 43 | NA | |
| CBX8 (h) | 27 | 31 | 23 | NA | |
| MBT domain | | | | | |
| L3MBTL1 | 41 | 61 | 59 | NA | |
| L3MBTL3 (h) | 22 | 29 | 33 | NA | |
| PHD domain | | | | | |
| SP140 (h) | 74 | 0 | 2 | NA | |
| TRIM 33 (h) | 59 | 3 | −2 | NA | |
| UHRF1 (108-286) (h) | 73 | 34 | 29 | NA | |
| Tudor domain | | | | | |
| PHF20(1) | 7 | 2 | 2 | NA | |

[A] % Inhibition of Control Specific Binding
NA Not-applicable

TABLE 5

ASH1L (h) bromodomain

| Conc. | 1$^{st}$ | 2$^{nd}$ | Mean |
|---|---|---|---|
| 3.0E−09M | −2.6 | −8.2 | −5.4 |
| 3.0E−08M | −12.3 | 1.8 | −5.2 |
| 3.0E−07M | −0.2 | −2.9 | −1.6 |
| 3.0E−06M | 17.0 | 28.0 | 22.5 |
| 3.0E−05M | 100.6 | 99.6 | 100.1 |

TABLE 6

CECR2(h) bromodomain binding curve

| Conc. | 1$^{st}$ | 2$^{nd}$ | Mean |
|---|---|---|---|
| 3.0E−09M | 5.9 | 2.4 | 4.2 |
| 3.0E−08M | −0.9 | −1.7 | −1.3 |
| 3.0E−07M | −1.5 | 0.9 | −0.3 |
| 3.0E−06M | 7.3 | 8.6 | 7.9 |
| 3.0E−05M | 99.4 | 99.6 | 99.5 |

TABLE 7

SP140 (h) bromodomain binding curve.

| Conc. | 1$^{st}$ | 2$^{nd}$ | Mean |
|---|---|---|---|
| 3.0E−09M | −6.0 | −8.6 | −7.3 |
| 3.0E−08M | −9.7 | −14.6 | −12.1 |
| 3.0E−07M | −14.1 | −11.0 | −12.6 |
| 3.0E−06M | 8.4 | 11.3 | 9.9 |
| 3.0E−05M | 102.3 | 102.3 | 102.3 |

TABLE 8

UHRF1(108-286) (h) binding curve.

| Conc. | 1$^{st}$ | 2$^{nd}$ | Mean |
|---|---|---|---|
| 3.0E−09M | −11.9 | −13.1 | −12.5 |
| 3.0E−08M | −13.3 | −12.6 | −12.9 |
| 3.0E−07M | −12.1 | −13.2 | −12.7 |
| 3.0E−06M | −1.8 | −0.1 | −0.9 |
| 3.0E−05M | 81.5 | 83.3 | 82.4 |

TABLE 9

IC$_{50}$ values from inhibition/concentration-response curves of compounds 1 and 2 for binding of epigenetic interacting protein modules against reference compounds.

| | Compound 1 IC$_{50}$ (µm) | 2 IC$_{50}$ (µm) | Reference Comp. | Reference IC$_{50}$ (µm) |
|---|---|---|---|---|
| Bromodomain | | | | |
| ASH1L (h) | 4.2 | | JQ-1 | 8.7 |
| ATAD2A (h) | 3.1 | | Ischemin | 5.2 |
| BRD2(1) (h) | | 22 | 1-BET 151 | 0.028 |
| BRD4(2) (h) | 5.6 | | PFI-1 | 1.1 |
| CECR2(h) | 5 | | Bromosporine | 0.14 |
| CREBBP (h) | 3.4 | | SGC-CBP30 | 0.046 |

TABLE 9-continued

IC$_{50}$ values from inhibition/concentration-response curves of compounds 1 and 2 for binding of epigenetic interacting protein modules against reference compounds.

| | Compound 1 IC$_{50}$ (μm) | Compound 2 IC$_{50}$ (μm) | Reference Comp. | Reference IC$_{50}$ (μm) |
|---|---|---|---|---|
| EP300 (h) | 4.5 | | SGC-CBP30 | 0.068 |
| KAT2A (GCN5L2) (h) | 3.9 | | GSK2801 | 10 |
| SP140 (h) | 3.8 | | Ischemin | 11 |
| PHD domain | | | | |
| SP140 (h) | 4.6 | | NA | NA |
| UHRF1(108-286) (h) | 11 | | NA | NA |

TABLE 10

Inhibition of compounds 1 to 3 at 10 μM on activity of epigenetic enzymes against references.

| Assay | % Inhibition[a] Comp 1 | Comp 2 | Comp 3 | Reference Compound | IC$_{50}$ μm |
|---|---|---|---|---|---|
| Cell-based detection methyl modifications | | | | | |
| H3K27 ac | −16 | −12 | −11 | (Not-applicable) | NA |
| H3K27 me2-1 | −2 | 3 | 2 | NA | |
| H3K27 me3 | −8 | −7 | 0 | NA | |
| H3K36 me2 | 10 | 7 | −8 | NA | |
| H3K4 me2 | −5 | −1 | −9 | NA | |
| H3K79 me2 | −2 | −16 | −5 | NA | |
| H3K9 ac | 17 | 3 | −1 | NA | |
| H3K9 me2 | 1 | 11 | 20 | NA | |
| Demethylases (KDMs) | | | | | |
| FBXL10 (h) | 37 | 7 | 22 | 2,4 PDCA | 0.61 |
| FBXL11 (h) | 34 | 2 | 11 | 2,4 PDCA | 1.5 |
| JARID1A (h) | 64 | −9 | 3 | 2,4 PDCA | 0.18 |
| JARID1B (h) | 70 | 6 | −2 | 2,4 PDCA | 0.15 |
| JARID1C (h) | 49 | −13 | 25 | 2,4 PDCA | 0.23 |
| JMJD1A (h) | 80 | 37 | −1 | 2,4 PDCA | 0.76 |
| JMJD2A (h) | 29 | −10 | 12 | 2,4 PDCA | 0.083 |
| JMJD2B (h) | 65 | 16 | 8 | 2,4 PDCA | 0.14 |
| JMJD2C (h) | 35 | 2 | 8 | 2,4 PDCA | 0.091 |
| JMJD2D (h) | 36 | −17 | 18 | 2,4 PDCA | 0.091 |
| JMJD2E (h) | 65 | 10 | 6 | 2,4 PDCA | 0.061 |
| JMJD3 (h) | 91 | 9 | 11 | 2,4 PDCA | 52 |
| LSD1 (h) | 10 | 10 | −3 | Tranylcypromine | 22 |
| PHF8(h) | 36 | −11 | 13 | Daminozide | 0.28 |
| UTX (h) | 68 | 5 | 27 | IOX1 | 0.15 |
| DNA methyltransferases (DNMTs) | | | | | |
| DNMT1 (h) | 10 | 4 | −5 | SAH | 0.23 |
| DNMT3b | −3 | −17 | −4 | SAH | 0.094 |
| DNMT3B/DNMT3L (h) | 23 | 27 | −20 | SAH | 0.045 |
| hDNMT3a | 3 | 3 | −31 | SAH | 0.052 |
| Histone acetyltransferases (HATs) | | | | | |
| CREBBP(h) | 74 | 78 | 43 | Garcinol | 1.5 |
| GCN5L2(h) | 11 | 5 | 1 | Anacardic Acid | 4.7 |
| HAT1(h) | −3 | 3 | −3 | Garcinol | 1.5 |
| MYST3(h) | 18 | 11 | 3 | Garcinol | 1.8 |
| MYST4(h) | 25 | 39 | 71 | Curcumin | 11 |
| pCAF(h) | −25 | −26 | −20 | Garcinol | 2.9 |
| TIP60(h) | 20 | 10 | −3 | Garcinol | 1.5 |
| Histone deacetylase (HDACs) | | | | | |
| HDAC1 (h) | −2 | −1 | −1 | trichostatin A | 0.0052 |
| HDAC2 (h) | 1 | 0 | −2 | trichostatin A | 0.024 |
| HDAC3 (h) | 1 | 1 | 3 | trichostatin A | 0.0068 |
| HDAC4 (h) | −73 | −20 | −11 | trichostatin A | 4.0 |

TABLE 10-continued

Inhibition of compounds 1 to 3 at 10 μM on activity of epigenetic enzymes against references.

| | % Inhibition[4] | | | Reference | |
|---|---|---|---|---|---|
| Assay | Comp 1 | Comp 2 | Comp 3 | Compound | IC$_{50}$ μm |
| HDAC5 (h) | −3 | −2 | −1 | trichostatin A | 1.0 |
| HDAC6 (h) | 12 | 2 | −18 | trichostatin A | 0.0074 |
| HDAC7 (h) | −111 | −6 | 16 | trichostatin A | 1.8 |
| HDAC8 (h) | −8 | −19 | 0 | trichostatin A | 0.41 |
| HDAC9 (h) | −50 | −1 | −9 | trichostatin A | 9.1 |
| HDAC10 (h) | 1 | 3 | 6 | trichostatin A | 0.0090 |
| HDAC11 (h) | 27 | −47 | −130 | scriptaid | 8.9 |
| Sirtuins | | | | | |
| sirtuin 1 (h) (inhibitor effect) | 2 | −3 | −5 | suramin | 7.9 |
| sirtuin 2 (h) (inhibitor effect) | −4 | 6 | −19 | suramin | 21 |
| sirtuin 3 (h) (inhibitor effect) | −14 | −8 | −3 | niacinamide | 21 |
| Sirtuin 6 (h) | 2 | 6 | −4 | EX-527 | 550 |
| Sirtuin 7 (h) | 7 | −2 | −8 | JFD00244 | 1300 |
| Methyltransferases (MTs) | | | | | |
| ASH1L | 3 | 20 | −54 | SAH | 9.1 |
| DOT1L (h) | −5 | 18 | 13 | SAH | 0.14 |
| EHMT1 (h) | 13 | 9 | 63 | SAH | 0.18 |
| EZH1/EED/SUZ12 (h) | −1 | 3 | −12 | SAH | 8.4 |
| EZH2/EED/SUZ12 (h) (PRC2 complex) | 19 | 26 | 4 | SAH | 22 |
| G9a (h) | 86 | 64 | 49 | SAH | 2.1 |
| hSMYD2 | 12 | 5 | −12 | SAH | 0.16 |
| MLL complex (h) | 2 | 22 | 11 | SAH | 0.97 |
| MLL2(h) complex | 6 | 3 | −15 | SAH | 24 |
| MLL3(h) complex | −22 | −21 | −33 | SAH | 9.0 |
| MLL4(h) complex | −16 | −18 | −4 | SAH | 0.55 |
| NSD1 (h) | 69 | 29 | −10 | chaetocin | 0.13 |
| NSD3/WHSC1L1 (h) | −17 | 11 | −35 | Suramin | 1.5 |
| PRDM9 (h) | 9 | 5 | 4 | SAH | 370 |
| PRMT1 (h) | 16 | 26 | −1 | SAH | 0.094 |
| PRMT3 (h) | 22 | 50 | 14 | SAH | 0.86 |
| PRMT4 (h) | 90 | 84 | 77 | SAH | 0.094 |
| PRMT5 complex (h) | 8 | −8 | 9 | SAH | 0.65 |
| PRMT6 (h) | 49 | 57 | 34 | SAH | 0.053 |
| PRMT7 (h) | −2 | 0 | −36 | SAH | 0.86 |
| PRMT8 (h) | 5 | 24 | −26 | SAH | 0.14 |
| SETD2(h) | −9 | −4 | −11 | SAH | 1.2 |
| SETD7 (h) | 12 | 16 | −2 | SAH | 24 |
| SETD8 (h) | 4 | 25 | −10 | mercurochrome | 2.4 |
| SETDB1 (h) | 53 | 43 | 52 | SAH | 1.8 |
| SUV39H2 (h) | −8 | −16 | 14 | SAH | 24 |
| SUV4-20H2 (h) | 11 | 20 | −45 | SAH | 4.7 |
| WHSC1(h) (NSD2(h)) | 3 | 14 | 7 | Chaetocin | 0.48 |
| Kinases | | | | | |
| Aurora B (h) (substrate histone H3 full length) | 6 | 4 | −1 | Staurosporine | 0.038 |
| DAPK3/ZIP (substrate histone H3 full length) | 4 | 9 | 8 | Staurosporine | 0.0073 |
| Haspin (h) (substrate histone H3 full length) | 2 | 11 | 7 | Staurosporine | 0.032 |
| IKK alpha(h) (substrate histone H3 full length) | 26 | 28 | 14 | Staurosporine | 0.03 |
| MSK1(h) (substrate histone H3 full length) | 6 | 2 | 10 | Staurosporine | 0.015 |
| MSK2(h) (substrate histone H3 full length) | 9 | 12 | −1 | Staurosporine | 0.0058 |
| PIM1(h) (histone H3 full length substrate) | 22 | 11 | 5 | Staurosporine | 0.025 |
| PKBalpha/AKT1(h) (substrate histone H3 full length) | −1 | −19 | −15 | Staurosporine | 0.0073 |
| PKBbeta/AKT2(h) (substrate histone H3 full length) | 13 | 11 | 12 | Staurosporine | 0.021 |

TABLE 10-continued

Inhibition of compounds 1 to 3 at 10 µM on activity of epigenetic enzymes against references.

| Assay | % Inhibition[4] | | | Reference | |
|---|---|---|---|---|---|
| | Comp 1 | Comp 2 | Comp 3 | Compound | $IC_{50}$ µm |
| PKBgamma/AKT3(h) (substrate histone H3 full length) | 5 | −7 | 3 | Staurosporine | 0.03 |
| Rsk2(h) (substrate histone H3 full length) | 5 | 7 | −4 | Staurosporine | 0.007 |
| Small molecule methyltransferases | | | | | |
| Catechol O-methyltransferase (h) | 6 | 1 | 0 | SAH-d4 | 14 |
| Glycine N-methyltransferase (h) | 55 | 5 | −11 | SAH-d4 | 17 |
| Guanidinoacetate N-methyltransferase (h) | 8 | −1 | −1 | SAH-d4 | 2.3 |
| Histamine N-methyltransferase (h) | 18 | −2 | 18 | SAH-d4 | 13 |
| Nicotinamide N-methyltransferase (h) | 13 | −2 | −2 | SAH-d4 | 13 |
| Phenylethanolamine N-methyltransferase (h) | 23 | 9 | 5 | SAH-d4 | 3.9 |
| Thiopurine S-methyltransferase (h) | 40 | 28 | 19 | SAH-d4 | 2.3 |
| Ubiquitin modifying enzymes | | | | | |
| BAP1 (h) | 1 | −9 | 24 | Ubiquitin Aldehyde | 0.23 |
| USP 10 (h) | 7 | 2 | −7 | N-Methylmaleimide | 1000 |
| USP 14 (h) | 1 | 0 | −24 | Ubiquitin Aldehyde | 0.004 |
| USP 16 (h) | 11 | 14 | 12 | Iodoacetamide | 3.5 |
| USP 21 (h) | −18 | 3 | 3 | Ubiquitin aldehyde | 0.17 |
| USP 7 (h) | −18 | −14 | 9 | Ubiquitin Aldehyde | 0.11 |

[4] % Inhibition of Control Values

TABLE 11

$IC_{50}$ values from inhibition/concentration-response curves of compounds 1, 2 and 4 for inhibition of epigenetic enzymes against reference compounds.

| Enzyme and Cell-based assays | Compound | | | Reference | |
|---|---|---|---|---|---|
| | 1 $IC_{50}$ (µM) | 2 $IC_{50}$ (µM) | 4 $IC_{50}$ (µM) | Reference Compound | $IC_{50}$ (µM) |
| Demethylases | | | | | |
| JARID1A (h) | 9.6 | | | 2,4 PDCA | 0.099 |
| JARID1B (h) | 3.6 | | | 2,4 PDCA | 0.12 |
| JMJD1A (h) | 4.5 | | | 2,4 PDCA | 3.9 |
| JMJD2B (h) | 12 | | | 2,4 PDCA | 0.095 |
| JMJD2E (h) | 4.7 | | | 2,4 PDCA | 0.11 |
| JMJD3 (h) | 14 | | | 2,4 PDCA | 73 |
| UTX (h) | 6.7 | | | IOX1 | 0.056 |
| Histone acetyltransferases | | | | | |
| CREBBP(h) | 3.9 | 6.1 | | Garcinol | 5.4 |
| MYST4 (h) | | | 4.2 | Curcumin | 8.9 |
| Histone methyltransferases | | | | | |
| G9a (h) | 11 | 5.4 | | SAH | 4.6 |
| NSD1 (h) | 4.9 | | | chaetocin | 0.24 |
| PRMT4 (h) | 4.7 | 5.4 | 4.7 | SAH | 0.056 |

Results: Epigenetic Targets, Diseases and Cancer

Epigenetic modifications can have a role in the development of a variety of diseases. Epigenetic regulation involves hierarchical covalent modification of DNA and proteins that package such as histones. DNA is regulated by methylation and demethylation on the cytosine residues. DNA methylation is mediated by members of the DNA-methyl transferase family (DNMT1, DNMT3A and DNMT3B) whereas demethylation is mediated by the family ten-eleven translocation (TET1-3). Besides methylation and demethylation, histone is also regulated by acetylation and deacetylation. The key proteins that mediate epigenetic signaling though acetylation and methylation of histones comprise histone acetyltransferases (HATs), histone deacetylases (HDMs), protein methyltransferases (PMTs) including lysine methyltransferases (KMTs) protein arginine methyltransferases (PRMTs), and bromodomain-containing proteins and proteins that bind to methylated histones (Arrowsmith et al., 2012; Plass et al., 2013; Tough et al., 2014; Biggar and Li, 2015).

Bromodomain Containing Proteins

Compound 1 showed significant inhibitory activity towards many of the bromodomain containing proteins (Table 10), in particular ASH1L, CECR2, EP300, KAT2A, PHIP(2), SP140, SMARCA2, TAF1(2), ATAD2A, BRD2(1), BRD4(2) and CREBBP. Compound 2 only showed significant activity towards BRD2(1). Recent studies have implicated bromodomain (BRD) containing proteins in a wide range of human diseases, including cancer (Taverna et al., 2007; Prinjha et al., 2012; Biggar and Li, 2015). The most investigated member of BRD containing proteins (BCPs) as drug targets is the BET family proteins. Currently, there are several BET inhibitors in various stages of clinical trials including RVX-208, I-BET 762, OTX 015, CPI-0610 and TEN-010 (see Table 14 in Tough et al., 2014).

In addition, JQ1 and I-BET have been shown to interact with NF-κB and induce apoptosis in drug resistant leukemia (Ciceri et al., 2014). NF-κB plays a central role inflammation and unresolved inflammation is involved in many disease states including cancer.

Several bromodomain containing proteins, including ASH1L, ATAD2A/B, BAZ2A/B, CECR2, EP300, KAT2A, PHIP(2), PB1, SMARCA2/4, BRD2/4 and CREBBP, have been shown to be up-regulated in many types of cancers (Tough et al., 2014; Fu et al, 2015). Hence, BRDs are therefore therapeutic targets for cancer. BRD-containing domains have been linked to the development of a number of extremely aggressive tumours containing BRD4-NUT and BRD3-NUT. CREBBP mutations have been identified in relapsed acute lymphoblastic leukaemia and are very common in diffuse large B-cell lymphoma and follicular lymphoma, Hodgkin's lymphoma. CREBBP and the related HAT are highly expressed in advanced prostate cancer and expression levels have been linked with patient survival. ATAD2 is over expressed in more than 70% of breast tumours and higher protein levels correlate with poor overall survival and disease recurrence (Ciro et al., 2009). ATAD2B is highly expressed in glioblastoma and oligodendroglioma as well as breast carcinoma (Krakstad et al., 2015). BRD4 is linked to development of cervical cancer (Weidner-Glunde et al.; 2010).

Compound 1 showed good inhibitory activity against domain PHD (plant homology domain) containing domain proteins SP140, TRIM 33, UHRF1 (108-286)).

Methyltransferases

Compound 1 was a strong inhibitor of the lysine methyltransferase enzyme G9a whereas compounds 2 and 3 were weaker (Table 10). G9a is a multipotent regulator of gene expression which has been shown to be over expressed in many different types of cancers (See reviews for details: Shankar et al., 2013; Casciello et al., 2015). Compounds 1 to 3 strongly inhibited the activity of PRMT4 and moderately inhibited the activity of PRMT6. Dysregulated PRMT expression and activity have been observed in a variety of cancers and PRMT1-5 and 7 have been shown to be overexpressed or otherwise contribute to tumorigenesis whereas PRMT8, and 9 have not been implicated in oncogenesis (Fuhrmann et al., 2015). PRMT4 (CARM1) is necessary for NFκB target gene expression. Further study showed a link between PRMT4 and p300 acetyltransferase activity in NFκB recruitment and gene activation.

Demethylases

Compound 1 showed significant inhibitory activity towards many of the lysine demethylase enzymes (Table 10), in particular JARID1A, JARID1B, JMJD1A, JMJD2B, JMJD2E, JMJD3 and UTX. Aberrant expression and mutations of lysine demethylases have been linked to various cancers (Hojfeldt et al., 2013; Tough et al., 2014). Mutation of lysine demethylases including FBXL10, JMJD2A, JMJDB, JMJD2C, JARID1B and PHF2 have been shown to be overexpressed in breast, colorectal, lung, prostrate, bladder and other tumours; the functional significance of JMJD2C overexpression is further suggested by the presence of the JMJD2C gene within an amplified region of a chromosome in multiple cancers (Xiang et al., 2007; Couvelard el al., 2008; Roesch et al., 2010; He et al., 2011a; Berry and Janknecht, 2013; Kogure et al., 2013; Tzatsos et al., 2013).

Histone Acetyltransferases

The serrulatanes diterpenes showed significant inhibitory activity on histone acetyltransferases CREBBP and MYST4 (Table 10). Misregulation of histone acetyltransferase activity has been linked to many different pathogenic states including cancers, neurodegenerative disorders, and metabolic, respiratory, inflammatory and cardiovascular diseases (Adcock and Lee, 2006; Avvakumov and Cote, 2007; Grabiec et al., 2008; Ghizzo et al., 2011, Iyer et al., 2011; Pirooznia and Elefant, 2013).

TABLE 12

Enzyme and Cell-based stimulation assays for compounds 1 to 3 at 10 µM concentration

| Assay | % Stimulation Relative to Control | | | Reference Compound | $EC_{50}$ (µM) |
|---|---|---|---|---|---|
| | Comp 1 | Comp 2 | Comp 3 | | |
| H3K9 ac (increase) | −21 | −26 | −8 | (Not-applicable) | NA |
| noneH3K27 ac (increase) | −28 | −17 | −25 | NA | |
| sirtuin 1 (h) (activator effect) | −5 | −3 | −4 | Resveratrol | 27 |

Pharmacology Assays

The in vitro pharmacological studies were conducted by Eurofins PanLab (Taiwan) using the parameters shown in Table 13 with respect to appropriate literature references.

TABLE 13

Pharmacology assay methods.

| | |
|---|---|
| Angiotensin system | |
| Angiotensin AT2 [Lee et al. 2001] | |
| Source | Human recombinant CHO-K1 cells |
| Vehicle | 1.00% DMSO |
| Ligand | 0.050 nM [$^{125}$I] CGP-42112A |
| Non-Specific Ligand | 10.0 µM (Sar$^1$, Ile$^8$)-Angiotensin II |
| Incubation (Time/Temperature) | 3 hours @ 37° C. |
| Incubation Buffer | 50 mM Tris-HCl, pH 7.4, 5 mM MgCl$_2$, 1 mM EDTA, 0.1% BSA |
| Quantitation Method | Radio ligand Binding |
| Angiotensin, AT$_1$/ACE [Rubin et al. 1978] | |
| Source | Dunkin Hartley Guinea pig 600 ± 80.0 g ileum |
| Vehicle | 0.10% DMSO |
| Incubation (Time/Temperature) | 5 minutes @ 32° C. |
| Incubation Buffer | Krebs, pH 7.4 |
| Quantitation Method | Isotonic (cm changes) |
| Peptidase, Angiotensin Converting Enzyme [Bunning et al. 1983] | |
| Source | Rabbit lung |
| Substrate | 500 µM (N-3[2-furyl] acryloyl)-Phe-Gly-Gly (FAPGG) |
| Vehicle | 1.00% DMSO |
| Pre incubation (Time/Temperature) | 15 minutes @ 25° C. |
| Incubation (Time/Temperature) | 30 minutes @ 25° C. |
| Incubation Buffer | 50 mM HEPES, pH 7.5, 300 mM NaCl |
| Quantitation Method | Spectrophotometric quantitation of FAPGG |

TABLE 13-continued

Pharmacology assay methods.

Chemokines

*Chemokine CCR1 [Hesselgesser et al. 1998]*

| | |
|---|---|
| Source | Human recombinant Chem-2 cells |
| Vehicle | 1.00% DMSO |
| Ligand | 0.10 nM [$^{125}$I] MIP-1α |
| Non-Specific Ligand | 0.10 μM MCP-3 |
| Incubation (Time/Temperature) | 3 hours @ 25° C. |
| Incubation Buffer | 50 mM HEPES, pH 7.4, 5 mM MgCl2, 1 mM CaCl2, 0.2% BSA |
| Quantitation Method | Radio ligand Binding |

*Chemokine CCR2B [Gong et al. 1997]*

| | |
|---|---|
| Source | Human recombinant CHO-K1 cells |
| Vehicle | 1.00% DMSO |
| Ligand | 0.10 nM [$^{125}$I] MCP-1 |
| Non-Specific Ligand | 0.030 μM MCP-1 |
| Incubation (Time/Temperature) | 60 minutes @ 25° C. |
| Incubation Buffer | 50 mM Tris-HCl, pH 7.4, 5 mM MgCl2, 1 mM EDTA, 0.1% BSA |
| Quantitation Method | Radio ligand Binding |

*Chemokine CX3CR1 [Combadiere et al. 1998]*

| | |
|---|---|
| Source | Human recombinant Chem-1 cells |
| Vehicle | 1.00% DMSO |
| Ligand | 20.0 pM [$^{125}$I] Fractalkine |
| Non-Specific Ligand | 10 nM Fractalkine |
| Incubation (Time/Temperature) | 90 minutes @ 25° C. |
| Incubation Buffer | 50 mM HEPES, pH 7.5, 1 mM CaCl2, 5 mM MgCl2, 0.5% BSA, 0.1% NaN3 |
| Quantitation Method | Radio ligand Binding |

*Chemokine CXCR1/2 (IL-8, Non-Selective) [Grob et al. 1990]*

| | |
|---|---|
| Source | Human neutrophils |
| Vehicle | 1.00% DMSO |
| Ligand | 15.0 pM [$^{125}$I] IL-8 |
| Non-Specific Ligand | 10 nM IL-8 |
| Incubation (Time/Temperature) | 2 hours @ 4° C. |
| Incubation Buffer | 50 mM Tris-HCl, pH 7.4 1 mM EDTA, 5 mM MgCl2, 5 mg/ml BSA |
| Quantitation Method | Radio ligand Binding |

*Chemokine CXCR2 (IL-8RB) [Ahuja and Murphy 1996]*

| | |
|---|---|
| Source | Human recombinant CHO-K1 cells |
| Vehicle | 1.00% DMSO |
| Ligand | 15.0 pM [$^{125}$I] IL-8 |
| Non-Specific Ligand | 10 nM IL-8 |
| Incubation (Time/Temperature) | 60 minutes @ 25° C. |
| Incubation Buffer | 25 mM HEPES, pH 7.4, 2 mM CaCl2, 1 mM MgCl2, 0.2% BSA |
| Quantitation Method | Radio ligand Binding |

*Chemokine CXCR4 [Valenzuela-Fernandez 2002]*

| | |
|---|---|
| Source | Human recombinant Chem-1 cells |
| Vehicle | 1.00% DMSO |
| Ligand | 0.030 nM [$^{125}$I] SDF-1α |
| Non-Specific Ligand | 0.030 μM SDF-1α |
| Incubation (Time/Temperature) | 90 minutes @ 25° C. |
| Incubation Buffer | 50 mM HEPES, pH 7.4, 5 mM MgCl2, 1 mM CaCl2, 0.2% BSA |
| Quantitation Method | Radio ligand Binding |

Histone Deacetylases (HDACs)

*Deacetylase, Histone 1 [Strahl and Allis 2000]*

| | |
|---|---|
| Source | Human recombinant Insect Sf9 cells |
| Substrate | 25.0 μM Fluor-de-Lys deacetylase |
| Vehicle | 1.00% DMSO |
| Pre incubation (Time/Temperature) | 15 minutes @ 25° C. |
| Incubation (Time/Temperature) | 60 minutes @ 25° C. |
| Incubation Buffer | 25 mM Tris-HCl, pH 8.0, 2.7 mM KCl, 1 mM MgCl2, 137 mM NaCl |
| Quantitation Method | Spectrofluorimetric quantitation of Fluor-de-Lys deacetylsubstrate |

*Deacetylase, Histone 2 [Strahl and Allis 2000]*

| | |
|---|---|
| Source | Human recombinant Insect Sf9 cells |
| Substrate | 25.0 μM Fluor-de-Lys deacetylase |
| Vehicle | 1.00% DMSO |
| Pre incubation (Time/Temperature) | 15 minutes @ 25° C. |
| Incubation (Time/Temperature) | 60 minutes @ 25° C. |
| Incubation Buffer | 25 mM Tris-HCl, pH 8.0, 2.7 mM KCl, 1 mM MgCl2, 137 mM NaCl |
| Quantitation Method | Spectrofluorimetric quantitation of Fluor-de-Lys deacetylsubstrate |

Growth Factor

*Epidermal Growth Factor (EGF) [Dittadi et al. 1990]*

| | |
|---|---|
| Source | Human A431 cells |
| Vehicle | 1.00% DMSO |
| Ligand | 0.080 nM [$^{125}$I] EGF (human) |
| Non-Specific Ligand | 0.10 μM EGF (human) |
| Incubation (Time/Temperature) | 60 minutes @ 25° C. |
| Incubation Buffer | 50 mM HEPES, pH 7.7, 0.1% BSA, 1.2 mM CaCl2, 5 mM KCl, 1.2 mM MgSO4, 138 mM NaCl |
| Quantitation Method | Radio ligand Binding |

Other classes

*Catechol-O-Methyl Transferase (COMT) [Muller-Enoch et al. 1976]*

| | |
|---|---|
| Source | Porcine liver |
| Substrate | 1.0 μM Esculetin |
| Vehicle | 1.00% DMSO |
| Pre incubation (Time/Temperature) | 15 minutes @ 37° C. |
| Incubation (Time/Temperature) | 30 minutes @ 37° C. |
| Incubation Buffer | 36 mM Tris-HCl, pH 8.0, 1.35 mM DTT, 0.54 mM MgCl2, 30.6 μM SAM |
| Quantitation Method | Spectrofluorimetric quantitation of scopoletin |

*Phospholipase sPLA2-V [Tietge et al. 2005]*

| | |
|---|---|
| Source | Human E. coli |
| Substrate | 250 μM diheptanoyl thio-PC |
| Vehicle | 1.00% DMSO |
| Pre incubation (Time/Temperature) | 15 minutes @ 25° C. |
| Incubation (Time/Temperature) | 30 minutes @ 25° C. |
| Incubation Buffer | 16.25 mM Tris-HCl, 6.5 mM CaCl2, 65 mM KCl, 0.2 mM Triton X-100 |
| Quantitation Method | Spectrophotometric quantitation of heptanoyl thio-PC |

*Protein Tyrosine Phosphatase, PTPN1 (PTP1B) [Montalibet et al. 2005]*

| | |
|---|---|
| Source | Human recombinant E. coli |
| Substrate | 10.0 μM DiFMUP |
| Vehicle | 1.00% DMSO |
| Pre incubation (Time/Temperature) | 15 minutes @ 37° C. |
| Incubation (Time/Temperature) | 60 minutes @ 37° C. |
| Incubation Buffer | 50 mM HEPES, pH 7.2, 0.1% BSA, 1 mM DTT |
| Quantitation Method | Spectrofluorimetric quantitation of DiFMU |

*Steroid 5α-Reductase [Sun and Tu 1998]*

| | |
|---|---|
| Source | Wistar Rat liver |
| Substrate | 0.90 μM Testosterone |
| Vehicle | 1.00% DMSO |
| Pre incubation (Time/Temperature) | 15 minutes @ 37° C. |
| Incubation (Time/Temperature) | 30 minutes @ 37° C. |

TABLE 13-continued

Pharmacology assay methods.

| | |
|---|---|
| Incubation Buffer | 40 mM Potassium Phosphate, pH 6.5 containing 1 mM DTT, 50 µM NADPH |
| Quantitation Method | EIA quantitation of Testosterone |

Thioredoxin Reductase [Becker et al. 2000]

| | |
|---|---|
| Source | E. coli |
| Substrate | 1.0 mM 5,5'-Dithiobis (2-nitrobenzoic acid) (DTNB) |
| Vehicle | 1.00% DMSO |
| Pre incubation (Time/Temperature) | 15 minutes @ 25° C. |
| Incubation (Time/Temperature) | 60 minutes @ 25° C. |
| Incubation Buffer | 100 mM Potassium Phosphate, pH 7.4, 2 mM EDTA, 0.2 mg/ml BSA |
| Quantitation Method | Spectrophotometric quantitation of 5-Mercapto-2-nitrobenzoic acid |

Xanthine Oxidase [Hatano et al. 1990]

| | |
|---|---|
| Source | Bovine buttermilk |
| Substrate | 165 µM Xanthine |
| Vehicle | 1.00% DMSO |
| Pre incubation (Time/Temperature) | 15 minutes @ 25° C. |
| Incubation (Time/Temperature) | 30 minutes @ 25° C. |
| Incubation Buffer | 33.3 mM Potassium Phosphate, pH 7.5 |
| Quantitation Method | Spectrophotometric quantitation of Uric acid |

Histamine H1 [De Backer et al., 1993]

| | |
|---|---|
| Source | Human recombinant Chem-1 cells |
| Substrate | 1.00% DMSO |
| Vehicle | 1.20 nM [$^3$H] Pyrilamine |
| Pre incubation (Time/Temperature) | 1.0 µM Pyrilamine |
| Incubation (Time/Temperature) | 3 hours @ 25° C. |
| Incubation Buffer | 50 mM Tris-HCl, pH 7.4, 5 mM MgCl2 |
| Quantitation Method | Radio ligand Binding |

Histamine H2 [Ruat et al., 1990]

| | |
|---|---|
| Source | Human recombinant CHO-K1 cells |
| Vehicle | 1.00% DMSO |
| Ligand | 0.10 nM [$^{125}$I] Aminopotentidine |
| Non-Specific Ligand | 3.0 µM Tiotidine |
| Incubation (Time/Temperature) | 2 hours @ 25° C. |
| Incubation Buffer | 50 mM Phosphate, pH 7.4 |
| Quantitation Method | Radio ligand Binding |

Histamine H3 [Krueger et al., 2005]

| | |
|---|---|
| Source | Human recombinant Chem-1 cells |
| Substrate | 1.00% DMSO |
| Vehicle | 0.40 nM [$^3$H] N-α-Methylhistamine (NAMH) |
| Pre incubation (Time/Temperature) | 1.0 µM R(−)-α-Methylhistamine (RAMH) |
| Incubation (Time/Temperature) | 2 hours @ 25° C. |
| Incubation Buffer | 50 mM Tris-HCl, pH 7.4, 5 mM MgCl2, 0.1% BSA |
| Quantitation Method | Radio ligand Binding |

Histamine H4 [Liu et al., 2001]

| | |
|---|---|
| Source | Human recombinant Chem-1 cells |
| Substrate | 1.00% DMSO |
| Vehicle | 8.20 nM [$^3$H] Histamine |
| Pre incubation (Time/Temperature) | 1.0 µM Histamine |
| Incubation (Time/Temperature) | 90 minutes @ 25° C. |
| Incubation Buffer | 50 mM Tris-HCl, pH 7.4, 1.25 mM EDTA |
| Quantitation Method | Radio ligand Binding |

HMG-CoA Reductase [Kubo and Strott, 1987]

| | |
|---|---|
| Source | Human recombinant E. coli |
| Substrate | 2.50 µM [$^{14}$C]HMG-CoA |
| Vehicle | 1.00% DMSO |
| Pre incubation (Time/Temperature) | 15 minutes @ 37° C. |
| Incubation (Time/Temperature) | 20 minutes @ 37° C. |
| Incubation Buffer | 100 mM KH2PO4, pH 7.5, 8 mM G-6-P, 1 mM NADP, 4 mM EDTA, 2 mM DTT, 0.6 U/ml G-6-P-DH |
| Quantitation Method | Quantitation of [$^{14}$C] Mevalonate |

5-Lipoxygenase [Pufahl et al., 2007]

| | |
|---|---|
| Source | Human recombinant Insect Sf9 cells |
| Substrate | 25.0 µM Arachidonic acid |
| Vehicle | 1.00% DMSO |
| Pre incubation (Time/Temperature) | 5 minutes @ 25° C. |
| Incubation (Time/Temperature) | 20 minutes @ 25° C. |
| Incubation Buffer | 50 mM Tris-HCl, pH 7.4, 5 mM CaCl2, 2 mM EDTA, 1 µM ATP |
| Quantitation Method | Spectrofluorimetric quantitation of rhodamine 123 |

Lipid Peroxidase [Mansuy et al., 1986]

| | |
|---|---|
| Source | Dunkin Hartley Guinea pig liver microsomes |
| Substrate | Polyunsaturated fatty acid |
| Vehicle | 1.00% DMSO |
| Pre incubation (Time/Temperature) | 15 minutes @ 37° C. |
| Incubation (Time/Temperature) | 20 minutes @ 37° C. |
| Incubation Buffer | 0.25M Potassium Phosphate, pH 7.4, 0.1 mM EDTA |
| Quantitation Method | Spectrophotometric quantitation of Malondialdehyde |

Lipoxygenase 12-LO [Romano et al., 1993]

| | |
|---|---|
| Source | Human platelets |
| Substrate | 30.0 µM Arachidonic acid |
| Vehicle | 1.00% DMSO |
| Pre incubation (Time/Temperature) | 15 minutes @ 25° C. |
| Incubation (Time/Temperature) | 15 minutes @ 25° C. |
| Incubation Buffer | 50 mM Tris-HCl, pH 7.4, 0.1% Triton X-100 |
| Quantitation Method | Spectrophotometric quantitation of 12-HETE |

Monoamine Oxidase MAO-A [Urban et al., 1991]

| | |
|---|---|
| Source | Human recombinant Insect Hi5 cells |
| Substrate | 50.0 µM Kynuramine |
| Vehicle | 1.00% DMSO |
| Pre incubation (Time/Temperature) | 15 minutes @ 37° C. |
| Incubation (Time/Temperature) | 60 minutes @ 37° C. |
| Incubation Buffer | 100 mM Potassium Phosphate, pH 7.4 |
| Quantitation Method | Spectrofluorimetric quantitation of 4-hydroxyquinoline |

Monoamine Oxidase MAO-B [Urban et al., 1991]

| | |
|---|---|
| Source | Human recombinant Insect Hi5 cells |
| Substrate | 50.0 µM Kynuramine |
| Vehicle | 1.00% DMSO |
| Pre incubation (Time/Temperature) | 15 minutes @ 37° C. |
| Incubation (Time/Temperature) | 60 minutes @ 37° C. |
| Incubation Buffer | 100 mM Potassium Phosphate, pH 7.4 |
| Quantitation Method | Spectrofluorimetric quantitation of 4-hydroxyquinoline |

Myeloperoxidase [Svensson et al., 1987]

| | |
|---|---|
| Source | Human PMN leukocytes |
| Substrate | 20.0 mM Guaiacol |
| Vehicle | 1.00% DMSO |
| Pre incubation (Time/Temperature) | 15 minutes @ 25° C. |
| Incubation (Time/Temperature) | 5 minutes @ 25° C. |

TABLE 13-continued

Pharmacology assay methods.

| | |
|---|---|
| Incubation Buffer | 0.1M Sodium Phosphate, pH 7.4 |
| Quantitation Method | Spectrophotometric quantitation of Tetraguaiacol |

[3H]-2-Deoxy-D-glucose uptake[Yamamoto et al., 2006]

| | |
|---|---|
| Source | Rat L6 skeletal muscle cells |
| Substrate | 0.10% DMSO |
| Vehicle | 24 hours @ 37° C. |
| Pre incubation (Time/Temperature) | 15 minutes @ 37° C. |
| Incubation (Time/Temperature) | KRPH, pH 7.4 |
| Incubation Buffer | Radiometric quantitation of insulin-induced 2-DG uptake |
| Quantitation Method | Rat L6 skelet al muscle cells |

Adhesion and Transcription response

Adhesion, ICAM-1-Mediated [Cobb et al. 1992]

| | |
|---|---|
| Source | Human |
| Vehicle | 0.40% DMSO |
| Ligand | 0.030 nM [$^{125}$I] SDF-1α |
| Non-Specific Ligand | 0.030 µM SDF-1α |
| Incubation (Time/Temperature) | 30 minutes @ 37° C. |
| Incubation Buffer | 25 mM HEPES, pH 7.4, RPMI-1640, 1% FBS |
| Quantitation Method | Spectrofluorimetric quantitation of adhesion |

Adhesion, VCAM-1-Mediated [Stoltenborg et al. 1994]

| | |
|---|---|
| Source | Human |
| Vehicle | 0.40% DMSO |
| Incubation (Time/Temperature) | 60 minutes @ 37° C. |
| Incubation Buffer | 25 mM HEPES, pH 7.4, RPMI-1640, 1% FBS |
| Quantitation Method | Spectrofluorimetric quantitation of adhesion |

Transcription Response, NF-κB [Lenardo and Baltimore 1989]

| | |
|---|---|
| Source | Human |
| Vehicle | 0.50% DMSO |
| Incubation (Time/Temperature) | 4 hours @ 37° C. |
| Incubation Buffer | RPMI-1640, pH 7.4 |
| Quantitation Method | Spectrofluorimetric quantitation of β-galactosidase |

The results of pharmacological assays are shown in Table 14.

TABLE 14

Pharmacological activity of compounds 1 to 3 at 10 µM.

| | % Control Response | | | Assay |
|---|---|---|---|---|
| Ascii Assay Name | 1 | 2 | 3 | Year |
| Angiotensin system | | | | |
| Angiotensin AT2 | 29 | 18 | 9 | 2015 |
| Angiotensin, AT 1/ACE - Agonist | 0 | 0 | 0 | 2015 |
| Angiotensin, AT 1/ACE - Antagonist | 34 | 10 | 17 | 2015 |
| Peptidase, Angiotensin Converting Enzyme | 0 | -3 | -3 | 2015 |
| Chemokines | | | | |
| Chemokine CCR1 | 33 | -3 | -5 | 2015 |
| Chemokine CCR2B | 1 | -23 | -10 | 2015 |
| Chemokine CX3CR1 | -1 | 5 | 7 | 2015 |
| Chemokine CXCR1/2 (IL-8, Non-Selective) | 30 | -28 | -1 | 2015 |
| Chemokine CXCR2 (IL-8RB) | 12 | -7 | 1 | 2015 |
| Chemokine CXCR4 | 14 | -27 | -13 | 2015 |
| Histone Deacetylases (HDACs) | | | | |
| Deacetylase, Histone 1 | 17 | 23 | NA | 2014 |
| Deacetylase, Histone 1 | -27 | -18 | -26 | 2015 |

TABLE 14-continued

Pharmacological activity of compounds 1 to 3 at 10 µM.

| | % Control Response | | | Assay |
|---|---|---|---|---|
| Ascii Assay Name | 1 | 2 | 3 | Year |
| Deacetylase, Histone 2 | 56 | 44 | NA | 2014 |
| Deacetylase, Histone 2 | 34 | 21 | 12 | 2015 |
| Deacetylase, Histone 3 | -5 | 25 | NA | 2014 |
| Deacetylase, Histone 4 | 4 | -5 | NA | 2014 |
| Deacetylase, Histone 5 | -9 | -11 | NA | 2014 |
| Deacetylase, Histone 6 | 0 | -17 | NA | 2014 |
| Deacetylase, Histone 7 | 1 | -16 | NA | 2014 |
| Deacetylase, Histone 8 | 29 | 13 | NA | 2014 |
| Deacetylase, Histone 9 | -14 | -13 | NA | 2014 |
| Deacetylase, Histone 10 | 11 | 9 | NA | 2014 |
| Deacetylase, Histone 11 | 9 | 5 | NA | 2014 |
| Sirtuins | | | | |
| Deacetylase, Sirtuin SIRT1 | 6 | -3 | NA | 2014 |
| Deacetylase, Sirtuin SIRT2 | 0 | 26 | NA | 2014 |
| Deacetylase, Sirtuin SIRT3 | -6 | -9 | NA | 2014 |
| Deacetylase, Sirtuin SIRT5 | -16 | 24 | NA | 2014 |
| Deacetylase, Sirtuin SIRT6 | 35 | 18 | NA | 2014 |
| Growth Factor | | | | |
| Epidermal Growth Factor (EGF) | -8 | -9 | 4 | 2015 |
| Nitric Oxide Synthases | | | | |
| Nitric Oxide Synthase, Endothelial (eNOS) | 6 | 5 | NA | 2014 |
| Nitric Oxide Synthase, Inducible (iNOS) | 16 | 7 | NA | 2014 |
| Nitric Oxide Synthase, Neuronal (nNOS) | 14 | 5 | NA | 2014 |
| Other classes | | | | |
| Catechol-O-Methyl Transferase (COMT) | 0 | -1 | 3 | 2015 |
| Histamine H1 | 85 | 66 | NA | 2014 |
| Histamine H1 | 97 | 60 | 50 | 2015 |
| Histamine H2 | 67 | 24 | NA | 2014 |
| Histamine H2 | 73 | -5 | 66 | 2015 |
| Histamine H3 | -10 | -5 | NA | 2014 |
| Histamine H3 | 12 | 24 | 1 | 2015 |
| Histamine H4 | 50 | 16 | NA | 2014 |
| Histamine H4 | 12 | -1 | 10 | 2015 |
| HMG-CoA Reductase | 29 | 27 | 24 | 2015 |
| 5-Lipoxygenase | 79 | 53 | 67 | 2015 |
| Lipid Peroxidase | 98 | 53 | 74 | 2015 |
| Lipoxygenase 12-LO | 60 | 40 | 29 | 2015 |
| Monoamine Oxidase MAO-A | 91 | 34 | 27 | 2015 |
| Monoamine Oxidase MAO-B | 75 | 39 | 18 | 2015 |
| Myeloperoxidase | 52 | 5 | NA | 2014 |
| Myeloperoxidase | 27 | 1 | -7 | 2015 |
| Phospholipase sPLA2-V | 4 | 3 | 0 | 2015 |
| Protein Tyrosine Phosphatase, PTPN1 (PTP1B) | 20 | 3 | -3 | 2015 |
| Steroid 5alpha-Reductase | 2 | -6 | 3 | 2015 |
| Thioredoxin Reductase | 71 | 6 | NA | 2014 |
| Thioredoxin Reductase | 35 | 12 | 9 | 2015 |
| Xanthine Oxidase | 14 | 20 | 27 | 2015 |

Pharmacological Assays: Further Lipoxygenase, Lipid Peroxidase and Monoamine Oxidase Assays Further in vitro pharmacological studies were conducted by Eurofins Panlabs (Taiwan) Ltd. using the parameters shown in Table 3 with respect to appropriate literature references.

For the Compound 1 5-lipoxygenase, lipid peroxidase and monoamine oxidase MAO-A assays, the inhibition/concentration-response curve concentrations were 10, 3, 1, 0.3, 0.1, 0.03 and 0.01 µM (Table 15).

TABLE 15

Activity of Compound 1 against 5-lipoxygenase, lipid peroxidase and monoamine oxidase (MAO-A) $IC_{50}$ (μM) and reference compounds

| Assay | Compound 1 $IC_{50}$ μM | Reference Compound | $IC_{50}$ μM |
|---|---|---|---|
| 5-Lipoxygenase | 2.31 | NDGA | 0.64 |
| Lipid Peroxidase | 1.47 | N-Propyl Gallate | 206 |
| Monoamine oxidase A (MAO-A) | 6.74 | Clorgyline | 0.00143 |

Compounds 1 to 3 are potent to moderately potent inhibitors of lipid oxidation (Tables 14 and 15). Therefore, they can be used in blocking inflammation induced by oxidative damage in cancer.

5-Lipoxygenase promotes lipid oxidation and produces leukotrienes. Compounds 1 to 3 are potent to moderately potent inhibitor of 5-lipoxygenase (Tables 14 and 15). Therefore, they can be used in blocking inflammation induced by oxidative damage and inflammatory pathophysiology in cancer.

12-Lipoxygenase promotes lipid oxidation and produces leukotrienes. Compounds 1 to 3 are moderately potent inhibitor of 12-lipoxygenase (Table 14). Therefore, they can be used in blocking inflammation induced by oxidative damage and inflammatory pathophysiology in cancer.

Compound 1 is a potent inhibitor of monoamine oxidase A and B (Tables 14 and 15). Therefore, it can be used in blocking oxidative damage induced by oxidation of monoamines and as an antidepressant in cancer.

Compounds 1 to 3 inhibit binding of the radioligand to histamine H1 and H2 receptors (Table 14). Therefore, they can be used in blocking inflammation induced by histamine resulting in anti-inflammatory action useful in cancer treatment.

Compound 1 inhibited the activity of thioredoxin reductase (Table 14). Inhibition of thioredoxin reductase activity can be used to selectively increasing oxidative stress in cancer cell while reducing oxidative stress in normal cells and Compound 1 inhibited the activity of myeloperoxidase (Table 14). Inhibition of myeloperoxidase activity can be used to selectively reduce oxidative stress in immune cells during cancer therapy.

Figure 7:
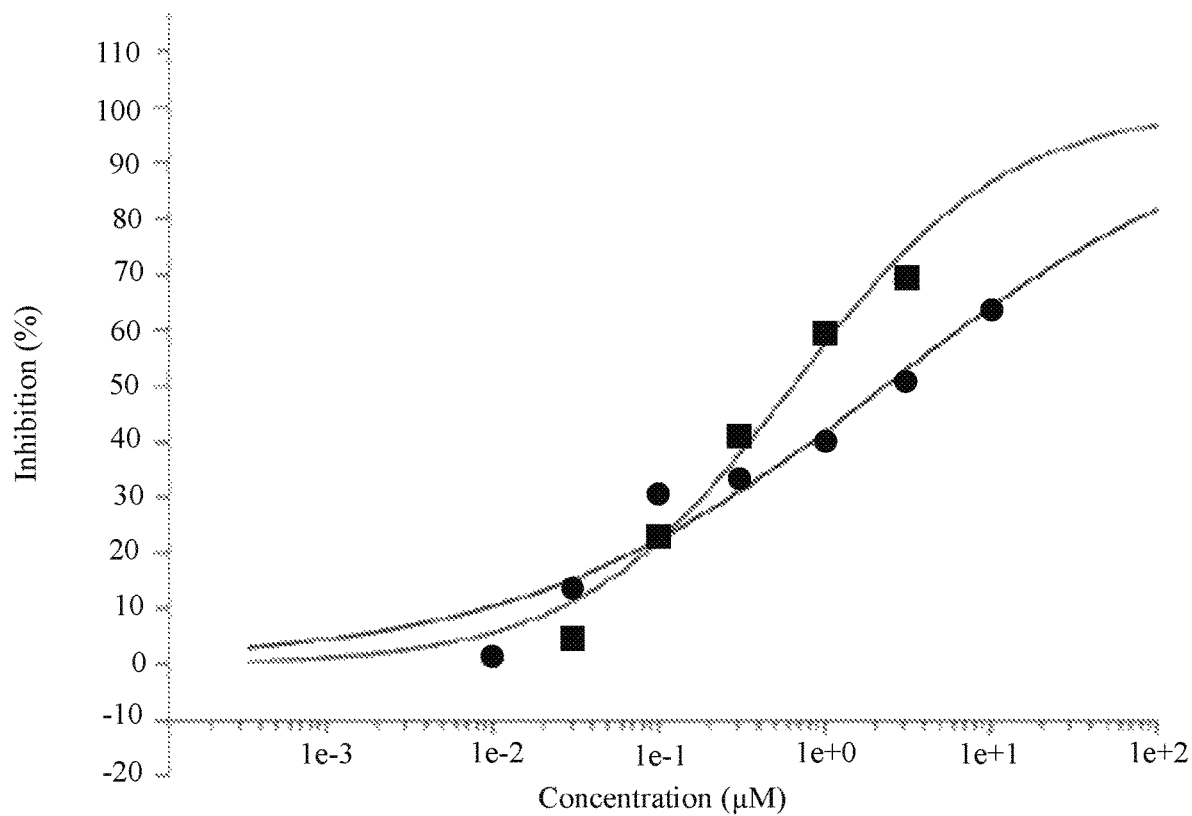
FIG. 7 shows binding against 5-lipoygenase for Compound 1 (circles, $IC_{50}$=2.3 μM) and a reference compound NSA (squares, $IC_{50}$=0.64 μM).
Figure 8:
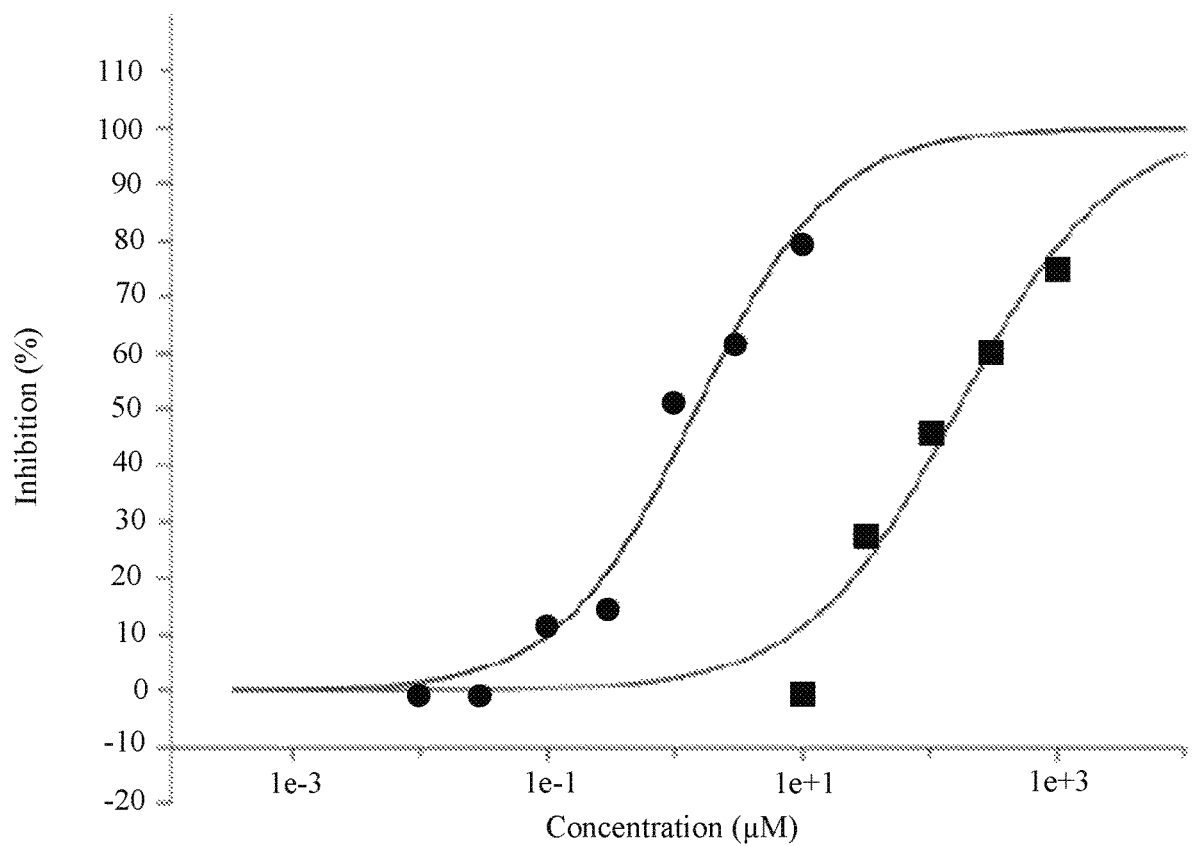
FIG. 8 shows binding against lipid peroxidase for Compound 1 (circles, $IC_{50}$=1.47 μM) and a reference compound N-propyl gallate (squares, $IC_{50}$=206 μM).
Figure 9:
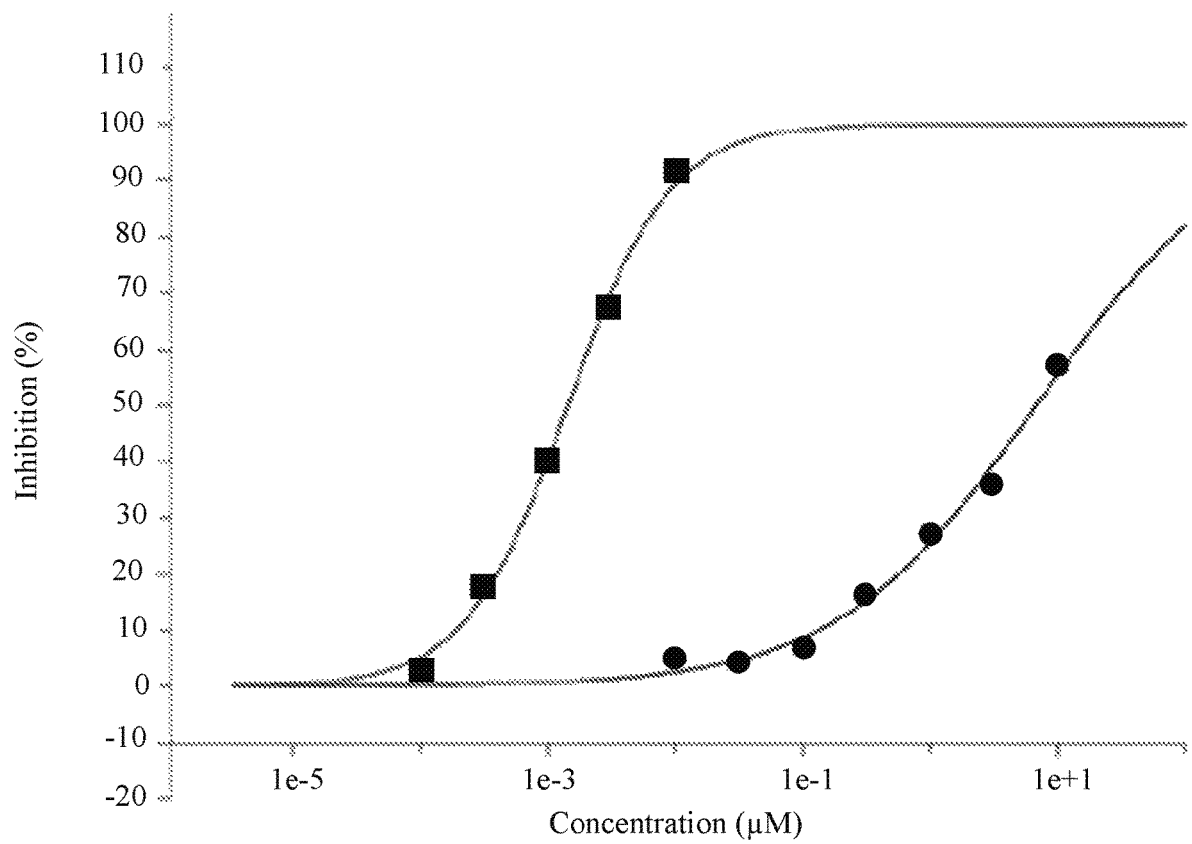
FIG. 9 shows binding against monoamine oxidase (MAO-A) for Compound 1 (circles, $IC_{50}$=6.47 μM) and a reference compound clorgyline (squares, $IC_{50}$=1.43 nM).

Curves showing binding against 5-lipoxygenase; lipid peroxidase; and monoamine oxidase (MAO-A) for Compound 1 are presented in FIGS. 7 to 9.

Pharmacology Assays: 2-Deoxy-D-Glucose Uptake into Muscle Cells

TABLE 16

Effect of compounds 1 to 4 at 10 μM on 2-deoxy-D-glucose uptake into muscle cells.

| Ascii Assay Name | % Control Response | | | | Assay Year |
|---|---|---|---|---|---|
| | 1 | 2 | 3 | 4 | |
| [3H]-2-Deoxy-D-glucose uptake - agonist* | −61 | 15 | −52 | −45 | 2016 |
| [3H]-2-Deoxy-D-glucose uptake - antagonist* | 152 | 67 | 195 | 151 | 2016 |

*agonist - Increase in 2-DG uptake relative to insulin response
*antagonist - Inhibition of insulin-induced 2-DG uptake Pharmacology Assays: Adhesion and Transcription Response

TABLE 17

Dose response and $IC_{50}$ values for the pharmacological activity of representative serrulatane diterpenes.

| Ascii Assay Name | Conc μM | Compound 1 Resp Av % | Compound 1 $IC_{50}$ μM | Compound 2 Resp Av % | Compound 2 $IC_{50}$ μM | Compound 3 Resp Av % | Compound 3 $IC_{50}$ μM |
|---|---|---|---|---|---|---|---|
| Adhesion, ICAM-1-Mediated | 10 | 6 | >10 | 5 | >10 | 7 | >10 |
| Adhesion, ICAM-1-Mediated | 1 | 3 | >10 | 4 | >10 | 6 | >10 |
| Adhesion, ICAM-1-Mediated | 0.1 | −2 | >10 | 3 | >10 | −4 | >10 |
| Adhesion, ICAM-1-Mediated | 0.01 | 1 | >10 | 0 | >10 | −5 | >10 |
| Adhesion, ICAM-1-Mediated | 0.001 | −4 | >10 | 7 | >10 | −7 | >10 |
| Adhesion, VCAM-1-Mediated - Antagonist | 10 | −7 | >10 | −18 | >10 | −4 | >10 |
| Adhesion, VCAM-1-Mediated - Antagonist | 1 | −9 | >10 | −18 | >10 | 7 | >10 |
| Adhesion, VCAM-1-Mediated - Antagonist | 0.1 | 3 | >10 | −8 | >10 | 13 | >10 |
| Adhesion, VCAM-1-Mediated - Antagonist | 0.01 | 0 | >10 | −17 | >10 | 18 | >10 |
| Adhesion, VCAM-1-Mediated - Antagonist | 0.001 | 13 | >10 | −7 | >10 | 13 | >10 |
| Transcription Response, NF-kappaB - Antagonist | 10 | 103 | 1.4 | 34 | >10 | −19 | >10 |
| Transcription Response, NF-kappaB - Antagonist | 1 | 17 | 1.4 | 10 | >10 | 1 | >10 |
| Transcription Response, NF-kappaB - Antagonist | 0.1 | 0 | 1.4 | −3 | >10 | −7 | >10 |
| Transcription Response, NF-kappaB - Antagonist | 0.01 | −5 | 1.4 | −7 | >10 | −11 | >10 |

TABLE 17-continued

Dose response and IC$_{50}$ values for the pharmacological activity of representative serrulatane diterpenes.

| | | Compound 1 | | Compound 2 | | Compound 3 | |
|---|---|---|---|---|---|---|---|
| Ascii Assay Name | Conc μM | Resp Av % | IC$_{50}$ μM | Resp Av % | IC$_{50}$ μM | Resp Av % | IC$_{50}$ μM |
| Transcription Response, NF-kappaB - Antagonist | 0.001 | −25 | 1.4 | −7 | >10 | −16 | >10 |

Nuclear factor kappa B (NF-κB) was first discovered as a factor in the nucleus of B lymphocytes that binds to the enhancer of kappa light chain of immunoglobulin and is also a lymphoid specific (Sen and Baltimore, 1986). The NF-κB family includes RelA/p65, NF-κB1 p50/p105, NF-κB2 p52/p100, C-Rel and RelB. These proteins contain an N-terminal Rel homology domain (RFID) that is responsible for binding to DNA and other proteins and harbour a nuclear leading sequence (NLS). NF-κB proteins function as a dimeric transcription factor that regulates the expression of genes influencing a broad range of biological processes including innate and adaptive immunity, inflammation, stress responses, B-cell development and lymphoid organogenesis (Pantano et al., 2006; Brigelius-Fohê and Fohê 2011; Ghosh et al., 2012; Akdis et al., 2017).

Figure 10:
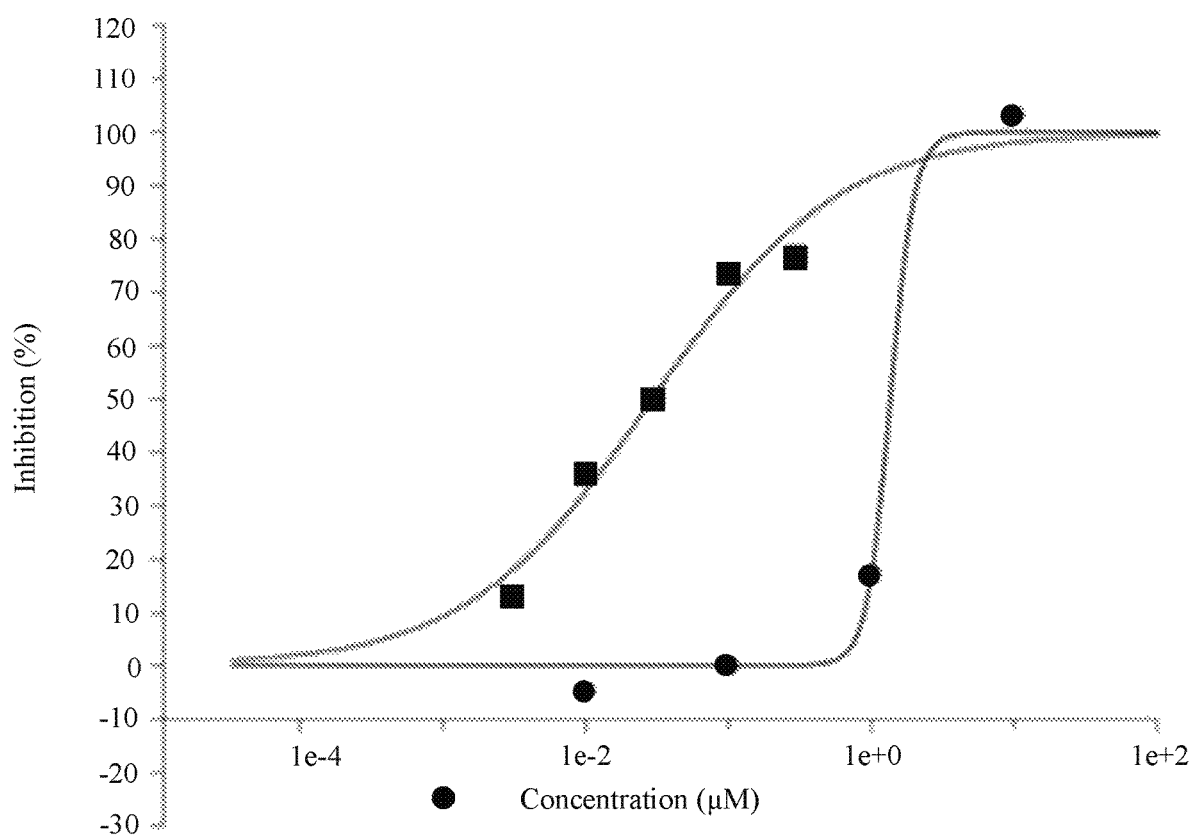
FIG. 10 shows transcription response and binding against NF-kB for Compound 1 (circles, $IC_{50}$=1.36 μM) and a reference compound cyclosporin (squares, $IC_{50}$=0.029 μM).
Figure 11:
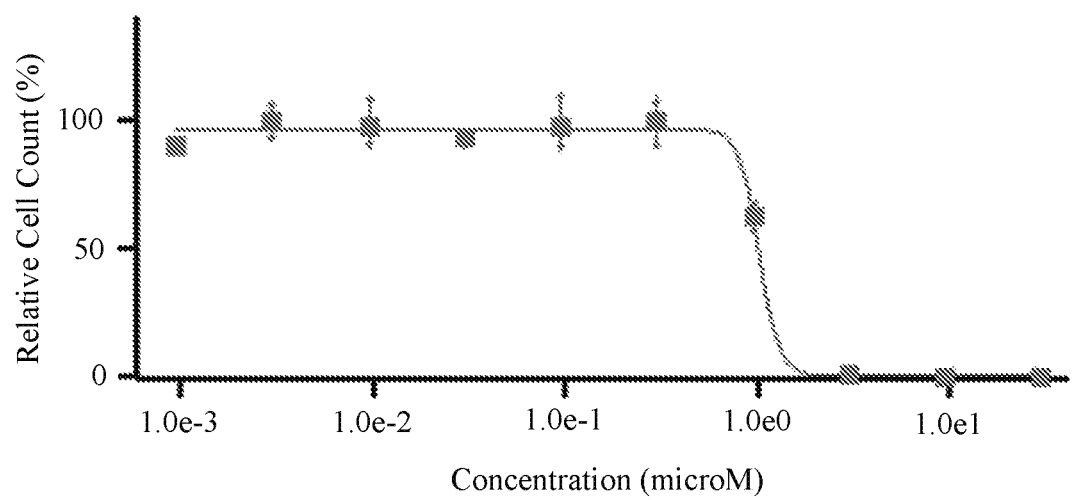
FIG. 11 shows proliferation response when cell line MDA-MB-415 is treated with Compound 1.
Figure 12:
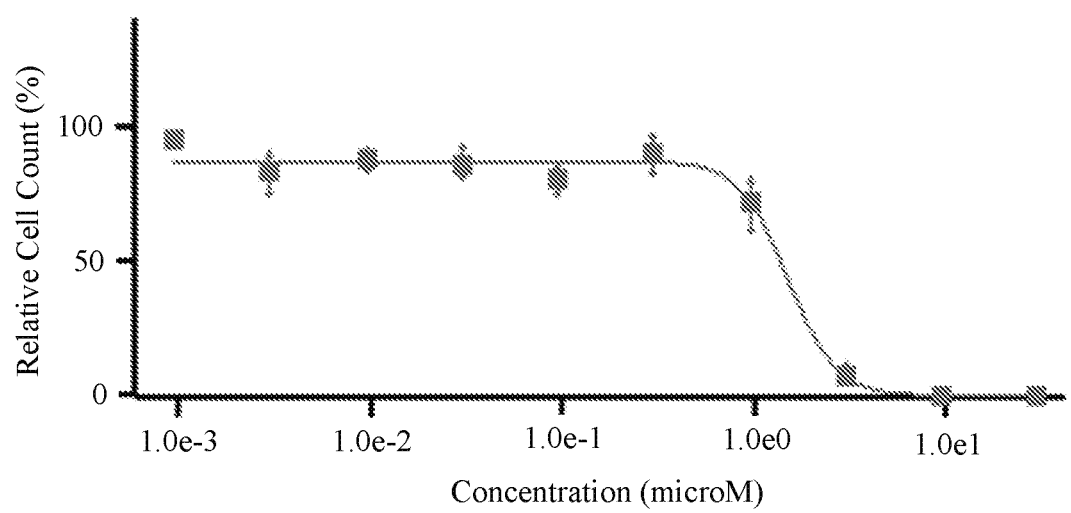
FIG. 12 shows proliferation response when cell line RKO-AS45-1 is treated with Compound 1.
Figure 13:
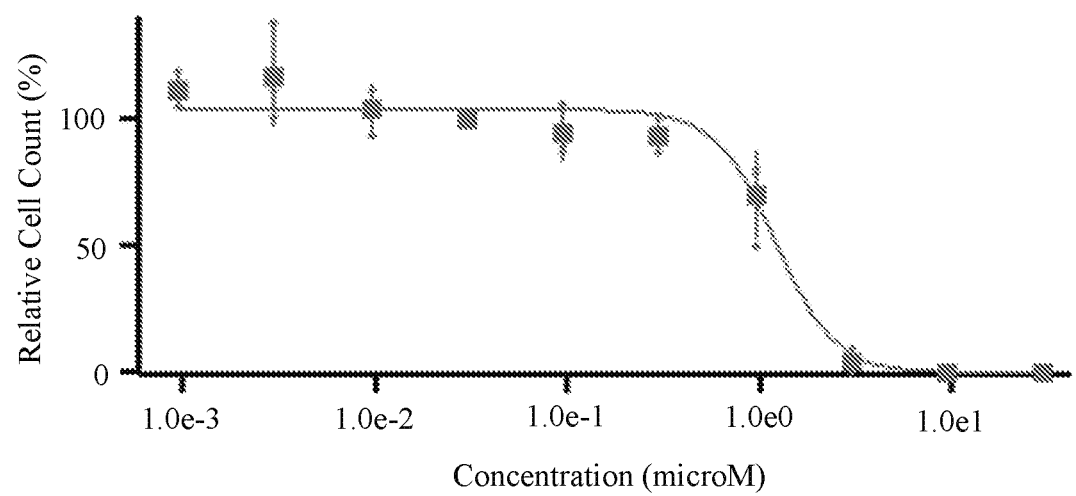
FIG. 13 shows proliferation response when cell line SW480 is treated with Compound 1.
Figure 14:
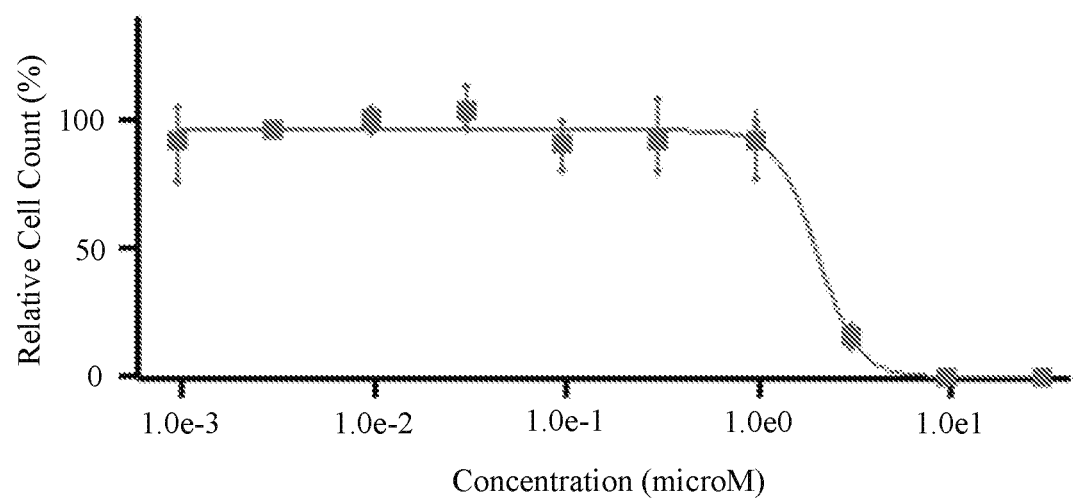
FIG. 14 shows proliferation response when cell line 639-V is treated with Compound 1.
Figure 15:
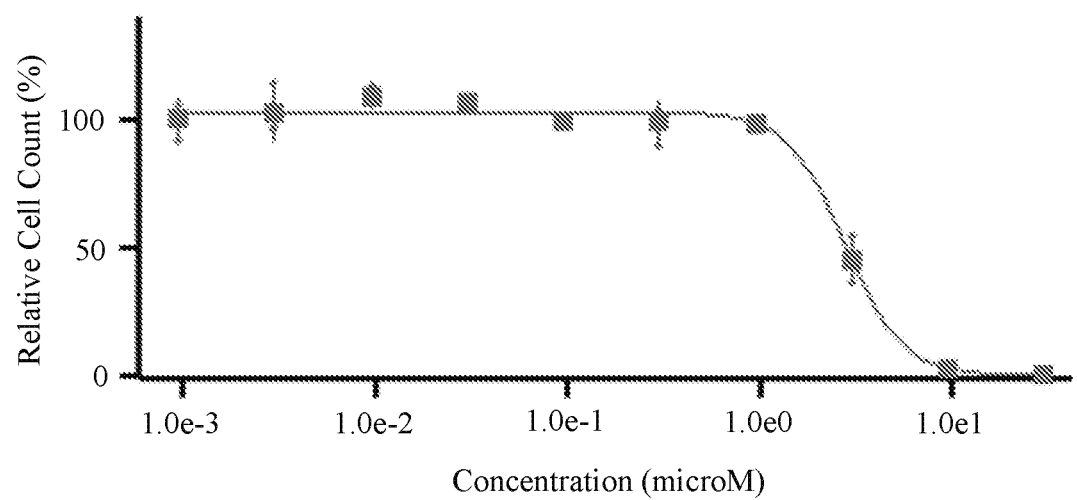
FIG. 15 shows proliferation response when cell line Hs 729 is treated with Compound 1.
Figure 16:
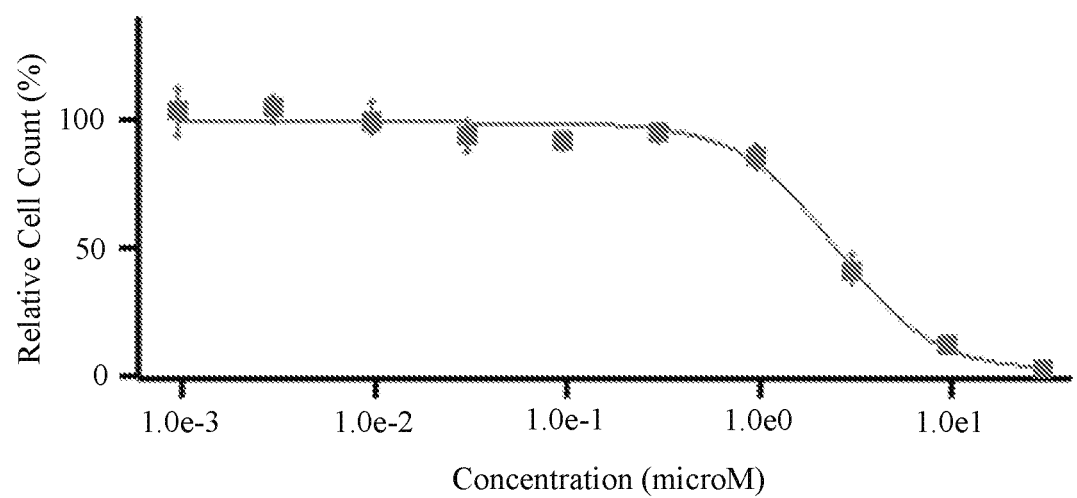
FIG. 16 shows proliferation response when cell line Hs 852.T is treated with Compound 1.
Figure 17:
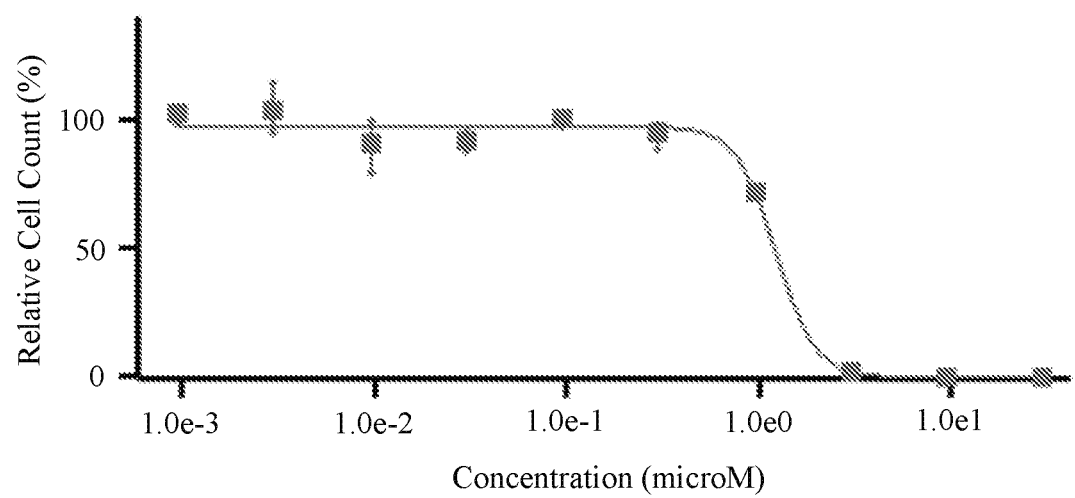
FIG. 17 shows proliferation response when cell line HCT-8 is treated with Compound 1.
Figure 18:
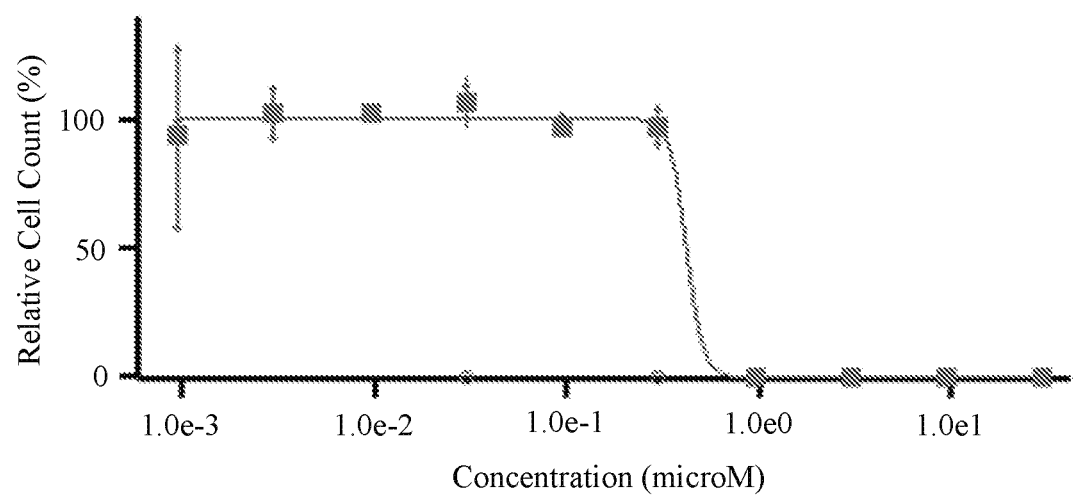
FIG. 18 shows proliferation response when cell line IM-9 is treated with Compound 1.

NF-κB has been shown to have diverse and complex roles in cancer and immune modulation (Perkins, 2012; Sethi et al., 2012; Parri and Chiarugi, 2013; D'Ignazio el al., 2015). Based on significant inhibitory activity against NF-κB (IC$_{50}$ 0.69 μM) and cytokines (IC$_{50}$ 6.6, 8.8, 4.3, 8.9 μM, for IL1β, IL-6, IL10, TNFα respectively, Compound 1 can potentially influence the expression of the aforementioned biological processes as well as modulation of immune responses. In support for these results, Eurofins Oncopanel Genomic analysis showed Compound 1 clustered near to ABT-199, a BH3 domain inhibitor of BCL-2. ABT-199 blocked anti-apoptotic of BCL-2 leading to programmed cell death. In addition to antitumor effect of BCL-2 therapeutics, the BH3 mimetics have been proposed in the context of immune modulation (Ludwig et al., 2016). Taken together, Compound 1 could target cancer cell death as well as immune modulation. FIG. 10 shows transcription response and binding against NF-κB for Compound 1.

In Vitro Cell Viability Assay of Serrulatane Terpenes

Four serrulatane diterpenes, namely compounds 1 to 4, and *Myoporum insulare* resin were evaluated for in vitro inhibition of cell growth in 43 cancer cell lines and one normal cell line as shown in Table 19. The assay is a 72 hour (three day) assay.

Methodology of the In Vitro Cell Viability Assay

Cell viability assays were carried out by Eurofins PanLab (Taiwan). The assays are based on the established principle that cell viability (survival) can be evaluated by measuring the intracellular levels of adenosine triphosphate (ATP) by bioluminescence in metabolically active cells (Xia, M et al. 2008). Assays are carried out by seeding cells in two plates (To and T$_{72}$). At time "zero" cell plate (To) is harvested, treated, and incubated for 72 h (three days) when the T$_{72}$ plate will be harvested. The intracellular levels of ATP are measured and represent the amount of viable cells.

Cell viability assay results for compounds 1 to 4 and *Myoporum insulare* resin/exudate extract towards 43 cancer cell lines and 1 normal cell line are shown in Table 18.

TABLE 18

Inhibition of cell growth at 10.5 μg/mL of *Myoporum insulare* resin and 10 μM of compounds 1 to 4.

| Cell lines | % Cell growth *Myoporum insulare* resin | 1 | 2 | 3 | 4 |
|---|---|---|---|---|---|
| Normal | | | | | |
| HUVEC, Endothelium | 32 | −90 | 97 | 91 | 37 |
| Brain | | | | | |
| U-87 MG | 36 | 7 | 101 | 111 | 81 |
| SK-N-MC | 4 | −87 | 73 | 82 | −92 |
| Leukemia | | | | | |
| HL-60 (TB) | 13 | −62 | −35 | 138 | −83 |
| K-562 | −20 | −55 | 69 | 93 | 60 |
| MV-411 | −96 | −96 | 37 | 76 | −94 |
| MOLT-4 | −97 | −94 | 38 | 77 | −93 |
| Non-Small Cell Lung Cancer | | | | | |
| A549/ATCC | 60 | −92 | 102 | 106 | 93 |
| LL/2 | 41 | −62 | 105 | 111 | 98 |
| NCI-H460 | 63 | −37 | 88 | 100 | 93 |
| PC-6 | 30 | −62 | 92 | 96 | 4 |
| Colon Cancer | | | | | |
| CT26.WT | 36 | 2 | 120 | 103 | 33 |
| SW-620 | −94 | −89 | 97 | 107 | 74 |
| DLD-1 | 29 | −65 | 95 | 101 | 68 |
| HCT-15 | 15 | −62 | 94 | 116 | 69 |
| HCT-116 | 45 | −74 | 81 | 99 | 64 |
| HT-29 | 69 | −66 | 107 | 101 | 91 |
| Melanoma | | | | | |
| B16-F0 | 84 | 7 | 123 | 116 | 56 |
| SK-MEL-5 | −69 | −96 | 95 | 118 | 88 |
| Ovarian Cancer | | | | | |
| OVCAR-3 | −33 | −93 | 67 | 86 | 60 |
| SK-OV-3 | 6 | −35 | 82 | 98 | 74 |
| Prostate Cancer | | | | | |
| LNCaP | −5 | −86 | 73 | 84 | 56 |
| PC-3 | −87 | 70 | 99 | 64 | |
| Breast Cancer | | | | | |
| BT474 | 56 | −67 | 118 | 108 | 64 |
| MCF7 | −51 | −71 | 114 | 112 | 77 |
| MCF-7 AdrR | −43 | −90 | 92 | 101 | 77 |
| MDA-MB-231 | −38 | −92 | 97 | 100 | 84 |
| MDA-MB-468 | −69 | −92 | 37 | 85 | 52 |
| T-47D | 102 | 20 | 104 | 119 | 47 |
| 4T1 | 75 | 52 | 60 | 99 | 26 |
| Kidney Cancer | | | | | |
| A-498 | 43 | −43 | 91 | 92 | 89 |
| ACHN | 34 | −41 | 101 | 105 | 105 |

TABLE 18-continued

Inhibition of cell growth at 10.5 µg/mL of *Myoporum insulare* resin and 10 µM of compounds 1 to 4.

| Cell lines | % Cell growth *Myoporum insulare* resin | 1 | 2 | 3 | 4 |
|---|---|---|---|---|---|
| Liver Cancer | | | | | |
| HC-4 | 80 | −91 | 104 | 105 | 91 |
| Hep3B | 20 | −84 | 87 | 84 | 93 |
| HepG2 | 27 | −23 | 95 | 103 | 90 |
| Lymphoma | | | | | |
| Ramos | −94 | −92 | 33 | 129 | −82 |
| H33HJ-JA1 | −73 | −90 | 57 | 90 | −87 |
| U937 | 28 | −86 | 102 | 105 | 20 |
| Pancreas | | | | | |
| MIA PaCa-2 | 20 | 3 | 92 | 106 | 92 |
| PANC-1 | 64 | 36 | 87 | 116 | 82 |
| Skin | | | | | |
| A-431 | 64 | −89 | 100 | 102 | 107 |
| A375 | 9 | −5 | 74 | 100 | 65 |
| Stomach | | | | | |
| KATO III | 12 | −91 | 84 | 105 | 83 |
| Uterus | | | | | |
| MES-SA | −57 | −88 | 75 | 94 | 68 |

Cell Viability Assay Results

At 10 µM Compound 1 showed potent reduction in cell viability (−80 to −100%) towards cancer cell lines. Moderate reduction in cell viability (−40 to −80%) was observed towards 12 cancer cell lines and weak effect towards cell viability for 4 cell lines. Growth inhibition was observed for the remaining cell lines.

At 10 µM Compound 2 showed weak reduction in cell viability (−35%) towards the HL-60 leukemia cells and no significant effect on the remaining cell lines. At 10 µM Compound 3 showed no significant effect on all 44 cell lines. At 10 µM Compound 4 showed potent reduction in cell viability (−82 to −94%) towards six lymphoma, leukemia and brain cancer cell lines: Ramos and H33HJ-JA1 (lymphoma); HL-60 (TB), MOLT-4 and MV-411 (leukemia), and SK-N-MC (brain). Compound 4 was selective with no significant reduction in the growth of HUVEC endothelium cells (normal cell line).

At 10.5 µg/mL *Myoporum insulare* resin showed potent reduction in cell viability (−80 to −100%) towards four cancer cell lines: SW-620 (colon); Ramos (lymphoma); and MV-411 and MOLT4 (leukemia). Moderate reduction in cell viability (−40 to −80%) was observed towards six cancer cell lines: MCF-7, MCF7 AdrR, MDA-MB-468 (breast); H33HJ-JA1 (lymphoma); SK-MEL-5 (melanoma); and MES-SA (uterus). Weak cell viability reduction (−5 to −38%) towards five cell lines: K-562 (leukemia); OVCAR-3 (ovarian); LNCaP (prostrate); MDA-MB-231 (breast); and A375 (skin). No significant effect was observed towards HUVEC endothelium cells (normal cell line).

OncoPanel Cell Proliferation Assay

The OncoPanel cell proliferation assay measures the proliferation response of cancer cell lines to drug treatments through high-content fluorescence imaging or bioluminescence. Whereas the cell viability assay described above is a three-day assay, the OncoPanel assay is a 10-day assay.

Experimental Procedure

Cells were grown in RPMI 1640, 10% FBS, 2 mM L-alanyl-L-glutamine, 1 mM Na pyruvate or a special medium. Cells were seeded into 384-well plates and incubated in a humidified atmosphere of 5% $CO_2$ at 37° C. Compounds were added the day following cell seeding. At the same time, a time zero untreated cell plate was generated. After a 10-day incubation period, cells were fixed and stained to allow fluorescence imaging of nuclei. At 7 days post-seeding, the growth media were replaced and the plates were re-dosed with the test compound.

Compounds were serially diluted in half-log steps from the highest test concentration specified in the above table, and assayed over 10 concentrations with a maximum assay concentration of 0.1% DMSO. Automated fluorescence microscopy was carried out using a Molecular Devices ImageXpress Micro XL high-content imager, and images were collected with a 4× objective. 16-bit TIFF images were acquired and analyzed with MetaXpress 5.1.0.41 software.

Data Analysis

Cell proliferation was measured by the fluorescence intensity of an incorporated nuclear dye. The output is referred to as the relative cell count, where the measured nuclear intensity is transformed to percent of control (POC) using the following formula:

$$POC = \frac{I_x}{I_0} \times 100$$

Where $I_x$ is the nuclear intensity at concentration x, and $I_0$ is the average nuclear intensity of the untreated vehicle wells.

Cellular response parameters were calculated using nonlinear regression to a sigmoidal single-site dose response model:

$$y = A + \frac{B-A}{1+(C/x)^D}$$

Where y is a response measured at concentration x, A and B are the lower and upper limits of the response, C is the concentration at the response midpoint ($EC_{50}$), and D is the Hill Slope (Fallahi-Sichani, M., S. et al. 2013).

Time zero non-treated plates were used to determine the number of doublings during the assay period, using the formula:

$$\text{Doublings} = \log_2\left(\frac{N}{N_{T0}}\right)$$

Where N is the cell number in untreated wells at the assay end point and NTO is the cell number at the time of compound addition.

Cell count $IC_{50}$ is the test compound concentration at 50% of maximal possible response. $EC_{50}$ is the test compound concentration at the curve inflection point or half the effective response (parameter C of the fitted curve solution). $GI_{50}$ is the concentration needed to reduce the observed growth by half (midway between the curve maximum and the time zero value). Activity area is an estimate of the integrated area above the curve (Barretina, J. G. et al. 2012). Activity area values range from 0-10, where a value of zero indicates no inhibition of proliferation at all concentrations, and a value of 10 indicates complete inhibition of proliferation at all concentrations. In rare instances, values <0 or >10 may be observed. In these instances, values <0 should be considered as equivalent to 0, whereas values >10 should be considered equivalent to 10.

Curve-fitting, calculations, and report generation were performed using a custom data reduction engine and MathIQ based software (AIM).

The OncoPanel cell proliferation results (OncoPanel, Eurofins PanLab, USA, across 280 human cancer cell lines) for compounds 1, 2 and 4 are shown below in Table 19. Tables 21 to 28 show representative proliferation response data (Table 21: MDA-MB-415; Table 22: RKO-AS45-1; Table 23: SW480; Table 24: 639-V; Table 25: Hs 729; Table 26: Hs 852.T; Table 27: HCT-8; Table 28: IM-9) and the cell proliferation results for *Myoporum insulare* resin are shown below in Table 29.

TABLE 19

OncoPanel cell proliferation results for compounds 1, 2 and 4.

| | | Compound 1 | | | Compound 2 | | | Compound 4 | | |
|---|---|---|---|---|---|---|---|---|---|---|
| Cell Line | Type | Cell Count $EC_{50}$ ($\mu$M) | Cell Count $IC_{50}$ ($\mu$M) | Cell Count $GI_{50}$ ($\mu$M) | Cell Count $EC_{50}$ ($\mu$M) | Cell Count $IC_{50}$ ($\mu$M) | Cell Count $GI_{50}$ ($\mu$M) | Cell Count $EC_{50}$ ($\mu$M) | Cell Count $IC_{50}$ ($\mu$M) | Cell Count $GI_{50}$ ($\mu$M) |
| 5637 | Bladder | 3.38 | 3.38 | 3.32 | >30 | >30 | >30 | 15.20 | 15.20 | 15.10 |
| 639-V | Bladder | 2.01 | 2.01 | 2.01 | 6.54 | 8.00 | 7.98 | 12.00 | 12.00 | 12.00 |
| 647-V | Bladder | 3.12 | 3.12 | 3.11 | 11.30 | 11.30 | 11.20 | 5.99 | 6.00 | 5.99 |
| BFTC-905 | Bladder | 1.79 | 1.79 | 1.78 | 8.03 | 8.03 | 8.01 | 9.70 | 9.70 | 9.68 |
| HT-1197 | Bladder | 2.31 | 2.34 | 2.28 | 10.70 | 10.70 | 10.30 | 15.60 | 15.60 | 15.20 |
| HT1376 | Bladder | 1.45 | 1.46 | 1.43 | 4.71 | 4.71 | 4.47 | 14.10 | 14.10 | 13.80 |
| J82 | Bladder | 1.06 | 1.06 | 1.05 | 12.90 | 12.90 | 12.70 | 6.22 | 6.22 | 6.09 |
| SCaBER | Bladder | 3.12 | 3.12 | 3.10 | 11.50 | 11.50 | 11.40 | 16.90 | 16.90 | 16.80 |
| T24 | Bladder | 1.44 | 1.44 | 1.44 | 20.40 | 20.40 | 20.30 | 12.20 | 12.20 | 12.20 |
| TCCSUP | Bladder | 1.75 | 1.75 | 1.72 | 8.20 | 8.20 | 7.78 | 8.91 | 8.91 | 8.67 |
| UM-UC-3 | Bladder | 1.85 | 1.85 | 1.84 | 5.30 | 5.75 | 5.74 | 3.83 | 3.83 | 3.82 |
| AU565 | Breast | 1.62 | 1.62 | 1.61 | 6.40 | 6.40 | 6.29 | 10.10 | 10.10 | 10.00 |
| BT20 | Breast | 1.59 | 1.61 | 1.53 | 12.20 | 12.70 | 12.30 | 14.10 | 14.30 | 13.90 |
| BT474 | Breast | 5.41 | 5.46 | 4.95 | >30 | >30 | >30 | 25.50 | 25.70 | 25.00 |
| BT-549 | Breast | 3.14 | 3.14 | 3.12 | 25.80 | 25.90 | 25.80 | 15.30 | 15.30 | 15.10 |
| CAMA-1 | Breast | 3.51 | 3.51 | 3.40 | >30 | >30 | >30 | >30 | >30 | >30 |
| EFM-19 | Breast | 1.61 | 1.61 | 1.54 | 11.20 | 11.20 | 10.60 | 11.90 | 11.90 | 11.30 |
| Hs 578T | Breast | 4.74 | 4.76 | 4.68 | 28.70 | 28.70 | 28.20 | 15.00 | 15.00 | 14.90 |
| KPL-1 | Breast | 0.81 | 0.81 | 0.81 | 4.70 | 4.73 | 4.70 | 4.18 | 4.18 | 4.13 |
| MCF7 | Breast | 1.37 | 1.37 | 1.35 | 10.40 | 10.40 | 9.96 | 12.10 | 12.10 | 11.90 |
| MDA MB 231 | Breast | 1.47 | 1.48 | 1.47 | 4.39 | 4.39 | 4.36 | 11.40 | 11.40 | 11.30 |
| MDA MB 453 | Breast | 0.78 | 0.78 | 0.77 | 3.68 | 3.69 | 3.65 | 3.76 | 3.76 | 3.68 |
| MDA MB 468 | Breast | 2.75 | 2.76 | 2.74 | 8.07 | 8.08 | 8.00 | 7.41 | 7.43 | 7.34 |
| MDA-MB-415 | Breast | 1.02 | 1.02 | 1.00 | 11.50 | 11.50 | 10.80 | 28.50 | 28.50 | 27.40 |
| MDA-MB-436 | Breast | 2.68 | 2.69 | 2.67 | 9.72 | 9.77 | 9.73 | 10.30 | 10.30 | 10.20 |
| SK-BR-3 | Breast | 1.79 | 1.80 | 1.76 | 12.20 | 12.20 | 11.90 | 10.30 | 10.30 | 9.97 |
| T47D | Breast | 4.63 | 4.63 | 4.28 | 10.20 | 10.20 | 9.40 | 3.28 | 3.28 | 2.92 |
| A172 | CNS - Glioma | 1.12 | 1.15 | 1.14 | 9.02 | 9.02 | 8.93 | 8.08 | 8.08 | 8.03 |
| CCF-STTG1 | CNS - Glioma | 5.79 | 6.60 | 5.24 | >30 | >30 | >30 | 19.70 | 19.70 | 16.00 |
| DBTRG-05MG | CNS - Glioma | 2.65 | 2.66 | 2.64 | 12.20 | 13.00 | 12.80 | 17.60 | 17.60 | 17.40 |
| DK-MG | CNS - Glioma | 6.16 | 6.41 | 6.12 | 1.64 | >30 | >30 | 17.20 | 17.20 | 16.40 |
| H4 | CNS - Glioma | 2.77 | 2.77 | 2.77 | 3.06 | >30 | >30 | 13.00 | 13.00 | 13.00 |
| Hs 683 | CNS - Glioma | 4.90 | 4.91 | 4.76 | 29.80 | 29.80 | 28.30 | 24.50 | 24.60 | 24.30 |
| M059J | CNS - Glioma | 3.09 | 3.09 | 3.02 | 9.98 | 15.80 | 14.20 | 13.00 | 13.00 | 12.90 |
| PFSK-1 | CNS - Glioma | 4.32 | 4.33 | 4.31 | 14.70 | 14.70 | 14.60 | 3.82 | 3.82 | 3.80 |
| SNB-19 | CNS - Glioma | 1.66 | 1.66 | 1.65 | 17.30 | 17.30 | 16.80 | 13.00 | 13.00 | 12.90 |
| SW1088 | CNS - Glioma | 2.44 | 2.44 | 2.43 | 10.70 | 10.70 | 10.50 | 8.77 | 8.77 | 8.69 |
| SW1783 | CNS - Glioma | 3.19 | 3.19 | 3.09 | 10.20 | 11.00 | 10.50 | 12.30 | 12.30 | 12.10 |
| T98G | CNS - Glioma | 2.05 | 2.05 | 2.05 | 19.10 | 19.10 | 19.00 | 24.50 | 24.50 | 24.50 |
| U-118 MG | CNS - Glioma | 4.56 | 4.58 | 4.49 | 29.60 | 29.60 | 29.40 | 13.90 | 13.90 | 13.60 |
| U-138MG | CNS - Glioma | 6.29 | 6.33 | 6.15 | >30 | >30 | >30 | 25.00 | 25.00 | 24.90 |
| U-87 MG | CNS - Glioma | 2.12 | 2.12 | 2.04 | >30 | >30 | >30 | 13.80 | 13.80 | 13.60 |
| D341 Med | CNS - Medulloblastoma | 9.09 | 9.46 | 9.37 | 19.20 | 19.20 | 18.70 | 8.57 | 8.57 | 8.40 |
| Daoy | CNS - Medulloblastoma | 1.06 | 1.06 | 1.06 | 8.64 | 8.65 | 8.64 | 3.19 | 3.19 | 3.19 |
| BE(2)C | CNS - Neuroblastoma | 4.23 | 4.23 | 4.18 | 6.91 | 7.52 | 7.48 | 13.10 | 13.10 | 13.00 |
| CHP-212 | CNS - Neuroblastoma | 1.43 | 1.43 | 1.41 | 11.40 | 11.40 | 11.10 | 9.77 | 9.78 | 9.74 |
| MC-IXC | CNS - Neuroblastoma | 4.01 | 4.01 | 4.00 | 16.90 | 16.90 | 16.90 | 6.88 | 6.88 | 6.88 |
| SK-N-AS | CNS - Neuroblastoma | 3.58 | 3.58 | 3.54 | 6.23 | 7.92 | 7.70 | 5.86 | 5.86 | 5.75 |
| SK-N-DZ | CNS - Neuroblastoma | 3.16 | 3.16 | 2.94 | >30 | >30 | >30 | 11.90 | 11.90 | 11.50 |
| SK-N-FI | CNS - Neuroblastoma | 7.31 | 7.31 | 6.32 | >30 | >30 | >30 | 21.50 | 21.50 | 20.60 |

TABLE 19-continued

OncoPanel cell proliferation results for compounds 1, 2 and 4.

| | | Compound 1 | | | Compound 2 | | | Compound 4 | | |
|---|---|---|---|---|---|---|---|---|---|---|
| Cell Line | Type | Cell Count EC$_{50}$ (μM) | Cell Count IC$_{50}$ (μM) | Cell Count GI$_{50}$ (μM) | Cell Count EC$_{50}$ (μM) | Cell Count IC$_{50}$ (μM) | Cell Count GI$_{50}$ (μM) | Cell Count EC$_{50}$ (μM) | Cell Count IC$_{50}$ (μM) | Cell Count GI$_{50}$ (μM) |
| Colo 201 | Colon | 0.92 | 0.92 | 0.92 | 8.51 | 8.51 | 8.45 | 4.07 | 4.07 | 4.04 |
| Colo 205 | Colon | 1.31 | 1.31 | 1.31 | 10.70 | 10.70 | 10.70 | 11.90 | 11.90 | 11.90 |
| Colo 320 HSR | Colon | 3.09 | 3.13 | 3.13 | 11.60 | 11.60 | 11.60 | 5.15 | 5.16 | 5.15 |
| Colo 320DM | Colon | 3.20 | 3.20 | 3.18 | 7.72 | 7.72 | 7.67 | 7.91 | 7.91 | 7.87 |
| DLD-1 | Colon | 2.96 | 2.96 | 2.96 | 10.70 | 11.20 | 11.20 | 15.70 | 15.70 | 15.70 |
| HCT-116 | Colon | 1.75 | 1.75 | 1.75 | 6.68 | 6.68 | 6.67 | 10.30 | 10.30 | 10.30 |
| HCT-15 | Colon | 1.84 | 1.84 | 1.83 | 8.64 | 9.49 | 9.48 | 13.40 | 13.40 | 13.40 |
| HCT-8 | Colon | 1.23 | 1.23 | 1.23 | 6.27 | 6.27 | 6.24 | 12.90 | 12.90 | 12.90 |
| HT-29 | Colon | 4.01 | 4.01 | 4.00 | 19.50 | 19.50 | 19.40 | 17.00 | 17.00 | 17.00 |
| LS1034 | Colon | 1.87 | 1.87 | 1.83 | 12.70 | 12.70 | 12.00 | 23.60 | 23.60 | 23.50 |
| LS123 | Colon | 1.13 | 1.16 | 1.03 | 6.57 | 18.40 | 13.40 | 12.00 | 12.00 | 10.70 |
| LS411N | Colon | 8.72 | 8.72 | 8.51 | 23.90 | 23.90 | 23.40 | 23.10 | 23.10 | 22.60 |
| MT-3 | Colon | 3.67 | 3.67 | 3.66 | 16.90 | 16.90 | 16.80 | 23.90 | 23.90 | 23.80 |
| NCI-H508 | Colon | 14.40 | 14.40 | 14.30 | >30 | >30 | >30 | >30 | >30 | >30 |
| NCI-H747 | Colon | 3.09 | 3.11 | 3.10 | 12.30 | >30 | >30 | 28.10 | 28.20 | 28.10 |
| RKO | Colon | 1.69 | 1.69 | 1.69 | 7.22 | 7.92 | 7.92 | 12.00 | 12.00 | 12.00 |
| RKO-AS45-1 | Colon | 1.50 | 1.50 | 1.50 | 9.64 | 9.64 | 9.62 | 12.80 | 12.80 | 12.80 |
| RKOE6 | Colon | 1.72 | 1.72 | 1.72 | 6.95 | 6.95 | 6.93 | 6.79 | 6.79 | 6.76 |
| SW1417 | Colon | 3.15 | 3.15 | 3.07 | 22.80 | 22.80 | 21.80 | >30 | >30 | 29.30 |
| SW1463 | Colon | 3.73 | 3.75 | 3.71 | >30 | >30 | >30 | 29.40 | 29.60 | 29.50 |
| SW403 | Colon | 8.09 | 8.11 | 7.89 | >30 | >30 | >30 | >30 | >30 | >30 |
| SW48 | Colon | 1.33 | 1.33 | 1.32 | 8.73 | 8.73 | 8.65 | 13.00 | 13.00 | 13.00 |
| SW480 | Colon | 1.21 | 1.21 | 1.20 | 10.10 | 10.10 | 9.93 | 12.30 | 12.30 | 12.30 |
| SW620 | Colon | 1.48 | 1.48 | 1.48 | 13.20 | 13.20 | 13.20 | 11.30 | 11.30 | 11.30 |
| SW837 | Colon | 2.35 | 2.37 | 2.33 | >30 | >30 | >30 | 18.90 | 18.90 | 18.70 |
| SW948 | Colon | 2.21 | 2.21 | 2.20 | 14.70 | 14.70 | 14.50 | 29.70 | >30 | >30 |
| WiDr | Colon | 2.32 | 2.32 | 2.31 | 14.50 | 14.50 | 14.40 | 12.80 | 12.80 | 12.80 |
| NCI-H295R | Endocrine - Adrenal gland | 14.70 | 14.70 | 13.50 | >30 | >30 | >30 | 25.60 | 25.60 | 21.60 |
| BHT-101 | Endocrine - Thyroid | 2.16 | 2.17 | 2.17 | 14.00 | 14.00 | 13.90 | 6.80 | 6.80 | 6.77 |
| CAL-62 | Endocrine - Thyroid | 1.69 | 1.69 | 1.69 | 5.60 | 5.79 | 5.78 | 5.36 | 5.36 | 5.36 |
| CGTH-W-1 | Endocrine - Thyroid | 1.20 | 1.20 | 1.20 | 5.83 | 5.83 | 5.81 | 3.45 | 3.48 | 3.47 |
| SW579 | Endocrine - Thyroid | 1.71 | 1.71 | 1.69 | 12.30 | 12.30 | 12.20 | 11.00 | 11.00 | 11.00 |
| Y79 | Eye | 5.60 | 5.60 | 5.33 | 6.57 | 7.65 | 7.41 | 5.65 | 5.65 | 5.34 |
| C-33A | Female GU - Cervix | 7.18 | 7.18 | 7.08 | 12.00 | 12.00 | 11.90 | 9.57 | 9.57 | 9.42 |
| C-4 II | Female GU - Cervix | 1.09 | 1.10 | 1.09 | 8.94 | 9.03 | 9.00 | 12.60 | 12.60 | 12.50 |
| HeLa | Female GU - Cervix | 2.99 | 2.99 | 2.98 | 16.60 | 16.60 | 16.50 | 21.10 | 21.10 | 21.10 |
| HT-3 | Female GU - Cervix | 3.88 | 3.89 | 3.84 | 17.60 | 19.30 | 18.60 | 14.50 | 14.50 | 14.30 |
| SiHa | Female GU - Cervix | 5.22 | 5.23 | 5.17 | 28.30 | 28.30 | 25.80 | 11.30 | 13.50 | 13.20 |
| Ca Ski | Female GU - Ovary | 5.28 | 5.29 | 5.24 | >30 | >30 | >30 | 17.60 | 17.60 | 17.60 |
| CaOV3 | Female GU - Ovary | 1.91 | 1.92 | 1.85 | 10.20 | 10.20 | 9.61 | 10.20 | 10.30 | 10.20 |
| ME-180 | Female GU - Ovary | 2.25 | 2.26 | 2.21 | >30 | >30 | >30 | 25.30 | 25.30 | 25.20 |
| MS751 | Female GU - Ovary | 2.23 | 2.23 | 2.21 | 7.55 | 8.78 | 8.72 | 12.10 | 12.10 | 12.00 |
| OVCAR3 | Female GU - Ovary | 1.53 | 1.57 | 1.52 | 14.40 | 14.40 | 13.70 | 15.60 | 15.60 | 14.90 |
| PA-1 | Female GU - Ovary | 4.21 | 4.21 | 4.21 | 11.60 | 16.30 | 16.20 | 7.89 | 7.90 | 7.89 |
| SKOV3 | Female GU - Ovary | 1.58 | 1.58 | 1.56 | 15.40 | 15.40 | 15.20 | 8.43 | 8.43 | 8.33 |
| AN3 CA | Female GU - Uterus | 1.52 | 1.52 | 1.49 | 11.30 | 11.30 | 11.10 | 9.62 | 9.62 | 9.43 |
| HEC-1-A | Female GU - Uterus | 2.57 | 2.57 | 2.56 | 12.10 | 12.10 | 12.00 | 12.30 | 12.30 | 12.20 |
| KLE | Female GU - Uterus | 3.70 | 3.82 | 3.56 | 26.30 | 26.30 | 20.50 | 18.20 | 18.20 | 16.60 |
| SW954 | Female GU - Vulva | 7.63 | 7.63 | 7.60 | >30 | >30 | >30 | 21.70 | 21.70 | 21.60 |

TABLE 19-continued

OncoPanel cell proliferation results for compounds 1, 2 and 4.

| Cell Line | Type | Compound 1 | | | Compound 2 | | | Compound 4 | | |
|---|---|---|---|---|---|---|---|---|---|---|
| | | Cell Count $EC_{50}$ (µM) | Cell Count $IC_{50}$ (µM) | Cell Count $GI_{50}$ (µM) | Cell Count $EC_{50}$ (µM) | Cell Count $IC_{50}$ (µM) | Cell Count $GI_{50}$ (µM) | Cell Count $EC_{50}$ (µM) | Cell Count $IC_{50}$ (µM) | Cell Count $GI_{50}$ (µM) |
| BV-173 | Leukemia | 3.80 | 3.80 | 3.79 | 9.33 | 9.33 | 9.33 | 3.56 | 3.56 | 3.55 |
| CCRFCEM | Leukemia | 4.73 | 4.73 | 4.71 | 11.50 | 11.50 | 11.40 | 4.92 | 4.93 | 4.91 |
| CEM-C1 | Leukemia | 1.96 | 1.96 | 1.95 | 3.26 | 3.26 | 3.26 | 1.47 | 1.47 | 1.47 |
| CML-T1 | Leukemia | 1.93 | 1.93 | 1.93 | 3.69 | 3.69 | 3.68 | 3.93 | 3.93 | 3.93 |
| EM-2 | Leukemia | 2.39 | 2.39 | 2.37 | 10.80 | 10.80 | 10.80 | 3.99 | 4.00 | 4.00 |
| HEL-92-1-7 | Leukemia | 13.90 | 13.90 | 13.90 | 13.40 | 13.40 | 13.40 | 4.05 | 4.05 | 4.05 |
| J-RT3-T3-5 | Leukemia | 0.01 | 0.01 | 0.010 | 2.08 | 2.08 | 2.06 | 2.71 | 2.71 | 2.71 |
| Jurkat | Leukemia | 2.25 | 2.25 | 2.24 | 2.66 | 2.66 | 2.65 | 3.59 | 3.59 | 3.58 |
| K562 | Leukemia | 4.60 | 4.60 | 4.58 | 10.20 | 10.20 | 10.10 | 12.20 | 12.20 | 12.20 |
| KG-1 | Leukemia | 0.12 | 0.12 | 0.11 | 11.30 | 12.00 | 11.90 | 13.30 | 13.30 | 13.10 |
| KU812 | Leukemia | 2.81 | 2.81 | 2.57 | 6.52 | 6.52 | 5.66 | 9.50 | 9.50 | 9.13 |
| MEG01 | Leukemia | 7.35 | 7.35 | 7.22 | 13.80 | 13.80 | 13.70 | 8.39 | 8.39 | 8.37 |
| MHH-PREB-1 | Leukemia | 6.17 | 6.17 | 6.17 | 7.85 | 7.85 | 7.85 | 5.71 | 5.71 | 5.71 |
| MOLT-16 | Leukemia | 1.84 | 1.84 | 1.84 | 13.30 | 13.30 | 13.30 | 4.02 | 4.02 | 4.01 |
| MOLT-3 | Leukemia | 2.13 | 2.13 | 2.11 | 1.27 | 1.27 | 1.26 | 3.15 | 3.15 | 3.13 |
| MV-4-11 | Leukemia | 3.58 | 3.58 | 3.57 | 8.56 | 8.56 | 8.52 | 3.81 | 3.81 | 3.80 |
| MX1 | Leukemia | 1.29 | 1.29 | 1.29 | 10.80 | 10.80 | 10.80 | 2.46 | 2.46 | 2.46 |
| NALM-6 | Leukemia | 1.81 | 1.81 | 1.81 | 1.67 | 1.68 | 1.68 | 2.61 | 2.61 | 2.61 |
| RS4; 11 | Leukemia | 1.77 | 1.77 | 1.71 | 6.43 | 6.43 | 6.30 | 4.15 | 4.23 | 4.16 |
| TF-1 | Leukemia | 2.11 | 2.11 | 1.98 | 2.75 | 2.75 | 2.44 | 6.57 | 6.57 | 6.26 |
| Thp1 | Leukemia | 1.38 | 1.38 | 1.34 | 5.32 | 5.69 | 5.61 | 12.00 | 12.00 | 11.90 |
| BC-1 | Lymphoma | 1.52 | 1.52 | 1.51 | 7.95 | 7.95 | 7.93 | 4.16 | 4.16 | 4.16 |
| BCP-1 | Lymphoma | 3.18 | 3.18 | 3.14 | 8.48 | 8.48 | 8.40 | 8.82 | 8.82 | 8.75 |
| CA46 | Lymphoma | 2.27 | 2.27 | 2.26 | 3.83 | 3.83 | 3.82 | 4.06 | 4.06 | 4.06 |
| CRO-AP2 | Lymphoma | 5.72 | 5.72 | 5.66 | 6.38 | 6.38 | 6.36 | 9.94 | 9.94 | 9.88 |
| Daudi | Lymphoma | 1.84 | 1.84 | 1.84 | 3.93 | 3.93 | 3.92 | 2.28 | 2.28 | 2.28 |
| DB | Lymphoma | 2.10 | 2.10 | 2.09 | 3.23 | 3.25 | 3.24 | 3.85 | 3.85 | 3.84 |
| DOHH-2 | Lymphoma | 1.41 | 1.41 | 1.41 | 3.24 | 3.24 | 3.24 | 2.24 | 2.24 | 2.24 |
| DoTc2 4510 | Lymphoma | 1.03 | 1.03 | 1.01 | 6.07 | 6.07 | 5.84 | 9.23 | 9.23 | 9.09 |
| EB2 | Lymphoma | 6.47 | 6.49 | 6.45 | 23.30 | 23.30 | 23.00 | 8.35 | 8.38 | 8.32 |
| EB-3 | Lymphoma | 3.56 | 3.56 | 3.56 | 9.72 | 9.72 | 9.71 | 3.93 | 3.93 | 3.93 |
| GA-10 | Lymphoma | 1.93 | 1.94 | 1.94 | 3.72 | 3.73 | 3.73 | 1.23 | 1.23 | 1.23 |
| Hs 445 | Lymphoma | 1.30 | 1.32 | 1.31 | 4.34 | 4.34 | 4.23 | 5.80 | 5.80 | 5.74 |
| Hs 611.T | Lymphoma | 2.92 | 2.94 | 2.91 | 10.70 | 10.70 | 10.60 | 5.11 | 5.11 | 5.05 |
| HT | Lymphoma | 1.52 | 1.53 | 1.51 | 6.51 | 6.51 | 6.43 | 4.49 | 4.49 | 4.46 |
| JeKo-1 | Lymphoma | 5.23 | 5.23 | 5.21 | 4.48 | 4.48 | 4.47 | 3.91 | 3.91 | 3.91 |
| Jiyoye | Lymphoma | 5.88 | 5.88 | 5.87 | 17.80 | 17.80 | 17.70 | 3.55 | 3.55 | 3.55 |
| L-428 | Lymphoma | 1.08 | 1.09 | 1.08 | 8.87 | 8.87 | 8.83 | 2.07 | 2.07 | 2.06 |
| MC116 | Lymphoma | 3.79 | 3.79 | 3.78 | 13.80 | 13.80 | 13.80 | 12.50 | 12.50 | 12.40 |
| NAMALWA | Lymphoma | 3.39 | 3.39 | 3.39 | 5.71 | 5.71 | 5.70 | 3.91 | 3.91 | 3.90 |
| Raji | Lymphoma | 4.60 | 4.60 | 4.59 | 8.04 | 8.04 | 8.04 | 3.92 | 3.92 | 3.92 |
| Ramos (RA 1) | Lymphoma | 2.96 | 2.96 | 2.96 | 4.39 | 4.39 | 4.39 | 4.17 | 4.17 | 4.17 |
| RPMI 6666 | Lymphoma | 3.53 | 3.53 | 3.44 | 10.40 | 10.70 | 10.70 | 23.10 | 23.10 | 23.00 |
| SR | Lymphoma | 3.80 | 3.80 | 3.80 | 10.70 | 10.70 | 10.70 | 4.39 | 4.39 | 4.39 |
| ST486 | Lymphoma | 1.09 | 1.09 | 1.08 | 3.87 | 3.87 | 3.86 | 2.66 | 2.66 | 2.65 |
| SU-DHL-10 | Lymphoma | 3.94 | 3.94 | 3.93 | 9.92 | 9.92 | 9.90 | 7.68 | 7.68 | 7.67 |
| SU-DHL-4 | Lymphoma | 2.01 | 2.01 | 2.01 | 4.20 | 4.20 | 4.20 | 5.74 | 5.74 | 5.74 |
| SU-DHL-5 | Lymphoma | 1.20 | 1.20 | 1.19 | 4.28 | 4.28 | 4.27 | 3.80 | 3.80 | 3.80 |
| SU-DHL-8 | Lymphoma | 1.77 | 1.77 | 1.77 | 7.40 | 7.40 | 7.40 | 3.90 | 3.90 | 3.90 |
| SUP-T1 | Lymphoma | 3.96 | 3.96 | 3.95 | 12.10 | 12.10 | 12.00 | 6.51 | 6.51 | 6.49 |
| TUR | Lymphoma | 5.09 | 5.09 | 5.08 | 2.63 | >30 | >30 | 8.98 | 8.98 | 8.98 |
| ARH-77 | Myeloma | 1.95 | 1.97 | 1.95 | 9.50 | 9.60 | 9.57 | 13.50 | 13.50 | 13.40 |
| IM-9 | Myeloma | 0.42 | 0.42 | 0.42 | 3.92 | 3.92 | 3.92 | 6.71 | 6.71 | 6.71 |
| RPMI 8226 | Myeloma | 0.68 | 0.68 | 0.67 | 2.02 | 2.02 | 1.95 | 3.03 | 3.03 | 3.03 |
| SKO-007 | Myeloma | 0.99 | 0.99 | 0.93 | 1.59 | 1.59 | 1.42 | 4.66 | 4.71 | 4.55 |
| U266B1 | Myeloma | 3.22 | 3.22 | 3.08 | 9.15 | 9.28 | 9.01 | 10.10 | 10.10 | 9.81 |
| A-253 | Head and Neck | 4.13 | 4.14 | 4.13 | 28.50 | 28.70 | 28.70 | 18.20 | 18.20 | 18.10 |
| A388 | Head and Neck | 1.66 | 1.67 | 1.66 | 13.50 | 13.50 | 13.40 | 7.66 | 7.66 | 7.59 |
| A431 | Head and Neck | 2.80 | 2.81 | 2.80 | >30 | >30 | >30 | 24.80 | 24.80 | 24.80 |
| Cal 27 | Head and Neck | 2.16 | 2.16 | 2.15 | 7.64 | 7.64 | 7.62 | 12.30 | 12.30 | 12.20 |
| Detroit 562 | Head and Neck | 1.96 | 1.97 | 1.96 | 14.50 | 14.50 | 14.40 | 25.00 | 25.00 | 25.00 |
| FaDu | Head and Neck | 0.87 | 0.87 | 0.87 | 8.66 | 8.66 | 8.66 | 8.28 | 8.28 | 8.28 |
| OE19 | Head and Neck | 3.23 | 3.23 | 3.21 | >30 | >30 | >30 | 20.70 | 20.70 | 20.50 |
| OE21 | Head and Neck | 3.68 | 3.68 | 3.67 | >30 | >30 | >30 | 12.70 | 12.70 | 12.70 |
| SCC-25 | Head and Neck | 3.94 | 3.96 | 3.95 | >30 | >30 | >30 | 25.00 | 25.00 | 25.00 |
| SCC-4 | Head and Neck | 4.66 | 4.72 | 4.63 | >30 | >30 | >30 | 15.80 | 15.80 | 15.50 |
| SCC-9 | Head and Neck | 3.44 | 3.45 | 3.44 | 26.70 | 27.30 | 27.30 | 16.50 | 16.50 | 16.40 |
| 769-P | Kidney | 0.85 | 0.85 | 0.85 | 6.95 | 6.95 | 6.94 | 3.72 | 3.72 | 3.71 |
| 786-O | Kidney | 2.05 | 2.05 | 2.05 | 27.90 | 27.90 | 27.90 | 14.00 | 14.00 | 13.90 |
| A498 | Kidney | 1.29 | 1.29 | 1.29 | 13.30 | 13.30 | 13.20 | 12.30 | 12.30 | 12.20 |
| A-704 | Kidney | 1.57 | 1.60 | 1.54 | >30 | >30 | >30 | 5.70 | 5.70 | 5.41 |

TABLE 19-continued

OncoPanel cell proliferation results for compounds 1, 2 and 4.

| | | Compound 1 | | | Compound 2 | | | Compound 4 | | |
|---|---|---|---|---|---|---|---|---|---|---|
| Cell Line | Type | Cell Count $EC_{50}$ (µM) | Cell Count $IC_{50}$ (µM) | Cell Count $GI_{50}$ (µM) | Cell Count $EC_{50}$ (µM) | Cell Count $IC_{50}$ (µM) | Cell Count $GI_{50}$ (µM) | Cell Count $EC_{50}$ (µM) | Cell Count $IC_{50}$ (µM) | Cell Count $GI_{50}$ (µM) |
| ACHN | Kidney | 1.74 | 1.74 | 1.74 | 8.79 | 8.79 | 8.76 | 9.50 | 9.50 | 9.47 |
| Caki-1 | Kidney | 2.86 | 2.86 | 2.75 | 0.17 | >30 | >30 | 14.40 | 14.40 | 14.10 |
| Caki-2 | Kidney | 4.38 | 4.38 | 4.35 | 28.80 | 29.10 | 28.90 | 13.10 | 13.60 | 13.50 |
| G-401 | Kidney | 4.00 | 4.00 | 3.99 | 26.00 | 26.20 | 26.20 | 8.08 | 8.08 | 8.05 |
| SK-NEP-1 | Kidney | 0.01 | 0.01 | 0.006 | 0.06 | 0.06 | 0.06 | 9.62 | 9.63 | 9.62 |
| HepG2 | Liver | 0.82 | 0.82 | 0.81 | 6.74 | 6.95 | 6.86 | 25.60 | 25.70 | 25.60 |
| HLE | Liver | 4.62 | 4.63 | 4.59 | 10.00 | 16.40 | 16.00 | 7.24 | 7.24 | 7.15 |
| HLF | Liver | 4.47 | 4.48 | 4.45 | 13.70 | 15.70 | 15.60 | 8.72 | 8.74 | 8.70 |
| HuCCT1 | Liver | 2.48 | 2.48 | 2.48 | 22.60 | 22.60 | 22.60 | 24.80 | 24.80 | 24.80 |
| HUH-6 Clone 5 | Liver | 1.52 | 1.52 | 1.51 | 15.50 | 15.50 | 15.30 | 9.63 | 9.63 | 9.46 |
| OCUG-1 | Liver | 4.30 | 4.30 | 4.29 | >30 | >30 | 29.90 | 15.60 | 15.60 | 15.50 |
| SNU-423 | Liver | 1.48 | 1.49 | 1.46 | 5.29 | 5.31 | 5.26 | 9.30 | 9.31 | 9.28 |
| A427 | Lung - NSCLC | 4.52 | 4.52 | 4.50 | 11.20 | 11.20 | 11.20 | 10.00 | 10.00 | 9.98 |
| A549 | Lung - NSCLC | 1.66 | 1.67 | 1.66 | 22.00 | 22.00 | 21.90 | 10.90 | 10.90 | 10.80 |
| Calu1 | Lung - NSCLC | 3.10 | 3.10 | 3.07 | 13.90 | 13.90 | 13.80 | 8.88 | 8.88 | 8.77 |
| Calu6 | Lung - NSCLC | 9.24 | 9.24 | 8.59 | 14.50 | 16.60 | 15.70 | 25.00 | 25.00 | 24.50 |
| ChaGoK1 | Lung - NSCLC | 1.53 | 1.54 | 1.53 | 8.32 | 8.32 | 8.26 | 8.92 | 8.92 | 8.82 |
| COR-L105 | Lung - NSCLC | 1.44 | 1.45 | 1.42 | 4.76 | 4.76 | 4.61 | 8.66 | 8.66 | 8.47 |
| COR-L23 | Lung - NSCLC | 7.18 | 7.18 | 7.14 | 23.80 | 23.80 | 23.60 | 13.30 | 13.30 | 13.20 |
| Hs 229.T | Lung - NSCLC | 2.88 | 2.94 | 2.89 | 29.30 | 29.80 | 28.60 | 25.90 | 26.30 | 25.20 |
| NCI-H292 | Lung - NSCLC | 3.20 | 3.20 | 3.18 | 16.70 | 16.70 | 16.60 | 9.21 | 9.21 | 9.19 |
| NCIH441 | Lung - NSCLC | 12.10 | 12.10 | 11.70 | >30 | >30 | >30 | 4.76 | >30 | >30 |
| NCI-H460 | Lung - NSCLC | 2.34 | 2.34 | 2.33 | 5.57 | 5.92 | 5.91 | 12.20 | 13.00 | 13.00 |
| NCI-H520 | Lung - NSCLC | 2.43 | 2.43 | 2.41 | 9.03 | 9.20 | 9.17 | 20.80 | 20.80 | 20.60 |
| NCI-H596 | Lung - NSCLC | 8.78 | 8.78 | 8.41 | 12.00 | 15.10 | 14.40 | 28.20 | >30 | >30 |
| NCI-H661 | Lung - NSCLC | 2.28 | 2.29 | 2.28 | 9.51 | 9.51 | 9.51 | 5.94 | 5.94 | 5.86 |
| SKMES1 | Lung - NSCLC | 1.06 | 1.06 | 1.06 | 7.80 | 7.80 | 7.67 | 11.60 | 11.60 | 11.50 |
| DMS114 | Lung - SCLC | 2.77 | 2.77 | 2.57 | 11.50 | 13.80 | 13.10 | 11.50 | 11.60 | 11.40 |
| DMS53 | Lung - SCLC | 0.81 | 0.81 | 0.77 | 5.91 | 5.95 | 5.75 | 8.95 | 8.95 | 8.60 |
| NCIH446 | Lung - SCLC | 10.30 | 10.30 | 10.00 | 9.75 | 9.85 | 9.77 | 7.81 | 7.81 | 7.62 |
| NCI-H69 | Lung - SCLC | 6.30 | 6.44 | 5.84 | 16.20 | 16.20 | 14.90 | 15.90 | 15.90 | 15.10 |
| SHP-77 | Lung - SCLC | 0.89 | 0.90 | 0.89 | 8.01 | 8.01 | 7.90 | 6.83 | 6.83 | 6.75 |
| SW900 | Lung - SCLC | 3.29 | 3.33 | 3.24 | 26.60 | 26.80 | 26.70 | 23.30 | 23.30 | 23.10 |
| AsPC-1 | Pancreas | 2.87 | 2.87 | 2.84 | 14.10 | 14.10 | 13.80 | 14.70 | 14.70 | 14.50 |
| BxPC-3 | Pancreas | 3.29 | 3.30 | 3.29 | 13.00 | >30 | >30 | 13.40 | 13.40 | 13.40 |
| Capan-1 | Pancreas | >30 | >30 | >30 | >30 | >30 | >30 | >30 | >30 | >30 |
| Capan-2 | Pancreas | 1.33 | 1.33 | 1.32 | 8.64 | 8.64 | 8.48 | 24.80 | 24.80 | 24.70 |
| CFPAC-1 | Pancreas | 3.65 | 3.66 | 3.65 | 12.30 | 13.50 | 13.40 | 25.20 | 25.20 | 25.10 |
| HPAF-II | Pancreas | 1.38 | 1.38 | 1.37 | 9.46 | 9.62 | 9.60 | 12.40 | 12.50 | 12.40 |
| Hs 766T | Pancreas | 1.61 | 1.61 | 1.54 | 28.40 | 28.40 | 26.20 | 9.34 | 9.34 | 9.08 |
| HuP-T4 | Pancreas | 4.52 | 4.54 | 4.53 | >30 | >30 | >30 | 13.70 | 13.70 | 13.60 |
| Mia PaCa-2 | Pancreas | 2.97 | 2.97 | 2.97 | 16.30 | 16.30 | 16.20 | 11.00 | 11.00 | 11.00 |
| PANC-1 | Pancreas | 2.87 | 2.87 | 2.83 | 7.06 | 7.06 | 7.01 | 11.70 | 11.70 | 11.60 |
| PSN-1 | Pancreas | 2.32 | 2.32 | 2.32 | 12.00 | 12.00 | 12.00 | 5.04 | 5.04 | 5.04 |
| SU.86.86 | Pancreas | 7.61 | 7.63 | 7.58 | 13.10 | >30 | >30 | >30 | >30 | >30 |
| YAPC | Pancreas | 1.91 | 1.91 | 1.90 | 13.00 | 13.00 | 12.90 | 18.00 | 18.20 | 18.20 |
| BeWo | Placenta | 9.06 | 9.06 | 8.92 | 7.68 | >30 | >30 | 15.60 | 15.60 | 15.50 |
| JAR | Placenta | 12.20 | 12.20 | 12.20 | >30 | >30 | >30 | 6.53 | 6.53 | 6.49 |
| JEG-3 | Placenta | 4.33 | 4.33 | 4.32 | >30 | >30 | >30 | 6.50 | 6.51 | 6.48 |
| 22Rv1 | Prostate | 4.08 | 4.08 | 4.06 | 11.40 | 11.40 | 11.30 | 9.08 | 9.08 | 9.00 |
| BM-1604 | Prostate | 2.58 | 2.58 | 2.56 | 19.10 | 19.10 | 18.90 | >30 | >30 | >30 |
| BPH1 | Prostate | 5.24 | 5.24 | 5.20 | >30 | >30 | >30 | 17.30 | 17.30 | 17.30 |
| DU145 | Prostate | 2.80 | 2.80 | 2.78 | 21.00 | 21.00 | 20.70 | 18.10 | 18.10 | 18.10 |
| LNCaP | Prostate | 3.90 | 3.90 | 3.47 | 0.86 | 0.86 | 0.28 | 11.50 | 12.90 | 12.40 |
| PC-3 | Prostate | 3.88 | 3.88 | 3.86 | 12.00 | 12.00 | 11.80 | 7.71 | 7.71 | 7.64 |
| A101D | Skin (Melanoma) | 8.42 | 8.42 | 8.25 | >30 | >30 | >30 | >30 | >30 | >30 |
| A375 | Skin (Melanoma) | 1.05 | 1.05 | 1.05 | 6.45 | 6.45 | 6.44 | 5.74 | 5.74 | 5.74 |
| A7 | Skin (Melanoma) | 0.94 | 0.94 | 0.94 | 5.54 | 5.63 | 5.60 | 10.50 | 10.50 | 10.50 |
| C32 | Skin (Melanoma) | 2.11 | 2.11 | 1.81 | 19.20 | 19.20 | 15.50 | 7.84 | 7.84 | 6.37 |
| CHL-1 | Skin (Melanoma) | 1.37 | 1.37 | 1.36 | 14.30 | 14.30 | 14.20 | 11.90 | 11.90 | 11.80 |
| COLO 829 | Skin (Melanoma) | 0.68 | 0.68 | 0.62 | 5.35 | 5.35 | 4.93 | 3.71 | 3.71 | 3.29 |
| G-361 | Skin (Melanoma) | 1.79 | 1.79 | 1.77 | 11.70 | 11.80 | 11.80 | 13.80 | 13.90 | 13.80 |
| HMCB | Skin (Melanoma) | 1.37 | 1.37 | 1.36 | 6.68 | 6.68 | 6.57 | 9.49 | 9.49 | 9.38 |
| Hs 294T | Skin (Melanoma) | 2.64 | 2.64 | 2.59 | 7.01 | 7.01 | 6.72 | 8.33 | 8.33 | 8.23 |
| Hs 688(A).T | Skin (Melanoma) | 1.33 | 1.44 | 1.27 | 11.60 | 13.20 | 12.20 | 7.43 | 7.68 | 6.88 |
| Hs 695T | Skin (Melanoma) | 1.18 | 1.27 | 1.16 | 9.07 | 9.48 | 8.99 | 5.00 | 5.18 | 4.02 |
| Hs 852.T | Skin (Melanoma) | 2.49 | 2.56 | 2.42 | 15.40 | 15.40 | 14.70 | 12.00 | 12.00 | 11.60 |
| Hs 934.T | Skin (Melanoma) | 2.53 | 3.27 | 2.34 | >30 | >30 | 24.10 | 11.10 | 11.60 | 10.20 |
| Hs 936.T(C1) | Skin (Melanoma) | 2.00 | 2.00 | 1.97 | 3.62 | 3.76 | 3.74 | 9.10 | 10.40 | 10.20 |
| MALME3M | Skin (Melanoma) | 1.79 | 1.79 | 1.66 | 19.80 | 19.80 | 17.30 | 20.60 | 20.60 | 17.80 |
| MeWo | Skin (Melanoma) | 1.32 | 1.32 | 1.31 | 9.45 | 9.97 | 9.91 | 9.66 | 9.66 | 9.51 |

TABLE 19-continued

OncoPanel cell proliferation results for compounds 1, 2 and 4.

| | | Compound 1 | | | Compound 2 | | | Compound 4 | | |
|---|---|---|---|---|---|---|---|---|---|---|
| Cell Line | Type | Cell Count EC$_{50}$ (μM) | Cell Count IC$_{50}$ (μM) | Cell Count GI$_{50}$ (μM) | Cell Count EC$_{50}$ (μM) | Cell Count IC$_{50}$ (μM) | Cell Count GI$_{50}$ (μM) | Cell Count EC$_{50}$ (μM) | Cell Count IC$_{50}$ (μM) | Cell Count GI$_{50}$ (μM) |
| RPMI-7951 | Skin (Melanoma) | 0.70 | 0.70 | 0.70 | 5.77 | 6.15 | 6.13 | 9.98 | 9.98 | 9.96 |
| SH-4 | Skin (Melanoma) | 1.95 | 1.95 | 1.94 | 9.60 | 11.90 | 11.80 | 11.60 | 11.60 | 11.50 |
| SK-MEL-1 | Skin (Melanoma) | 4.29 | 4.41 | 4.11 | 15.70 | 15.70 | 14.70 | >30 | >30 | >30 |
| SK-MEL-28 | Skin (Melanoma) | 1.54 | 1.54 | 1.53 | 9.46 | 9.89 | 9.85 | 11.20 | 11.20 | 11.10 |
| SK-MEL-3 | Skin (Melanoma) | 4.37 | 4.38 | 4.28 | 22.00 | 22.00 | 20.80 | >30 | >30 | >30 |
| WM-266-4 | Skin (Melanoma) | 1.15 | 1.15 | 1.14 | 6.39 | 6.39 | 6.25 | 10.90 | 10.90 | 10.80 |
| G-292, clone A141B1 | Soft Tissue - Osteosarcoma | 4.55 | 4.57 | 4.41 | 8.80 | 8.80 | 8.57 | 6.23 | 6.25 | 6.07 |
| HOS | Soft Tissue - Osteosarcoma | 0.96 | 0.96 | 0.96 | 4.82 | 4.82 | 4.81 | 3.08 | 3.08 | 3.08 |
| Hs 888.Sk | Soft Tissue - Osteosarcoma | 2.20 | 2.38 | 2.05 | 28.30 | 28.50 | 27.90 | 12.30 | 12.70 | 12.10 |
| KHOS-240S | Soft Tissue - Osteosarcoma | 0.95 | 0.95 | 0.95 | 4.59 | 4.59 | 4.58 | 4.96 | 4.96 | 4.96 |
| MG-63 | Soft Tissue - Osteosarcoma | 9.24 | 9.24 | 9.16 | >30 | >30 | >30 | 11.20 | 11.20 | 11.10 |
| SaOS2 | Soft Tissue - Osteosarcoma | 1.98 | 2.10 | 2.04 | 15.70 | 15.70 | 15.10 | 10.60 | 10.70 | 10.70 |
| SJSA1 | Soft Tissue - Osteosarcoma | 1.41 | 1.41 | 1.41 | 7.11 | 7.11 | 7.02 | 7.45 | 7.45 | 7.45 |
| SW1353 | Soft Tissue - Osteosarcoma | 1.00 | 1.00 | 0.99 | 9.49 | 9.49 | 9.46 | 4.15 | 4.15 | 4.14 |
| U2OS | Soft Tissue - Osteosarcoma | 1.66 | 1.66 | 1.65 | 12.70 | 12.70 | 12.70 | 4.21 | 4.21 | 4.20 |
| A204 | Soft Tissue - Sarcoma | 0.52 | 0.54 | 0.52 | 8.46 | 8.54 | 8.50 | 0.72 | 0.72 | 0.68 |
| A-673 | Soft Tissue - Sarcoma | 1.54 | 1.55 | 1.54 | 10.80 | 11.10 | 11.10 | 2.88 | 2.88 | 2.87 |
| Hs 729 | Soft Tissue - Sarcoma | 2.77 | 2.78 | 2.67 | 23.30 | 23.30 | 21.80 | 11.90 | 11.90 | 11.60 |
| Hs 821.T | Soft Tissue - Sarcoma | 4.22 | 4.22 | 1.80 | >30 | >30 | 13.90 | 12.60 | 12.90 | 9.99 |
| HT-1080 | Soft Tissue - Sarcoma | 0.96 | 0.96 | 0.96 | 3.31 | 3.31 | 3.30 | 4.42 | 4.42 | 4.42 |
| MES-SA | Soft Tissue - Sarcoma | 1.23 | 1.23 | 1.22 | 9.26 | 9.26 | 9.22 | 6.49 | 6.49 | 6.44 |
| RD | Soft Tissue - Sarcoma | 0.81 | 0.81 | 0.81 | 2.98 | 2.98 | 2.96 | 5.19 | 5.19 | 5.17 |
| SJRH30 | Soft Tissue - Sarcoma | 1.42 | 1.42 | 1.41 | 5.09 | 5.10 | 5.07 | 3.68 | 3.68 | 3.68 |
| SK-LMS-1 | Soft Tissue - Sarcoma | 1.57 | 1.57 | 1.56 | 6.79 | 11.30 | 11.20 | 9.04 | 9.04 | 8.98 |
| SK-UT-1 | Soft Tissue - Sarcoma | 2.23 | 2.23 | 2.22 | 11.70 | 11.70 | 11.60 | 5.49 | 5.49 | 5.46 |
| SW684 | Soft Tissue - Sarcoma | 9.37 | 9.37 | 8.28 | >30 | >30 | >30 | >30 | >30 | >30 |
| SW872 | Soft Tissue - Sarcoma | 0.96 | 0.96 | 0.96 | 4.46 | 4.46 | 4.45 | 4.39 | 4.39 | 4.38 |
| SW982 | Soft Tissue - Sarcoma | 1.07 | 1.07 | 1.07 | 7.63 | 7.63 | 7.53 | 7.29 | 7.30 | 7.26 |
| TE 125.T | Soft Tissue - Sarcoma | 6.47 | 9.21 | 1.48 | >30 | >30 | 28.70 | 23.60 | 23.60 | 17.00 |
| TE 381.T | Soft Tissue - Sarcoma | 1.62 | 1.62 | 1.59 | 8.14 | 8.14 | 7.99 | 6.28 | 6.28 | 6.08 |
| VA-ES-BJ | Soft Tissue - Sarcoma | 3.67 | 3.67 | 3.55 | >30 | >30 | >30 | 15.20 | 15.20 | 15.00 |
| AGS | Stomach | 0.70 | 0.70 | 0.70 | 4.69 | 4.69 | 4.69 | 5.25 | 5.25 | 5.24 |
| HS 746T | Stomach | 5.58 | 5.74 | 4.64 | >30 | >30 | >30 | 20.00 | 20.00 | 17.10 |
| KATO III | Stomach | 3.28 | 3.28 | 3.27 | 8.98 | 16.80 | 16.60 | 10.90 | 11.10 | 11.10 |
| SK-PN-DW | Stomach | 4.66 | 4.66 | 4.63 | 10.80 | 10.90 | 10.90 | 4.91 | 4.91 | 4.88 |
| SNU-1 | Stomach | 1.25 | 1.25 | 1.25 | 8.51 | 9.42 | 9.41 | 6.99 | 6.99 | 6.98 |
| SNU-16 | Stomach | 1.31 | 1.31 | 1.31 | 9.96 | 9.96 | 9.91 | 11.00 | 11.00 | 11.00 |
| SNU-5 | Stomach | 3.92 | 3.92 | 3.87 | >30 | >30 | >30 | 14.40 | 14.40 | 14.20 |
| NTERA-2 cl.D1 | Testis | 2.25 | 2.25 | 2.20 | 12.50 | 12.50 | 12.30 | 7.41 | 7.41 | 7.39 |

TABLE 20

Oncopanel cell proliferation results for Compounds 11 and 12.

| | | Compound 11 and 12 | | |
| --- | --- | --- | --- | --- |
| Cell Line | Type | Cell Count $EC_{50}$ (μM) | Cell Count $IC_{50}$ (μM) | Cell Count $GI_{50}$ (μM) |
| 647-V | Bladder | >30 | >30 | >30 |
| AU565 | Breast | 16.4 | 17.1 | 16.9 |
| CAMA-1 | Breast | >30 | >30 | >30 |
| MCF7 | Breast | 27.5 | 27.5 | 27 |
| MDA MB 231 | Breast | >30 | >30 | >30 |
| MDA MB 453 | Breast | 10.6 | 10.6 | 10.4 |
| MDA-MB-415 | Breast | 17.8 | 17.8 | 15.7 |
| Hs 683 | CNS - Glioma | 27 | 27 | 25.6 |
| M059J | CNS - Glioma | >30 | >30 | >30 |
| HuTu 80 | Colon | 8.61 | 8.7 | 8.65 |
| LS-174T | Colon | >30 | >30 | >30 |
| HeLa | Female GU - Cervix | >30 | >30 | >30 |
| OVCAR3 | Female GU - Ovary | >30 | >30 | >30 |
| AN3 CA | Female GU - Uterus | 10.8 | 13.3 | 13.1 |
| MEG01 | Leukemia | 17.5 | 17.5 | 17.3 |
| MOLT-16 | Leukemia | 21.8 | 21.8 | 21.7 |
| MOLT-3 | Leukemia | 11.8 | 14.1 | 14 |
| MV-4-11 | Leukemia | >30 | >30 | >30 |
| MX1 | Leukemia | 14.9 | 14.9 | 14.9 |
| A427 | Lung - NSCLC | 16 | 16 | 15.8 |
| Calu1 | Lung - NSCLC | >30 | >30 | >30 |
| Calu6 | Lung - NSCLC | >30 | >30 | >30 |
| Hs 229.T | Lung - NSCLC | >30 | >30 | >30 |
| NCI-H292 | Lung - NSCLC | 12.1 | >30 | >30 |
| NCI-H520 | Lung - NSCLC | >30 | >30 | >30 |
| NCI-H596 | Lung - NSCLC | >30 | >30 | >30 |
| DOHH-2 | Lymphoma | 12.2 | 13.4 | 13.4 |
| EB2 | Lymphoma | >30 | >30 | >30 |
| Jiyoye | Lymphoma | >30 | >30 | >30 |
| L-428 | Lymphoma | 21.3 | 21.3 | 21.1 |
| NAMALWA | Lymphoma | >30 | >30 | >30 |
| Raji | Lymphoma | >30 | >30 | >30 |
| SUP-T1 | Lymphoma | >30 | >30 | >30 |
| PSN-1 | Pancreas | >30 | >30 | >30 |
| Hs 934.T | Skin (Melanoma) | 21.9 | >30 | 16.3 |
| HOS | Soft Tissue - Osteosarcoma | >30 | >30 | >30 |
| KHOS-240S | Soft Tissue - Osteosarcoma | >30 | >30 | >30 |
| SW1353 | Soft Tissue - Osteosarcoma | >30 | >30 | >30 |
| Hs 729 | Soft Tissue - Sarcoma | 26.4 | >30 | >30 |
| HT-1080 | Soft Tissue - Sarcoma | 12.7 | 12.7 | 12.7 |

TABLE 21

Representative data for proliferation response when cell line MDA-MB-415 is treated with Compound 1

| | Relative cell count (%) | |
| --- | --- | --- |
| Concentration (microM) | Mean | StdDev |
| 9.55E−04 | 90.2 | 1.3 |
| 3.02E−03 | 100.0 | 6.4 |
| 9.53E−03 | 98.0 | 8.7 |
| 3.01E−02 | 93.4 | 2.7 |
| 9.52E−02 | 98.1 | 10.3 |
| 3.01E−01 | 100.2 | 8.6 |
| 9.51E−01 | 62.3 | 5.3 |
| 3.00E+00 | 1.3 | 0.2 |
| 9.49E+00 | 0.3 | 0.0 |
| 3.00E+01 | 0.2 | 0.0 |

TABLE 22

Representative data for proliferation response when cell line RKO-AS45-1 is treated with Compound 1

| | Relative cell count (%) | |
| --- | --- | --- |
| Concentration (microM) | Mean | StdDev |
| 9.55E−04 | 95.4 | 2.0 |
| 3.02E−03 | 83.7 | 7.7 |
| 9.53E−03 | 88.3 | 3.7 |
| 3.01E−02 | 86.2 | 5.6 |
| 9.52E−02 | 80.5 | 4.7 |
| 3.01E−01 | 90.0 | 6.9 |
| 9.51E−01 | 72.1 | 9.7 |
| 3.00E+00 | 7.6 | 3.5 |
| 9.49E+00 | 0.1 | 0.0 |
| 3.00E+01 | 0.1 | 0.0 |

TABLE 23

Representative data for proliferation response when cell line SW480 is treated with Compound 1

| | Relative cell count (%) | |
| --- | --- | --- |
| Concentration (microM) | Mean | StdDev |
| 9.55E−04 | 111.8 | 7.0 |
| 3.02E−03 | 116.5 | 19.3 |
| 9.53E−03 | 103.7 | 9.4 |
| 3.01E−02 | 99.5 | 0.5 |
| 9.52E−02 | 94.1 | 10.2 |
| 3.01E−01 | 93.5 | 6.4 |
| 9.51E−01 | 69.9 | 17.0 |
| 3.00E+00 | 4.1 | 4.6 |
| 9.49E+00 | 0.2 | 0.0 |
| 3.00E+01 | 0.4 | 0.4 |

TABLE 24

Representative data for proliferation response when cell line 639-V is treated with Compound 1

| | Relative cell count (%) | |
| --- | --- | --- |
| Concentration (microM) | Mean | StdDev |
| 9.55E−04 | 92.0 | 14.3 |
| 3.02E−03 | 96.1 | 1.9 |
| 9.53E−03 | 101.2 | 5.0 |
| 3.01E−02 | 103.6 | 8.6 |
| 9.52E−02 | 91.6 | 9.6 |
| 3.01E−01 | 92.6 | 14.1 |
| 9.51E−01 | 91.9 | 12.2 |
| 3.00E+00 | 15.8 | 4.2 |
| 9.49E+00 | 0.3 | 0.1 |
| 3.00E+01 | 0.0 | 0.0 |

TABLE 25

Representative data for proliferation response when cell line Hs 729 is treated with Compound 1

| | Relative cell count (%) | |
| --- | --- | --- |
| Concentration (microM) | Mean | StdDev |
| 9.55E−04 | 100.6 | 7.6 |
| 3.02E−03 | 103.0 | 10.5 |
| 9.53E−03 | 108.7 | 4.1 |
| 3.01E−02 | 107.0 | 2.1 |
| 9.52E−02 | 99.9 | 0.7 |
| 3.01E−01 | 99.4 | 7.7 |

TABLE 25-continued

Representative data for proliferation response when cell line Hs 729 is treated with Compound 1

| Concentration (microM) | Relative cell count (%) Mean | StdDev |
|---|---|---|
| 9.51E−01 | 98.9 | 1.2 |
| 3.00E+00 | 46.0 | 8.8 |
| 9.49E+00 | 3.2 | 0.2 |
| 3.00E+01 | 1.0 | 0.3 |

TABLE 26

Representative data for proliferation response when cell line Hs 852.T is treated with Compound 1

| Concentration (microM) | Relative cell count (%) Mean | StdDev |
|---|---|---|
| 9.55E−04 | 104.3 | 9.1 |
| 3.02E−03 | 104.5 | 5.1 |
| 9.53E−03 | 100.2 | 6.2 |
| 3.01E−02 | 94.5 | 5.6 |
| 9.52E−02 | 92.2 | 2.4 |
| 3.01E−01 | 95.3 | 2.9 |
| 9.51E−01 | 85.5 | 4.3 |
| 3.00E+00 | 41.6 | 5.1 |
| 9.49E+00 | 13.1 | 1.7 |
| 3.00E+01 | 2.7 | 0.5 |

TABLE 27

Representative data for proliferation response when cell line HCT-8 is treated with Compound 1

| Concentration (microM) | Relative cell count (%) Mean | StdDev |
|---|---|---|
| 9.55E−04 | 102.6 | 3.7 |
| 3.02E−03 | 104.1 | 9.7 |
| 9.53E−03 | 91.0 | 10.1 |
| 3.01E−02 | 91.8 | 3.5 |
| 9.52E−02 | 100.8 | 2.6 |
| 3.01E−01 | 94.9 | 4.8 |
| 9.51E−01 | 72.6 | 2.3 |
| 3.00E+00 | 1.9 | 0.5 |
| 9.49E+00 | 0.0 | 0.0 |
| 3.00E+01 | 0.0 | 0.0 |

TABLE 28

Representative data for proliferation response when cell line IM-9 is treated with Compound 1

| Concentration (microM) | Relative cell count (%) Mean | StdDev |
|---|---|---|
| 9.55E−04 | 94.9 | 34.7 |
| 3.02E−03 | 102.8 | 9.5 |
| 9.53E−03 | 103.1 | 2.4 |
| 3.01E−02 | 107.3 | 9.3 |
| 9.52E−02 | 97.7 | 3.4 |
| 3.01E−01 | 97.5 | 8.6 |
| 9.51E−01 | 0.0 | 0.0 |
| 3.00E+00 | 0.1 | 0.0 |
| 9.49E+00 | 0.1 | 0.1 |
| 3.00E+01 | 0.0 | 0.0 |

TABLE 29

Oncopanel cell proliferation results for *Myoporum insulare* resin extract.

| | | *M. insulare* resin extract | | | |
|---|---|---|---|---|---|
| Cell Line | Type | Cell Count $EC_{50}$ (µg/mL) | Cell Count $IC_{50}$ (µg/mL) | Cell Count $GI_{50}$ (µg/mL) | |
| 5637 | Bladder | 3.71 | 3.75 | 3.75 | A |
| 639-V | Bladder | 3.18 | 3.18 | 3.17 | B |
| 647-V | Bladder | 2.69 | 2.69 | 2.69 | C |
| BFTC-905 | Bladder | 3.28 | 3.28 | 3.28 | B |
| HT-1197 | Bladder | 3.18 | 3.20 | 3.17 | C |
| HT1376 | Bladder | 1.31 | 1.31 | 1.27 | C |
| J82 | Bladder | 1.26 | 1.26 | 1.26 | D |
| SCaBER | Bladder | 2.74 | 2.74 | 2.73 | C |
| T24 | Bladder | 1.70 | 1.70 | 1.70 | A |
| TCCSUP | Bladder | 2.76 | 2.77 | 2.73 | B |
| UM-UC-3 | Bladder | 0.98 | 0.98 | 0.97 | C |
| AU565 | Breast | 1.62 | 1.62 | 1.61 | A |
| BT20 | Breast | 1.57 | 1.61 | 1.50 | B |
| BT474 | Breast | 5.60 | 5.60 | 4.94 | A |
| BT-549 | Breast | 3.25 | 3.25 | 3.16 | A |
| CAMA-1 | Breast | 3.57 | 3.57 | 3.50 | A |
| EFM-19 | Breast | 1.59 | 1.59 | 1.50 | A |
| Hs 578T | Breast | 8.96 | 9.00 | 8.96 | A |
| KPL-1 | Breast | 0.61 | 0.61 | 0.61 | A |
| MCF7 | Breast | 1.72 | 1.73 | 1.71 | C |
| MDA MB 231 | Breast | 2.03 | 2.03 | 2.03 | A |
| MDA MB 453 | Breast | 0.53 | 0.53 | 0.52 | A |
| MDA MB 468 | Breast | 2.86 | 2.86 | 2.84 | A |
| MDA-MB-415 | Breast | 1.12 | 1.12 | 1.05 | A |
| MDA-MB-436 | Breast | 2.70 | 2.70 | 2.67 | A |
| SK-BR-3 | Breast | 2.15 | 2.16 | 2.10 | C |
| T47D | Breast | 4.80 | 4.80 | 4.59 | B |
| A172 | CNS - Glioma | 1.46 | 1.46 | 1.45 | B |
| CCF-STTG1 | CNS - Glioma | 9.00 | 9.00 | 7.35 | C |
| DBTRG-05MG | CNS - Glioma | 3.23 | 3.24 | 3.22 | C |
| DK-MG | CNS - Glioma | 5.99 | 6.23 | 6.06 | C |
| H4 | CNS - Glioma | 3.32 | 3.32 | 3.32 | C |
| Hs 683 | CNS - Glioma | 5.01 | 5.01 | 4.87 | B |
| M059J | CNS - Glioma | 4.62 | 4.62 | 4.55 | B |
| PFSK-1 | CNS - Glioma | 3.89 | 3.89 | 3.85 | B |
| SNB-19 | CNS - Glioma | 1.39 | 1.41 | 1.41 | C |
| SW1088 | CNS - Glioma | 1.79 | 1.79 | 1.78 | C |
| SW1783 | CNS - Glioma | 3.06 | 3.06 | 2.96 | B |
| T98G | CNS - Glioma | 3.06 | 3.06 | 3.06 | B |
| U-118 MG | CNS - Glioma | 4.20 | 4.24 | 4.20 | B |
| U-138MG | CNS - Glioma | 5.92 | 5.92 | 5.74 | C |
| U-87 MG | CNS - Glioma | 2.46 | 2.50 | 2.45 | C |
| D341 Med | CNS - Medulloblastoma | 3.78 | 3.96 | 3.92 | B |
| Daoy | CNS - Medulloblastoma | 1.10 | 1.11 | 1.10 | A |
| BE(2)C | CNS - Neuroblastoma | 3.07 | 3.07 | 3.05 | B |
| CHP-212 | CNS - Neuroblastoma | 1.19 | 1.19 | 1.14 | B |
| MC-IXC | CNS - Neuroblastoma | 3.32 | 3.32 | 3.30 | B |
| SK-N-AS | CNS - Neuroblastoma | 3.18 | 3.20 | 3.19 | A |
| SK-N-DZ | CNS - Neuroblastoma | 3.35 | 3.42 | 3.39 | B |
| SK-N-FI | CNS - Neuroblastoma | 3.37 | 5.39 | 4.66 | C |
| Colo 201 | Colon | 1.08 | 1.08 | 1.08 | D |
| Colo 205 | Colon | 1.46 | 1.46 | 1.46 | D |
| Colo 320 HSR | Colon | 2.45 | 2.45 | 2.44 | B |
| Colo 320DM | Colon | 3.19 | 3.19 | 3.17 | B |
| DLD-1 | Colon | 3.19 | 3.19 | 3.19 | A |
| HCT-116 | Colon | 1.44 | 1.44 | 1.44 | B |
| HCT-15 | Colon | 1.92 | 1.92 | 1.92 | C |
| HCT-8 | Colon | 2.56 | 2.56 | 2.55 | D |
| HT-29 | Colon | 4.31 | 4.31 | 4.31 | A |
| LS1034 | Colon | 1.96 | 1.96 | 1.93 | B |
| LS123 | Colon | 1.28 | 1.38 | 1.29 | B |

TABLE 29-continued

Oncopanel cell proliferation results for *Myoporum insulare* resin extract.

| Cell Line | Type | M. insulare resin extract Cell Count EC$_{50}$ (µg/mL) | Cell Count IC$_{50}$ (µg/mL) | Cell Count GI$_{50}$ (µg/mL) | |
|---|---|---|---|---|---|
| LS411N | Colon | 6.41 | 6.41 | 6.30 | B |
| MT-3 | Colon | 4.10 | 4.10 | 4.10 | A |
| NCI-H508 | Colon | >10.5 | >10.5 | >10.5 | B |
| NCI-H747 | Colon | 3.64 | 3.71 | 3.68 | B |
| RKO | Colon | 1.88 | 1.88 | 1.87 | C |
| RKO-AS45-1 | Colon | 2.78 | 2.78 | 2.78 | C |
| RKOE6 | Colon | 2.49 | 2.49 | 2.49 | B |
| SW1417 | Colon | 3.27 | 4.03 | 3.92 | D |
| SW1463 | Colon | 3.64 | 3.68 | 3.64 | B |
| SW403 | Colon | 9.10 | 9.42 | 9.31 | B |
| SW48 | Colon | 1.14 | 1.14 | 1.14 | C |
| SW480 | Colon | 1.04 | 1.04 | 1.03 | C |
| SW620 | Colon | 2.32 | 2.32 | 2.32 | B |
| SW837 | Colon | 2.92 | 3.20 | 3.14 | C |
| SW948 | Colon | >10.5 | >10.5 | >10.5 | D |
| WiDr | Colon | 1.12 | 1.12 | 1.11 | B |
| NCI-H295R | Endocrine - Adrenal gland | >10.5 | >10.5 | >10.5 | A |
| BHT-101 | Endocrine - Thyroid | 2.72 | 2.72 | 2.71 | C |
| CAL-62 | Endocrine - Thyroid | 1.18 | 1.18 | 1.18 | A |
| CGTH-W-1 | Endocrine - Thyroid | 1.03 | 1.03 | 1.03 | B |
| SW579 | Endocrine - Thyroid | 3.01 | 3.01 | 3.00 | C |
| Y79 | Eye | 3.08 | 3.10 | 3.02 | D |
| C-33A | Female GU - Cervix | 4.27 | 4.27 | 4.24 | C |
| C-4 II | Female GU - Cervix | 1.19 | 1.19 | 1.19 | B |
| HeLa | Female GU - Cervix | 3.75 | 3.75 | 3.71 | C |
| HT-3 | Female GU - Cervix | 3.99 | 4.03 | 3.99 | B |
| SiHa | Female GU - Cervix | 5.60 | 5.60 | 5.53 | B |
| Ca Ski | Female GU - Ovary | 5.53 | 5.53 | 5.46 | A |
| CaOV3 | Female GU - Ovary | 2.59 | 2.60 | 2.52 | B |
| ME-180 | Female GU - Ovary | 3.22 | 3.22 | 3.20 | B |
| MS751 | Female GU - Ovary | 2.65 | 2.65 | 2.63 | B |
| OVCAR3 | Female GU - Ovary | 2.01 | 2.08 | 2.02 | D |
| PA-1 | Female GU - Ovary | 4.73 | 4.73 | 4.73 | B |
| SKOV3 | Female GU - Ovary | 1.73 | 1.73 | 1.72 | B |
| AN3 CA | Female GU - Uterus | 1.61 | 1.61 | 1.58 | B |
| HEC-1-A | Female GU - Uterus | 1.60 | 1.68 | 1.67 | A |
| KLE | Female GU - Uterus | 3.28 | 3.28 | 2.92 | C |
| SW954 | Female GU - Vulva | 8.51 | 8.51 | 8.47 | C |
| BV-173 | Leukemia | 2.17 | 2.17 | 2.17 | B |
| CCRFCEM | Leukemia | 3.85 | 3.85 | 3.82 | A |
| CEM-C1 | Leukemia | 1.13 | 1.13 | 1.12 | A |
| CML-T1 | Leukemia | 1.43 | 1.43 | 1.43 | A |
| EM-2 | Leukemia | 2.58 | 2.58 | 2.56 | A |
| HEL-92-1-7 | Leukemia | 5.29 | 5.29 | 5.25 | A |
| J-RT3-T3-5 | Leukemia | 1.29 | 1.29 | 1.29 | D |
| Jurkat | Leukemia | 0.91 | 0.91 | 0.91 | B |
| K562 | Leukemia | 3.75 | 3.75 | 3.75 | A |
| KG-1 | Leukemia | 4.73 | 5.39 | 5.32 | B |
| KU812 | Leukemia | 4.52 | 4.52 | 4.45 | C |
| MEG01 | Leukemia | 4.55 | 4.55 | 4.55 | A |
| MHH-PREB-1 | Leukemia | 3.82 | 3.82 | 3.82 | C |
| MOLT-16 | Leukemia | 2.49 | 2.49 | 2.48 | A |
| MOLT-3 | Leukemia | 1.42 | 1.42 | 1.42 | C |
| MV-4-11 | Leukemia | 2.76 | 2.76 | 2.75 | A |
| MX1 | Leukemia | 1.28 | 1.28 | 1.28 | C |
| NALM-6 | Leukemia | 1.03 | 1.03 | 1.03 | C |
| RS4; 11 | Leukemia | 1.86 | 1.86 | 1.82 | A |
| TF-1 | Leukemia | 4.55 | 4.55 | 4.45 | C |
| Thp1 | Leukemia | 1.78 | 1.78 | 1.74 | A |
| BC-1 | Lymphoma | 1.73 | 1.73 | 1.73 | A |
| BCP-1 | Lymphoma | 3.26 | 3.26 | 3.23 | A |
| CA46 | Lymphoma | 2.03 | 2.03 | 2.03 | A |
| CRO-AP2 | Lymphoma | 3.99 | 3.99 | 3.99 | A |
| Daudi | Lymphoma | 1.33 | 1.33 | 1.33 | A |
| DB | Lymphoma | 1.09 | 1.10 | 1.10 | B |
| DOHH-2 | Lymphoma | 1.01 | 1.01 | 1.01 | A |
| DoTc2 4510 | Lymphoma | 1.38 | 1.38 | 1.36 | A |
| EB2 | Lymphoma | 5.60 | 5.60 | 5.57 | A |
| EB-3 | Lymphoma | 1.68 | 1.68 | 1.68 | B |
| GA-10 | Lymphoma | 1.42 | 1.42 | 1.42 | A |
| Hs 445 | Lymphoma | 1.46 | 1.46 | 1.44 | C |
| Hs 611.T | Lymphoma | 3.29 | 3.29 | 3.28 | D |
| HT | Lymphoma | 1.61 | 1.61 | 1.60 | c |
| JeKo-1 | Lymphoma | 2.58 | 2.58 | 2.57 | A |
| Jiyoye | Lymphoma | 4.24 | 4.24 | 4.24 | A |
| L-428 | Lymphoma | 1.24 | 1.24 | 1.24 | A |
| MC116 | Lymphoma | 3.15 | 3.15 | 3.15 | A |
| NAMALWA | Lymphoma | 1.68 | 1.69 | 1.68 | D |
| Raji | Lymphoma | 3.92 | 3.92 | 3.92 | A |
| Ramos (RA 1) | Lymphoma | 2.33 | 2.33 | 2.33 | C |
| RPMI 6666 | Lymphoma | 3.28 | 3.32 | 3.27 | C |
| SR | Lymphoma | 1.74 | 1.74 | 1.74 | A |
| ST486 | Lymphoma | 1.08 | 1.08 | 1.08 | A |
| SU-DHL-10 | Lymphoma | 4.17 | 4.17 | 4.17 | A |
| SU-DHL-4 | Lymphoma | 1.82 | 1.82 | 1.82 | C |
| SU-DHL-5 | Lymphoma | 1.02 | 1.02 | 1.02 | B |
| SU-DHL-8 | Lymphoma | 1.74 | 1.74 | 1.74 | A |
| SUP-T1 | Lymphoma | 3.75 | 3.75 | 3.75 | A |
| TUR | Lymphoma | 4.48 | 4.48 | 4.48 | C |
| ARH-77 | Myeloma | 2.66 | 2.67 | 2.65 | A |
| IM-9 | Myeloma | 0.68 | 0.68 | 0.68 | B |
| RPMI 8226 | Myeloma | 0.99 | 1.00 | 0.99 | C |
| SKO-007 | Myeloma | 0.99 | 1.00 | 0.99 | B |
| U266B1 | Myeloma | 2.82 | 2.82 | 2.71 | B |
| A-253 | Head and Neck | 8.23 | 8.23 | 8.23 | B |
| A388 | Head and Neck | 1.92 | 1.94 | 1.93 | B |
| A431 | Head and Neck | 3.29 | 3.30 | 3.30 | A |
| Cal 27 | Head and Neck | 2.17 | 2.17 | 2.17 | B |
| Detroit 562 | Head and Neck | 2.99 | 3.00 | 2.99 | B |
| FaDu | Head and Neck | 0.90 | 0.90 | 0.90 | B |
| OE19 | Head and Neck | 2.97 | 2.98 | 2.96 | C |
| OE21 | Head and Neck | 3.89 | 3.89 | 3.89 | C |
| SCC-25 | Head and Neck | 5.99 | 5.99 | 5.95 | C |
| SCC-4 | Head and Neck | 8.51 | 8.51 | 8.47 | B |
| SCC-9 | Head and Neck | 7.35 | 7.42 | 7.39 | B |
| 769-P | Kidney | 1.05 | 1.05 | 1.05 | B |
| 786-O | Kidney | 2.81 | 2.81 | 2.81 | B |
| A498 | Kidney | 1.80 | 1.80 | 1.79 | B |
| A-704 | Kidney | 2.99 | 3.01 | 2.98 | B |
| ACHN | Kidney | 3.26 | 3.26 | 3.25 | A |
| Caki-1 | Kidney | 4.66 | 4.66 | 4.59 | C |
| Caki-2 | Kidney | 4.76 | 4.80 | 4.80 | A |
| G-401 | Kidney | 4.13 | 4.13 | 4.13 | B |
| SK-NEP-1 | Kidney | 3.99 | 3.99 | 3.99 | D |
| HepG2 | Liver | 1.54 | 1.54 | 1.54 | C |
| HLE | Liver | 3.92 | 3.92 | 3.89 | B |
| HLF | Liver | 3.99 | 3.99 | 3.96 | C |
| HuCCT1 | Liver | 3.64 | 3.64 | 3.64 | B |

TABLE 29-continued

Oncopanel cell proliferation results for *Myoporum insulare* resin extract.

| Cell Line | Type | Cell Count EC$_{50}$ (μg/mL) | Cell Count IC$_{50}$ (μg/mL) | Cell Count GI$_{50}$ (μg/mL) | |
|---|---|---|---|---|---|
| HUH-6 Clone 5 | Liver | 1.70 | 1.70 | 1.69 | B |
| OCUG-1 | Liver | 3.61 | 3.64 | 3.64 | B |
| SNU-423 | Liver | 1.47 | 1.47 | 1.45 | B |
| A427 | Lung - NSCLC | 4.13 | 4.13 | 4.10 | A |
| A549 | Lung - NSCLC | 2.98 | 2.98 | 2.98 | C |
| Calu1 | Lung - NSCLC | 2.72 | 2.72 | 2.69 | A |
| Calu6 | Lung - NSCLC | 9.56 | 9.77 | 9.59 | B |
| ChaGoK1 | Lung - NSCLC | 1.69 | 1.69 | 1.68 | A |
| COR-L105 | Lung - NSCLC | 2.85 | 2.86 | 2.84 | A |
| COR-L23 | Lung - NSCLC | 4.59 | 4.62 | 4.59 | D |
| Hs 229.T | Lung - NSCLC | 3.09 | 3.31 | 3.15 | A |
| NCI-H292 | Lung - NSCLC | 3.50 | 3.50 | 3.49 | A |
| NCIH441 | Lung - NSCLC | >10.5 | >10.5 | >10.5 | A |
| NCI-H460 | Lung - NSCLC | 2.99 | 2.99 | 2.99 | A |
| NCI-H520 | Lung - NSCLC | 3.02 | 3.02 | 3.01 | A |
| NCI-H596 | Lung - NSCLC | 8.89 | 8.93 | 8.86 | A |
| NCI-H661 | Lung - NSCLC | 1.70 | 1.70 | 1.69 | A |
| SKMES1 | Lung - NSCLC | 1.26 | 1.26 | 1.25 | A |
| DMS114 | Lung - SCLC | 4.62 | 4.69 | 4.55 | C |
| DMS53 | Lung - SCLC | 0.51 | 0.51 | 0.48 | A |
| NCIH446 | Lung - SCLC | 3.75 | 3.75 | 3.75 | B |
| NCI-H69 | Lung - SCLC | 5.01 | 5.01 | 4.73 | A |
| SHP-77 | Lung - SCLC | 1.03 | 1.03 | 1.03 | B |
| SW900 | Lung - SCLC | 3.64 | 3.68 | 3.61 | C |
| AsPC-1 | Pancreas | 2.51 | 2.51 | 2.45 | A |
| BxPC-3 | Pancreas | 4.48 | 4.48 | 4.48 | A |
| Capan-1 | Pancreas | >10.5 | >10.5 | >10.5 | C |
| Capan-2 | Pancreas | 1.34 | 1.34 | 1.33 | A |
| CFPAC4 | Pancreas | 3.57 | 3.57 | 3.57 | A |
| HPAF-II | Pancreas | 2.30 | 2.31 | 2.29 | C |
| Hs 766T | Pancreas | 2.44 | 2.47 | 2.42 | A |
| HuP-T4 | Pancreas | >10.5 | >10.5 | >10.5 | C |
| Mia PaCa-2 | Pancreas | 3.15 | 3.15 | 3.15 | A |
| PANC-1 | Pancreas | 2.20 | 2.20 | 2.17 | A |
| PSN-1 | Pancreas | 2.70 | 2.70 | 2.70 | B |
| SU.86.86 | Pancreas | >10.5 | >10.5 | >10.5 | C |
| YAPC | Pancreas | 3.37 | 3.37 | 3.34 | A |
| BeWo | Placenta | 10.05 | >10.5 | >10.5 | B |
| JAR | Placenta | 8.65 | 8.65 | 8.65 | C |
| JEG-3 | Placenta | 4.38 | 4.38 | 4.34 | B |
| 22Rv1 | Prostate | 4.13 | 4.13 | 4.10 | A |
| BM-1604 | Prostate | 3.89 | 3.89 | 3.85 | C |
| BPH1 | Prostate | 4.10 | 8.82 | 7.98 | A |
| DU145 | Prostate | 3.61 | 3.61 | 3.57 | A |
| LNCaP | Prostate | 3.17 | 3.17 | 2.62 | C |
| PC-3 | Prostate | 4.06 | 4.06 | 4.03 | A |
| A101D | Skin (Melanoma) | 6.23 | 6.23 | 6.09 | B |
| A375 | Skin (Melanoma) | 1.41 | 1.41 | 1.41 | B |
| A7 | Skin (Melanoma) | 0.92 | 0.92 | 0.91 | B |
| C32 | Skin (Melanoma) | 1.71 | 1.71 | 1.36 | B |
| CHL-1 | Skin (Melanoma) | 1.59 | 1.59 | 1.59 | D |
| COLO 829 | Skin (Melanoma) | 1.01 | 1.03 | 0.98 | D |
| G-361 | Skin (Melanoma) | 2.70 | 2.70 | 2.69 | B |
| HMCB | Skin (Melanoma) | 1.46 | 1.47 | 1.46 | C |
| Hs 294T | Skin (Melanoma) | 1.73 | 1.73 | 1.67 | B |
| Hs 688(A).T | Skin (Melanoma) | 2.11 | 2.22 | 1.99 | B |
| Hs 695T | Skin (Melanoma) | 0.22 | 0.22 | 0.11 | C |
| Hs 852.T | Skin (Melanoma) | 3.64 | 3.64 | 3.50 | B |
| Hs 934.T | Skin (Melanoma) | 3.01 | 4.52 | 3.02 | B |
| Hs 936.T(C1) | Skin (Melanoma) | 2.26 | 2.26 | 2.22 | B |
| MALME3M | Skin (Melanoma) | 2.69 | 2.69 | 2.53 | C |
| MeWo | Skin (Melanoma) | 1.93 | 1.93 | 1.91 | B |
| RPMI-7951 | Skin (Melanoma) | 0.74 | 0.74 | 0.73 | C |
| SH-4 | Skin (Melanoma) | 2.60 | 2.60 | 2.58 | B |
| SK-MEL-1 | Skin (Melanoma) | 3.96 | 4.27 | 4.13 | B |
| SK-MEL-28 | Skin (Melanoma) | 2.38 | 2.39 | 2.37 | A |
| SK-MEL-3 | Skin (Melanoma) | 5.25 | 5.25 | 5.15 | C |
| WM-266-4 | Skin (Melanoma) | 1.19 | 1.19 | 1.18 | B |
| G-292, clone A141B1 | Soft Tissue - Osteosarcoma | 2.26 | 2.26 | 2.16 | B |
| HOS | Soft Tissue - Osteosarcoma | 1.06 | 1.06 | 1.06 | B |
| Hs 888.Sk | Soft Tissue - Osteosarcoma | 3.09 | 3.19 | 3.10 | B |
| KHOS-240S | Soft Tissue - Osteosarcoma | 2.18 | 2.18 | 2.18 | D |
| MG-63 | Soft Tissue - Osteosarcoma | 9.66 | 9.70 | 9.66 | A |
| SaOS2 | Soft Tissue - Osteosarcoma | 3.36 | 3.43 | 3.33 | B |
| SJSA1 | Soft Tissue - Osteosarcoma | 1.51 | 1.51 | 1.50 | B |
| SW1353 | Soft Tissue - Osteosarcoma | 1.76 | 1.76 | 1.76 | B |
| U2OS | Soft Tissue - Osteosarcoma | 2.35 | 2.35 | 2.34 | C |
| A204 | Soft Tissue - Sarcoma | 0.65 | 0.65 | 0.64 | A |
| A-673 | Soft Tissue - Sarcoma | 1.15 | 1.15 | 1.15 | B |
| Hs 729 | Soft Tissue - Sarcoma | 3.07 | 3.11 | 3.01 | C |
| Hs 821.T | Soft Tissue - Sarcoma | 2.79 | 5.43 | 2.56 | B |
| HT-1080 | Soft Tissue - Sarcoma | 0.59 | 0.59 | 0.59 | A |
| MES-SA | Soft Tissue - Sarcoma | 1.53 | 1.53 | 1.53 | B |
| RD | Soft Tissue - Sarcoma | 0.69 | 0.69 | 0.69 | C |
| SJRH30 | Soft Tissue - Sarcoma | 1.46 | 1.46 | 1.46 | A |
| SK-LMS-1 | Soft Tissue - Sarcoma | 2.23 | 2.23 | 2.21 | C |
| SK-UT-1 | Soft Tissue - Sarcoma | 2.39 | 2.39 | 2.38 | B |
| SW684 | Soft Tissue - Sarcoma | 9.14 | 9.14 | 7.95 | C |
| SW872 | Soft Tissue - Sarcoma | 0.35 | 0.35 | 0.35 | A |
| SW982 | Soft Tissue - Sarcoma | 1.20 | 1.20 | 1.19 | B |
| TE 125.T | Soft Tissue - Sarcoma | 2.05 | 6.34 | 1.31 | B |
| TE 381.T | Soft Tissue - Sarcoma | 1.56 | 1.56 | 1.55 | A |

TABLE 29-continued

Oncopanel cell proliferation results for *Myoporum insulare* resin extract.

| | | *M. insulare* resin extract | | |
|---|---|---|---|---|
| Cell Line | Type | Cell Count $EC_{50}$ (µg/mL) | Cell Count $IC_{50}$ (µg/mL) | Cell Count $GI_{50}$ (µg/mL) |
| VA-ES-BJ | Soft Tissue - Sarcoma | 4.17 | 4.17 | 4.13 $^B$ |
| AGS | Stomach | 0.85 | 0.85 | 0.85 $^B$ |
| HS 746T | Stomach | 3.99 | 6.51 | 4.94 $^A$ |
| KATO III | Stomach | 4.62 | 4.62 | 4.62 $^C$ |
| SK-PN-DW | Stomach | 2.16 | 2.16 | 2.15 $^B$ |
| SNU-1 | Stomach | 1.51 | 1.51 | 1.51 $^C$ |
| SNU-16 | Stomach | 1.44 | 1.44 | 1.44 $^D$ |
| SNU-5 | Stomach | 4.80 | 4.80 | 4.73 $^D$ |
| NTERA-2 cl.D1 | Testis | 1.98 | 1.99 | 1.96 $^B$ |

$^A$ 14 Jul. 2016;
$^B$ 22 Aug. 2016;
$^C$ 22 Sep. 2016;
$^D$ 5 Oct. 2016

For Compound 1, a broad spectrum of activity was observed over the 280 cell types with very potent to strong ($GI_{50}$=0.006 to 2.98 µM) activity towards 174 cell lines. Very potent activity was observed towards SK-NEP-1 kidney ($GI_{50}$=0.00618 µM) and J-RT3-T3-5 leukemia ($GI_{50}$=0.0101 µM) cell lines. Moderately potent activity was observed ($GI_{50}$=0.11 µM) towards KG-1 leukemia cell line. Moderately potent activity ($GI_{50}$=0.4 to 1.0 µM) was observed towards the following cell lines: 2 breast cell lines KPL-1, MDA-MB-453; 3 myeloma cell lines IM-9, RPMI8226, SKO-007; 3 melanoma cell lines A7, COLO829, RPMI-7951; 7 soft tissue cell lines HOS (osteosarcoma), KHOS-240S (osteosarcoma), SW1353 (osteosarcoma), A204 (sarcoma), HT-1080 (sarcoma), RD (sarcoma), SW 872 (sarcoma); 2 small cell lung carcinoma cell lines DMS53, SHP-77; and also Colo 201 (colon); FaDu (head and neck), 769-P (kidney), HepG2 (liver), and AGS (stomach). Strong activity ($GI_{50}$=1 to 2.98 µM) was shown towards 149 cell lines: 16 melanoma; 15 lymphoma; 9 female genitourinary; 14 soft tissue (sarcoma); 16 colon; 12 leukemia; 8 non-small cell lung carcinoma; 8 pancreas; 9 breast; 10 CNS; 8 bladder; 5 kidney; 4 head and neck, 4 endocrine, 1 myeloma, 3 liver, 2 small cell lung carcinoma, 2 prostate, 2 stomach and 1 testis.

For Compound 2, a narrow spectrum of activity was observed over the 280 cell types with potent to strong ($GI_{50}$=0.06 to 2.96 µM) activity towards 10 cell lines. Potent activity was observed towards SK-NEP-1 kidney ($GI_{50}$=0.0606 µM) Strong activity ($GI_{50}$=1 to 2.96 µM) was observed towards the following cell lines: 5 leukemia cell lines J-RT3-T3-5, Jurkat, MOLT-3, NALM-6, TF-1; 2 myeloma cell lines RPMI8226, SKO-007; 1 soft tissue cell line RD (sarcoma). For Compound 2 activities towards Jurkat, MOLT-3, NALM-6, TF-1 (leukemia) and SKO-007 (myeloma) were similar in magnitude to Compound 1.

For Compound 4, a narrow spectrum of activity was observed over the 280 cell types with moderately potent to strong ($GI_{50}$=0.68 to 2.92 µM) activity towards 12 cell lines. One strong activity ($GI_{50}$=0.684 µM) was observed towards A204 (soft tissue sarcoma) similar in magnitude to that observed for Compound 1. Strong activity ($GI_{50}$=1.23 to 2.92 µM) for Compound 4 was observed towards the following cell lines: 5 lymphoma (Daudi, DOHH-2, GA-10, L-428, ST486); 2 leukemia (MX1, NALM-6); also for T47D (breast), CEM-C1 (leukemia), A-673 (soft tissue sarcoma). The activity towards these cell lines is comparable in magnitude to Compound 1, however, Compound 4 show strong activity towards the J-RT3-T3-5 leukemia cell line ($GI_{50}$=2.71 µM) approximately 270 times less activity than the very potent activity observed for Compound 1 ($GI_{50}$=0.0101 µM) towards this cell line.

The plant resin extract showed strong activity ($GI_{50}$=0.11 to 1.03 µg/mL) towards 24 cell lines: 4 soft tissue sarcoma (A204, HT-1080, RD, SW 872); 4 melanoma (A7, COLO829, Hs695T, RPMI-7951); 3 myeloma (IM-9, RPMI8226, SKO-007); 2 breast (KPL-1, MDA-MB-453); 2 lymphoma (DOHH-2, SU-DHL-5); 2 small cell carcinoma (DMS53, SHP-77); 2 leukemia (Jurkat, NALM-6) and also bladder (UM-UC-3); colon (SW480); thyroid (CGTH-W-1); head and neck (FaDu); and stomach (AGS). For the Hs695T melanoma cell line, calculated on a weight-weight basis, the plant resin extract ($GI_{50}$=0.11 µg/mL) was approximately 3 times more active than Compound 1 ($GI_{50}$=0.37 µg/mL) towards this particular cell line. From weight comparison for all other cell lines the plant extract was less active than Compound 1.

Overall, Compound 1 provides a broad spectrum of anticancer activity towards a wide range of cell lines. Compound 2 shows specificity for the LNCaP prostate cell line, also specific activity towards SK-NEP-1 (kidney), Jurkat, MOLT-3, NALM-6, TF-1 (leukemia) and SKO-007, RPMI8226 (myeloma) similar in magnitude to Compound 1. Compound 4 showed moderately potent to strong activity ($GI_{50}$=0.68 to 2.92 µM) towards a narrow range of cell lines (12 out of 280) compared with Compound 1 (174 out of 280),

TABLE 30

Number of cancer cell types for levels of growth inhibitory activity for Compounds 1, 2 and 4

| | | Number of cell types | | |
|---|---|---|---|---|
| GI Activity | $GI_{50}$ range (µM) | Comp 1 | Comp 2 | Comp 4 |
| very potent | 0.001-0.029 | 2 | 0 | 0 |
| Potent | 0.03-0.099 | 0 | 1 | 0 |
| moderately potent | 0.1-0.99 | 23 | 1 | 1 |
| Strong | 1-2.99 | 149 | 8 | 11 |
| moderately strong | 3-9.99 | 99 | 110 | 125 |
| weak | 10-30.00 | 6 | 118 | 130 |
| very weak | >30 | 1 | 42 | 13 |
| TOTAL | | 280 | 280 | 280 |

TABLE 31

Number of cancer cell types for levels of growth inhibitory activity for *M. insulare* extract

| GI Activity | $GI_{50}$ range (µg/mL) | Number of cell types *M. insulare* extract |
|---|---|---|
| very potent | 0.00035-0.0104 | 0 |
| Potent | 0.0105-0.034 | 0 |
| moderately potent | 0.035-0.34 | 1 |
| Strong | 0.35-1.04 | 23 |
| moderately strong | 1.05-3.49 | 165 |
| weak | 3.5-10.49 | 83 |
| very weak | >10.5 | 8 |
| TOTAL | | 280 |

Inhibition of Toll-Like Receptor 4 (TLR4) Activation on Human Peripheral Blood Mononuclear Cells (PBMC's).

Study Objective

To evaluate compound capability to inhibit Toll-like receptor 4 (TLR4) activation on human peripheral blood mononuclear cells (PBMC's).

Experimental Protocol

Compound 1 was evaluated for ability to inhibit TLR4 in human PBMC's, as measured by release of specific cytokines. Evaluation was conducted by Eurofins Panlabs Inc., St Charles, Mo., USA.

TLR4 Inhibition Assay Protocol
a) Cryopreserved human PBMC's were drip-thawed.
b) Cells were diluted to the appropriate density (1×105 per well) and seeded into 96-well polypropylene plates with 150 µL per well of culture medium (RPMI 1640, 10% heat-inactivated FBS, 1% penicillin/streptomycin, 2 mM L-glutamine).
c) Cells were incubated at 37° C., 5% $CO_2$ for 1 hour prior to the addition of test compounds or controls.
d) Test compounds were solubilized in DMSO to make stock solutions, and then diluted further with cell culture medium. The positive control, LPS (from *S. minnesota* R595), was resuspended in endotoxin-free water at 0.5 mg/mL to make working stock solutions. Dexamethasone was used as a reference control compound.
e) Compounds and controls, including appropriate vehicle controls, were added to the PBMC's in volumes of 10 µL and incubated for 1 hour at 37° C., 5% $CO_2$. Compounds were tested in duplicate at final assay concentrations of 10, 3, 1, 0.3, 0.1, and 0.03 µM. Vehicle control wells simply received 10 µL of the appropriate vehicle.
f) After a 1-hour incubation, 40 µL of diluted working stock LPS were added to the test compound and control wells to give final assay volumes of 200 µL. Plates were incubated for 24 hours at 37° C., 5% $CO_2$.
g) Plates were centrifuged at 200×g for 10 minutes. Cell culture supernatants were collected and stored at −80° C. until needed for analysis.
h) Cytokine levels in each sample were determined using Luminex methodology, per the manufacturer's protocol.

PBMC Donor: Human donor 1 (lot #100)

Results and Discussion

Stimulation of human PBMC's with LPS for 24 hours elicited the measurable release of appropriate cytokines within expected ranges. Conversely, dexamethasone inhibited the LPS-stimulated release of cytokines from human PBMC's, also within expected ranges. Compound 1 elicited measurable inhibition of the LPS-induced release of specific cytokines from human PBMC's, following a 24-hour stimulation.

As seen from the results shown in Table 32, Compound 1 elicited a moderate to strong inhibition of the secretion of all cytokines at the top test concentration, giving measured $IC_{50}$ values of 4.3 µM, 6.6 µM, 8.8 µM, and 8.9 µM for IL-10, IL-1β, IL-6, and TNFα, respectively. ($IC_{50}$ values could not be measured for IL-8 and MIP-1α.)

TABLE 32

| Compound 1 activity against certain LPS-induced cytokines | |
|---|---|
| Assay | Compound 1 LPS-induced cytokine $IC_{50}$ (µM) |
| I-1β | 6.6 |
| IL-6 | 8.8 |
| IL-8 | NA |
| IL-10 | 4.3 |
| MIP-1α | NA |
| TNF-α | 8.9 |

Bioprint Assays

The Bioprint assay (conducted by Eurofins Cerep, France) provides a profile that is designed with the dual purpose of assessing safety at targets with known safety liabilities as well as providing a rich enough profile to search for compounds with similar profiles.

Methodology

Compound 1 was tested at 10 µM. For Compound 1 at 10 µM, the agonist radioligand assays for control specific inhibition of interest for biological activity or safety are as follows:—

GPCR Family:—adenosine A3 (h), 92%; adrenergic alpha 2C (h), 92%; cannabinoid CB2 (h), 71%; cholecystokinin CCK1 (CCKA) (h), 81%; dopamine D1 (h), 67%; dopamine D3 (h), 85%; histamine H1 (h), 64%; melatonin MT1 (ML1A) (h), 91%.

Transporters:—norepinephrine transporter (h), 76%.

Non-steroid Nuclear Receptors:—PPARgamma (h), 91%.

For Compound 1 at 10 µM, the enzyme assays for control specific inhibition of interest for biological activity or safety are as follows:—

AA Metabolism:—COX1 (h), 81%; COX2 (h), 74%.

Compound binding was calculated as a % inhibition of the binding of a radioactively labeled ligand specific for each target. Compound enzyme inhibition effect was calculated as a % inhibition of control enzyme activity. Results showing an inhibition or stimulation higher than 50% are considered to represent significant effects of the test compounds.

Results

Compound 1 results for inhibition of control specific binding to receptors are shown in Table 33 whilst results for inhibition of control specific binding inhibition of enzymes in enzyme and cell-based assays are shown in Table 34.

TABLE 33

Bioprint results for Compound 1 tested at 10 μM for inhibition of control specific binding to receptors.

| Family | Binding Assay | Compound 1 % Inhibition of Control Specific Binding | Reference Compound | IC$_{50}$ (μM) |
|---|---|---|---|---|
| GPCR | | | | |
| ADENOSINE | A1 (h) (agonist radioligand) | 10 | CPA | 0.0021 |
| ADENOSINE | A2A (h) (agonist radioligand) | 18 | NECA | 0.036 |
| ADENOSINE | A2B (h) (antagonist radioligand) | 8 | NECA | 0.59 |
| ADENOSINE | A3 (h) (agonist radioligand) | 92 | IB-MECA | 4.5E−04 |
| ADRENERGIC | alpha 1A (h) (antagonist radioligand) | 17 | WB 4101 | 2.7E−04 |
| ADRENERGIC | alpha 1B (h) (antagonist radioligand) | 41 | prazosin | 1.7E−04 |
| ADRENERGIC | alpha 2A (h) (antagonist radioligand) | 35 | yohimbine | 0.0065 |
| ADRENERGIC | alpha 2B (h) (antagonist radioligand) | 7 | yohimbine | 0.0065 |
| ADRENERGIC | alpha 2C (h) (antagonist radioligand) | 92 | yohimbine | 0.004 |
| ADRENERGIC | beta 1 (h) (agonist radioligand) | 19 | atenolol | 0.34 |
| ADRENERGIC | beta 2 (h) (agonist radioligand) | 2 | ICI 118551 | 7.8E−04 |
| ADRENERGIC | Adrenergic beta3 | 33 | Alprenolol | 0.25 |
| ANGIOTENSIN II | AT1 (h) (antagonist radioligand) | 60 | saralasin | 0.0019 |
| ANGIOTENSIN II | AT2 (h) (agonist radioligand) | 54 | angiotensin-II | 1.4E−04 |
| APELIN | APJ (apelin) (h) (agonist radioligand) | 24 | apelin-13, TFA | 3.4E−04 |
| BOMBESIN | BB3 (h) (agonist radioligand) | 26 | Bn(6-14) | 0.0048 |
| BRADYKININ | B2 (h) (agonist radioligand) | −37 | NPC 567 | 0.038 |
| CANNABINOID | CB1 (h) (agonist radioligand) | 46 | CP 55940 | 0.001 |
| CANNABINOID | CB2 (h) (agonist radioligand) | 71 | WIN 55212-2 | 0.0022 |
| CYTOKINES | TNF-alpha (h) (agonist radioligand) | −23 | TNF-alpha | 1.6E−04 |
| CHOLECYSTOKININ | CCK1 (CCKA) (h) (agonist radioligand) | 81 | CCK-8s | 1.5E−04 |
| CHOLECYSTOKININ | CCK2 (CCKB) (h) (agonist radioligand) | 6 | CCK-8s | 1.7E−04 |
| CORTICOTROPIN RELEASING FACTOR | CRF1 (h) (agonist radioligand) | 34 | sauvagine | 2.5E−04 |
| DOPAMINE | D1 (h) (antagonist radioligand) | 67 | SCH 23390 | 3.9E−04 |
| DOPAMINE | D2S (h) (agonist radioligand) | 59 | 7-OH-DPAT | 0.0033 |
| DOPAMINE | D3 (h) (antagonist radioligand) | 85 | (+)butaclamol | 0.0024 |
| ENDOTHELIN | ETA(h) (agonist radioligand) | 6 | endothelin-1 | 4.9E−05 |
| ENDOTHELIN | ETB (h) (agonist radioligand) | 40 | endothelin-3 | 1.7E−05 |
| GABA | GABAB(1b) (h) (antagonist radioligand) | −17 | CGP 54626 | 0.0022 |
| GLUCAGON | glucagon (h) (agonist radioligand) | −20 | glucagon | 0.001 |
| CHEMOKINES | CCR2 (h) (agonist radioligand) | 48 | MCP-1 | 8.7E−05 |

TABLE 33-continued

Bioprint results for Compound 1 tested at 10 µM for
inhibition of control specific binding to receptors.

| Family | Binding Assay | Compound 1 % Inhibition of Control Specific Binding | Reference Compound | IC$_{50}$ (µM) |
|---|---|---|---|---|
| HISTAMINE | H1 (h) (antagonist radioligand) | 64 | pyrilamine | 0.0023 |
| HISTAMINE | H2 (h) (antagonist radioligand) | 37 | cimetidine | 0.66 |
| HISTAMINE | H3 (h) (agonist radioligand) | 10 | (R)alpha-Me-histamine | 0.0016 |
| HISTAMINE | H4 (h) (agonist radioligand) | 23 | imetit | 0.0047 |
| LEUKOTRIENES | BLT1 (LTB4) (h) (agonist radioligand) | 27 | LTB4 | 3.7E−04 |
| LEUKOTRIENES | CysLT1 (LTD4) (h) (agonist radioligand) | 10 | LTD4 | 6.3E−04 |
| MELANIN-CONCENTRATING-HORMONE | MCH1 (h) (agonist radioligand) | −5 | human MCH | 7.8E−05 |
| MELANOCORTIN | MC1 (agonist radioligand) | 11 | NDP-alpha -MSH | 1.2E−04 |
| MELANOCORTIN | MC3 (h) (agonist radioligand) | 60 | NDP-alpha -MSH | 2.7E−04 |
| MELANOCORTIN | MC4 (h) (agonist radioligand) | 37 | NDP-alpha -MSH | 4.0E−04 |
| MELATONIN | MT1 (ML1A) (h) (agonist radioligand) | 91 | melatonin | 2.8E−04 |
| MOTOLIN | motilin(h) (agonist radioligand) | −12 | [Nleu13]-motilin | 8.9E−04 |
| MUSCARINIC | M1 (h) (antagonist radioligand) | 8 | pirenzepine | 0.031 |
| MUSCARINIC | M2 (h) (antagonist radioligand) | 1 | methoctramine | 0.032 |
| MUSCARINIC | M3 (h) (antagonist radioligand) | −3 | 4-DAMP | 0.001 |
| MUSCARINIC | M4 (h) (antagonist radioligand) | 19 | 4-DAMP | 9.2E−04 |
| NEUROKININ | NK1 (h) (agonist radioligand) | 62 | [Sar9, Met(O2)11]-SP | 3.7E−04 |
| NEUROKININ | NK2 (h) (agonist radioligand) | 52 | [Nleu10]-NKA (4-10) | 0.0029 |
| NEUROPEPTIDE Y | Y1 (h) (agonist radioligand) | 29 | NPY | 1.6E−04 |
| OPIOD & OPIOID-LIKE | delta (DOP) (h) (agonist radioligand) | 62 | DPDPE | 0.002 |
| OPIOD & OPIOID-LIKE | kappa (KOP) (agonist radioligand) | 39 | U 50488 | 0.0012 |
| OPIOD & OPIOID-LIKE | mu (MOP) (h) (agonist radioligand) | 43 | DAMGO | 5.3E−04 |
| OPIOD & OPIOID-LIKE | NOP (ORL1) (h) (agonist radioligand) | −4 | nociceptin | 8.4E−04 |
| PLATELET ACTIVATED FACTOR | PAF (h) (agonist radioligand) | 39 | C16-PAF | 0.0034 |
| PROSTANOID | EP2 (h) (agonist radioligand) | 53 | PGE2 | 0.0027 |
| PROSTANOID | FP (h) (agonist radioligand) | 54 | PGF2alpha | 0.003 |
| PROSTANOID | IP (PGI2) (h) (agonist radioligand) | 16 | iloprost | 0.017 |
| SEROTONIN | 5-HT1A (h) (agonist radioligand) | −18 | 8-OH-DPAT | 8.3E−04 |
| SEROTONIN | 5-HT1B (antagonist radioligand) | 42 | serotonin | 0.013 |
| SEROTONIN | 5-HT1D (agonist radioligand) | 18 | serotonin | 0.0026 |
| SEROTONIN | 5-HT2A (h) (agonist radioligand) | 9 | (±)DOI | 4.7E−04 |
| SEROTONIN | 5-HT2B (h) (agonist radioligand) | 70 | (±)DOI | 0.0067 |
| SEROTONIN | 5-HT2C (h) (agonist radioligand) | 32 | (±)DOI | 2.4E−04 |
| SEROTONIN | 5-HT4e (h) (antagonist radioligand) | 2 | serotonin | 0.19 |

TABLE 33-continued

Bioprint results for Compound 1 tested at 10 μM for inhibition of control specific binding to receptors.

| Family | Binding Assay | Compound 1 % Inhibition of Control Specific Binding | Reference Compound | IC$_{50}$ (μM) |
|---|---|---|---|---|
| SEROTONIN | 5-HT6 (h) (agonist radioligand) | 42 | serotonin | 0.18 |
| SEROTONIN | 5-HT7 (h) (agonist radioligand) | 14 | serotonin | 4.4E−04 |
| SOMASTATIN | sst1 (h) (agonist radioligand) | 18 | somatostatin-28 | 5.5E−04 |
| SOMASTATIN | sst4 (h) (agonist radioligand) | 40 | somatostatin-14 | 0.0042 |
| UROTENSIN-II | UT (h) (agonist radioligand) | 46 | urotensin-II | 9.5E−04 |
| VASOACTIVE INTESTINAL PEPTIDE | VPAC1 (VIP1) (h) (agonist radioligand) | −9 | VIP | 2.7E−04 |
| VASOPRESSIN | V1a (h) (agonist radioligand) | 12 | [d(CH2)51, Tyr(Me)2]-AVP | 0.0015 |
| VASOPRESSIN | V2 (h) (agonist radioligand) | 11 | AVP | 0.0013 |
| TRANSPORTERS | | | | |
| CHOLINE | choline transporter (CHT1) (h) (antagonist radioligand) | −41 | hemicholinium-3 | 0.0046 |
| DOPAMINE | dopamine transporter (h) (antagonist radioligand) | 63 | BTCP | 0.012 |
| GABA | GABA transporter (antagonist radioligand) | −10 | nipecotic acid | 2.3 |
| NOREPINEPHRINE | norepinephrine transporter (h) (antagonist radioligand) | 76 | protriptyline | 0.0039 |
| SEROTONIN | 5-HT transporter (h) (antagonist radioligand) | 56 | imipramine | 0.0044 |
| ION-CHANNELS | | | | |
| GABA | GABAA1 (h) (alpha 1, beta 2, gamma 2) (agonist radioligand) | −36 | muscimol | 0.053 |
| GABA CHANNELS | BZD (central) (agonist radioligand) | −31 | diazepam | 0.0094 |
| GABA CHANNELS | Cl- channel (GABA-gated) (antagonist radioligand) | 42 | picrotoxinin | 0.33 |
| GLUTAMATE CHANNELS | PCP (antagonist radioligand) | −11 | MK 801 | 0.0096 |
| GLUTAMATE CHANNELS | AMPA (agonist radioligand) | 4 | L-glutamate | 0.37 |
| GLUTAMATE CHANNELS | kainate (agonist radioligand) | 15 | kainic acid | 0.023 |
| GLUTAMATE CHANNELS | NMDA (antagonist radioligand) | 9 | CGS 19755 | 0.35 |
| GLYCINE CHANNELS | glycine (strychnine-insensitive) (antagonist radioligand) | 4 | glycine | 0.28 |
| NICOTINIC CHANNELS | N neuronal alpha 4beta 2 (h) (agonist radioligand) | −3 | nicotine | 0.0046 |
| NICOTINIC CHANNELS | N muscle-type (h) (antagonist radioligand) | 1 | alpha -bungarotoxin | 0.0019 |
| SEROTONIN CHANNELS | 5-HT3 (h) (antagonist radioligand) | −2 | MDL 72222 | 0.0086 |
| Ca$^{2+}$ CHANNELS | Ca2+ channel (L, dihydropyridine site) (antagonist radioligand) | 55 | nitrendipine | 1.3E−04 |
| Ca$^{2+}$ CHANNELS | Ca2+ channel (L, diltiazem site) (benzothiazepines) (antagonist radioligand) | −30 | diltiazem | 0.057 |
| Ca$^{2+}$ CHANNELS | Ca2+ channel (L, verapamil site) (phenylalkylamine) (antagonist radioligand) | −4 | D 600 | 0.027 |

TABLE 33-continued

Bioprint results for Compound 1 tested at 10 μM for inhibition of control specific binding to receptors.

| Family | Binding Assay | Compound 1 % Inhibition of Control Specific Binding | Reference Compound | IC$_{50}$ (μM) |
|---|---|---|---|---|
| Ca$^{2+}$ CHANNELS | Ca2+ channel (N) (antagonist radioligand) | 5 | omega-conotoxin GVIA | 1.7E−06 |
| K$^+$ CHANNELS | SKCa channel (antagonist radioligand) | 14 | apamin | 9.7E−06 |
| Na$^+$ CHANNELS | Na+ channel (site 2) (antagonist radioligand) | 48 | veratridine | 5.9 |
| NUCLEAR RECEPTORS | | | | |
| NON-STEROID NUCLEAR RECEPTORS | PPARgamma (h) (agonist radioligand) | 91 | rosiglitazone | 0.015 |
| STEROID NUCLEAR RECEPTORS | AR (h) (agonist radioligand) | −9 | mibolerone | 0.0021 |
| STEROID NUCLEAR RECEPTORS | Estrogen ER alpha (h) (agonist radioligand) | 40 | Diethylstilbestrol | 4.5E−04 |
| STEROID NUCLEAR RECEPTORS | GR (h) (agonist radioligand) | 47 | dexamethasone | 0.0035 |
| OTHER RECEPTORS | | | | |
| SIGMA | sigma (non-selective) (h) (agonist radioligand) | 11 | haloperidol | 0.045 |
| THYROID HORMONE | Thyroid Hormone | 9 | Triiodothyronine | 3.9E−05 |

TABLE 34

Bioprint results for Compound 1 tested at 10 μM for inhibition of control specific binding inhibition of enzymes in enzyme and cell-based assays.

| Family | Enzyme and Cell-based Assays | Compound 1 % Inhibition of Control Values | Reference Compound | IC$_{50}$ (μM) |
|---|---|---|---|---|
| KINASES | | | | |
| RTK | FLT-1 kinase (h) (VEGFR1) | 36 | staurosporine | 0.0098 |
| RTK | IRK (h) (InsR) | −15 | staurosporine | 0.052 |
| CTK | Abl kinase (h) | 14 | staurosporine | 0.11 |
| CTK | Fyn kinase (h) | 6 | PP1 | 0.11 |
| CTK | Lyn A kinase (h) | 9 | staurosporine | 0.012 |
| CTK | ZAP70 kinase (h) | 33 | staurosporine | 0.021 |
| CMGC | CDK2 (h) (cycA) | 12 | staurosporine | 0.011 |
| CMGC | ERK2 (h) (P42mapk) | 6 | staurosporine | 1 |
| CMGC | p38alpha kinase (h) | 4 | SB202190 | 0.033 |
| CAMK | CaMK2alpha (h) | 2 | AIP | 0.092 |
| OTHER NON-KINASE ENZYMES | | | | |
| AA METABOLISM | COX1(h) | 81 | Diclofenac | 0.0078 |
| AA METABOLISM | COX2(h) | 74 | NS398 | 0.19 |
| ATPASE | ATPase (Na+/K+) | 22 | ouabain | 0.25 |
| MONOAMINE & NEUROTRANSMITTER | acetylcholinesterase (h) | 32 | galanthamine | 0.57 |
| MONOAMINE & NEUROTRANSMITTER | COMT (catechol-O-methyl transferase) | −6 | Ro 41-0960 | 0.061 |
| MONOAMINE & NEUROTRANSMITTER | MAO-A (antagonist radioligand) | 15 | clorgyline | 0.0012 |
| NO SYNTHASES | inducible NOS | −1 | 1400 W | 0.029 |
| PHOSPHODIESTERASES | PDE2A1 (h) | 43 | EHNA | 1.2 |
| PHOSPHODIESTERASES | PDE3B (h) | −3 | milrinone | 1.2 |

TABLE 34-continued

Bioprint results for Compound 1 tested at 10 μM for inhibition of control specific binding inhibition of enzymes in enzyme and cell-based assays.

| Family | Enzyme and Cell-based Assays | Compound 1 % Inhibition of Control Values | Reference Compound | IC$_{50}$ (μM) |
|---|---|---|---|---|
| PHOSPHODIESTERASES | PDE4D2 (h) | 55 | Ro 20-1724 | 0.15 |
| PHOSPHODIESTERASES | PDE5 (h) (non-selective) | 11 | dipyridamole | 0.84 |
| PHOSPHODIESTERASES | PDE6 (non-selective) | 4 | zaprinast | 0.16 |
| SERINE PROTEASES | caspase-3 (h) | −3 | Ac-DEVD-CHO | 0.0029 |
| ASPARTIC PROTEASES | BACE-1 (h) (beta - secretase) | 0 | OM 99-2 | 0.081 |
| ASPARTIC PROTEASES | HIV-1 protease | 9 | pepstatin A | 2.4 |
| METALLOPROTEASES | ACE (h) | 14 | captopril | 5.8E−04 |
| METALLOPROTEASES | ACE-2 (h) | −3 | AC-GG-26-NH2 | 0.2 |
| METALLOPROTEASES | MMP-1 (h) | −2 | GM6001 | 0.0054 |
| METALLOPROTEASES | MMP-2 (h) | 0 | GM6001 | 7.9E−04 |
| METALLOPROTEASES | MMP-9 (h) | 1 | GM6001 | 3.6E−04 |
| MISCELLANEOUS ENZYMES | MT3 (ML2) (agonist radioligand) | 31 | melatonin | 0.16 |
| MISCELLANEOUS ENZYMES | xanthine oxidase/superoxide O2- scavenging | −140 | allopurinol | 7.8 |

In Vitro Toxicity: Normal Cell Panel Toxicity Assay

The OncoPanel (Eurofins Panlabs Inc., St Charles, Mo., USA) normal cell proliferation assay measures the proliferation response of normal cells to drug treatments through high-content fluorescence imaging.

Methodology

Normal cells (see description in Table 35) were grown in special medium for each cell type. Cells were seeded into 384-well plates and incubated in a humidified atmosphere of 5% $CO_2$ at 37° C. Compounds (information in Table 36) were added the day following cell seeding. At the same time, a time zero untreated cell plate was generated. After a 3-day incubation period, cells were fixed and stained to allow fluorescence imaging of nuclei.

TABLE 35

Description of cells used in normal cell panel toxicity assay

| Normal cell name | Cell type | Source | Catalog number |
|---|---|---|---|
| CCD 841 CoN | Colon epithelial | ATCC | CRL-1790 |
| HMEC | Mammary epithelial | ATCC | PCS-600-010 |
| HREC | Renal mixed epithelial | ATCC | PCS-400-012 |
| Wi38 | Lung fibroblast | ATCC | CCL-75 |

TABLE 36

Information for compounds used in normal cell panel toxicity assay

| Compound ID | F.W. | Amount received (mg) | Stock conc. (mM) | Stock volume (microL) | Max final test conc. (microM) |
|---|---|---|---|---|---|
| Carbonyl cyanide 3-chlorophenylhydrazone | 204.62 | 5.70 | 10.00 | 2786 | 10.00 |
| Compound 1 | 318.00 | 4.80 | 30.00 | 500 | 30.00 |
| Cycloheximide | 281.35 | 5.40 | 10.00 | 1919 | 10.00 |
| Paclitaxel | 853.91 | N/A | 0.30 | 1000 | 0.30 |
| Staurosporine | 466.50 | 1.00 | 1.00 | 2144 | 1.00 |

Compounds were serially diluted in half-log steps from the highest test concentration specified in the above table, and assayed over 10 concentrations with a maximum assay concentration of 0.1% DMSO.

The experimental procedure and calculations are similar to the Oncopanel 10-day incubation cell proliferation assay described previously.

Results

Compound 1 activity ($EC_{50}$ $IC_{50}$ and $GI_{50}$ (μM)) is shown against the reference compound paclitaxel in Table 37. Data on other reference compounds for comparison purposes is shown in Table 38.

TABLE 37

Compound 1 activity ($EC_{50}$ $IC_{50}$ and $GI_{50}$ (μM)) against paclitaxel

| Cell Line | normal human primary cells | Compound 1 | | | Paclitaxel | | |
|---|---|---|---|---|---|---|---|
| | | Cell Count $EC_{50}$ (μM) | Cell Count $IC_{50}$ (μM) | Cell Count $GI_{50}$ (μM) | Cell Count $EC_{50}$ (μM) | Cell Count $IC_{50}$ (μM) | Cell Count $GI_{50}$ (μM) |
| CCD 841 CoN | colon epithelial | 4.86 | 14.3 | 5.27 | 0.0119 | N/A | 0.0221 |
| HMEC | mammary epithelial | 30 | 30 | 6.39 | >30 | >30 | >30 |
| HREC | renal mixed epithelial | 6.45 | 7.98 | 4.3 | 0.00172 | 0.0484 | 0.0016 |
| Wi38 | lung fibroblast | 5.45 | 10.4 | 5.92 | 0.0039 | 0.00941 | 0.0036 |

TABLE 38

Further reference compound activity

| Cell Line | Cycloheximide | | | Carbonyl cyanide 3-chlorophenylhydrazone | | | Staurosporine | | |
|---|---|---|---|---|---|---|---|---|---|
| | Cell Count $EC_{50}$ (μM) | Cell Count $IC_{50}$ (μM) | Cell Count $GI_{50}$ (μM) | Cell Count $EC_{50}$ (μM) | Cell Count $IC_{50}$ (μM) | Cell Count $GI_{50}$ (μM) | Cell Count $EC_{50}$ (μM) | Cell Count $IC_{50}$ (μM) | Cell Count $GI_{50}$ (μM) |
| CCD 841 CoN | 0.505 | 2.77 | 0.588 | 10 | 10 | 6.21 | 0.00024 | 0.00057 | 0.00019 |
| HMEC | 3.65 | 10 | 0.306 | >10 | >10 | 0.175 | 0.00229 | >1 | 0.00091 |
| HREC | 0.117 | 0.593 | 0.0369 | 0.553 | 1.52 | 0.308 | 0.00055 | 0.0027 | 0.0005 |
| Wi38 | 0.285 | 0.871 | 0.369 | 8.84 | 8.84 | 6.15 | 0.00049 | 0.00074 | 0.00033 |

Table 39 shows representative data for the response when the cell line HREC is treated with Compound 1 in an OncoPanel Normal Cell Proliferation Assay.

TABLE 39

Compound 1 against HREC

| | Relative cell count (%) | |
|---|---|---|
| Concentration (microM) | Mean | StdDev |
| 9.55E−04 | 98.5 | 8.8 |
| 3.02E−03 | 94.0 | 7.4 |
| 9.53E−03 | 93.3 | 6.6 |
| 3.01E−02 | 96.0 | 8.3 |
| 9.52E−02 | 95.8 | 4.5 |
| 3.01E−01 | 96.7 | 8.7 |
| 9.51E−01 | 89.3 | 4.7 |
| 3.00E+00 | 85.1 | 14.4 |
| 9.49E+00 | 40.4 | 3.3 |
| 3.00E+01 | 20.9 | 5.7 |

Figure 19:
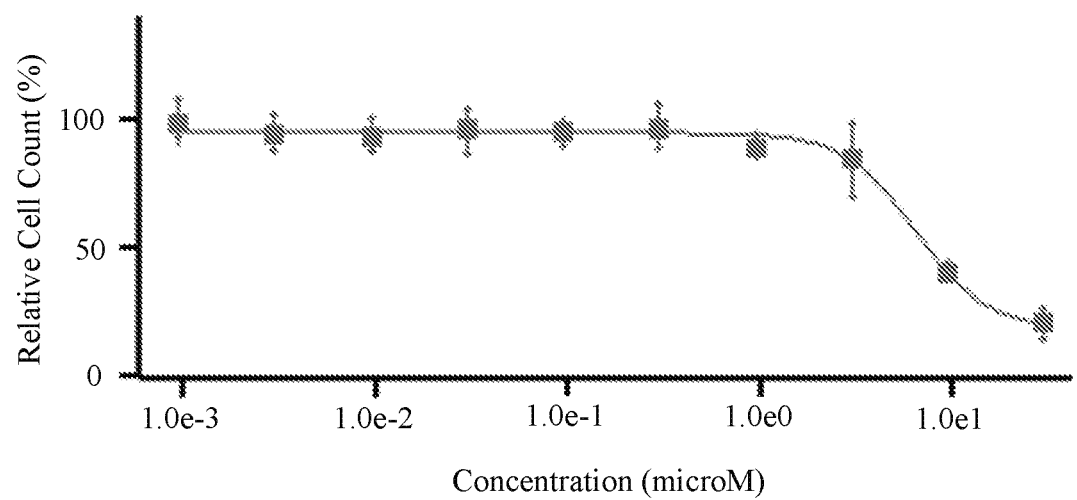
FIG. 19 shows the response when the cell line HREC is treated with Compound 1 in an OncoPanel Normal Cell Proliferation Assay.

The data displayed in Table 39 is graphed in FIG. 19.

DISCUSSION

Compound 1 and reference compounds, paclitaxel, cycloheximide, carbonyl cyanide m-chlorophenylhydrazone (CCCP) and staurosporine, were tested on 4 normal cell types, CCD 841 CoN, HMEC, HREC and Wi38. In summary, Compound 1 showed relatively low toxicity towards all 4 cell lines. Paclitaxel showed low toxicity towards the HMEC cell line and high toxicity towards the other three cell lines. Based on average $GI_{50}$ for the 4 normal cell lines, the order of toxicity is staurosporine>paclitaxel> cycloheximide>CCCP>Compound 1.

In Vitro Toxicity: ADME-Toxicity Study

ADME-Toxicity study of compounds 1, 2 and 4 was conducted by Eurofins Panlabs Inc, St Charles, Mo., USA using a CYP panel.

Methodology

Cytochrome P450 Inhibition was monitored through HPLC-UV/VIS and HPLC-MS/MS detection. Peak areas corresponding to the metabolite of each substrate were recorded. The percent of control activity was then calculated by comparing the peak area obtained in the presence of the test compound to that obtained in the absence of the test compound. Subsequently, the percent inhibition was calculated by subtracting the percent control activity from 100 for each compound. $IC_{50}$ values (concentration causing a half-maximal inhibition of control values) were determined by non-linear regression analysis of the concentration-response curve using Hill equation curve fitting [Dierks, E. A. et al. (2001)].

Results

CYP3A (Testosterone Substrate)

Compounds 1, 2 and 4 are relatively weak inhibitors (7-20% at 1 µM) compared with the reference compound ketoconazole ($IC_{50}$ 0.18 µM).

In Vivo Toxicity: Compound 1 Maximum Tolerated Dose for Mice

Two studies were conducted by Eurofins Panlabs Taiwan, Ltd. The purpose of Study 1 was to assess the possible adverse effects of Compound 1 alone or in combination with carboplatin in Maximum Tolerated Dose (MTD) assay. The purpose of Study 2 is a follow-up study performed at escalating doses.

The vehicle information and dosing volume used in the studies are shown in Table 41. Table 42 and Table 43 show results for Study 1 in terms of mortality and body weight

TABLE 40

Inhibition of CYPs by compounds 1, 2 and 4 against reference compounds

| Human liver microsomes | % Inhibition of Control Values | | | | | | Reference | |
|---|---|---|---|---|---|---|---|---|
| | Compound 1 | | Compound 2 | | Compound 4 | | | |
| In Vitro Metabolism | 1 µM | 10 µM | 1 µM | 10 µM | 1 µM | 10 µM | Compound | $IC_{50}$ µM |
| CYP1A (phenacetin sub.) | 28 | 92 | 38 | 63 | 14 | 85 | Furafylline | 16 |
| CYP2B6 (bupropion sub.) | 13 | 55 | 15 | 38 | 16 | 49 | Clopidogrel | 0.39 |
| CYP2C8 (paclitaxel sub.) | 14 | 76 | 12 | 52 | 24 | 61 | Montelukast | 0.57 |
| CYP2C9 (diclofenac sub.) | 5 | 77 | 20 | 72 | 31 | 91 | Sulfaphenazole | 0.28 |
| CYP2C19 (omeprazole sub.) | 37 | 90 | 34 | 73 | 25 | 78 | Oxybutynin | 6.7 |
| CYP2D6 (dextromethorphan sub.) | 13 | 45 | 18 | 44 | 21 | 45 | Quinidine | 0.12 |
| CYP3A (midazolam sub.) | 16 | 65 | 15 | 37 | 15 | 50 | Ketoconazole | 0.18 |
| CYP3A (testosterone sub.) | 7 | 77 | 17 | 57 | 20 | 48 | Ketoconazole | 0.18 |

Summary of Results

Enzyme—Substrates

CYP1A (Phenacetin Substrate)

Compounds 1, 2 and 4 are strong inhibitors at 10 µM (63-92%). With $IC_{50}$ values estimated to be <10, Compounds 1, 2 and 4 are stronger inhibitors the reference standard furafylline ($IC_{50}$ 16 µM). Compounds 1 and 2 showed moderate inhibition at 1 µM (28% and 38% respectively).

CYP2B6 (Bupropion Substrate)

Compounds 1, 2 and 4 are relatively weak inhibitors (13-16% at 1 µM) compared with the reference compound clopidogrel ($IC_{50}$ 0.39 µM).

CYP2C8 (Paclitaxel Substrate)

Compounds 1, 2 and 4 are relatively weak inhibitors (12-24% at 1 µM) compared with the reference compound montelukast ($IC_{50}$ 0.57 µM).

CYP2C9 (Diclofenac Substrate)

Compounds 1 was a very weak at 1 µM (5%) and Compounds 2 and 4 relatively weak inhibitors (20 and 31%) compared with the reference compound sulfaphenazole ($IC_{50}$ 0.28 µM).

CYP2C19 (Omeprazole Substrate)

Compounds 1, 2 and 4 are moderately strong inhibitors (25-37% at 1 µM) with activity comparable with oxybutynin ($IC_{50}$ 6.7 µM).

CYP2D6 (Dextromethorphan Substrate)

Compounds 1, 2 and 4 are relatively weak inhibitors (12-21% at 1 µM) compared with the reference compound quinidine ($IC_{50}$ 0.12 µM).

CYP3A (Midazolam Substrate)

Compounds 1, 2 and 4 are relatively weak inhibitors (15-16% at 1 µM) compared with the reference compound ketoconazole ($IC_{50}$ 0.18 µM).

observations. In regard to Study 2, Table 44 and Table 45 show results for mortality and body weight observations and behavioral, symptomatic i.e. neurological and autonomic signs for Compound 1, alone and in combination with carboplatin, are shown in Table 46 and Table 47. Corresponding signs for the vehicles are shown in Table 48 and Table 49.

TABLE 41

Vehicle information and dosing volume for MTD assay studies

| Study | Test article | Vehicle | Concentration (mg/mL) | Dosing volume (mL/kg) | Dosage (mg/kg) |
|---|---|---|---|---|---|
| 1 | Compound 1 | 10% Tween 20/ 90% PBS | 10 | 10 | 100 |
| 2 | Compound 1 | 20% Tween 20/ 80% PBS | 20 | 10 | 200 |

Test Substance and Dosing Pattern

Compound 1 was dissolved in 10% Tween 20/90% PBS or 20% Tween 20/80% PBS for IP injections. Compound 1 was administrated alone or in combination with carboplatin at a dosing volume of 10 or 20 mL/kg for each substance.

Study 1

For mortality, test substance (Compound 1; 100 mg/kg) alone or in combination with carboplatin (8.75, 17.5, or 35 mg/kg; given on the same day) was administered to mice by IP injection to evaluate the possible adverse effects in MTD assay. The mice were a group of 3 female NOD/SCID mice at 6-7 weeks of age. The mortality was observed at 30 min and again at 3, 24, 48 and 72 hours after compound administrations.

For body weight, test substance (Compound 1; 100 mg/kg) alone or in combination with carboplatin (8.75 or 17.5 mg/kg; given on the same day) was administered to a group of 3 female NOD/SCID mice at 6-7 weeks of age. The body weight of each animal was measured and recorded daily for 3 days.

Compound 1 alone did not elicit significant adverse effects and were considered tolerated. All test animals survived over the 72-hour observation period (Table 42). However, Compound 1 in combination with carboplatin was associated with slight to moderate limb tone, and resulted in a 33% mortality after 72 hours of dosing, reflecting the dose level was not well-tolerated (Table 42)

Compound 1, in combination with the lower doses of carboplatin (8.75 and 17.5 mg/kg), was further investigated in the MTD study. Compound 1, injected with two doses of carboplatin on the same day, was associated with slight to moderate abdominal tone during the first 30 minutes of administrations (Table 42 and Table 43). However, no mortality and body weight losses were observed in test animals over the experimental period, signifying the dose levels were tolerated (Table 42 and Table 43).

Study 2

A follow-up MTD study was performed to evaluate for the adverse effects of the test substance (Compound 1) at escalating doses alone or in combination with carboplatin (17.5 mg/kg) via IP in a group of 3 female NOD/SCID mice at 6-7 weeks of age.

For mortality, treatment with Compound 1 at escalating doses (200 mg/kg) alone and in combination with carboplatin (17.5 mg/kg; given on the same day) were administered by IP injection to a group of 3 female NOD/SCID mice at 6-7 weeks of age. The mortality was monitored at 30 min and again at 3, 24, 48 and 72 hours after compound administrations.

For body weight, test substance (Compound 1) at escalating doses (200 mg/kg) alone or in combination with carboplatin (17.5 mg/kg; given on the same day) were administered by IP injection to a group of 3 female NOD/SCID mice at 6-7 weeks of age. The body weight of each animal was measured and recorded daily for 3 days.

On treatment with Compound 1 (200 mg/g) alone and in combination with carboplatin (17.5 mg/kg) exhibited a 33-100% mortality, but no marked weight loss during the study period (Table 44 and Table 45).

TABLE 42

MTD in mice (Study 1, Round 1 & 2)

| Compound | Route | Dose (mg/kg) | Response (death/test) | | | | |
|---|---|---|---|---|---|---|---|
| | | | 30 min | 3 hrs | Day 1 | Day 2 | Day 3 |
| Vehicle[a] | IP | 10 mL/kg | 0/3 | 0/3 | 0/3 | 0/3 | 0/3 |
| Vehicle[a] + Vehicle[b] | IP | 10 mL/kg + 10 mL/kg | 0/3 | 0/3 | 0/3 | 0/3 | 0/3 |
| Compound 1 | IP | 100 mg/kg | 0/3 | 0/3 | 0/3 | 0/3 | 0/3 |
| Carboplatin | IP | 35 mg/kg | 0/3 | 0/3 | 0/3 | 0/3 | 0/3 |
| Compound 1 + carboplatin | IP | 100 mg/kg + 35 mg/kg | 0/3 | 0/3 | 0/3 | 0/3 | 1/3 |
| Vehicle[a] + Vehicle[b] | IP | 10 mL/kg + 10 mL/kg | 0/3 | 0/3 | 0/3 | 0/3 | 0/3 |
| Compound 1 + carboplatin | IP | 100 mg/kg + 17.5 mg/kg | 0/3 | 0/3 | 0/3 | 0/3 | 0/3 |
| Compound 1 + carboplatin | IP | 100 mg/kg + 8.75 mg/kg | 0/3 | 0/3 | 0/3 | 0/3 | 0/3 |

Legend:
[a]10% Tween 20/90% PBS
[b]0.9% NaCl

TABLE 43

MTD in mice (Study 1; Round 2)

| Compound | Route | Dose (mg/kg) | No. | Body Weight (g) | | | |
|---|---|---|---|---|---|---|---|
| | | | | Day 0 | Day 1 | Day 2 | Day 3 |
| Vehicle[a] + Vehicle[b] | IP | 10 mL/kg + 10 mL/kg | 1 | 20 | 20 | 19 | 19 |
| | | | 2 | 20 | 20 | 20 | 19 |
| | | | 3 | 22 | 21 | 21 | 21 |
| Compound 1 + carboplatin | IP | 100 mg/kg + 17.5 mg/kg | 1 | 22 | 21 | 21 | 20 |
| | | | 2 | 22 | 22 | 22 | 21 |
| | | | 3 | 21 | 21 | 21 | 21 |
| Compound 1 + carboplatin | IP | 100 mg/kg + 8.75 mg/kg | 1 | 22 | 20 | 20 | 20 |
| | | | 2 | 21 | 21 | 22 | 21 |
| | | | 3 | 21 | 21 | 21 | 20 |

Legend:
[a]10% Tween 20/90% PBS
[b]0.9% NaCl

TABLE 44

MTD in mice (Study 2)

| Compound | Route | Dose (mg/kg) | Response (death/test) | | | | |
|---|---|---|---|---|---|---|---|
| | | | 30 min | 3 hrs | Day 1 | Day 2 | Day 3 |
| Vehicle[a] | IP | 10 mL/kg | 0/3 | 0/3 | 0/3 | 0/3 | 0/3 |
| Vehicle[a] + Vehicle[b] | IP | 10 mL/kg + 10 mL/kg | 0/3 | 0/3 | 0/3 | 0/3 | 0/3 |
| PT# 1206425 (UOS-70) (Compound 1) | IP | 200 mg/kg | 0/3 | 0/3 | 1/3 | 3/3 | 3/3 |
| PT# 1206425 (UOS-70) (Compound 1) + carboplatin | IP | 200 mg/kg + 17.5 mg/kg | 0/3 | 0/3 | 0/3 | 1/3 | 1/3 |
| Vehicle[a] (20% Tween20/ 80% PBS) | IP | 20 mL/kg | 0/3 | 0/3 | 1/3 | 2/3 | 2/3 |

Legend:
[a] 20% Tween 20/80% PBS
[b] 0.9% NaCl

TABLE 45

MTD in mice (Study 2; Round 1 & 2)

| Compound | Route | Dose (mg/kg) | No. | Body Weight (g) | | | |
|---|---|---|---|---|---|---|---|
| | | | | Day 0 | Day 1 | Day 2 | Day 3 |
| Vehicle[a] (20% Tween20/80% PBS) | IP | 10 mL/kg | 1 | 23 | 22 | 23 | 23 |
| | | | 2 | 24 | 23 | 23 | 23 |
| | | | 3 | 23 | 22 | 22 | 22 |
| Vehicle[a] + Vehicle[b] | IP | 10 mL/kg + 10 mL/kg | 1 | 22 | 21 | 20 | 19 |
| | | | 2 | 22 | 22 | 21 | 19 |
| | | | 3 | 22 | 20 | 20 | 20 |
| Compound 1 | IP | 200 mg/kg | 1 | 22 | 21 | NA | NA |
| | | | 2 | 21 | NA | NA | NA |
| | | | 3 | 21 | 21 | NA | NA |
| Compound 1 + carboplatin | IP | 200 mg/kg + 17.5 mg/kg | 1 | 21 | 20 | 20 | 21 |
| | | | 2 | 22 | 22 | NA | NA |
| | | | 3 | 21 | 20 | 19 | 20 |
| Vehicle[a] | IP | 20 mL/kg | 1 | 23 | NA | NA | NA |
| | | | 2 | 22 | 22 | NA | NA |
| | | | 3 | 23 | 22 | 22 | 21 |

Legend:
[a] 20% Tween 20/80% PBS
[b] 0.9% NaCl

For behavioral, symptomatic i.e. neurological and autonomic signs, test substance (Compound 1; 200 mg/kg) alone or in combination with carboplatin (17.5 mg/kg; given on the same day) were administered by IP injection to a group of 3 female NOD/SCID mice at 6-7 weeks of age. The animals were then observed for presences of acute toxic symptoms and autonomic effects for 30 min after the first dose.

Pronounced behavioral effects such as decreased startle, touch response, pinna and placing were observed on Compound 1 treatment, alone and in combination with carboplatin (see Table 46). Decreased neurologic signs, such as spontaneous activity, righting, ataxia and low limb post were observed on Compound 1 treatment (Table 46). Hypothermia (decreased body temperature) was observed as an autonomic sign (Table 47)

TABLE 46

Behavioral and neurologic signs in mice for compound 1 (Study 2; Round 1)

| | Treatment | | | | | |
|---|---|---|---|---|---|---|
| | Compound 1 | | | Compound 1 + carboplatin | | |
| | Route | | | | | |
| | IP | | | IP | | |
| | Dosage | | | | | |
| | 200 mg/kg | | | 200 mg/kg + 17.5 mg/kg | | |
| | No. 1 | No. 2 | No. 3 | No. 1 | No. 2 | No. 3 |
| BEHAVIORAL | | | | | | |
| B.W. (g) | 22 | 21 | 21 | 21 | 22 | 21 |
| Irritability | – | – | – | – | – | – |
| Hyperactivity | – | – | – | – | – | – |
| Inc. Startle | – | – | – | – | – | – |

TABLE 46-continued

Behavioral and neurologic signs in mice for compound 1 (Study 2; Round 1)

| | Treatment | | | | | |
|---|---|---|---|---|---|---|
| | Compound 1 | | | Compound 1 + carboplatin | | |
| | Route | | | | | |
| | IP | | | IP | | |
| | Dosage | | | | | |
| | 200 mg/kg | | | 200 mg/kg + 17.5 mg/kg | | |
| | No. 1 | No. 2 | No. 3 | No. 1 | No. 2 | No. 3 |
| Inc. Touch | − | − | − | − | − | − |
| Dec. Startle Response | + | + | + | + | + | + |
| Dec. Touch Response | + | + | + | + | + | + |
| Inc. Exploration | − | − | − | − | − | − |
| Dec. Exploration | + | + | + | + | + | + |
| Pinna | + | + | + | + | + | + |
| Placing | ± | ± | ± | ± | + | ± |
| NEUROLOGIC | | | | | | |
| Tremor | − | − | − | + | − | + |
| Dec. Spont. Activity | + | + | + | + | + | + |
| Straub Tail | − | − | − | − | − | − |
| Reactivity | − | + | + | + | ± | + |
| Righting | + | + | ± | ± | + | + |
| Ataxia | + | + | ± | ± | + | + |
| Convulsion C.T.C-T | − | − | − | − | − | − |
| Low Limb Post | + | + | + | + | + | + |
| Abdominal Tone | + | + | + | + | + | + |
| Limb Tone | + | + | + | + | + | + |
| Grip Strength | − | ± | + | − | + | ± |

TABLE 47

Autonomic signs in mice for compound 1 (Study 2; Round 1)

| | Treatment | | | | | |
|---|---|---|---|---|---|---|
| | Compound 1 | | | Compound 1 + carboplatin | | |
| | Route | | | | | |
| | IP | | | IP | | |
| | Dosage | | | | | |
| | 200 mg/kg | | | 200 mg/kg + 17.5 mg/kg | | |
| AUTONOMIC | No. 1 | No. 2 | No. 3 | No. 1 | No. 2 | No. 3 |
| Skin Color | − | − | − | − | − | − |
| Respiration | D± | D+ | D+ | D+ | D+ | D+ |
| Salivation F.V. | − | − | − | − | − | − |
| Lacrimation | − | − | − | − | − | − |
| Diarrhea | − | − | − | − | − | − |
| Body Temperature | ↓+ | ↓+ | ↓+ | ↓+ | ↓+ | ↓+ |
| Piloerection | − | − | − | − | − | − |
| Inc. Palpebral Size | − | − | − | − | − | − |
| Dec. Palpebral Size | − | − | − | − | ± | − |
| Others | − | − | − | − | − | − |
| Death | − | − | − | − | − | − |

TABLE 48

Behavioral and neurologic signs in mice for vehicles (Study 2; Round 1)

| | Treatment | | | | | |
|---|---|---|---|---|---|---|
| | Vehicle[a] | | | Vehicle[a] + Vehicle[b] | | |
| | Route | | | | | |
| | IP | | | IP | | |
| | Dosage | | | | | |
| | 10 mL/kg | | | 10 mL/kg + 10 mL/kg | | |
| | No. 1 | No. 2 | No. 3 | No. 1 | No. 2 | No. 3 |
| BEHAVIORAL | | | | | | |
| B.W. (g) | 23 | 24 | 23 | 22 | 22 | 22 |
| Irritability | − | − | − | − | − | − |
| Hyperactivity | − | − | − | − | − | − |
| Inc. Startle | − | − | − | − | − | − |
| Inc. Touch | − | − | − | − | − | − |
| Dec. Startle Response | − | − | − | − | − | − |
| Dec. Touch Response | − | − | − | − | − | − |
| Inc. Exploration | − | − | − | − | − | − |
| Dec. Exploration | − | − | − | − | − | − |
| Pinna | − | − | − | − | − | − |
| Placing | − | − | − | − | − | − |
| NEUROLOGIC | | | | | | |
| Tremor | − | − | − | − | − | − |
| Dec. Spont. Activity | − | − | − | − | − | − |
| Straub Tail | − | − | − | − | − | − |
| Reactivity | − | − | − | − | − | − |
| Righting | − | − | − | − | − | − |
| Ataxia | − | − | − | − | − | − |
| Convulsion C.T.C-T | − | − | − | − | − | − |
| Low Limb Post | − | − | − | − | − | − |
| Abdominal Tone | − | − | ± | ± | ± | ± |
| Limb Tone | − | − | − | − | − | − |
| Grip Strength | − | − | − | − | − | − |

TABLE 49

Autonomic signs in mice for vehicles (Study 2; Round 1)

| | Treatment | | | | | |
|---|---|---|---|---|---|---|
| | Vehicle[a] | | | Vehicle[a] + Vehicle[b] | | |
| | Route | | | | | |
| | IP | | | IP | | |
| | Dosage | | | | | |
| | 10 mL/kg | | | 10 mL/kg + 10 mL/kg | | |
| AUTONOMIC | No. 1 | No. 2 | No. 3 | No. 1 | No. 2 | No. 3 |
| Skin Color | − | − | − | − | − | − |
| Respiration | − | − | − | − | − | − |
| Salivation F.V. | − | − | − | − | − | − |
| Lacrimation | − | − | − | − | − | − |
| Diarrhea | − | − | − | − | − | − |
| Body Temperature | − | − | − | − | − | − |
| Piloerection | − | − | − | − | − | − |
| Inc. Palpebral Size | − | − | − | − | − | − |
| Dec. Palpebral Size | | | | | | |

TABLE 49-continued

Autonomic signs in mice for vehicles (Study 2; Round 1)

| | Treatment | | | | | |
|---|---|---|---|---|---|---|
| | Vehicle[a] | | | Vehicle[a] + Vehicle[b] | | |
| | Route | | | | | |
| | IP | | | IP | | |
| | Dosage | | | | | |
| | 10 mL/kg | | | 10 mL/kg + 10 mL/kg | | |
| AUTONOMIC | No. 1 | No. 2 | No. 3 | No. 1 | No. 2 | No. 3 |
| Others | − | − | − | − | − | − |
| Death | − | − | − | − | − | − |

Legend for Tables 46 to 49
[a] 20% Tween 20/80% PBS
[b] 0.9% NaCl
−: no effects
±: Slight to moderate effects
+: Severe effects
Inc.: Increased
Dec.: Decreased
Spont.: Spontaneous
C.: Chronic
T.: Tonic
C-T: Chronic-Tonic
↓: Low
D: Deep In Vivo Anti-Cancer Activity: Compound 1 and Gemcitabine An in vivo study indicates that Compound 1 is effective in combination with gemcitabine. The study design is detailed below and in Table 50. There is evidence for synergy from the study results which are shown in Table 51 and Table 52. Monotherapy and combinations were well tolerated.

Estimated Timeline

Animal Arrival: Within one month receiving test compounds

Tumor cells implantation: Within two weeks after animals are obtained

Dosing: Approximately 1-2 weeks after tumor cell implantation

Sample Requirements

Compound 1 150 mg; Gemcitabine 256 mg.

Protocol

Tumor, Xenograft Pancreas, MIA PaCa-2

Procedure: Groups of (8) female nu/nu mice (7-8 weeks old), bred in an animal isolator (IVC racks) under specific pathogens free (SPF) condition at 22 plus or minus 2° C. are used. Viable human pancreatic carcinoma MIA PaCa-2 (ATCC CRL-1420) cells (1.0×107 in 0.2 mL) are injected subcutaneously into the right flank of experimental mice. When tumor volumes reach ~80-150 mm$^3$ (about 8-10 days post implant), the animals are randomly assigned into groups of eight, and test compounds and/or vehicle dose administrations are initiated (denoted as Day 1). Test compounds are administered as detailed in the "Study Design" section (Table 50). Tumor volumes and body weights are measured and recorded twice weekly over the course of the study period. Animals are monitored as a group. The endpoint of the experiment is a mean tumor volume in the negative control group of 2000 mm$^3$ or 28 days, whichever comes first.

Tumor volume (mm$^3$) is estimated according to the formula for a prolate ellipsoid: length (mm)×[width (mm)]2× 0.5. Tumor growth inhibition (% TGI) will be determined twice weekly during the dosing period by the formula: % TGI=(1−[(T−T0)/(C−C0)])×100 where T=mean tumor volume of treated group, T0=mean tumor volume of treated group at study start, C=mean tumor volume of control group and C0=mean tumor volume of control group at study start [Mohammed et al. 1998],

TABLE 50

Tumor, Xenograft, Pancreas, MIA PaCa-2 in female nu/nu mice study design

| Group | Test Article | Route | Conc. mg/mL | Dosage mL/kg | Dosage mg/kg | Mice[a] (female) |
|---|---|---|---|---|---|---|
| 1[#] | Vehicle[b] | IP | NA | 10 | NA qwk x 3[c] | 8 |
| 2 | Gemcitabine | IP | 8 | 10 | 80 q4d x 4[d] | 8 |
| 4 | Compound 1 | IP | 10 | 10 | 100 qwk x 3[c] | 8 |
| 6 | Compound 1 + Gemcitabine | IP + IP | 10 + 8 | 10 | 100, qwk x 3[c] + 80, q4d x 4[d] | 8 |

[#] Negative control group
[a] Female nu/nu mice aged 7-8 weeks are implanted with 1 x 10$^7$ MIA PaCa-2 cells (0.2 mL/mouse), and dosing is initiated when group mean tumor volumes reach ~80-150 mm$^3$.
[b] Test substance vehicle (10% Tween20/90% Saline)
[c] Doses are administered once weekly for 3 weeks.
[d] Doses are administered once every four days (four total administrations).
Body weight and tumor volumes are recorded twice weekly beginning on Day 1 and continuing until study completion.
Tumor growth inhibition (% TGI) is determined twice weekly during the dosing period by the formula: % TGI = (1 − [(T − T0)/(C − C0)]) x 100 where T = mean tumor volume of treated group, T0 = mean tumor volume of treated group at study start, C = mean tumor volume of control group and C0 = mean tumor volume of control group at study start.
Study is designed to continue for 28 days, or until the mean tumor volume within negative control group reaches 2000 mm$^3$, whichever comes first.
After TGI is determined, study may be converted to determine Tumor Growth Delay (TGD).
Animals are to be sacrificed if/when:
1. Body weight loss >25%
2. Severe tumor ulceration All aspects of this work including housing, experimentation, and animal disposal are performed in general accordance with the "Guide for the Care and Use of Laboratory Animals: Eighth Edition" (2011) in an AAALAC-accredited laboratory animal facility.

TABLE 51

Tumor volume change in a pancreas MIA PaCa-2 tumor xenograft model in response to treatment with compound 1 alone or in combination with Gemcitabine.
Assay Tumor Xenograft, Pancreas, MIA PaCa-2
WO#1060729 (AB67928)
Female nu/nu mice

| Gr. | Treatment | Dose (mg/kg) (Route) | No. | Day 1 | Day 4 | Day 8 | Day 11 | Day 15 |
|---|---|---|---|---|---|---|---|---|
| 1 | Vehicle | NA (mg/kg) | 1 | 64 | 125 | 186 | 326 | 574 |
| | | QWK x 3 | 2 | 74 | 65 | 87 | 128 | 151 |
| | | IP | 3 | 103 | 97 | 175 | 238 | 476 |
| | | | 4 | 122 | 111 | 142 | 179 | 422 |
| | | | 5 | 76 | 63 | 135 | 160 | 258 |
| | | | 6 | 90 | 79 | 81 | 96 | 171 |
| | | | 7 | 90 | 84 | 73 | 140 | 326 |
| | | | 8 | 103 | 125 | 180 | 315 | 629 |
| | | | Mean | 90 | 94 | 132 | 198 | 376 |
| | | | SEM | 7 | 9 | 17 | 31 | 63 |
| 2 | Gemcitabine | 80 mg/kg | 1 | 65 | 65 | 114 | 165 | 213 |
| | | Q4D x 4 | 2 | 74 | 82 | 104 | 97 | 160 |
| | | IP | 3 | 104 | 128 | 151 | 215 | 419 |
| | | | 4 | 115 | 123 | 162 | 228 | 335 |
| | | | 5 | 76 | 73 | 75 | 103 | 130 |
| | | | 6 | 88 | 100 | 70 | 85 | 128 |
| | | | 7 | 91 | 58 | 70 | 94 | 115 |
| | | | 8 | 101 | 119 | 113 | 127 | 156 |
| | | | Mean | 89 | 94 | 107 | 139 | 207 |
| | | | SEM | 6 | 10 | 13 | 20 | 39 |
| | | | % T/C | 99 | 100 | 81 | 70 | 55 |
| | | | % TGI | 1 | 0 | 19 | 30 | 45 |
| 4 | Compound 1 | 100 mg/kg | 1 | 67 | 56 | 126 | 368 | 600 |
| | | QWK x 3 | 2 | 72 | 59 | 95 | 110 | 244 |
| | | IP | 3 | 104 | 105 | 125 | 192 | 276 |
| | | | 4 | 115 | 103 | 107 | 121 | 197 |
| | | | 5 | 81 | 129 | 187 | 266 | 414 |
| | | | 6 | 87 | 70 | 111 | 188 | 309 |
| | | | 7 | 93 | 92 | 177 | 251 | 409 |
| | | | 8 | 100 | 107 | 138 | 188 | 312 |
| | | | Mean | 90 | 90 | 133 | 211 | 345 |
| | | | SEM | 6 | 9 | 12 | 30 | 45 |
| | | | % T/C | 100 | 96 | 101 | 107 | 92 |
| | | | % TGI | 0 | 4 | −1 | −7 | 8 |
| 6 | Compound 1 + Gemcitabine | 100 mg/kg QWK x 3 IP + 80 mg/kg Q4D x 4 IP | 1 | 69 | 46 | 48 | 57 | 80 |
| | | | 2 | 70 | 111 | 94 | 104 | 116 |
| | | | 3 | 108 | 86 | 101 | 97 | 103 |
| | | | 4 | 111 | 132 | 124 | 157 | 265 |
| | | | 5 | 84 | 68 | 71 | 35 | 95 |
| | | | 6 | 86 | 67 | 77 | 105 | 123 |
| | | | 7 | 96 | 55 | 28 | 25 | 23 |
| | | | 8 | 98 | 94 | 98 | 127 | 210 |
| | | | Mean | 90 | 82 | 80 | 88 | 127 |
| | | | SEM | 6 | 10 | 11 | 16 | 27 |
| | | | % T/C | 100 | 87 | 61 | 44 | 34 |
| | | | % TGI | 0 | 13 | 39 | 56 | 66 |

TABLE 52

Body weight change in a pancreas MIA PaCa-2 tumor xenograft model in response
to treatment with Compound 1 alone or in combination with Gemcitabine.
Assay # 581500 Tumor Xenograft, Pancreas, MIA PaCa-2
WO#1060729 (AB67928)
Female nu/nu mice

| Gr. | Treatment | Dose (mg/kg) (Route) | No. | Body Weight (g) | | | | |
|---|---|---|---|---|---|---|---|---|
| | | | | Day 1 | Day 4 | Day 8 | Day 11 | Day 15 |
| 1 | Vehicle | NA (mg/kg) QWK x 3 IP | 1 | 28 | 27 | 27 | 27 | 26 |
| | | | 2 | 27 | 26 | 27 | 27 | 27 |
| | | | 3 | 25 | 24 | 25 | 26 | 27 |
| | | | 4 | 24 | 24 | 24 | 24 | 24 |
| | | | 5 | 26 | 25 | 25 | 25 | 25 |
| | | | 6 | 25 | 25 | 25 | 26 | 26 |
| | | | 7 | 25 | 23 | 23 | 24 | 24 |
| | | | 8 | 25 | 25 | 24 | 25 | 26 |
| | | | Mean | 25.6 | 24.9 | 25.0 | 25.5 | 25.6 |
| | | | SEM | 0.5 | 0.4 | 0.5 | 0.4 | 0.4 |
| 2 | Gemcitabine | 80 mg/kg Q4D x 4 IP | 1 | 24 | 23 | 25 | 25 | 26 |
| | | | 2 | 30 | 28 | 30 | 31 | 31 |
| | | | 3 | 25 | 22 | 25 | 26 | 27 |
| | | | 4 | 26 | 25 | 27 | 27 | 27 |
| | | | 5 | 24 | 24 | 25 | 25 | 25 |
| | | | 6 | 25 | 24 | 25 | 25 | 25 |
| | | | 7 | 25 | 24 | 24 | 25 | 25 |
| | | | 8 | 26 | 25 | 25 | 25 | 25 |
| | | | Mean | 25.6 | 24.4 | 25.8 | 26.1 | 26.4 |
| | | | SEM | 0.7 | 0.6 | 0.7 | 0.7 | 0.7 |
| 4 | Compound 1 | 100 mg/kg QWK x 3 IP | 1 | 29 | 27 | 29 | 29 | 29 |
| | | | 2 | 26 | 24 | 26 | 25 | 25 |
| | | | 3 | 25 | 24 | 26 | 25 | 26 |
| | | | 4 | 25 | 23 | 25 | 25 | 24 |
| | | | 5 | 25 | 25 | 25 | 27 | 26 |
| | | | 6 | 23 | 23 | 23 | 25 | 23 |
| | | | 7 | 25 | 25 | 25 | 27 | 26 |
| | | | 8 | 26 | 26 | 26 | 27 | 26 |
| | | | Mean | 25.5 | 24.6 | 25.6 | 26.3 | 25.6 |
| | | | SEM | 0.6 | 0.5 | 0.6 | 0.5 | 0.6 |
| 6 | Compound 1 + Gemcitabine | 100 mg/kg QWK x 3 IP + 80 mg/kg Q4D x 4 IP | 1 | 25 | 24 | 24 | 24 | 24 |
| | | | 2 | 24 | 23 | 23 | 24 | 24 |
| | | | 3 | 27 | 27 | 26 | 26 | 26 |
| | | | 4 | 27 | 25 | 26 | 26 | 26 |
| | | | 5 | 23 | 22 | 23 | 23 | 23 |
| | | | 6 | 26 | 25 | 25 | 25 | 24 |
| | | | 7 | 27 | 26 | 26 | 26 | 26 |
| | | | 8 | 25 | 24 | 24 | 23 | 23 |
| | | | Mean | 25.5 | 24.5 | 24.6 | 24.6 | 24.5 |
| | | | SEM | 0.5 | 0.6 | 0.5 | 0.5 | 0.5 |

Evaluation of Compound 1 to Treat Skin Diseases

Aim

To evaluate compounds 1 with skin disease relevant in vitro assays. Evaluation was conducted by LEO Pharma Open Innovation, USA (openinnovation.leo-pharma.com).

Specific Objectives

1. Determination of inhibition of CCL2 release from IL-4, IL-13, IL-22 and IFN-γ-stimulated primary human keratinocytes [assay number 1280] and determination of the effect on cell viability [assay number 1243],
2. Determination of inhibition of IL-8 release from IL-17A and TNFα-induced primary human keratinocytes [assay number 1250] and determination of the effect on cell viability [assay number 1244],
3. Determination of inhibition of IL-17A secretion from human PBMC stimulated with antiCD3/antiCD28-coated beads [assay number 1321] and determination of the effect on cell viability [assay number 1322],
4. Determination of inhibition of IL-4 and IL-2 secretion from human CD4-positive T-cells stimulated with antiCD2/antiCD3/antiCD28-coated beads [assay number 1297, 1298] and determination of the effect on cell viability [assay number 1299], Disease Relevance Summary 1. Compounds which inhibit keratinocyte CCL2 secretion may be expected to have efficacy in atopic dermatitis.
2. Compounds which inhibit keratinocyte IL-8 secretion may be expected to have efficacy in psoriasis.
3. Compounds which inhibit IL-17A secretion may be expected to have efficacy in psoriasis.
4. Compounds which inhibit IL-4 secretion may be expected to have efficacy in atopic dermatitis. Compounds which also inhibit IL-2 secretion have a broader immunosuppressive effect since IL-2 is an autocrine growth factor for T-cells.

Results

Figure 20A:
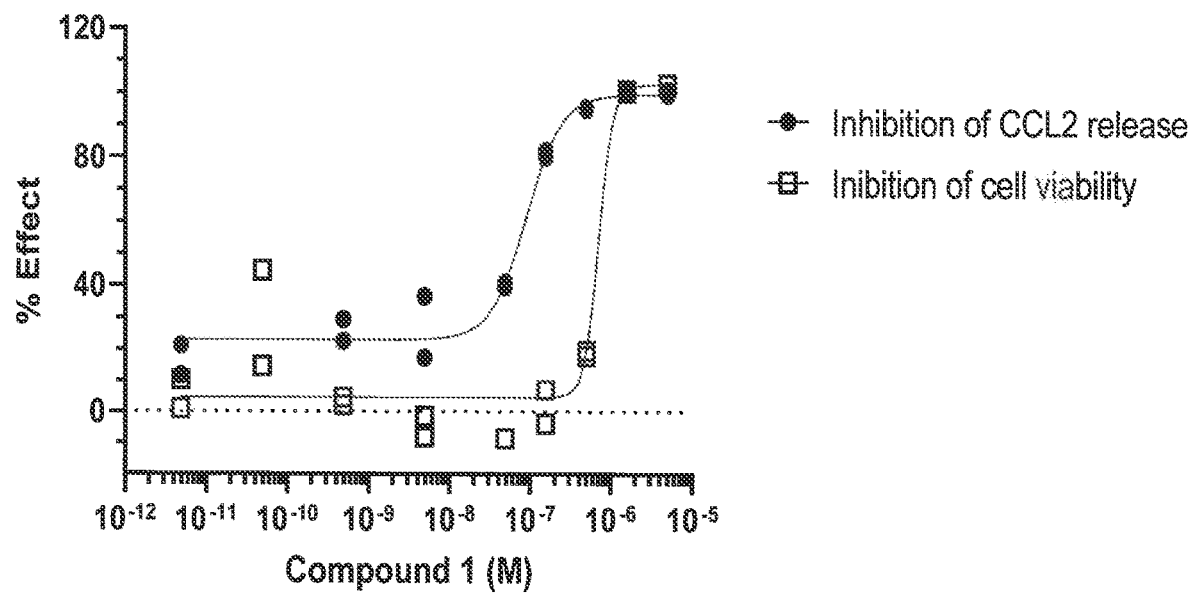
FIGS. 20A to 20D show various dose-responsive effects of an example compound on A) CCL2 release in human keratinocytes, B) IL-8 release in human keratinocytes, C) IL-17A release in human PBMC inflammation, and D) IL-2 and IL-4 release in T-cell inflammation, respectively.

1. Effect of Compound 1 on monocyte chemoattractant protein-1 (MCP-1/CCL2) release in human keratinocytes induced by IL-4, IL-13, IL-22 and IFN-γ.
   FIG. 20A shows dose-responsive effect of Compound 1 on chemokine CCL2 release in human keratinocytes induced by IL-4, IL-13, IL-22 and IFN-γ.

Inhibition of CCL2 release: Rel $EC_{50}$=92.2 nM, Max Effect=101%.

Inhibition of cell viability: Rel $EC_{50}$=708.0 nM, Max Effect=103%.

Compound 1 showed medium potency in reduction of CCL2 release without significant reduction of cell viability as shown in FIG. 20A.

2. Effect of Compound 1 on IL-8 release in human keratinocytes induced by IL-17 and TNF-α.

Figure 20B:
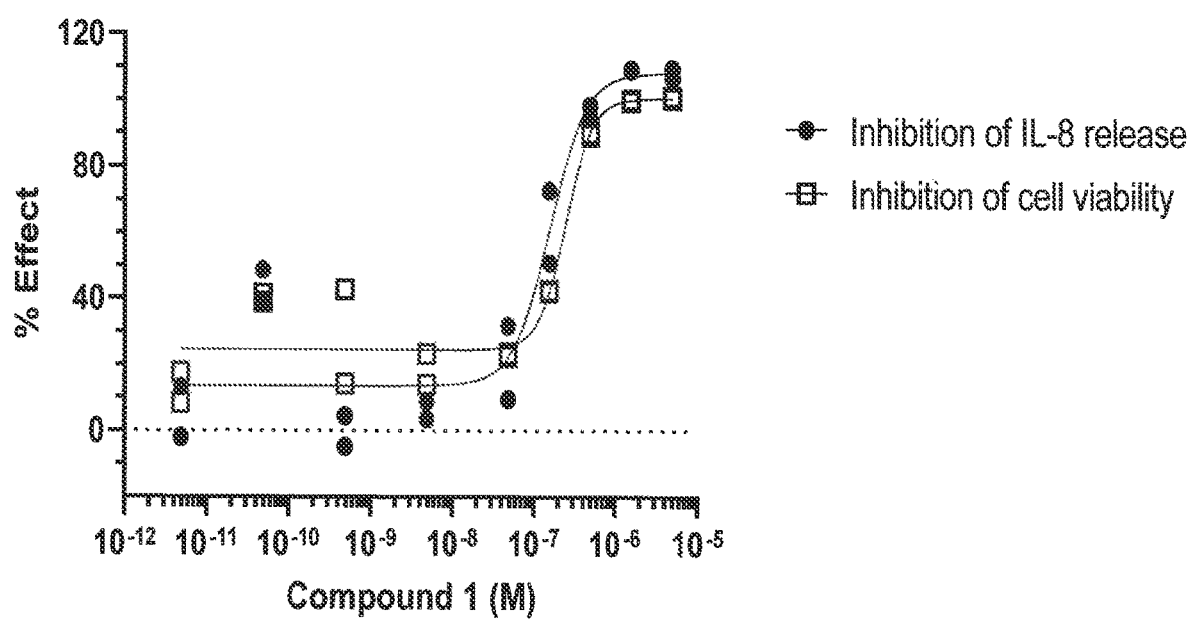

FIG. 20B shows dose-responsive effect of Compound 1 on IL-8 release in human keratinocytes induced by IL-17 and TNF-α.

Inhibition of IL-8 release: Rel $EC_{50}$=157 nM, Max Effect=110%.

Inhibition of cell viability: Rel $EC_{50}$=246 nM, Max Effect=101%.

There is similar reduction of IL-8 release and cell viability.

3. Effect of Compound 1 on IL-17A release in Human PBMC inflammation induced by CD3, CD28 and IL-23.

Figure 20C:
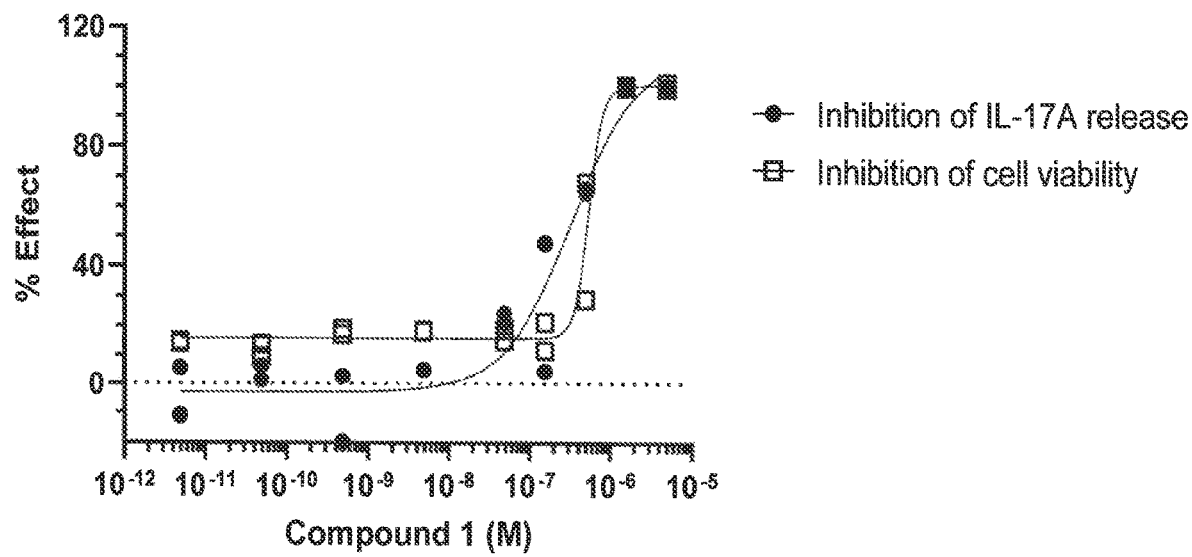

FIG. 20C shows dose-responsive effect of Compound 1 on IL-17A release in Human PBMC inflammation induced by CD3, CD28 and IL-23.

Inhibition of IL-17A release: Rel $EC_{50}$=320 nM, Max Effect=100%.

Inhibition of cell viability: Rel $EC_{50}$=542 nM, Max Effect=101%.

There is similar reduction of IL-17 release and cell viability.

4. Effect of Compound 1 on IL-2 and IL-4 releases in T-cell inflammation induced by CD2, CD3 and CD28.

Figure 20D:
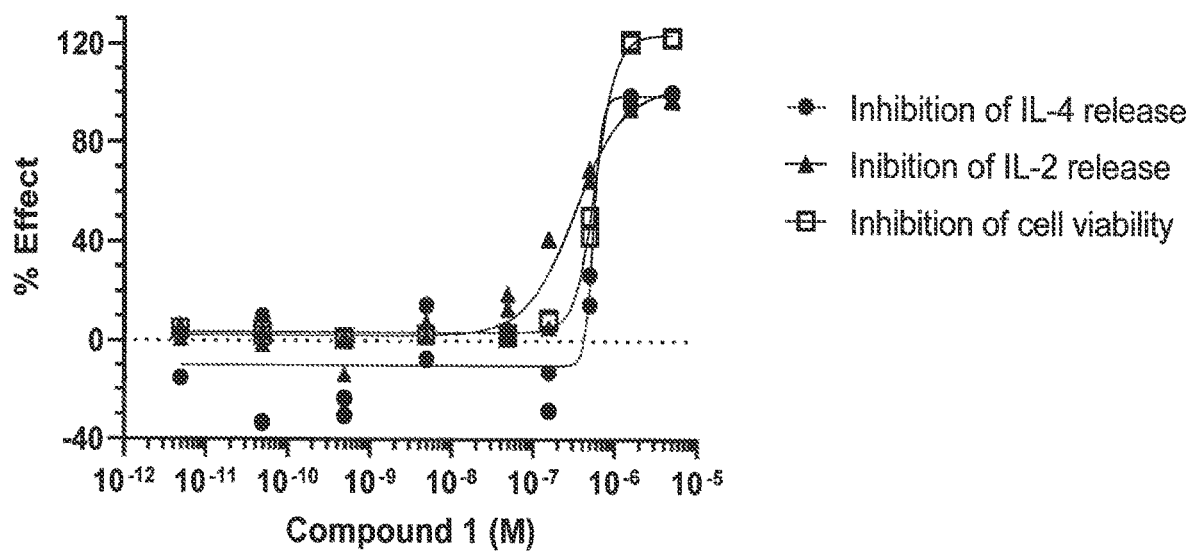

FIG. 20D. Dose-responsive effect of Compound 1 on IL-2 and IL-4 releases in T-cell inflammation induced by CD2, CD3 and CD28.

Inhibition of IL-2 release: Rel $EC_{50}$=327 nM, Max Effect=98%.

Inhibition of IL-4 release: Rel $EC_{50}$=523 nM, Max Effect=100%.

Inhibition of cell proliferation: Rel $EC_{50}$=587 nM, Max Effect=123%.

There is similar effect on IL-2, IL-4 and cell proliferation.

Discussion

Compound 1 showed pronounced effect in CCL2-release without significant effect on cell viability (FIG. 20A) compared to IL-8, IL-17A, IL-2 and IL-4 where the effect on release and cell viability are similar (FIGS. 20B to 20D). These results indicate that Compound 1 is a potential candidate for effective treatment of skin inflammatory diseases such as atopic dermatitis.

Methods

1. Keratinocyte CCL2 Release

Inhibition of CCL2 release from IL-4, IL-13, IL-22 and IFN-γ-stimulated primary human keratinocytes LEO Pharma Open Innovation assay number 1280

Disease Relevance

The inflammatory skin disease atopic dermatitis (AD) is characterized by the T-cell cytokines including IL-4, IL-13, IL-22 and IFN-γ. In the present assay, keratinocytes are stimulated with a mixture of these cytokines, and the release of CCL2 (C—C chemokine ligand 2, also called monocyte chemoattractant protein 1 (MCP-1)) is measured in the culture supernatant by proximity time-resolved homogenous fluorescence (HTRF). The purpose of the assay is to measure if test compounds inhibit the levels of CCL2 released by the keratinocytes. Compound which inhibit keratinocyte CCL2 secretion may be expected to have efficacy in atopic dermatitis.

A known steroid, Betamethasone, inhibits CCL2 release in this assay with an $EC_{50}$ of approximately 15 nM, and an Emax (plateau of the fitted curve) of approximately 60%. A high Emax shows that the compound inhibits a large proportion of the secreted CCL2. A low $EC_{50}$ value indicates that the compound is potent and to perform the inhibition at low concentrations.

| Key assay parameters | Description |
|---|---|
| Human primary keratinocytes (HEKa) | Cells are frozen in passage 2. Cells are used in passage 3-6 |
| IL-4, IL-13, IL-22 and IFN-γ | Atopic dermatitis-like stimulation: Recombinant human interleukin (IL) 4, 13 and 22 at 10 ng/mL and Interferon-γ at 1 ng/mL |
| Effect | Inhibition of AD stimuli induced CCL2 release from HEKa cells |
| Positive control (~100% effect) | AD-like stimulation + Terfenadine (CAS: 50679-08-8) at 10 microM |
| Negative control (~0% effect) | AD-like stimulation and 0.1% DMSO |
| Reference compound | Betamethasone (CAS: 378-44-9) |
| Incubation time | 48 h |
| Capacity, run-time and requirements | The assay takes 3 days to perform. |

Method Description

CELL Culture:

HEKa are human epidermal keratinocytes isolated from adult skin. The cells have been cryopreserved at the end of the primary culture stage in a medium containing 10% DMSO. Sterile cell culture work applies.

Initiating Cultures from Cryopreserved HEKa Cells:

Thaw a vial of the frozen HEKa stock in a 37° C. water/bead bath.

Transfer the cell suspension into 30 ml T75 cell culture flask.

Take 15 ml out and dispense over into 2×T75 (15 ml each).

Set up for assay 5-6 days later or pass it on.

Maintenance of Stock Cultures

Change the culture medium to freshly supplemented medium, 24 to 36 hours after establishing a secondary culture from cryopreserved cells. For subsequent subcultures, change the medium 48-72 hours after establishing the subculture.

Only passage up to 3-5 in the assay.

Subculture of HEKa

View and confirm 80% confluence.

Remove all of the culture medium from the flask.

Add 3 ml of TrypLE Express solution to the flask. Rock the flask to ensure that the entire surface is covered.

Immediately remove all 3 ml of TrypLE Express solution from the flask.

Add 1½ ml (T75) (3 ml T175) of fresh TrypLE Express solution to the flask.

View the culture under a microscope. Incubate the flask at room temperature until the cells have become completely round, approximately 8-10 minutes.

Tap the flask very gently to dislodge cells from the surface of the flask.

Add 3-4 ml (T75) (7 ml T175) of Trypsin Neutralizer solution to the flask and transfer the detached cells to a sterile conical tube.

Centrifuge the cells at 170×g for 7-10 minutes. Observe the cell pellet.

Remove the supernatant from the tube, being careful not to dislodge the cell pellet.

Resuspend the cell pellet in 15 ml medium with HKGS supplemented (cat no S-001-K) but without hydrocortisone (when use for assay). Pipette the cells up and down with a 10 ml pipette to ensure a homogeneous cell suspension.

Determine the concentration of cells in the suspension.

Dilute the cells in supplemented medium and seed new culture in a T175 flask. Incubate the cultures in a 37° C., 5% $CO_2$/95% air, humidified cell culture incubator.

Assay Day 0:

Trypsinize the cells as described above.

Resuspend pellet in 10 ml assay medium (EpiLife Medium with HKGS Kit but without hydrocortisone)

Filter the cells though a 37 μm strainer.

Count cells using a cell counter.

Seed HEKa cells in 384-well view plates 3500 c/w/40 μL.

Place the plates with lids on in a humidity chamber with lid (24.5×24.5 cm box added $H_2O$ in the bottom).

Incubate plates over night at 37° C., 5% $CO_2$/95% air

Assay Day 1:

Prepare compound-containing source plate, i.e. titrations in DMSO to be transferred to the assay plate.

Add 80 nL compounds and controls from the source plate to the assay plate (with cells).

Add 40 μL stimulation (recombinant human interleukin (IL) 4, 13, 22 at 10 ng/mL and Interferon-gamma at 1 ng/mL) in medium with supplement, but without hydrocortisone.

Incubate plates at 37° C., 5% $CO_2$/95% air for 2 days.

Assay Day 3:

Remove plates from incubation and equilibrate to room temperature for 30 minutes.

Transfer 8 μL supernatant to white proxi 384-well plates for CCL2 detection.

Add 8 μL media to the detection plate.

Add 4 μL CCL2 HTRF detection reagent (to the white proxi 384w).

Seal and incubate for 4 hours and read in a plate reader.

Data Analysis and Calculations

CCL2 concentration in the supernatants is measured using homogeneous time-resolved fluorescence resonance (TR-FRET). The assay is quantified by measuring fluorescence at 665 nm (proportional to CCL2 concentration) and 620 nm (control). A ratio 665/620*1000 is calculated.

% Effect:

The capacity of the test compound to inhibit CCL2 release is normalized to the signal in the control wells with keratinocytes incubated with 0.1% DMSO (0%) and 10 μM Terfenadine (100%), which fully inhibits the CCL2 release.

2. Keratinocyte IL-8 Release

Inhibition of IL-8 release from IL-17A and TNFα-induced primary human keratinocytes LEO Pharma Open Innovation assay number 1250.

Disease Relevance

The inflammatory skin disease psoriasis is characterized by cytokines IL-17A and TNFα. In the present assay, primary human keratinocytes are stimulated with a mixture of these cytokines, and the release of IL-8 (also called CXCL8) is measured in the culture supernatant by proximity homogenous time-resolved fluorescence (HTRF). The purpose of the assay is to measure if the test compound is able to inhibit the levels of IL-8 released by the keratinocytes, indicating that it is able to inhibit part of the inflammation occurring in cells.

Compounds which inhibit keratinocyte IL-8 secretion may be expected to have efficacy in psoriasis.

A known steroid, Betamethasone, inhibits IL-8 release in this assay with an $EC_{50}$ of approximately 10 nM, and an Emax (plateau of the fitted curve) of approximately 50%. A high Emax indicates that the compound inhibits a large proportion of the IL-8 secretion. A low $EC_{50}$ value indicates that the compound is potent and performs the inhibition at low concentrations.

| Key assay parameters | Description |
|---|---|
| Human epidermal keratinocytes, adult (HEKa) | Cells are frozen in passage 2. Cells are used in passage 3-5 |
| IL-17A and TNFα | Psoriasis-like stimulation: Recombinant human interleukin (IL) 17A and tumor necrosis factor alpha (TNFα) both at 10 ng/mL |
| Effect | Inhibition of IL-17A/TNFα-induced IL-8 release from HEKa |
| Positive control (~100% effect) | No stimulation and 0.1% DMSO |
| Negative control (~0% effect) | IL-17A/TNFα stimulation and 0.1% DMSO |
| Reference compound | Betamethasone (CAS: 378-44-9) |
| Incubation time | 72 h |
| Capacity, run-time and requirements | The assay takes 3 days to perform. |

Method Description

CELL Culture:

HEKa are human epidermal keratinocytes isolated from adult skin (See Cell Culture Method described for Keratinocyte CCL2 release above).

Assay Day 0:

Detach the cells as described above.

Resuspend pellet in 10 ml EpiLife Medium with HKGS Kit but without hydrocortisone Filter the cells though a 37 μm strainer.

Count cells using a cell counter.

Seed Human Epidermal Keratinocytes, adult (HEKa) cells in 384-well view plates 3500 c/w/40 μL. Use cell media with supplement but without hydrocortisone as assay medium.

Place the plates with lids on in a humidity chamber with lid (24.5×24.5 cm box added $H_2O$ in the bottom).

Incubate plates over night at 37° C., 5% $CO_2$/95% air.

Assay Day 1:

Prepare compound-containing source plate, i.e. titrations in DMSO to be transferred to the assay plate.

Empty the assay plate, and re-add 25 μL assay medium.

Add 75 nL compounds and controls from the source plate to the assay plate (with cells).

Add 25 μL assay medium and incubate for 2 hours.

Add 25 μL stimulation mix in assay medium (recombinant human interleukin 17A and Tumor necrosis factor-alpha) to give a final concentration of 10 ng/mL of both cytokines.

Incubate plates at 37° C., 5% $CO_2$/95% air for 3 days.

Assay Day 4:

Remove plates from incubation and equilibrate to room temperature for 30 minutes.

Transfer 2 μL supernatant to white proxi 384-well plates for IL-8 detection.

Add 2 µL assay medium
Prepare IL-8 HTRF mix (according to manufactory protocol) and add 2 µL pr well.
Seal and incubate for 3 hours and read fluorescence in a plate reader.

Data Analysis and Calculations

IL-8 concentration in the supernatant is measured using homogeneous time-resolved fluorescence resonance (TR-FRET). The assay is quantified by measuring fluorescence at 665 nm (proportional to IL8 concentration) and 620 nm (control). A ratio 665/620*1000 is calculated as a representation of the amount of IL-8 in the supernatant.

% Effect:

The capacity of the test compound to inhibit IL-8 release is normalized to the signal in the negative control wells with keratinocytes incubated with 0.1% DMSO (0%) and 10 µM Terfenadine (100%), which fully inhibits the release of IL-8.

3. PBMC IL-17 Assay

Inhibition of IL-17A secretion from human PBMC stimulated with antiCD3/antiCD28-coated beads. LEO Pharma Open Innovation assay number 1321

Disease Relevance

The inflammatory skin disease psoriasis is characterized by cytokines IL-17A and TNFα. In the present assay, human peripheral blood mononuclear cells (PBMC) are stimulated with beads coated with antibodies against CD3 and CD28 to activate the T-cell receptor, and stimulated with IL-23 to promote T-helper17 activity. The cells are incubated for three days, then the secreted level of IL-17A is measured in the culture supernatant using AlphaLISA and the amount of living cells is measured by addition of resazurin (Presto-Blue®) to identify compounds that inhibit cell proliferation or viability. The purpose of the assay is to measure if test compounds inhibit the secretion of IL-17A by the PBMC. Compounds which inhibit IL-17A secretion may be expected to have efficacy in psoriasis.

The reference compound in this assay is the calcineurin inhibitor Tacrolimus and inhibits IL-17A release with an EC 50 of approximately 0.34 nM, and with an Emax (plateau of the fitted curve) of approximately 90%. A high Emax shows that the compound inhibits a large proportion of the secreted IL-17. A low $EC_{50}$ value indicates that the compound is potent and performs the inhibition at low concentrations.

Key Assay Parameters

| Parameter | Description |
| --- | --- |
| Cells | Human PBMC isolated from huffy coats and kept at −150° C. until day of assay |
| Stimulation | Beads coated with antibodies to CD3 and CD28 (T-cell activation/expansion kit Miltenyi Biotec cat no 130-091-441) One bead/cell. |
| Effect | Inhibition of IL-17A release |
| 0% effect of test compound | Bead stimulation, 0.1% DMSO |
| 100% effect of test compound | Bead stimulation, 0.1% DMSO, Terfenadine 10 uM |
| Reference compound | Tacrolimus (Cas no 104987-11-3-P) |
| Incubation time | 3 days |
| Capacity, run-time and requirements | The assay takes 3 days to perform. |

Method Description

PBMC Isolation:

PBMC are isolated from fresh human huffy coats by centrifugation on Lymphoprep® following instructions from Sebmate®

Cells are spun down and resuspended in freezing medium (RPMI1640+20% FBS+5% DMSO)

Cells are frozen in aliquots of $8 \times 10^7$ cells/vial matching one 384 plate. Cells are placed in Coolcell box and placed in −80° C. freezer for one day. Vials are moved to the −150° C. freezer in a prechilled box.

Assay Day 1:

Prepare assay medium: RPMI1640+10% heat inactivated FBS and 1% pen/strep, supplemented with human IL-23, 20 ng/mL (R&D systems, cat no 1290-IL-010)

Test compounds: Prepare compound-containing source plate, i.e. titrations in DMSO to be transferred to the assay plate.

Add 70 nL compounds and controls from the source plate to the assay plate.

Thaw the cells by adding 1 vial to 20 ml warm assay medium

Centrifuge the cells down at 170 G in 10 minutes, remove the supernatant and resuspend in new medium.

Filter the cells though a 37 µm strainer.

Count the cells in the cell counter.

Beads (T Cell Activation/Expansion Kit-human, Miltenyi Biotech, cat. no. 130-091-441): Coat beads with antibodies (antiCD3 and antiCD28) according to the kit procedure.

Add the beads to the cells, one bead per cell, 2.1e+06 cells/ml. Use a pipette to mix the cells and beads carefully.

Seed the cell/bead mixture into the assay plate, 70 µL/well (1.3e+05 cells/well)

Place the plates in a humidity chamber with lid (24.5× 24.5 cm box added $H_2O$ in the bottom).

Incubate plates at 37° C., 5% $CO_2$/95% air for 3 days.

Assay Day 4:

IL-17A concentration in the supernatants is measured using an alphaLISA kit (Perkin Elmer, cat no. AL219F).

Pretest to find optima dilution of samples: Test 5 µL supernatant from control wells and run IL-17A alphaLISA assay with only 2 hours of incubation.

When data are available, remove assay plates from incubation and equilibrate to room temperature for 30 minutes.

Transfer 5 µL or corrected amounts of supernatant to a 384-proxy plate

Add 5 µL alphaLISA acceptor beads.

Incubate 1 hour at room temperature

Add 5 µL donor beads

Incubate overnight at room temperature protected from light.

Add 7 µL PrestoBlue reagent (resazurin)/well to the assay plate and incubated for 2-4 hours at 37° C./5% $CO_2$. The fluorescence in the wells is measured (Ex615/Em 535).

Assay Day 5:

Read alphaLISA plate in a plate reader

Data Analysis and Calculations

IL-17A concentration in the supernatants is measured using an alphaLISA kit (Perkin Elmer, cat no. AL219F).

% Effect IL-17:

The capacity of the test compound to inhibit IL-17A release is normalized to the signal in the negative control wells treated with atoxic compound, Terfenadine.

The level of living cells in the wells is measured by the addition of PrestoBlue® and the conversion of Resazurin to Resorufin (fluorescent) in living cells is measured.

% Effect Viability/Proliferation:

The effect of the test compounds on viability/proliferation is normalized to the PrestoBlue signal in the negative control wells treated with a toxic compound, Terfenadine.

4 and 5. T-Cell IL-2 & IL-4 Assay

Inhibition of IL-4 and IL-2 secretion from human CD4-positive T-cells stimulated with antiCD2/antiCD3/antiCD28-coated beads. LEO Pharma Open Innovation assay number 1297, 1298, 1299

Disease Relevance

The inflammatory skin disease atopic dermatitis is characterized by the T-cell cytokines IL-4, IL-13 and IL-22. In the present assay, human T-cells are stimulated with beads coated with antibodies against CD2, CD3 and CD28 to activate the T-cell receptor. Then the level of secreted of IL-4 is measured in the culture supernatant using electrochemiluminescence (MSD kits, Meso Scale Discovery), IL-2 is measured by proximity homogenous time-resolved fluorescence (HTRF) and the amount of living cells is measured by addition of resazurin (PrestoBlue®) to allow identifying compounds that inhibit T-cell proliferation or viability. The purpose of the assay is to measure if a test compound is able to inhibit the secretion of IL-4 by the T-cells, indicating that it is able to inhibit part of the inflammation occurring in the skin. Compounds which inhibit IL-4 secretion may be expected to have efficacy in atopic dermatitis. Compounds which also inhibit IL-2 secretion have a broader immunosuppressive effect since IL-2 is an autocrine growth factor for T-cells. A known steroid, Betamethasone, inhibits IL-4 release in this assay with an $EC_{50}$ of approximately 15 nM, and with an Emax (plateau of the fitted curve) of approximately 80%. A high Emax shows that the compound is able to inhibit a large proportion of the secreted IL-4. A low EC 50 value indicates that the compound is potent and is able to perform the inhibition at low concentrations.

Key Assay Parameters

| Human CD4-postive T-cells isolated from buffy coats and kept at −150 degree C. until day of assay | |
| --- | --- |
| Stimulation | Beads coated with antibodies to CD2, CD3 and CD28 (T-cell activation/expansion kit Miltenyi Biotec cat no 130-091- 441) One bead/cell. |
| Effect | Inhibition of IL-4 release from T-cells |
| 0% effect of test compound | Bead stimulation, 0.1% DMSO |
| 100% effect of test compound | Unstimulated cells, 0.1% DMSO |
| Reference compound | Betamethasone (CAS: 378-44-9) |
| Incubation time | 48 h |
| Capacity, run-time and requirements | The assay takes 3 days to perform. |

Method Description

CD4+ T-Cell Isolation:
Peripheral blood mononuclear cells (PBMC) are isolated from fresh human buffy coats by centrifugation on Lymphoprep® following instructions from Sebmate™ (Stemcell).
The cells are resuspended in 30 ml of PBS+2% Serum and counted.
CD4 positive T-cells are isolated from freshly isolated PBMC using EasySep™ humane CD4+ T-cell Isolation Kit (Catalog #17952) and following the manufacturer's protocol.
Cells are spun down and resuspended in freezing medium (X-vivo 15+10% FBS+5% DMSO)
Cells are frozen in aliquots of $3 \times 10^7$ cells/vial matching one 384 plate. Cells are place in Coolcell box and place in −80° C. freezer for one day then transferred to the −150° C. freezer in a prechilled box.

Assay Day 1:
Prepare assay medium: 500 ml X-Vivo 15+5 ml Glutamax (2 mM final)+5 ml pen/strep (100 U/ml final).
Add 5 µL medium to the wells of a 384 well plate (Greiner cat. No 788986).
CD4+ Cells: Thaw frozen cells from −150° C. freezer in 37° C. bath, and pipette the cells into 10 ml medium. Spin 10 min @ 170 g.
Resuspend pellet in 3.5 ml per $2.5 \times 10^7$ cells and add 10 µL per well to the plate (40000 cells/well)
Test compounds: Prepare compound-containing source plate, i.e. titrations in DMSO to be transferred to the assay plate.
Add 25 nL compounds and controls from the source plate to the assay plate (with cells).
Beads (T Cell Activation/Expansion Kit-human, Miltenyi Biotech, cat. no. 130-091-441): Coat beads with antibodies according to the kit procedure.
Add 10 µL beads to each well except for the negative controls. One bead per cell. Add 10 µL medium to the negative controls.
Incubate plates at 37° C., 5% $CO_2$/95% air for 2 days.

Assay Day 3:
Remove plates from incubation and equilibrate to room temperature for 30 minutes.
IL-4 concentration in 10 µL supernatant is measured using an MSD IL-4 384-plate kit (Custom made) according to manufacturer protocol.
IL-2 concentrations in the supernatant is measured by an IL-2 HTRF kit, CisBio, cat. No 62HIL02PEH.
Add 4 µL medium to white proxi 384-well plates
Add 1 µL supernatant.
Add 4 µL mHTRF mix (each diluted 1:300 in ⅔ reconstitution buffer and ⅓ assay medium).
Spin the plates for 1 minute at 170 g
Seal and incubate overnight and read fluorescence in a plate reader
The amount of viable cells is measured by PrestoBlue® reagent
Add 15 µL diluted PrestoBlue® reagent (resazurin) corresponding to 2.5 µL Prestoblue/well to the assay plate.
Incubate overnight at 37° C./5% $CO_2$. The fluorescence in the wells is measured (Ex615/Em 535).

Data Analysis and Calculations

IL-4 concentration in the supernatants is measured using electrochemiluminescence (MSD kits, Meso Scale Discovery). IL-2 concentration in the supernatants is measured using homogeneous time-resolved fluorescence resonance (TR-FRET). The assay is quantified by measuring fluorescence at 665 nm (proportional to IL-2 concentration) and 620 nm (control). A ratio 665/620*1000 is calculated.

% Effect for IL-2 and IL-4:

The capacity of the test compound to inhibit IL-4 and IL-2 release is normalized to the signal in the negative control wells with un-stimulated T-cells.

The level of living cells in the wells is measured by the addition of PrestoBlue® and the conversion of Resazurin to Resorufin (fluorescent) in living cells is measured.

% Effect for Viability/Proliferation:

The effect of the test compounds on viability/proliferation is normalized to the PrestoBlue signal in the negative control wells treated with a toxic compound, Terfenadine.

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

REFERENCES

Ghisalberti E L (1994) The phytochemistry of the Myoporaceae. *Phytochemistry*, 35: 7-33.
Davis R A, Caroll A R, Pierens G K (1999). New lamellarin alkaloids from the Australian ascidian, *Didemnum chartaceum. J. Nat. Prod*, 62(3), 419-24.
Ullman E F, Kirakossian H, Singh S, Wu Z P, Irvin B R, Pease J S, Switchenko A C, Irvine J D, Daffom A, Skold C N (1994) Luminescent oxygen channeling immunoassay: Measurement of particle binding kinetics by chemiluminescence. *Proc. Natl. Acad. Sci. USA* Vol. 91, 5426-5430.
Ma H, Deacon S, Horiuchi K (2008). The challenge of selecting protein kinase assays for lead discovery optimization. *Expert Opin Drug Discov.* 3(6): 607-621.
Filippakopoulos, P., Picaud S, Mangos M, Keates T, Lambert J P, Barsyte-Lovejoy D, Felletar I, Volkmer R, Müller S, Pawson T, Gingras A C, Arrowsmith C H, Knapp S. (2012) Histone recognition and large-scale structural analysis of the human bromodomain family. *Cell*, 149(1): 214-31.
Filippakopoulos, P. and S. Knapp (2012) The bromodomain interaction module. *FEBS Lett*, 586(17): 2692-704.
Philpott, M., Yang J, Tumber T, Fedorov O, Uttarkar S, Filippakopoulos P, Picaud S, Keates T, Felletar I, Ciulli A, Knapp S, Heightman T D (2011) Bromodomain-peptide displacement assays for interactome mapping and inhibitor discovery. *Mol Biosyst*, 7(10): 2899-908.
Kaustov, L., Ouyang H, Amaya M, Lemak A, Nady N, Duan S, Wasney G A, Li Z, Vedadi M, Schapira M, Min J, Arrowsmith C H (2011) Recognition and specificity determinants of the human cbx chromodomains. *J Biol Chem* 286(1): 521-9.
Kim, J., Daniel J, Espejo A, Lake A, Krishna M, Xia L, Zhang Y, Bedford M T (2006) Tudor, MBT and chromo domains gauge the degree of lysine methylation. *EMBO Rep*, 7(4): 397-403.
Org, T., Chignola F, Hetenyi C, Gaetani M, Rebane A, Liiv I, Maran U, Mollica L, Bottomley M J, Musco G, Peterson P (2008) The autoimmune regulator PHD finger binds to non-methylated histone H3K4 to activate gene expression. *EMBO Rep*, 9(4): 370-6.
Venturing L., You J, Stadler M, Galien R, Lallemand V, Koken M H, Mattei M G, Ganser A, Chambon P, Losson R, de Thé H. (1999) TIF1 gamma, a novel member of the transcriptional intermediary factor 1 family. *Oncogene*, 18(5): 1209-17.
Xie, S., J. Jakoncic, and C. Qian (2012) UHRF1 double tudor domain and the adjacent PHD finger act together to recognize K9me3-containing histone H3 tail. *J Mol Biol*, 415(2): 318-28.
Adams-Cioaba, M. A., Li Z, Tempel W, Guo Y, Bian C, Li Y, Lam R, Min J. (2012) Crystal structures of the Tudor domains of human PHF20 reveal novel structural variations on the Royal Family of proteins. *FEBS Lett*, 586(6): 859-65.

Hayashi-Takanaka Y, Yamagata K, Wakayama T, Stasevich T J, Kainuma T, Tsurimoto T, Tachibana M, Shinkai Y, Kurumizaka H, Nozaki N, Kimura H (2011) *Nucleic Acids Res.* 39(15): 6475-88.
Kubicek, S. et al. (2007), *Mol. Cell.* 25:473-481.
Ken-ichi Noma and Shiv I. S. Grewal (2002), *Proc Natl Acad Sci USA*. Dec. 10, 1999 (Suppl 4): 16438-16445.
Rotili, D. and Mai, A. (2011), *Genes & Cancer*, 2: 663-679.
Chowdhury, R. et al. (2011), *Eur. Mol. Biol. Org.*, 12: 463-469.
Nottke, A. et al. (2009), *Development*, 136:879-889.
Kristensen, L. H. et al. (2012), *FEBS Journal*, 279:1905-1914.
Heightman T. D. (2011), *Current Chemical Genomics*, 5: 62-71.
King O. N. F. et al. (2010), *PLoS ONE*, 5:1-12.
Hong, S. et al. (2007), *PNAS*, 104:18439-18444.
Pradhan, S. et al. (1999), *J. Biol. Chem.*, 274: 33002-33010.
Suetake I, Shinozaki F, Miyagawa J, Takeshima H, Tajima S. (2004), *J Biol Chem.* 279(26): 27816-23.
Aoki, A. et al. (2001), *Nucleic. Acids. Res.*, 29: 3506-3512.
Zhang, H. et al. (2012), *J Biol Chem.*, 287(9):6573-81.
Strahl, B. D. and C. D Allis (2000) The language of covalent histone modifications. *Nature*, 403(6765): 41-5.
Michan, S. and Sinclair, D. (2007), *Biochem. J.*, 404: 1-13.
Michishita, E. et al. (2008), *Nature*, 452, 492-496.
Kim, W. and Kim, J. E. (2013), *J. Physiol. Pharmacol.*, 64(5):531-534.
An S I, Yeo K J, Jeon Y H, Song J J. (2011), *J Biol Chem.* 286(10): 8369-74.
Yost, J. M. et al. (2011), *Curr. Chem. Genomics*, 5: 72-84.
Shen, X, Liu, Y. et al. (2008), *Mol. Cell*, 32: 491-502
Nayak, V. et al. (2011), *Nucleus*, 1:2.
Jiang H I, Lu X, Shimada M, Dou Y, Tang Z, Roeder R G. (2013), *Nat Struct Mol Biol.*, 10:1156-63.
Ali M1, Horn R A1, Blakeslee W1, Ikenouye L1, Kutateladze T G2. (2014), *Biochim Biophys Acta.*; 1843(2):366-71.
Allali-Hassani A1, Kuznetsova E1, Hajian T1, Wu H1, Dombrovski L1, Li Y1, Graslund S1, Arrowsmith C H2, Schapira M3, Vedadi M4. (2014), *J Biomol Screen.*; 19(6):928-935.
Selvi B. R. et al. (2010), *Biochim Biophys Acta.*, 1799(10-12): 810-28.
Munoz-Fuentes, V. et al. (2011), *PLoS ONE*, 6: 1-7.
Cheng, D. et al. (2004), *J. Biol. Chem.*, 279: 23892-23899.
Li, K. K. et al. (2012), *Med Res Rev.* 32(4):815-67.
Selvi, B. R. et al. (2010), *J. Biol. Chem.*, 285: 7143-7152.
Yost, J. M. et al. (2011), *Curr. Chem. Genomics*, 5: 72-84.
Iberg, A. N. et al. (2007), *J Biol. Chem.*, 283: 3006-3010.
Zurita-Lopez C I1, Sandberg T, Kelly R, Clarke S G. (2012), *J Biol Chem.* 287(11):7859-70.
Lee, J. et al. (2005), *The journal of biological chemistry*, vol. 280, 38: 32890-32896.
Du, H.-N. et al. (2008), *Gene Dev*, 22: 2786-2798
Schultz, D. C. et al. (2002), *Genes Dev.*, 16: 919-932.
Kang, H. B. et al. (2009), *FEBS LETT* 583: 1880-1886.
Sabbattini P, Canzonetta C, Sjoberg M, Nikic S, Georgiou A, Kemball-Cook G, Auner H W, Dillon N. (2007), *EMBO J.* 26(22):4657-69.
Preuss U, Landsberg G, Scheidtmann K H. (2003), *Nucleic Acids Res.*, 31(3):878-85.
Han A, Lee K H, Hyun S, Lee N J, Lee S J, Hwang H, Yu J. (2011), *Bioorg Med Chem.*, 19(7):2373-7.
Baek S H. (2011), *Mol Cell*, 42(3):274-84
Barnett, S. F. et al. (2005), *Biochem. J.*, 385: 399-408.
Misaghi, S. et al. (2009), *Mol. Cell. Biol.* 29: 2181-2192.

Horton, R. A. et al. (2007), *Anal. Biochem.*, 360:138-143.
Hu, M. et al. (2005), *The EMBO Journal* 24, 3747-3756.
Ye Y. et al. (2011), *EMBO reports*, 12: 350-357.
Tian, X. et al. (2011), *Assay and Drug Dev. Technol.*, 9:165-173.
Arrowsmith C H, Bountra C, Fish P V, Lee K, Schapira M (2012) Epigenetic protein families: a new frontier for drug discovery. *Nature Reviews Drug Discovery*, 11, 384-400.
Plass C, Pfister S M, Lindroth A M, Bogatyrova O, Claus R and Lichter P. (2013). Mutations in regulators of the epigenome and their connections to global chromatin patterns in cancer. *Nature Reviews Genetics* 14: 765-780.
Taverna S D, Li H, Ruthenburg A J, Allis C D, Patel D J. (2007) How chromatin-binding modules interpret histone modifications: lessons from professional pocket pickers *Nature Structural & Molecular Biology* 14, 1025-1040.
Prinjha R K, Witherington J, Lee K. (2012) Place your BETs: the therapeutic potential of bromodomains *Trends in Pharmacological Sciences* 33, 3, 146-153.
Biggar K L, Li S S-C. (2015) Non-histone protein methylation as a regulator of cellular signalling and function. *Nature Rev Mol Cell Biol,* 16, 5-17.
Tough D F, Lewis H D, Rioja I, Lindon M J, Prinjha R K (2014). Epigenetic pathways targets for the treatment of disease: accelerating progress in the development of pharmacological tools: IUPHAR Review 11. *Br J Pharmacol* 171: 4981-5010
Ciceri P, Müller S, O'Mahony A, Fedorov O, Filippakopoulos P, Hunt J P, Lasater E A, Pallares G, Picaud S, Wells C, Martin S, Wodicka L M, Shah N P, Treiber D K, Knapp S (2014) Dual kinase-bromodomain inhibitors for rationally designed polypharmacology. *Nature Chemical Biology,* 10, 305-312.
Fu L, Tian M, Li X, Li J-J, Huang J L, Zhang Y, Liu B. (2015). Inhibition of BET bromodomains as a therapeutic strategy for cancer drug discovery. *Oncotarget.* 2015 Mar. 20; 6(8): 5501-5516.
Ciro M, Prosperini E, Quarto M, Grazini U, Walfridsson J, McBlane F, Nucifero P, Pacchiana G, Capra M, Christensen J, Helin K. (2009) ATAD2 is a novel cofactor for MYC, overexpressed and amplified in aggressive tumors. *Cancer Res.,* 69: 8491-8498.
Krakstad C, Tangen I L, Hoivik E A, Halle M K, Berg A, Werner H M, Salvesen, H B. (2015) ATAD2 overexpression links to enrichment of B-MYB-translational signatures and development of aggressive endometrial carcinoma. *Oncotarget,* 6: 28440-28452.
Weidner-Glunde M, Ottinger M, Schulz T F. (2010) WHAT do viruses BET on? *Front Biosci.* 15: 537-549.
Blus B J, Wiggins K, S. (2011) Epigenetic virtues of chromodomains. *Critical Reviews in Biochemistry and Molecular Biology.* 46, 6, 507-526
Cyr A R, Dormann F E. The redox basis of epigenetic modifications: from mechanism to functional consequences. (2011) *Antioxidant & Redox Signaling,* 15(2), 551-589.
Copeland R A, Solomon M E, Richon V M. (2009) Protein methyl transferase as a target class for drug discovery. *Nat. Rev. Drug Discovery,* 8, 724-732.
Shankar R S, Bahirvani A G, Rao V K, Bharathy N, Ow J R, Taneja R. (2013) G9a a multipotent regulator of gene expression. *Epigenetics,* 8:1, 16-22.
Casciello F, Winloch K, Gannon F, Lee J S. (2015) Functional role of G9a histone methyltransferase in cancer. *Front. Immunol.,* 6:487-498.

Fuhrmann J, Clancy K W, Thompson P R. (2015) Chemical biology of protein arginine modifications in epigenetic regulation. *Chem Rev.,* 115, 5413-5461.
Hojfelt J W, Agger K, Helin K. (2013) Histone lysine demethylases as targets for anticancer therapy. *Nat. Rev. Drug Discov.* 917.
Xiang Y, Zhu Z, Han G, Ye X, Xu B, Peng Z et al. (2007). JARID1B is a histone H3 lysine 4 demethylase up-regulated in prostate cancer. *Proc Natl Acad Sci USA* 104: 19226-19231.
Couvelard A, Deschamps L, Rebours V, Sauvanet A, Gatter K, Pezzella F et al. (2008). Overexpression of the oxygen sensors PHD-1, PHD-2, PHD-3, and FIH is associated with tumor aggressiveness in pancreatic endocrine tumors. *Clin Cancer Res* 14: 6634-6639.
Roesch A, Fukunaga-Kalabis M, Schmidt E C, Zabierowski S E, Brafford P A, Vultur A et al. (2010). A temporarily distinct subpopulation of slow-cycling melanoma cells is required for continuous tumor growth. *Cell* 141: 583-594.
He J, Nguyen A T, Zhang Y (2011). KDM2b/JHDMlb, an H3K36me2-specific demethylase, is required for initiation and maintenance of acute myeloid leukemia. *Blood* 111: 3869-3880.
Berry W L, Janknecht R (2013). KDM4/JMJD2 histone demethylases: epigenetic regulators in cancer cells. *Cancer Res* 73: 2936-2942.
Kogure M, Takawa M, Cho H-S, Toyokawa G, Hayashi K, Tsunoda T et al. (2013). Deregulation of the histone demethylase JMJD2A is involved in human carcinogenesis through regulation of the G1/S transition. *Cancer Lett* 336: 76-84.
Tzatsos A, Paskaleva P, Ferrari F, Deshpande V, Stoykova S, Contino G et al. (2013). KDM2B promotes pancreatic cancer via polycomb dependent and -independent transcriptional programs. *J Clin Invest* 123: 727-739.
Adcock I M, Lee K Y (2006). Abnormal histone acetylase and deacetylase expression and function in lung inflammation. *Inflamm Res* 55:311-321.
Avvakumov N, Cote J (2007). The MYST family of histone acetyltransferases and their intimate links to cancer. *Oncogene* 26: 5395-5407.
Grabiec A, Tak P, Reedquist K (2008). Targeting histone deacetylase activity in rheumatoid arthritis and asthma as prototypes of inflammatory disease: should we keep our HATs on? *Arthritis Res Ther* 10: 226.
Ghizzoni M, Haisma H J, Maarsingh H, Dekker F J (2011). Histone acetyltransferases are crucial regulators in NF-kB mediated inflammation. *Drug Discov Today* 16: 504-511.
Iyer A, Fairlie D P, Brown L (2011). Lysine acetylation in obesity, diabetes and metabolic disease. *Immunol Cell Biol* 90: 39-46.
Pirooznia S K and Elefant F (2013). Targeting specific HATs for neurodegenerative disease treatment: translating basic biology to therapeutic possibilities. *Front Cell Neurosci* 7: 30.
Lee, S., et al., (2001) *Combined angiotensin converting enzyme inhibition and* angiotensin AT(1) receptor blockade up-regulates myocardial AT(2) receptors in remodeled myocardium post-infarction. *Cardiovasc Res,* 51(1): 131-9.
Rubin, B., Laffan R J, Kotler D G, O'Keefe E H, Demaio D A, Goldberg M E (1978) S Q 14,225 (D-3-mercapto-2-methylpropanoyl-1-proline), a novel orally active inhibitor of angiotensin I-converting enzyme. *J Pharmacol Exp Ther,* 204(2): 271-80.

Bunning, P., B. Holmquist, and J. F. Riordan, *Substrate specificity and kinetic characteristics of angiotensin converting enzyme*. Biochemistry, 1983. 22(1): p. 103-10.

Hesselgesser, J., et al., *Identification and characterization of small molecule functional antagonists of the CCR1 chemokine receptor*. J Biol Chem, 1998. 273(25): p. 15687-92.

Gong, X., Gong W, Kuhns D B, Ben-Baruch A, Howard O M, Wang J M (1997) Monocyte chemotactic protein-2 (MCP-2) uses CCR1 and CCR2B as its functional receptors. *J Biol Chem*, 272(18): 11682-5.

Combadiere, C., Salzwedel K, Smith E D, Tiffany H L, Berger E A, Murphy P M (1998) Identification of CX3CR1. A chemotactic receptor for the human CX3C chemokine fractalkine and a fusion coreceptor for HIV-1. *J Biol Chem*, 273(37): 23799-804.

Grob, P. M., David E, Warren T C, DeLeon R P, Farina P R, Homon C A. (1990) Characterization of a receptor for human monocyte-derived neutrophil chemotactic factor/interleukin-8. *J Biol Chem*, 265(14): 8311-6.

Ahuja, S. K. and P. M. Murphy (1996) The CXC chemokines growth-regulated oncogene (GRO) alpha, GRObeta, GROgamma, neutrophil-activating peptide-2, and epithelial cell-derived neutrophil-activating peptide-78 are potent agonists for the type B, but not the type A, human interleukin-8 receptor. *J Biol Chem*, 271(34): 20545-50.

Valenzuela-Femandez, A., Planchenault T, Baleux F, Staropoli I, Le-Barillec K, Leduc D, Delaunay T, Lazarini F, Virelizier J L, Chignard M, Pidard D, Arenzana-Seisdedos F. (2002) Leukocyte elastase negatively regulates Stromal cell-derived factor-1 (SDF-1)/CXCR4 binding and functions by amino-terminal processing of SDF-1 and CXCR4. *J Biol Chem*, 277(18): 15677-89.

Dittadi, R., et al., Radioligand binding assay of epidermal growth factor receptor: causes of variability and standardization of the assay. Clin Chem, 1990. 36(6): p. 849-54.

Muller-Enoch, D., E. Seidl, andH. Thomas, [6,7-Dihydroxycoumarin (Aesculetin) as a substrate for catechol-o-methyltransferase (author's transl)]. *Z Naturforsch C*, 1976. 31(5-6): 280-4.

Tietge, U. J., Pratico D, Ding T, Funk C D, Hildebrand R B, Van Berkel T, Van Eck M. (2005). Macrophage-specific expression of group IIA sPLA2 results in accelerated atherogenesis by increasing oxidative stress. *J Lipid Res*, 46(8): 1604-14.

Montalibet, J., K. I. Skorey, and B. P. Kennedy (2005) Protein tyrosine phosphatase: enzymatic assays. *Methods* 35(1): 2-8.

Sun, Z. Y. and Z. H. Tu, *A novel in vitro model to screen steroid 5 alpha-reductase inhibitors against benign prostatic hyperplasia*. Methods Find Exp Clin Pharmacol, 1998. 20(4): p. 283-7.

Becker, K., Gromer, S., Schirmer, R. H., Müller, S. (2000) Thioredoxin reductase as a pathophysiological factor and drug target. *Eur J Biochem*, 267(20): 6118-25.

Hatano, T., et al. (1990). Effects of interaction of tannins with co-existing substances. VII. Inhibitory effects of tannins and related polyphenols on xanthine oxidase. *Chem Pharm Bull (Tokyo)*, 38(5): 1224-9.

De Backer et al, (1993). Genomic cloning, heterologous expression and pharmacological characterization of a human histamine H1 receptor. *Biochem Biophys Res Commun* 197(3): 1601-1608.

Ruat et al., (1990). Reversible and irreversible labeling and autoradiographic localization of the cerebral histamine H2 receptor using [125I]iodinated probes. *Proc Natl Acad Sci USA*. 87(5): 1658-1662.

Krueger et al, (2005). G protein-dependent pharmacology of histamine H3 receptor ligands: evidence for heterogeneous active state receptor conformations. *J Pharmacol Exp Ther.* 314(1): 271-281.

Liu et al, (2001). Comparison of human, mouse, rat, and guinea pig histamine H4 receptors reveals substantial pharmacological species variation. *J Pharmacol Exp Ther.* 299(1): 121-130.

Kubo and Strott, (1987). Differential activity of 3-hydroxy-3-methylglutaryl coenzyme A reductase in zones of the adrenal cortex. *Endocrinology*. 120:214-221.

Pufahl et al., (2007). Development of a fluorescence-based enzyme assay of human 5-lipoxygenase. *Anal Biochem*. 364(2): 204-212.

Mansuy et al., (1986). A new potent inhibitor of lipid peroxidation in vitro and in vivo, the hepatoprotective drug anisylditholthione. *Biochem Biophys Res Comm*. 135:1015-1021.

Romano et al., (1993). Lipoxin synthase activity of human platelet 12-lipoxygenase. *Biochem J*. 296: 127-133.

Urban et al., (1991). Comparative membrane locations and activities of human monoamine oxidases expressed in yeast. *FEBSLett*. 286(1-2): 142-146.

Svensson et al., (1987). Peroxidase and peroxidase-oxidase activities of isolated human myeloperoxidase. *Biochem J*. 242:673-680.

Yamamoto et al., (2006). A nonradioisotope, enzymatic assay for 2-deoxyglucose uptake in L6 skeletal muscle cells cultured in a 96-well microplate. *Anal Biochem*. 351(1): 139-45.

Cobb, R. R., et al., (1992) *Functional expression of soluble ICAM-1 by baculovirus-infected Sf9 cells*. Biochem Biophys Res Commun, 185(3): 1022-33.

Stoltenborg, J. K., Tsao P W, George H J, Bouchard P J, Wexler E J, Hausner E A (1994). A fluorescent cellular adhesion assay using insect cell produced human VCAM1. *J Immunol Methods*, 175(1): 59-68.

Lenardo, M. J. and D. Baltimore (1989) NF-kappa B: a pleiotropic mediator of inducible and tissue-specific gene control. Cell, 58(2): 227-9.

Sen R., Baltimore D. (1986). Multiple nuclear factors interact with immunoglobulin enhancer sequences. *Cell*, 46, 705-716.

Pantano C., Reynaert N. L., van der Vliet A. V., Janssen-Heininger Y. M. W. (2006). Redox-sensitive kinases of the nuclear factor κB signalling pathway. *Antioxidants & Redox Signaling* 8(9-10), 1791-1807.

Brigelius-Flohé R., Flohé L. (2011). Basic principle and emerging concepts in redox control of transcription factors. *Antioxidants & Redox Signaling*, 15(8), 2335-2380.

Ghosh G., Wang V. Y-F., Huang D-B., Fusco A. (2015). NF-κB regulation: lessons from structures. *Immunol. Rev.* 246(1), 36-58.

Akdis M., Aab A., Altunbulakli C., Azkur K., Costa R. A., Crameri R., Duan S., Eiwegger T., Eljaszewicz A., Ferstl R., Frei R., Garbani M., Globinska A., Hess L., Huitema C., Kubo T., Komlosi Z., Konieczna P., Kovacs N., Kucuksezer U. C., Meyer N., Morita H., Olzhausen J., O'Mahony L., Perzer M., Prati M., Rabane A., Rhyner C., Rinaldi A., Sokolowska M., Stanic B., Sugita K., Treis A., van der Veen W., Wanke K., Wawrzyniak M., Wawrzyniak P., Wirz O. F., Zakzuk J. S, Akdis C. A. (2016). Interleukins (from IL-1 to IL-38), interferons, transforming growth factor β, and TNF-α: receptors, functions, and role in diseases. Fundamentals of allergy and Immunology, 138, 4, 984-1010.

Perkins N. D. (2012). The diverse and complex roles of NF-κB subunits in cancer. Nature Reviews Cancer, 12, 121-133.

Sethi G., Shanmugam M. K., Ramachandran L., Kumar A. P., Tergaonkar V. (2012). Multifacet link between cancer and inflammation. Biosci. Rep. 32, 1-15.

Parri M., Chiarugi P. (2013). Redox molecular machines involved in tumour progression. Antioxidants & Redox Signaling, 19(15), 1828-1846.

D'Ignazio L., Bandarra D., Rocha S. (2016). NF-κB cross talk in immune responses. FEBS Journal 283, 413-424.

Ludwig L. M., Nassin M. L., Hadji A., Labelle, J. L. (2016). Killing two cells with one stone: Pharmacologic BCL-2 family targeting for cancer cell death and immune modulation. Frontiers in Peadiatrics, Vol 4, Article 135, page 1-13.

Xia, M, Huang R, Witt K L, Southall N, Fostel J, Cho M H, Jadhav A, Smith C S, Inglese J, Portier C J, Tice R R, Austin C P (2008) Compound cytotoxicity profiling using quantitative high-throughput screening. *Environ Health Perspect.* 116(3):284-91.

Fallahi-Sichani, M., S. Honardejad, L. M. Heiser, J. W. Gray, and P. K. Sorger (2013). Metrics other than potency reveal systematic variation in responses to cancer drugs. *Nat. Chem. Biol.* 9: 708-714.

Barretina, J., G. Caponigro, N. Stransky, K. Venkatesan, A. A. Margolin, et al. (2012). The Cancer Cell Line Encyclopedia enables predictive modelling of anticancer drug sensitivity. *Nature* 483: 603-607.

Dierks E A, Stams K R, Lim H K, Cornelius G, Zhang H, Ball S E (2001). A method for the simultaneous evaluation of the activities of seven major human drug-metabolizing cytochrome P450s using an in vitro cocktail of probe substrates and fast gradient liquid chromatography tandem mass spectrometry. *Drug Metab. Dispos.*, 29: 23-29.

Mohammad R. H., Dugan, M. C., Mohamed, A. N., Almatchy, V. P., Flake, T. M., Dergham, S. T., Shields, A. F., Al-Katib, A. A., Vaitkevicius, V. K. and Sarkar, F. H (1998). Establishment of a human pancreatic tumor xenograft model: Potential application for preclinical evaluation of novel therapeutic agents. *Pancreas* 16:19-25.

"Guide for the Care and Use of Laboratory Animals: Eighth Edition" (2011), The National Academies Press, Washington, D.C.

What is claimed is:

1. A method of treating a disease or disorder selected from the group consisting of a cancer, a skin disease, or a skin disorder, the method comprising:
   administering a therapeutically effective amount of a compound according to a compound of Formula (I),

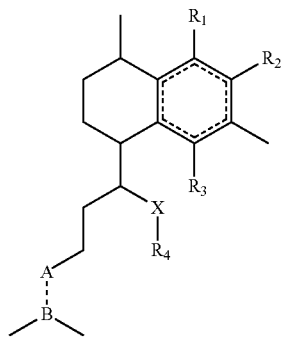

a geometric isomer, stereoisomer, or pharmaceutically acceptable salt thereof,
wherein:
$R_1$ is independently H, OH, $OC_{1-5}$alkyl, $OCH_2Ph$, $OC_{2-5}$ alkenyl, $OC_{4-5}$alkadienyl, $OC(O)C_{1-5}$alkyl, $OC(O)Ph$, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$ alkenyl, $OC_{4-5}$alkadienyl, $OC(O)C_{1-5}$alkyl, $OC(O)Ph$, $OC(O)C_{2-5}$alkenyl, $OC(P)C_{4-5}$alkadienyl or =O;

$R_3$ is independently H, OH, $OC_{1-5}$alkyl or $OC(O)C_{1-5}$alkyl or =O, no more than one of $R_1$, $R_2$ and $R_3$ can be H;

A-B is CH=C or $CH_2$—CH; and (a) X is $CH_2$, or C(O), and $R_4$ is OH, $OC_{1-5}$alkyl, $OCH_2Ph$, $OC_{2-5}$alkenyl, $OC_{4-5}$alkadienyl, $OC(O)C_{1-5}$ alkyl, $OC(O)Ph$, $OC(O)C_{2-5}$alkenyl or $OC(O)C_{4-5}$alkadienyl;

or (b) X and $R_3$ are directly joined with each other to form a six membered ring, provided that X is CH, $CH_2$, or C(O), and $R_3$ is O, wherein when X is CH then $R_4$ is OH, $OC_{1-5}$alkyl, $OCH_2Ph$, $OC_{2-5}$alkenyl, $OC_{4-5}$ alkadienyl, $OC(O)C_{1-5}$alkyl, $OC(O)Ph$, $OC(O)C_{2-5}$ alkenyl or $OC(O)C_{4-5}$alkadienyl, or when X is $CH_2$ or C(O) then $R_4$ is absent.

2. The method according to claim 1, wherein,
(i) when $R_2$ is H, X is not $CH_2$; and
(ii) when $R_2$ is H, and when X and $R_3$ form a six membered ring, then A-B is CH=C.

3. The method according to claim 1, wherein the compound is
(i) a compound of Formula (Ia):

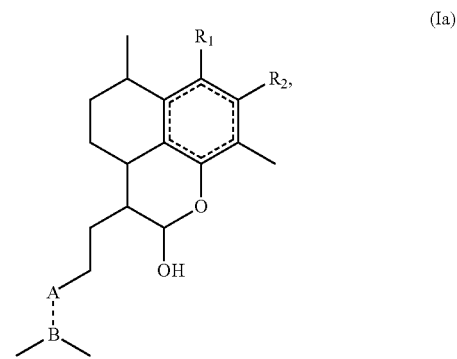

or (ii) a compound of Formula (Ic):

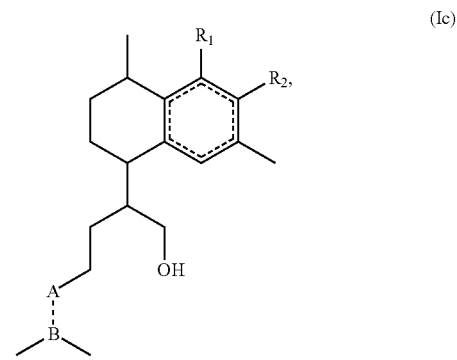

or
(iii) a compound of Formula (Ii):
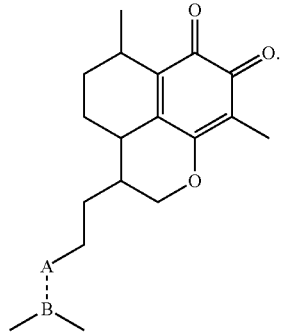
(Ii)
4. The method according to claim 1, wherein A-B is CH=C.
5. The method according to claim 1, wherein the compound is selected from the group consisting of:
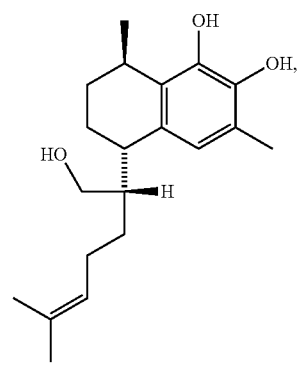
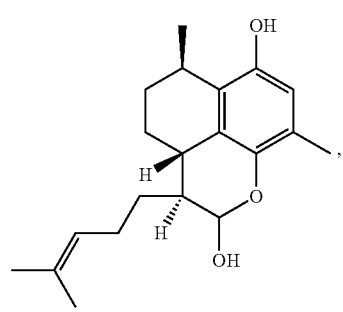
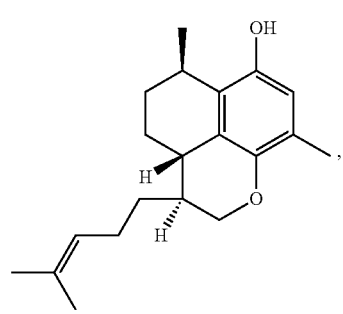
-continued
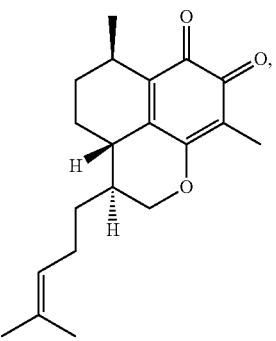
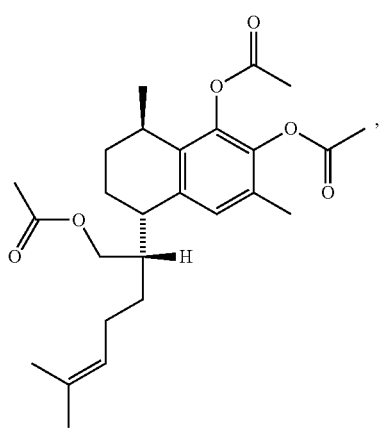
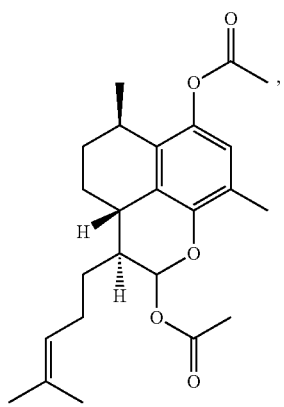
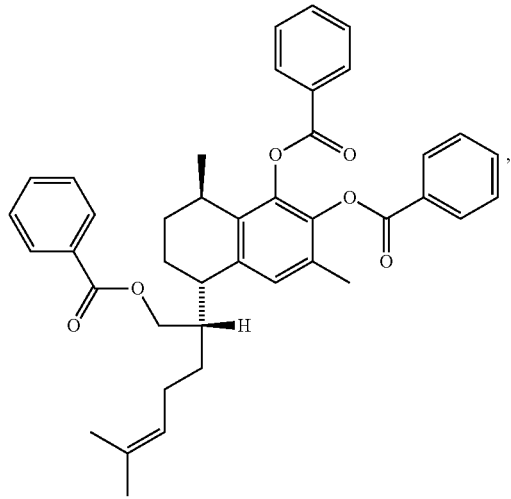

-continued

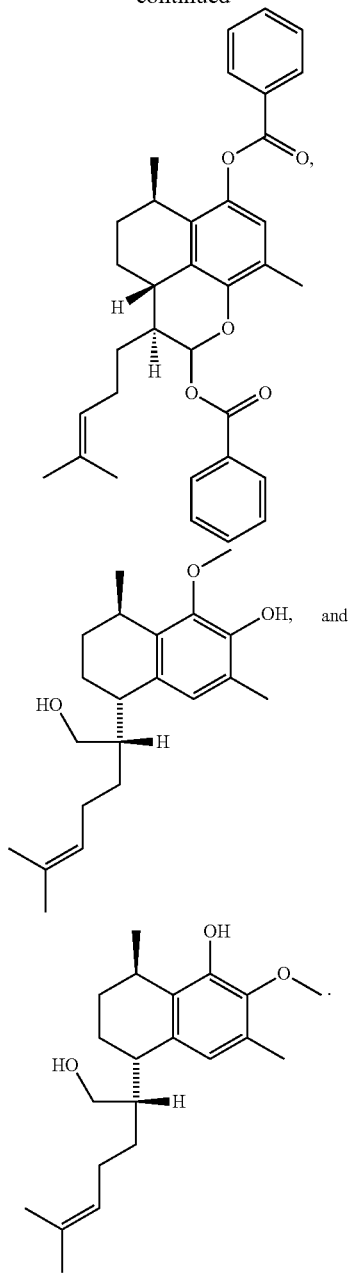

and

6. The method according to claim 5, wherein the compound is:

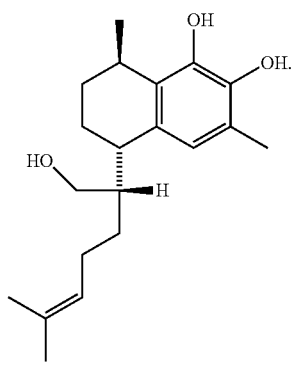

7. The method according to claim 5, wherein the compound is:

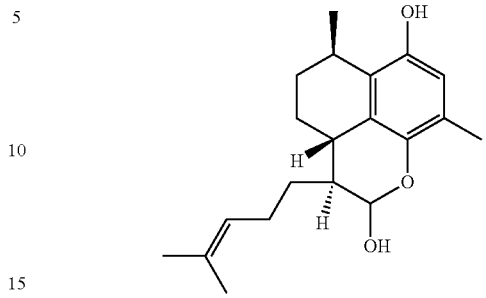

8. The method according to claim 1, wherein the compound is isolated from propolis, and wherein the propolis originates from plants of the *Myoporum* genus.

9. The method according to claim 8, wherein the propolis originates from *Myoporum insulare*.

10. The method as defined in claim 1, wherein the compound is isolated from the resin, gum or exudate of *Myoporum* genus.

11. The method according to claim 10, wherein the compound is isolated from the resin, the gum, or the exudate of *Myoporum insulare*.

12. The method according to claim 1, wherein the skin disease or the skin disorder is selected from the group consisting of eczema, psoriasis, acne, a wound, a scar, inflammation, a burn, sunburn, skin damage and skin irritation.

13. The method according to claim 1, wherein the disease or the disorder is the cancer, and wherein the cancer is selected from the group consisting of bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

14. The method according to claim 13, wherein the cancer is of the central nervous system and is a glioma.

15. The method according to claim 13, wherein the cancer is of the central nervous system and is a medulloblastoma.

16. The method according to claim 13, wherein the cancer is of the central nervous system and is a neuroblastoma.

17. The method according to claim 13, wherein the cancer is the lung cancer and the lung cancer is a non-small cell lung cancer.

18. The method according to claim 13, wherein the cancer is the lung cancer and the lung cancer is a small cell lung cancer.

19. The method according to claim 13, wherein the cancer is the carcinoma and the carcinoma is adenosquamous cell carcinoma or squamous cell carcinoma.

20. The method according to claim 13, wherein the cancer is the sarcoma and the sarcoma is a liposarcoma, a rhabdomyosarcoma, or a fibrosarcoma.

21. The method according to claim 13, wherein the cancer is the sarcoma and the sarcoma is a soft tissue sarcoma.

22. The method according to claim 21, wherein the soft tissue sarcoma is a soft tissue osteosarcoma.

23. The method according to claim 13, wherein the cancer is the lymphoma and the lymphoma is Burkitt's lymphoma, Hodgkin's lymphoma, or non-Hodgkin's lymphoma.

24. A method of manufacturing a medicament for treating a disease or disorder selected from the group consisting of a cancer, a skin disease, or a skin disorder, comprising, dissolving an effective amount of a compound according to Formula (I) for treating the cancer, the skin disease or the disorder with a pharmaceutically acceptable excipient, wherein Formula (I) is

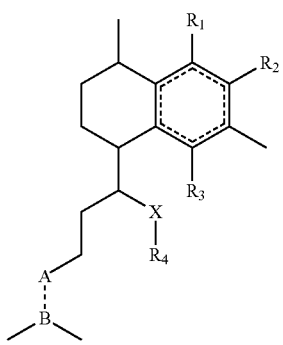

(I)

a geometric isomer, stereoisomer, or a pharmaceutically acceptable salt thereof, wherein:

$R_1$ is independently H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl, $OC(O)C_{4-5}$alkadienyl or =O;

$R_2$ is independently H, OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl, $OC(O)C_{4-5}$alkadienyl or =O;

$R_3$ is independently H, OH, $OC_{1-5}$alkyl or $OC(O)C_{1-5}$alkyl or =O;

and no more than one of $R_1$, $R_2$ and $R_3$ can be H;

A-B is CH=C or $CH_2$—CH; and (a) X is $CH_2$, or C(O), and $R_4$ is OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$alkadienyl; or (b) X and $R_3$ are directly joined with each other to form a six-membered ring, and X is CH, CH2, or C(O), and R3 is O, wherein when X is CH then $R_4$ is OH, $OC_{1-5}$alkyl, $OCH_2Ph$, $OC_{2-5}$alkenyl, $OC_{4-5}$alkadienyl, $OC(O)C_{1-5}$alkyl, $OC(O)Ph$, $OC(O)C_{2-5}$alkenyl or $OC(O)C_{4-5}$alkadienyl, or when X is CH2 or C(O) then R4 is absent.

25. The method according to claim 24, wherein (i) when $R_2$ is H then, X is not $CH_2$; and (ii) when $R_2$ is H, and X and $R_3$ form a six membered ring, then A-B is CH=C.

26. The method according to claim 24, wherein:

(i) the compound is a compound of Formula (Ia):

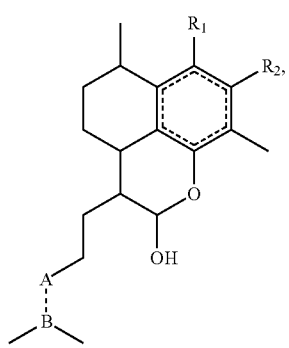

(Ia)

or (ii) a compound of Formula (Ic):

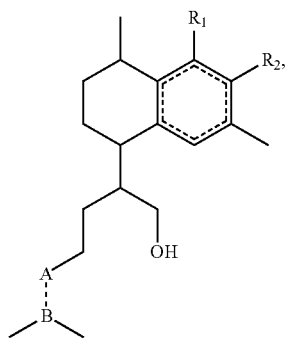

(Ic)

or (iii) a compound of Formula (Ii):

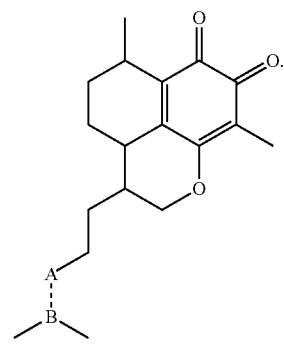

(Ii)

27. The use method according to claim 24, wherein A-B is CH=C.

28. The method according to claim 24, wherein the compound is a compound selected from the group consisting of:
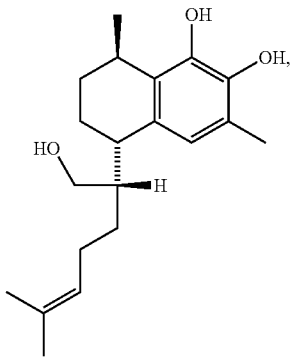
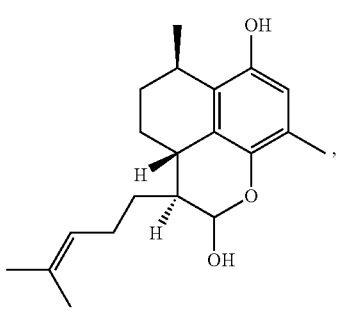
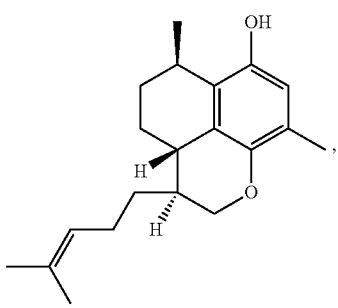
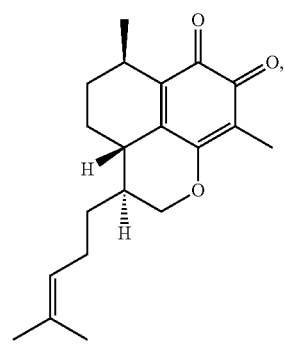
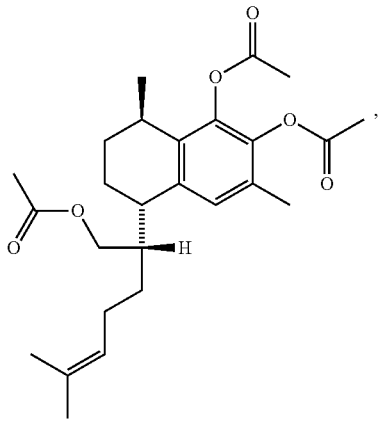
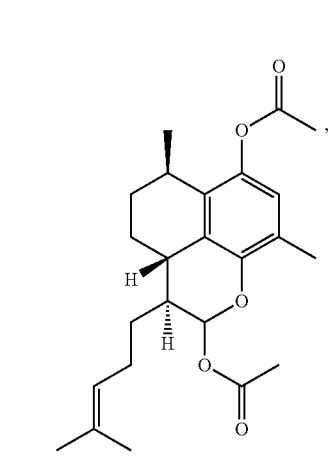
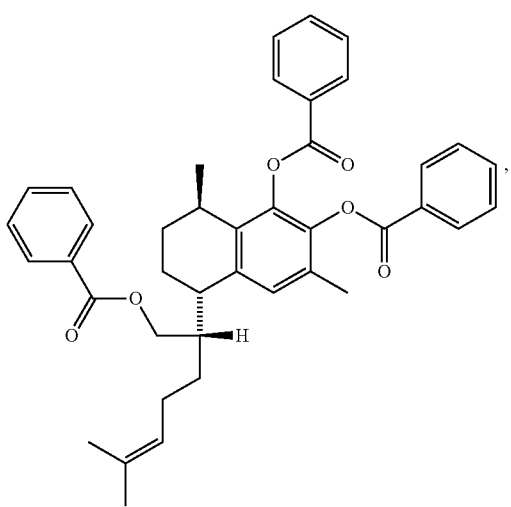

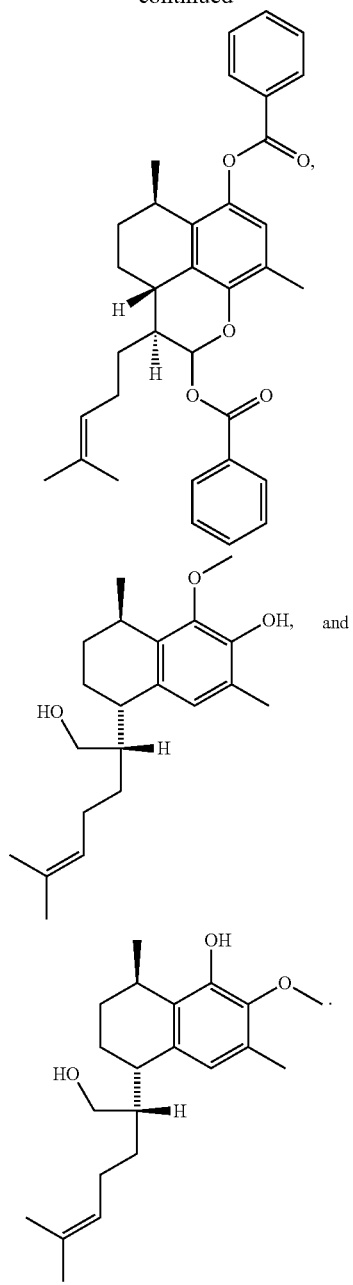

29. The method according to claim 24, wherein the skin disease or the skin disorder is the cancer and the cancer is selected from the group consisting of bladder cancer, bone cancer, brain cancer, breast cancer, a cancer of the central nervous system, cancer of the adrenal glands, cancer of the placenta, cancer of the testis, cervical cancer, colon cancer, kidney cancer, head and neck cancer, myeloma, leukemia, liver cancer, lung cancer, melanoma, ovarian cancer, pancreatic cancer, prostate cancer, skin cancer, stomach cancer, thyroid cancer, uterine cancer, a carcinoma, a lymphoma, a sarcoma, eye cancer, esophageal cancer, bile duct cancer or vulva cancer.

30. The method according to claim 24, wherein the disease or the disorder is the skin disease or the skin disorder and the skin disease or the skin disorder is selected from the group consisting of: eczema, psoriasis, acne, a wound, a scar, inflammation, a burn, sunburn, skin damage and skin irritation.

31. The method according to claim 1, wherein:
$R_1$ is independently H, OH, $OC_{1-5}$alkyl, $OCH_2Ph$, $OC(O)C_{1-5}$alkyl, $OC(O)Ph$, or =O;
$R_2$ is independently H, OH, $OC_{1-5}$alkyl, $OCH_2Ph$, $OC(O)C_{1-5}$alkyl, $OC(O)Ph$ or =O;
$R_3$ is independently H, OH, $OC_{1-5}$alkyl, $OC(O)C_{1-5}$alkyl or =O;
no more than one of $R_1$, $R_2$ and $R_3$ can be H;
A-B is CH=C or CH2-CH; and
(a) X is $CH_2$, and $R_4$ is OH, $OC_{1-5}$alkyl, $OCH_2Ph$, $OC(O)C_{1-5}$alkyl, or $OC(O)Ph$, or
(b) X and $R_3$ are directly joined with each other to form a six membered ring, provided that X is CH or CH2 and R3 is O, wherein when X is CH then R4 is OH, $OC_{1-5}$alkyl, $OCH_2Ph$, $OC(O)C_{1-5}$alkyl, or $OC(O)Ph$, or when X is CH2 then R4 is absent.

32. The method of claim 1, wherein:
X is $CH_2$;
$R_1$ is independently OH, $OC_{1-5}$alkyl, $OC(O)C_{1-5}$alkyl or =O;
$R_2$ is independently OH, $OC_{1-5}$alkyl, $OC(O)C_{1-5}$alkyl or =O;
$R_3$ is H;
$R_4$ is OH, $OC_{1-5}$alkyl, or $OC(O)C_{1-5}$alkyl; and
A-B is CH=C or $CH_2$—CH.

33. The method of claim 1, wherein:
X is $CH_2$;
$R_1$ is independently OH or $OC_{1-5}$alkyl;
$R_2$ is independently OH or $OC_{1-5}$alkyl;
$R_3$ is H;
$R_4$ is OH or $OC_{1-5}$alkyl; and
A-B is CH=C.

34. The method of claim 24, wherein:
$R_1$ is independently selected from H, OH, $OC_{1-5}$alkyl, $OCH_2Ph$, $OC(O)C_{1-5}$alkyl, $OC(O)Ph$, or =O;
$R_2$ is independently selected from H, OH, $OC_{1-5}$alkyl, $OCH_2Ph$, $C(O)C_{1-5}$alkyl, $OC(O)Ph$, or =O;
$R_3$ is independently selected from H, OH, $OC_{1-5}$alkyl, $OC(O)C_{1-5}$alkyl or =O;
wherein, no more than one of $R_1$, $R_2$ and $R_3$ can be H;
A-B is CH=C or $CH_2$—CH; and
(a) X is $CH_2$ and R4 is OH, $OC_{1-5}$alky, $OCH_2Ph$, $OC(O)C_{1-5}$alkyl, or $OC(O)Ph$, or
(b) X and R3 are directly joined with each other to form a six membered ring, provided that X is CH or CH2 and R3 is O, wherein when X is CH then R4 is OH, $OC_{1-5}$alkyl, $OCH_2Ph$, $OC(O)C_{1-5}$alkyl, or $OC(O)Ph$, or when X is CH2 then R4 is absent.

35. The method according to claim 24, wherein:
$R_1$ is independently selected from H, OH, $OC_{1-5}$alkyl, $OCH_2Ph$, $OC(O)C_{1-5}$alkyl, $OC(O)Ph$ or =O;
$R_2$ is independently selected from H, OH, $OC_{1-5}$alkyl, $OCH_2Ph$, $OC(O)C_{1-5}$alkyl, $OC(O)Ph$ or =O,
$R_3$ is independently selected from H, OH, $OC_{1-5}$alkyl, $OC(O)C_{1-5}$alkyl or =O;
wherein, no more than one of $R_1$, $R_2$ and $R_3$ can be H;
A-B is CH=C or $CH_2$—CH; and
(a) X is $CH_2$ and $R_4$ is OH, $OC_{1-5}$alkyl, $OCH_2Ph$, $OC(O)C_{1-5}$alkyl or $OC(O)Ph$; or
(b) X and $R_3$ are directly joined with each other to form a six-membered ring, provided that X is CH or CH2 and R3 is O, wherein when X is CH then $R_4$ is OH, $OC_{1-5}$alkyl, $OCH_2Ph$, $OC(O)C_{1-5}$alkyl or $OC(O)Ph$, or when X is CH2 then R4 is absent.

36. The method of claim 24, wherein:
X is $CH_2$;
$R_1$ is OH or $OC_{1-5}$alkyl;
$R_2$ is OH or $OC_{1-5}$alkyl;
$R_3$ is H;
$R_4$ is OH or $OC_{1-5}$alkyl; and
A-B is CH=C.

\* \* \* \* \*